(12) United States Patent
Ahrens et al.

(10) Patent No.: US 9,167,819 B2
(45) Date of Patent: Oct. 27, 2015

(54) HERBICIDAL 3-(SULFIN-/SULFONIMIDOYL)-BENZAMIDES

(71) Applicant: BAYER INTELLECTUAL PROPERTY GMBH, Monheim (DE)

(72) Inventors: Hartmut Ahrens, Egelsbach (DE); Ralf Braun, Ramberg (DE); Simon Doerner-Rieping, Neu-Anspach (DE); Arnim Koehn, Klein-Winternheim (DE); Stefan Lehr, Lyons (FR); Hansjoerg Dietrich, Liederbach am Taunus (DE); Dirk Schmutzler, Hattersheim (DE); Elmar Gatzweiler, Bad Nauheim (DE); Christopher Hugh Rosinger, Hofheim am Taunus (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/379,525

(22) PCT Filed: Feb. 18, 2013

(86) PCT No.: PCT/EP2013/053149
§ 371 (c)(1),
(2) Date: Aug. 19, 2014

(87) PCT Pub. No.: WO2013/124228
PCT Pub. Date: Aug. 29, 2013

(65) Prior Publication Data
US 2015/0018209 A1    Jan. 15, 2015

(30) Foreign Application Priority Data
Feb. 21, 2012 (EP) .................. 12156308

(51) Int. Cl.
| C07D 413/00 | (2006.01) |
| A01N 43/713 | (2006.01) |
| C07D 249/14 | (2006.01) |
| C07D 257/06 | (2006.01) |
| C07D 271/08 | (2006.01) |
| C07D 271/113 | (2006.01) |
| A01N 43/653 | (2006.01) |
| A01N 43/82 | (2006.01) |
| C07D 271/04 | (2006.01) |

(52) U.S. Cl.
CPC ............ *A01N 43/713* (2013.01); *A01N 43/653* (2013.01); *A01N 43/82* (2013.01); *C07D 249/14* (2013.01); *C07D 257/06* (2013.01); *C07D 271/04* (2013.01); *C07D 271/08* (2013.01); *C07D 271/113* (2013.01)

(58) Field of Classification Search
CPC .. C07D 271/12; C07D 285/14; C07D 513/04; C07D 498/04; C07D 513/18
USPC ................................ 548/126, 264.4; 504/105
See application file for complete search history.

(56) References Cited

U.S. PATENT DOCUMENTS

| 2011/0152084 A1 | 6/2011 | Koehn et al. |
| 2012/0058892 A1 | 3/2012 | Braun et al. |

FOREIGN PATENT DOCUMENTS

| WO | 2011035874 A1 | 3/2011 |
| WO | WO 2012018635 A2 * | 2/2012 |

OTHER PUBLICATIONS

International Search Report from corresponding PCT/EP2013/053149, mailed Apr. 8, 2013.

* cited by examiner

*Primary Examiner* — Nyeemah A Grazier
*Assistant Examiner* — Sagar Patel
(74) *Attorney, Agent, or Firm* — Miles & Stockbridge P.C.

(57) ABSTRACT

The invention relates to suifin- and sulfonimidoylbenzamides of general formula (S) used as herbicides. In said formula (I), R, R', R", X, W and Z represent radicals such as hydrogen, organic radicals such as alkyl, and other radicals such as halogens. Q represents a tetrazolyl-, triazolyl or oxadiazolyl radicals.

18 Claims, No Drawings

HERBICIDAL 3-(SULFIN-/SULFONIMIDOYL)-BENZAMIDES

CROSS REFERENCE TO RELATED APPLICATIONS

This application is a §371 National Stage Application of PCT/EP2013/053149, filed Feb. 18, 2013, which claims priority to EP 12156308.4, filed Feb. 21, 2012.

BACKGROUND

1. Field of the Invention

The invention relates to the technical field of the herbicides, in particular to that of the herbicides for the selective control of broad-leafed leaves and weed grasses in crops of useful plants.

2. Description of Related Art

WO 2011/035874 A1 discloses herbicidally active N-(1,2,5-oxadiazol-3-yl)benzamides. Certain N-(tetrazol-5-yl)- and N-(triazol-5-yl)benzamides and -nicotinamides are known as herbicides from the European patent application EP10174893, which has an earlier priority date than the present invention but was unpublished at the priority date of the present invention. However, the herbicidal activity and/or the crop plant compatibility of the compounds mentioned in these publications is not always sufficient.

SUMMARY

It is an object of the present invention to provide herbicidally active compounds having improved properties compared to the compounds known from the prior art.

It has now been found that certain sulfin- and sulfonimidoylbenzamides are especially suitable as herbicides. Accordingly, the present invention provides sulfin- and sulfonimidoylbenzamides of the formula (I) and salts thereof

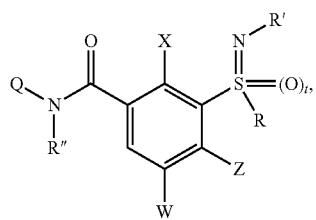

(I)

in which the symbols and indices are as defined below:
Q is a radical Q1, Q2, Q3 or Q4,

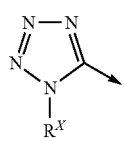

(Q1)

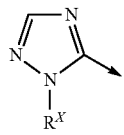

(Q2)

-continued

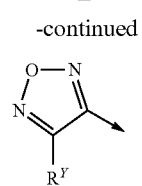

(Q3)

(Q4)

X is nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkenyl, halo-$(C_3-C_6)$-cycloalkenyl, $(C_3-C_6)$-cycloalkyl-$(C_1-C_6)$-alkyl, halo-$(C_3-C_6)$-cycloalkyl-$(C_1-C_6)$-alkyl, $(C_3-C_6)$-cycloalkenyl-$(C_1-C_6)$-alkyl, halo-$(C_3-C_6)$-cycloalkenyl-$(C_1-C_6)$-alkyl, $R^1(O)C$, $R^1(R^1ON\!\!=\!\!)C$, $R^1O(O)C$, $(R^1)_2N(O)C$, $R^1(R^1O)N(O)C$, $(R^1)_2N(R^1)N(O)C$, $R^1(O)C(R^1)N(O)C$, $R^2O(O)C(R^1)N(O)C$, $(R^1)_2N(O)C(R^1)N(O)C$, $R^2(O)_2S(R^1)N(O)C$, $R^1O(O)_2S(R^1)N(O)C$, $(R^1)_2N(O)_2S(R^1)N(O)C$, $R^1O$, $R^1(O)CO$, $R^2(O)_2SO$, $R^2O(O)CO$, $(R^1)_2N(O)CO$, $(R^1)_2N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $(R^5O)_2(O)P$, $R^1(O)C\!-\!(C_1-C_6)$-alkyl, $R^1O(O)C\!-\!(C_1-C_6)$-alkyl, $(R^1)_2N(O)C\!-\!(C_1-C_6)$-alkyl, $(R^1O)(R^1)N(O)C\!-\!(C_1-C_6)$-alkyl, $(R^1)_2N(R^1)N(O)C\!-\!(C_1-C_6)$-alkyl, $R^1(O)C(R^1)N(O)C\!-\!(C_1-C_6)$-alkyl, $R^2O(O)C(R^1)N(O)C\!-\!(C_1-C_6)$-alkyl, $(R^1)_2N(O)C(R^1)N(O)C\!-\!(C_1-C_6)$-alkyl, $R^2(O)_2S(R^1)N(O)C\!-\!(C_1-C_6)$-alkyl, $R^1O(O)_2S(R^1)N(O)C\!-\!(C_1-C_6)$-alkyl, $(R^1)_2N(O)_2S(R^1)N(O)C\!-\!(C_1-C_6)$-alkyl, NC$\!-\!(C_1-C_6)$-alkyl, $R^1O\!-\!(C_1-C_6)$-alkyl, $R^1(O)CO\!-\!(C_1-C_6)$-alkyl, $R^2(O)_2SO\!-\!(C_1-C_6)$-alkyl, $R^2O(O)CO\!-\!(C_1-C_6)$-alkyl, $(R^1)_2N(O)CO\!-\!(C_1-C_6)$-alkyl, $(R^1)_2N\!-\!(C_1-C_6)$-alkyl, $R^1(O)C(R^1)N\!-\!(C_1-C_6)$-alkyl, $R^2(O)_2S(R^1)N\!-\!(C_1-C_6)$-alkyl, $R^2O(O)C(R^1)N\!-\!(C_1-C_6)$-alkyl, $(R^1)_2N(O)C(R^1)N\!-\!(C_1-C_6)$-alkyl, $R^1O(O)_2S(R^1)N\!-\!(C_1-C_6)$-alkyl, $(R^1)_2N(O)_2S(R^1)N\!-\!(C_1-C_6)$-alkyl, $R^2(O)_nS\!-\!(C_1-C_6)$-alkyl, $R^1O(O)_2S\!-\!(C_1-C_6)$-alkyl, $(R^1)_2N(O)_2S\!-\!(C_1-C_6)$-alkyl, $R^1(O)C(R^1)N(O)_2S\!-\!(C_1-C_6)$-alkyl, $R^2O(O)C(R^1)N(O)_2S\!-\!(C_1-C_6)$-alkyl, $(R^1)_2N(O)C(R^1)N(O)_2S\!-\!(C_1-C_6)$-alkyl, $(R^5O)_2(O)P\!-\!(C_1-C_6)$-alkyl, phenyl, heteroaryl, heterocyclyl, phenyl-$(C_1-C_6)$-alkyl, heteroaryl-$(C_1-C_6)$-alkyl, heterocyclyl-$(C_1-C_6)$-alkyl, where the six last-mentioned radicals are each substituted by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O\!-\!(C_1-C_6)$-alkyl, and where heterocyclyl carries n oxo groups, Z is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkenyl, halo-$(C_3-C_6)$-cycloalkenyl, $(C_3-C_6)$-cycloalkyl-$(C_1-C_6)$-alkyl, halo-$(C_3-C_6)$-cycloalkyl-$(C_1-C_6)$-alkyl, $(C_3-C_6)$-cycloalkenyl-$(C_1-C_6)$-alkyl, halo-$(C_3-C_6)$-cycloalkenyl-$(C_1-C_6)$-alkyl, $R^1(O)C$, $R^1(R^1ON\!\!=\!\!)C$, $R^1O(O)C$, $(R^1)_2N(O)C$, $R^1(R^1O)N(O)C$, $(R^1)_2N(R^1)N(O)C$, $R^1(O)C(R^1)N(O)C$, $R^2O(O)C(R^1)N(O)C$, $(R^1)_2N(O)C(R^1)N(O)C$, $R^2(O)_2S(R^1)N(O)C$, $R^1O(O)_2S(R^1)N(O)C$, $(R^1)_2N(O)_2S(R^1)N(O)C$, $R^1O$, $R^1(O)CO$, $R^2(O)_2SO$, $R^2O(O)CO$, $(R^1)_2N(O)CO$, $(R^1)_2N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $(R^5O)_2(O)P$, $R^1(O)C$—$(C_1$-$C_6)$-alkyl, $R^1O(O)C$—$(C_1$-$C_6)$-alkyl, $(R^1)_2N(O)C$—$(C_1$-$C_6)$-alkyl, $(R^1O)(R^1)N(O)C$—$(C_1$-$C_6)$-alkyl, $(R^1)_2N(R^1)N(O)C$—$(C_1$-$C_6)$-alkyl, $R^1(O)C(R^1)N(O)C$—$(C_1$-$C_6)$-alkyl, $R^2O(O)C(R^1)N(O)C$—$(C_1$-$C_6)$-alkyl, $(R^1)_2N(O)C(R^1)N(O)C$—$(C_1$-$C_6)$-alkyl, $R^2(O)_2S(R^1)N(O)C$—$(C_1$-$C_6)$-alkyl, $R^1O(O)_2S(R^1)N(O)C$—$(C_1$-$C_6)$-alkyl, $(R^1)_2N(O)_2S(R^1)N(O)C$—$(C_1$-$C_6)$-alkyl, $NC$—$(C_1$-$C_6)$-alkyl, $R^1O$—$(C_1$-$C_6)$-alkyl, $R^1(O)CO$—$(C_1$-$C_6)$-alkyl, $R^2(O)_2SO$—$(C_1$-$C_6)$-alkyl, $R^2O(O)CO$—$(C_1$-$C_6)$-alkyl, $(R^1)_2N(O)CO$—$(C_1$-$C_6)$-alkyl, $(R^1)_2N$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, $R^2O(O)C(R^1)N$—$(C_1$-$C_6)$-alkyl, $(R^1)_2N(O)C(R^1)N$—$(C_1$-$C_6)$-alkyl, $R^1O(O)_2S(R^1)N$—$(C_1$-$C_6)$-alkyl, $(R^1)_2N(O)_2S(R^1)N$—$(C_1$-$C_6)$-alkyl, $R^2(O)_nS$—$(C_1$-$C_6)$-alkyl, $R^1O(O)_2S$—$(C_1$-$C_6)$-alkyl, $(R^1)_2N(O)_2S$—$(C_1$-$C_6)$-alkyl, $R^1(O)C(R^1)N(O)_2S$—$(C_1$-$C_6)$-alkyl, $R^2O(O)C(R^1)N(O)_2S$—$(C_1$-$C_6)$-alkyl, $(R^1)_2N(O)C(R^1)N(O)_2S$—$(C_1$-$C_6)$-alkyl, $(R^5O)_2(O)P$—$(C_1$-$C_6)$-alkyl, phenyl, heteroaryl, heterocyclyl, phenyl-$(C_1$-$C_6)$-alkyl, heteroaryl-$(C_1$-$C_6)$-alkyl, heterocyclyl-$(C_1$-$C_6)$-alkyl, where the six last-mentioned radicals are each substituted by s radicals from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1$-$C_6)$-alkyl, and where heterocyclyl carries n oxo groups, W is hydrogen, halogen, nitro, cyano, thiocyanato, $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, $(C_3$-$C_7)$-cycloalkyl, halo-$(C_3$-$C_7)$-cycloalkyl, $(C_1$-$C_6)$-alkoxy, halo-$(C_1$-$C_6)$-alkoxy, $(C_1$-$C_6)$-alkyl-$(O)_nS$—, $(C_1$-$C_6)$-haloalkyl-$(O)_nS$—, $(C_1$-$C_6)$-alkoxy-$(C_1$-$C_4)$-alkyl, $(C_1$-$C_6)$-alkoxy-$(C_1$-$C_4)$-haloalkyl, $R^1(O)C$, $R^1(R^1ON=)C$, $R^1O(O)C$, $(R^1)_2N$, $R^1(O)C(R^1)N$ or $R^2(O)_2S(R^1)N$, R is $(C_1$-$C_6)$-alkyl, $(C_2$-$C_6)$-alkenyl or $(C_2$-$C_6)$-alkynyl, each of which is substituted by s radicals from the group consisting of nitro, halogen, cyano, thiocyanato, $(C_3$-$C_6)$-cycloalkyl, $R^1(O)C$, $R^1(R^1ON=)C$, $R^1O(O)C$, $(R^1)_2N(O)C$, $R^1(R^1O)N(O)C$, $R^2(O)_2S(R^1)N(O)C$, $R^1O(O)_2S(R^1)N(O)C$, $(R^1)_2N(O)_2S(R^1)N(O)C$, $R^1S(O)C$, $R^1O$, $R^1(O)CO$, $R^2(O)_2SO$, $R^2O(O)CO$, $(R^1)_2N(O)CO$, $(R^1)_2N$, $R^1O(R^1)N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1C(O)S$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$ and $(R^5O)_2(O)P$, or is $(C_3$-$C_6)$-cycloalkyl, $(C_3$-$C_6)$-cycloalkenyl, phenyl, phenyl-$(C_1$-$C_6)$-alkyl, heteroaryl, heteroaryl-$(C_1$-$C_6)$-alkyl, heterocyclyl, heterocyclyl-$(C_1$-$C_6)$-alkyl, phenyl-O—$(C_1$-$C_6)$-alkyl, heteroaryl-O—$(C_1$-$C_6)$-alkyl, heterocyclyl-O—$(C_1$-$C_6)$-alkyl, phenyl-$N(R^1)$—$(C_1$-$C_6)$-alkyl, heteroaryl-$N(R^1)$—$(C_1$-$C_6)$-alkyl, heterocyclyl-$N(R^1)$—$(C_1$-$C_6)$-alkyl, phenyl-$S(O)_n$—$(C_1$-$C_6)$-alkyl, heteroaryl-$S(O)_n$—$(C_1$-$C_6)$-alkyl or heterocyclyl-$S(O)_n$—$(C_1$-$C_6)$-alkyl, each of which is substituted in the cyclic moiety by s radicals from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^1(O)C$, $R^1(R^1ON=)C$, $R^1O(O)C$, $(R^1)_2N(O)C$, $R^1(R^1O)N(O)C$, $R^2(O)_2S(R^1)N(O)C$, $R^1O(O)_2S(R^1)N(O)C$, $(R^1)_2N(O)_2S(R^1)N(O)C$, $R^1S(O)C$, $R^1O$, $R^1(O)CO$, $R^2(O)_2SO$, $R^2O(O)CO$, $(R^1)_2N(O)CO$, $(R^1)_2N$, $R^1O(R^1)N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1C(O)S$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $(R^5O)_2(O)P$ and $R^1O$—$(C_1$-$C_6)$-alkyl, and where heterocyclyl carries n oxo groups, R' is hydrogen, nitro, halogen, cyano, $(C_1$-$C_6)$-alkyl, halo-$(C_1$-$C_6)$-alkyl, $(C_3$-$C_6)$-alkenyl, halo-$(C_3$-$C_6)$-alkenyl, $(C_2$-$C_6)$-alkynyl, halo-$(C_3$-$C_6)$-alkynyl, $(C_3$-$C_6)$-cycloalkyl, halo-$(C_3$-$C_6)$-cycloalkyl, $(C_3$-$C_6)$-cycloalkyl-$(C_1$-$C_6)$-alkyl, halo-$(C_3$-$C_6)$-cycloalkyl-$(C_1$-$C_6)$-alkyl, $R^1(O)C$, $R^2O(O)C$, $(R^1)_2N(O)C$, $R^2S(O)C$, $(R^1)_2N(S)C$, $R^1(R^1O)N(O)C$, $R^2(O)_2S(R^1)N(O)C$, $(R^1)_2N(O)_2S(R^1)N(O)C$, $R^1O$, $(R^1)_2N$, $R^2(O)_nS$, $(R^2)_3Si$—$(C_1$-$C_6)$-alkyl-$(O)_nS$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $R^2(O)_2S(R^1)N(O)_2S$, $(R^5O)_2(O)P$, $(R^2)_3Si$, $R^1(O)C$—$(C_1$-$C_6)$-alkyl, $R^1O(O)C$—$(C_1$-$C_6)$-alkyl, $(R^1)_2N(O)C$—$(C_1$-$C_6)$-alkyl, $(R^1O)(R^1)N(O)C$—$(C_1$-$C_6)$-alkyl, $R^2(O)_2S(R^1)N(O)C$—$(C_1$-$C_6)$-alkyl, $R^1O(O)_2S(R^1)N(O)C$—$(C_1$-$C_6)$-alkyl, $(R^1)_2N(O)_2S(R^1)N(O)C$—$(C_1$-$C_6)$-alkyl, $R^1O$—$(C_1$-$C_6)$-alkyl, $R^1(O)CO$—$(C_1$-$C_6)$-alkyl, $R^2(O)_2SO$—$(C_1$-$C_6)$-alkyl, $R^2O(O)CO$—$(C_1$-$C_6)$-alkyl, $(R^1)_2N(O)CO$—$(C_1$-$C_6)$-alkyl, $(R^1)_2N$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, $R^2O(O)C(R^1)N$—$(C_1$-$C_6)$-alkyl, $(R^1)_2N(O)C(R^1)N$—$(C_1$-$C_6)$-alkyl, $R^1O(O)_2S(R^1)N$—$(C_1$-$C_6)$-alkyl, $(R^1)_2N(O)_2S(R^1)N$—$(C_1$-$C_6)$-alkyl, $R^2(O)_nS$—$(C_1$-$C_6)$-alkyl, $R^1O(O)_2S$—$(C_1$-$C_6)$-alkyl, $(R^1)_2N(O)_2S$—$(C_1$-$C_6)$-alkyl, $R^1(O)C(R^1)N(O)_2S$—$(C_1$-$C_6)$-alkyl, $R^{20}(O)C(R^1)N(O)_2S$—$(C_1$-$C_6)$-alkyl, $(R^1)_2N(O)C(R^1)N(O)_2S$—$(C_1$-$C_6)$-alkyl, $(R^5O)_2(O)P$—$(C_1$-$C_6)$-alkyl, $(R^2)_3Si$—$(C_1$-$C_6)$-alkyl, or is phenyl, heteroaryl, heterocyclyl, phenyl-$(C_1$-$C_6)$-alkyl, heteroaryl-$(C_1$-$C_6)$-alkyl or heterocyclyl-$(C_1$-$C_6)$-alkyl, each of which is substituted in the cyclic moiety by s radicals from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1$-$C_6)$-alkyl, and where heterocyclyl carries n oxo groups, R" is hydrogen, $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, $(C_3$-$C_6)$-cycloalkyl, halo-$(C_3$-$C_6)$-cycloalkyl, $(C_3$-$C_6)$-cycloalkyl-$(C_1$-$C_6)$-alkyl, halo-$(C_3$-$C_6)$-cycloalkyl-$(C_1$-$C_6)$-alkyl, $R^1(O)C$—$(C_1$-$C_6)$-alkyl, $R^1O(O)C$—$(C_1$-$C_6)$-alkyl, $(R^1)_2N(O)C$—$(C_1$-$C_6)$-alkyl, $NC$—$(C_1$-$C_6)$-alkyl, $R^1O$—$(C_1$-$C_6)$-alkyl, $R^1(O)CO$—$(C_1$-$C_6)$-alkyl, $R^2(O)_2SO$—$(C_1$-$C_6)$-alkyl, $(R^1)_2N$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, $R^2(O)_nS$—$(C_1$-$C_6)$-alkyl, $R^1O(O)_2S$—$(C_1$-$C_6)$-alkyl, $(R^1)_2N(O)_2S$—$(C_1$-$C_6)$-alkyl, $R^1(O)C$, $R^1O(O)C$, $(R^1)_2N(O)C$, $R^1O$, $(R^1)_2N$, $R^2O(O)C(R^1)N$, $(R^1)_2N(O)C(R^1)N$, $R^2(O)_2S$, or is benzyl which is in each case substituted by s radicals from the group consisting of methyl, ethyl, methoxy, nitro, trifluoromethyl and halogen-substituted benzyl, $R^X$ is $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, where the six above-mentioned radicals are each substituted by s radicals from the group consisting of nitro, cyano, $(R^6)_3Si$, $(R^5O)_2(O)P$, $R^2(O)_nS$, $(R^1)_2N$, $R^1O$, $R^1(O)C$, $R^1O(O)C$, $R^1(O)CO$, $R^2O(O)CO$, $R^1(O)C(R^1)N$, $R^2(O)_2S(R^1)N$, $(C_3$-$C_6)$-cycloalkyl, heteroaryl, heterocyclyl and phenyl, where the four last-mentioned radicals are substituted by s radicals from the group consisting of $(C_1$-$C_6)$-alkyl, halo-$(C_1$-$C_6)$-alkyl, $(C_1$-$C_6)$-alkoxy, halo-$(C_1$-$C_6)$-alkoxy and halogen, and where heterocyclyl carries n oxo groups, or $R^X$ is $(C_3-C_7)$-cycloalkyl, heteroaryl, heterocyclyl or phenyl, where the four above-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $(C_1-C_6)$-alkyl-S(O)$_n$, $(C_1-C_6)$-alkoxy, halo-$(C_1-C_6)$-alkoxy and $(C_1-C_6)$-alkoxy-$(C_1-C_4)$-alkyl, $R^Y$ is hydrogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_7)$-cycloalkyl, $(C_1-C_6)$-alkoxy, halo-$(C_1-C_6)$-alkoxy, $(C_2-C_6)$-alkenyloxy, $(C_2-C_6)$-alkynyloxy, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or is heteroaryl, heterocyclyl or phenyl, each of which is substituted by s radicals from the group consisting of $(C_1-C_6)$-alkyl, halo-$(C_1-C_6)$-alkyl, $(C_1-C_6)$-alkoxy, halo-$(C_1-C_6)$-alkoxy and halogen, and where heterocyclyl carries n oxo groups, $R^Z$ is hydrogen, $(C_1-C_6)$-alkyl, $R^1O$—$(C_1-C_6)$-alkyl, $R^7CH_2$, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $R^1O$, $R^1(H)N$, methoxycarbonyl, ethoxycarbonyl, methylamino, dimethylamino, trifluoromethylcarbonyl, acetylamino, methylsulfenyl, methylsulfinyl, methylsulfonyl or is heteroaryl, heterocyclyl, benzyl or phenyl, each of which is substituted by s radicals from the group consisting of halogen, nitro, cyano, $(C_1-C_6)$-alkyl, halo-$(C_1-C_6)$-alkyl, $(C_3-C_6)$-cycloalkyl, $(C_1-C_6)$-alkyl-S(O)$_n$, $(C_1-C_6)$-alkoxy, halo-$(C_1-C_6)$-alkoxy and $(C_1-C_6)$-alkoxy-$(C_1-C_4)$-alkyl, where heterocyclyl carries n oxo groups, $R^1$ is hydrogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl, heterocyclyl-O—$(C_1-C_6)$-alkyl, phenyl-N($R^3$)—$(C_1-C_6)$-alkyl, heteroaryl-N($R^3$)—$(C_1-C_6)$-alkyl, heterocyclyl-N($R^3$)—$(C_1-C_6)$-alkyl, phenyl-S(O)$_n$—$(C_1-C_6)$-alkyl, heteroaryl-S(O)$_n$—$(C_1-C_6)$-alkyl, heterocyclyl-S(O)$_n$—$(C_1-C_6)$-alkyl, where the fifteen last-mentioned radicals are each substituted by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^3O(O)C$, $(R^3)_2N(O)C$, $R^3O$, $(R^3)_2N$, $R^4(O)_nS$, $R^3O(O)_2S$, $(R^3)_2N(O)_2S$ and $R^3O$—$(C_1-C_6)$-alkyl, and where heterocyclyl carries n oxo groups, $R^2$ is $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl, heterocyclyl-O—$(C_1-C_6)$-alkyl, phenyl-N($R^3$)—$(C_1-C_6)$-alkyl, heteroaryl-N($R^3$)—$(C_1-C_6)$-alkyl, heterocyclyl-N($R^3$)—$(C_1-C_6)$-alkyl, phenyl-S(O)$_n$—$(C_1-C_6)$-alkyl, heteroaryl-S(O)$_n$—$(C_1-C_6)$-alkyl, heterocyclyl-S(O)$_n$—$(C_1-C_6)$-alkyl, where the fifteen last-mentioned radicals are each substituted by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^3O(O)C$, $(R^3)_2N(O)C$, $R^3O$, $(R^3)_2N$, $R^4(O)_nS$, $R^3O(O)_2S$, $(R^3)_2N(O)_2S$ and $R^3O$—$(C_1-C_6)$-alkyl, and where heterocyclyl carries n oxo groups, $R^3$ is hydrogen, $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^4$ is $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^5$ is hydrogen or $(C_1-C_4)$-alkyl, $R^6$ is $(C_1-C_4)$-alkyl, $R^7$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_3-C_6)$-cycloalkyl or is heteroaryl or heterocyclyl, each of which is substituted by s radicals from the group consisting of methyl, ethyl, methoxy, trifluoromethyl and halogen, n is 0, 1 or 2, s is 0, 1, 2 or 3, t is 0 or 1.

DETAILED DESCRIPTION OF A PREFERRED EMBODIMENT

In formula (I) and all formulae given below, alkyl radicals which have more than two carbon atoms may be straight-chain or branched. Alkyl radicals are, for example, methyl, ethyl, n- or isopropyl, n-, iso-, t- or 2-butyl, pentyls, hexyls, such as n-hexyl, isohexyl and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. In each case, the multiple bond may be located in any position of the unsaturated radical. Cycloalkyl is a carbocyclic saturated ring system having three to six carbon atoms, for example cyclopropyl, cyclobutyl, cyclopentyl or cyclohexyl. Analogously, cycloalkenyl is a monocyclic alkenyl group having three to six carbon ring members, for example cyclopropenyl, cyclobutenyl, cyclopentenyl and cyclohexenyl, where the double bond may be located in any position.

Halogen is fluorine, chlorine, bromine or iodine.

Heterocyclyl is a saturated, partially saturated or completely unsaturated cyclic radical which comprises 3 to 6 ring atoms, 1 to 4 of which are from the group consisting of oxygen, nitrogen and sulfur, and which may additionally be condensed with a benzo ring. Heterocyclyl is, for example, piperidinyl, pyrrolidinyl, tetrahydrofuranyl, dihydrofuranyl and oxetanyl.

Heteroaryl is an aromatic cyclic radical which comprises 3 to 6 ring atoms, 1 to 4 of which are from the group consisting of oxygen, nitrogen and sulfur, and which may additionally be condensed with a benzo ring. Heteroaryl is, for example, benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

If a group is substituted by a plurality of radicals, this means that this group is substituted by one or more identical or different of the radicals mentioned. This applies analogously to the construction of ring systems from different atoms and elements.

Here, compounds which the skilled worker knows to be chemically unstable under standard temperature and pressure conditions are excluded from the claims.

Depending on the nature and the attachment of the substituents, the compounds of the formula (I) may be present as stereoisomers. If, for example, one or more asymmetrically substituted carbon atoms are present, it is possible for enantiomers and diastereomers to occur. Stereoisomers also occur when n in the grouping $S(O)_n$ is 1 (sulfoxides). Moreover, the sulfur atom in the sulfoximino group or the sulfilimino group is a center of chirality. Stereoisomers can be obtained by customary separation methods, for example by chromatographic separation procedures, from the mixtures obtained in the preparation. It is also possible to selectively prepare stereoisomers by employing stereoselective reactions using optically active starting materials and/or auxiliaries. The invention also relates to all stereoisomers embraced by the formula (I) but not shown in their specific stereoform, and mixtures thereof. The invention also relates to all E/Z isomers embraced by the formula (I) but not specifically defined, and mixtures thereof.

The compounds of the formula (I) are capable of forming salts. Salt formation may occur by action of a base on those compounds of the formula (I) which carry an acidic hydrogen atom, for example in the case of R". Suitable bases are, for example, organic amines, such as trialkylamines, morpholine, piperidine or pyridine, and also ammonium, alkali metal or alkaline earth metal hydroxides, carbonates and bicarbonates, in particular sodium hydroxide and potassium hydroxide, sodium carbonate and potassium carbonate and sodium bicarbonate and potassium bicarbonate. These salts are compounds in which the acidic hydrogen is replaced by an agriculturally suitable cation, for example metal salts, in particular alkali metal salts or alkaline earth metal salts, especially sodium salts and potassium salts, or else ammonium salts, salts with organic amines or quaternary ammonium salts, for example with cations of the formula [NRR*RR*]+ in which R, R*, R and R* independently of one another each denote an organic radical, in particular alkyl, aryl, aralkyl or alkylaryl. Also suitable are alkylsulfonium and alkylsulfoxonium salts such as $(C_1$-$C_4)$-trialkylsulfonium and $(C_1$-$C_4)$-trialkylsulfoxonium salts.

By forming an adduct with a suitable inorganic or organic acid, for example mineral acids such as HCl, HBr, $H_2SO_4$, $H_3PO_4$ or $HNO_3$ or organic acids, for example carboxylic acids such as formic acid, acetic acid, propionic acid, oxalic acid, lactic acid or salicylic acid, or sulfonic acids such as p-toluenesulfonic acid, at a basic group, such as, for example, amino, alkylamino, dialkylamino, piperidino, morpholino or pyridino, the compounds of the formula (I) are capable of forming salts. In this case, the salts contain the conjugated base of the acid as anion.

Preference is given to compounds of the formula (I) in which
Q is a radical Q1, Q2, Q3 or Q4,

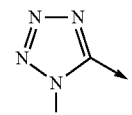
(Q1)

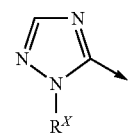
(Q2)

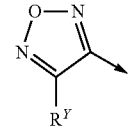
(Q3)

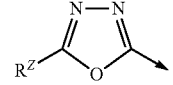
(Q4)

X is nitro, halogen, cyano, $(C_1$-$C_6)$-alkyl, halo-$(C_1$-$C_6)$-alkyl, $(C_2$-$C_6)$-alkenyl, $(C_2$-$C_6)$-alkynyl, $(C_3$-$C_6)$-cycloalkyl, halo-$(C_3$-$C_6)$-cycloalkyl, $(C_3$-$C_6)$-cycloalkyl-$(C_1$-$C_6)$-alkyl, halo-$(C_3$-$C_6)$-cycloalkyl-$(C_1$-$C_6)$-alkyl, $R^1(O)C$, $R^1(R^1ON=)C$, $R^1O(O)C$, $(R^1)_2N(O)C$, $R^1O$, $(R^1)_2N$, $R^1(O)C(R^1)N$, $R^2(O)_2S(R^1)N$, $R^2O(O)C(R^1)N$, $(R^1)_2N(O)C(R^1)N$, $R^2(O)_nS$, $R^1O(O)_2S$, $(R^1)_2N(O)_2S$, $(R^5O)_2(O)P$, $R^1(O)C$—$(C_1$-$C_6)$-alkyl, $R^1O(O)C$—$(C_1$-$C_6)$-alkyl, $(R^1)_2N(O)C$—$(C_1$-$C_6)$-alkyl, NC—$(C_1$-$C_6)$-alkyl, $R^1O$—$(C_1$-$C_6)$-alkyl, $(R^1)_2N$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, $R^2O(O)C(R^1)N$—$(C_1$-$C_6)$-alkyl, $(R^1)_2N(O)C(R^1)N$—$(C_1$-$C_6)$-alkyl, $R^2(O)_nS$—$(C_1$-$C_6)$-alkyl, $R^1O(O)_2S$—$(C_1$-$C_6)$-alkyl, $(R^1)_2N(O)_2S$—$(C_1$-$C_6)$-alkyl, $(R^5O)_2(O)P$—$(C_1$-$C_6)$-alkyl, phenyl, heteroaryl, heterocyclyl, phenyl-$(C_1$-$C_6)$-alkyl, heteroaryl-$(C_1$-$C_6)$-alkyl, heterocyclyl-$(C_1$-$C_6)$-alkyl, where the six last-mentioned radicals are each substituted by s radicals from the group consisting of nitro, halogen, cyano, thiocyanato, $(C_1$-$C_6)$-alkyl, halo-$(C_1$-$C_6)$-alkyl, $R^1O$, $(R^1)_2N$, $R^2(O)_nS$, $R^1O(O)_2S$, $(R^1)_2N(O)_2S$ and $R^1O$—$(C_1$-$C_6)$-alkyl and where heterocyclyl carries n oxo groups, Z is hydrogen, nitro, halogen, cyano, $(C_1$-$C_6)$-alkyl, halo-$(C_1$-$C_6)$-alkyl, $(C_2$-$C_6)$-alkenyl, $(C_2$-$C_6)$-alkynyl, $(C_3$-$C_6)$-cycloalkyl, halo-$(C_3$-$C_6)$-cycloalkyl, $(C_3$-$C_6)$-cycloalkyl-$(C_1$-$C_6)$-alkyl, halo-$(C_3$-$C_6)$-cycloalkyl-$(C_1$-$C_6)$-alkyl, $R^1(O)C$, $R^1(R^1ON=)C$, $R^1O(O)C$, $(R^1)_2N(O)C$, $R^1O$, $(R^1)_2N$, $R^1(O)C(R^1)N$, $R^2(O)_2S(R^1)N$, $R^2O(O)C(R^1)N$, $(R^1)_2N(O)C(R^1)N$, $R^2(O)_nS$, $R^1O(O)_2S$, $(R^1)_2N(O)_2S$, $(R^5O)_2(O)P$, $R^1(O)C$—$(C_1$-$C_6)$-alkyl, $R^1O(O)C$—$(C_1$-$C_6)$-alkyl, $(R^1)_2N(O)C$—$(C_1$-$C_6)$-alkyl, NC—$(C_1$-$C_6)$-alkyl, $R^1O$—$(C_1$-$C_6)$-alkyl, $(R^1)_2N$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, $R^2O(O)C(R^1)N$—$(C_1$-$C_6)$-alkyl, $(R^1)_2N(O)C(R^1)N$—$(C_1$-$C_6)$-alkyl, $R^2(O)_nS$—$(C_1$-$C_6)$-alkyl, $R^1O(O)_2S$—$(C_1$-$C_6)$-alkyl, $(R^1)_2N(O)_2S$—$(C_1$-$C_6)$-alkyl, $(R^5O)_2(O)P$—$(C_1$-$C_6)$-alkyl, phenyl, heteroaryl, heterocyclyl, phenyl-$(C_1$-$C_6)$-alkyl, heteroaryl-$(C_1$-$C_6)$-alkyl, heterocyclyl-$(C_1$-$C_6)$-alkyl, where the six last-mentioned radicals are each substituted by s radicals from the group consisting of nitro, halogen, cyano, thiocyanato, $(C_1$-$C_6)$-alkyl, halo-$(C_1$-$C_6)$-alkyl, $R^1O$, $(R^1)_2N$, $R^2(O)_nS$, $R^1O(O)_2S$, $(R^1)_2N(O)_2S$ and $R^1O$—$(C_1$-$C_6)$-alkyl and where heterocyclyl carries n oxo groups, W is hydrogen, halogen, nitro, cyano, $(C_1-C_6)$-alkyl, halo-$(C_1-C_6)$-alkyl, $(C_3-C_7)$-cycloalkyl, $(C_1-C_6)$-alkoxy, $(C_1-C_6)$-alkyl-$(O)_n$S—, $R^1O(O)C$, $(R^1)_2N$, $R^1(O)C(R^1)N$ or $R^2(O)_2S(R^1)N$, R is $(C_1-C_6)$-alkyl which is in each case substituted by s radicals from the group consisting of halogen, cyano, $(C_3-C_6)$-cycloalkyl, $R^1(O)C$, $R^1(R^1ON=)C$, $R^1O(O)C$, $(R^1)_2N(O)C$, $R^2(O)_2S(R^1)N(O)C$, $R^1O$, $(R^1)_2N$, $R^1(O)C(R^1)N$, $R^2(O)_2S(R^1)N$, $R^2O(O)C(R^1)N$, $(R^1)_2N(O)C(R^1)N$, $R^2(O)_nS$, $R^1O(O)_2S$, $(R^1)_2N(O)_2S$, $R^1(O)C(R^1)N(O)_2S$, $R^2O(O)C(R^1)N(O)_2S$ and $(R^1)_2N(O)C(R^1)N(O)_2S$ or is $(C_3-C_6)$-cycloalkyl which is in each case substituted by s radicals from the group consisting of halogen, $(C_1-C_6)$-alkyl, halo-$(C_1-C_6)$-alkyl, $(C_3-C_6)$-cycloalkyl, $R^1O(O)C$ and $(R^1)_2N(O)C$, R' is hydrogen, nitro, cyano, $(C_1-C_6)$-alkyl, halo-$(C_1-C_6)$-alkyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^2O(O)C$, $(R^1)_2N(O)C$, $R^2(O)_2S$, $R^1(O)C$—$(C_1-C_6)$-alkyl, $R^1O(O)C$—$(C_1-C_6)$-alkyl, $(R^1)_2N(O)C$—$(C_1-C_6)$-alkyl, $R^1O$—$(C_1-C_6)$-alkyl, $(R^1)_2N$—$(C_1-C_6)$-alkyl, $R^2(O)_nS$—$(C_1-C_6)$-alkyl, R" is hydrogen, $R^X$ is $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, where the six above-mentioned radicals are each substituted by s radicals from the group consisting of $R^2(O)_nS$, $(R^1)_2N$, $R^1O$, $R^1(O)C$, $R^1O(O)C$, $R^1(O)CO$, $R^2O(O)CO$, $R^1(O)C(R^1)N$, $R^2(O)_2S(R^1)N$, $(C_3-C_6)$-cycloalkyl, heteroaryl, heterocyclyl and phenyl, where the four last-mentioned radicals for their part are substituted by s radicals from the group consisting of $(C_1-C_6)$-alkyl, halo-$(C_1-C_6)$-alkyl, $(C_1-C_6)$-alkoxy and halogen, and where heterocyclyl carries n oxo groups, or $R^X$ is $(C_3-C_7)$-cycloalkyl, where this radical is in each case substituted by s radicals from the group consisting of halogen, $(C_1-C_6)$-alkyl and halo-$(C_1-C_6)$-alkyl, $R^Y$ is hydrogen, $(C_1-C_6)$-alkyl, halo-$(C_1-C_6)$-alkyl, $(C_3-C_7)$-cycloalkyl, $(C_1-C_6)$-alkoxy, methoxycarbonyl, methoxycarbonylmethyl, halogen, amino, aminocarbonyl or methoxymethyl, $R^Z$ is hydrogen, $(C_1-C_6)$-alkyl, $R^1O$—$(C_1-C_6)$-alkyl, $R^7CH_2$, $(C_3-C_7)$-cycloalkyl, halo-$(C_1-C_6)$-alkyl, $R^1O$, $R^1(H)N$, methoxycarbonyl, acetylamino or methylsulfonyl, $R^1$ is hydrogen, $(C_1-C_6)$-alkyl, halo-$(C_1-C_6)$-alkyl, $(C_3-C_6)$-cycloalkyl, halo-$(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl, heterocyclyl-O—$(C_1-C_6)$-alkyl, where the nine last-mentioned radicals are in each case substituted by s radicals from the group consisting of nitro, halogen, $(C_1-C_6)$-alkyl, halo-$(C_1-C_6)$-alkyl, $R^3O(O)C$, $(R^3)_2N(O)C$, $R^3O$, $(R^3)_2N$, $R^4(O)_nS$ and $R^3O$—$(C_1-C_6)$-alkyl, and where heterocyclyl carries n oxo groups, $R^2$ is $(C_1-C_6)$-alkyl, halo-$(C_1-C_6)$-alkyl, $(C_3-C_6)$-cycloalkyl, halo-$(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl, heterocyclyl-O—$(C_1-C_6)$-alkyl, where the nine last-mentioned radicals are in each case substituted by s radicals from the group consisting of nitro, halogen, $(C_1-C_6)$-alkyl, halo-$(C_1-C_6)$-alkyl, $R^3O(O)C$, $(R^3)_2N(O)C$, $R^3O$, $(R^3)_2N$, $R^4(O)_nS$ and $R^3O$—$(C_1-C_6)$-alkyl, and where heterocyclyl carries n oxo groups, $R^3$ is hydrogen or $(C_1-C_6)$-alkyl,
$R^4$ is $(C_1-C_6)$-alkyl,
$R^5$ is hydrogen or $(C_1-C_4)$-alkyl,
$R^7$ is acetoxy, acetamido, methoxycarbonyl or $(C_3-C_6)$-cycloalkyl,
n is 0, 1 or 2,
s is 0, 1, 2 or 3,
t is 0 or 1.

Particular preference is given to compounds of the formula (I) in which

Q is a radical Q1, Q2, Q3 or Q4,

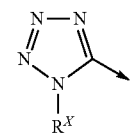

(Q1)

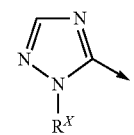

(Q2)

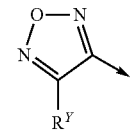

(Q3)

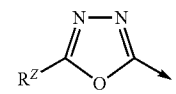

(Q4)

X is nitro, halogen, methyl, ethyl, n-propyl, isopropyl, trifluoromethyl, difluoromethyl, chlorodifluoromethyl, dichlorofluoromethyl, trichloromethyl, pentafluoroethyl, heptafluoroisopropyl, cyclopropyl, methoxy, ethoxy, methylsulfanyl, methylsulfinyl, methylsulfonyl, methoxymethyl, ethoxymethyl, methoxyethyl, methoxyethoxymethyl, methylthiomethyl, methylsulfinylmethyl or methylsulfonylmethyl, Z is hydrogen, nitro, cyano, halogen, methyl, ethyl, n-propyl, isopropyl, trifluoromethyl, difluoromethyl, chlorodifluoromethyl, dichlorofluoromethyl, trichloromethyl, pentafluoroethyl, heptafluoroisopropyl, cyclopropyl, methoxy, ethoxy, methylsulfanyl, methylsulfinyl or methylsulfonyl, W is hydrogen, chlorine or methyl,
R is methyl, ethyl or n-propyl,
R' is hydrogen, cyano or trifluoroacetyl,
R" is hydrogen,
$R^X$ is methyl, ethyl, n-propyl, prop-2-en-1-yl, methoxyethyl, ethoxyethyl or methoxyethoxyethyl,
$R^Y$ is methyl, ethyl, n-propyl, chlorine or amino,
$R^Z$ is methyl, ethyl, n-propyl or methoxymethyl,
t is 0 or 1.

Compounds according to the invention in which Q is Q1 or Q2 can, for example, be prepared stepwise initially at the thioether stage of the formula (I-thioether) using the method shown in Scheme 1 by base-catalyzed reaction of a benzoyl chloride (II) with a 5-amino-1-H-1,2,4-triazole or 5-amino-1H-tetrazole (III). The thioether intermediates can then be converted according to Scheme 13 into the sulfin- and sulfonimidoylbenzamides of the formula (I) according to the invention.

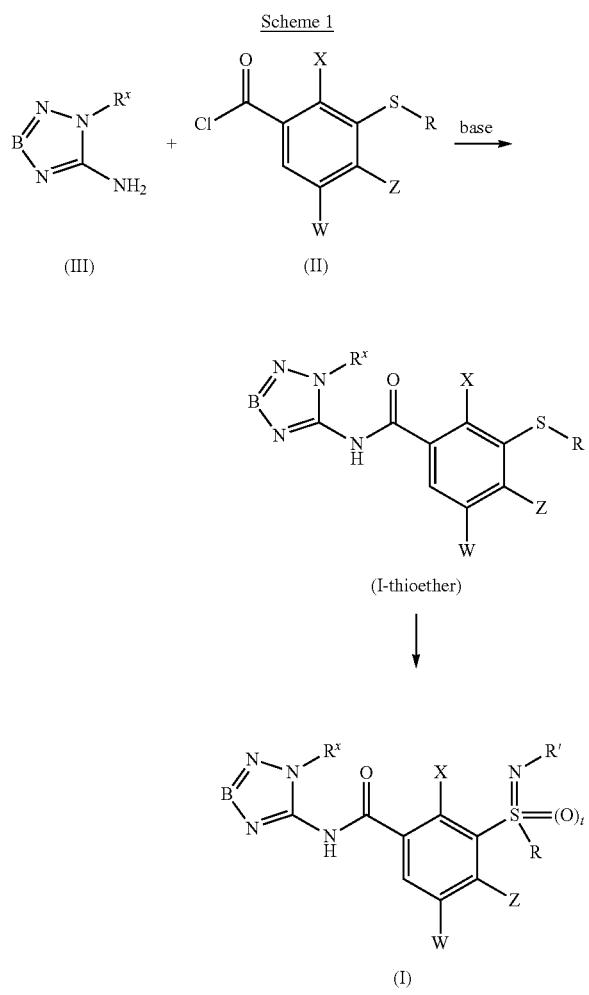

Here, B is CH or N.

Compounds according to the invention in which Q is Q1 or Q2 can also, for example, be prepared stepwise initially at the thioether stage of the formula (I-thioether) using the method shown in Scheme 2 by reacting a benzoic acid of the formula (IV) with a 5-amino-1-H-1,2,4-triazole or 5-amino-1H-tetrazole (III). The thioether intermediates can then be converted according to Scheme 13 into the sulfin- and sulfonimidoylbenzamides of the formula (I) according to the invention.

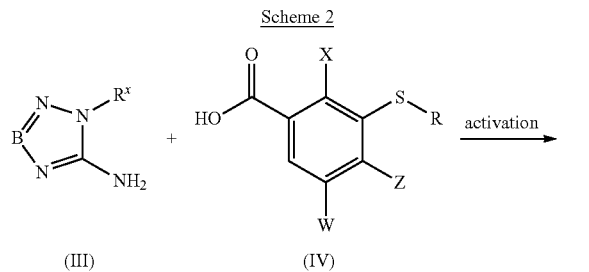

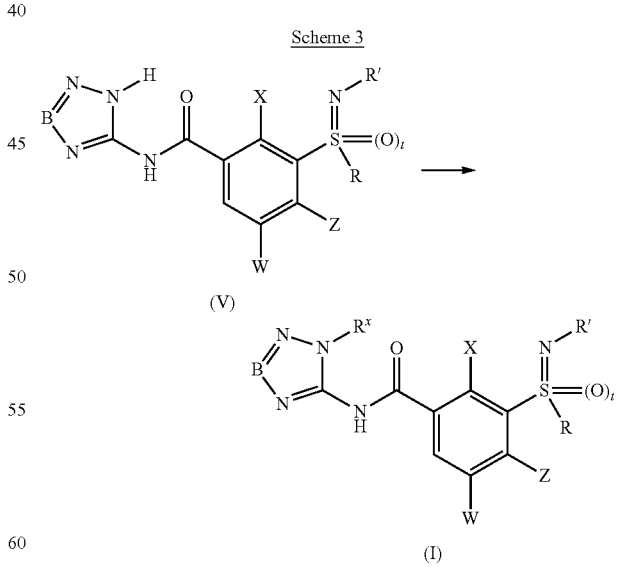

For activation, it is possible to employ reagents customarily used for amidation reactions such as, for example, 1,1'-carbonyldiimidazole (CDI), dicyclohexyl-carbodiimide (DCC), 2,4,6-tripropyl-1,3,5,2,4,6-trioxatriphosphinane 2,4,6-trioxide (T3P).

The benzoyl chlorides of the formula (II) and the benzoic acids of the formula (IV) that they are based on are known in principle and can be prepared, for example, according to the methods described in WO 03/014071 A1, WO 2008/125214 A1, WO 2011/12246 A1 and WO 2011/012247 A1.

Compounds according to the invention in which Q is Q1 or Q2 can also be prepared according to the method described in Scheme 3, by reacting an N-(1H-1,2,4-triazol-5-yl)benzamide or N-(1H-tetrazol-5-yl)benzamide:

For the reaction shown in Scheme 3, it is possible to employ, for example, alkylating agents such as alkyl halides, alkyl sulfonates or dialkyl sulfates in the presence of a base.

The 5-amino-1H-tetrazoles of the formula (III) are either commercially available or can be prepared analogously to methods known from the literature. Substituted 5-aminotetrazoles, for example, can be prepared by the method described in Journal of the American Chemical Society (1954), 76, 923-924 from aminotetrazole:

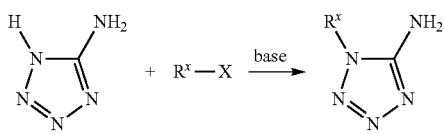

In the reaction mentioned above, X is a leaving group such as iodine. Substituted 5-aminotetrazoles can also be synthesized, for example, as described in Journal of the American Chemical Society (1954) 76, 88-89:

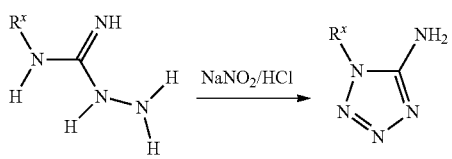

The 5-amino-1H-triazoles of the formula (III) are either commercially available or can be prepared analogously to methods known from the literature. Substituted 5-aminotriazoles, for example, can be prepared by the method described in Zeitschrift für Chemie (1990), 30(12), 436-437 from aminotriazole:

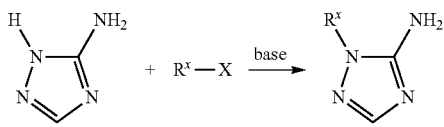

Substituted 5-aminotriazoles can also be synthesized, for example, as described in Chemische Berichte (1964), 97(2), 396-404:

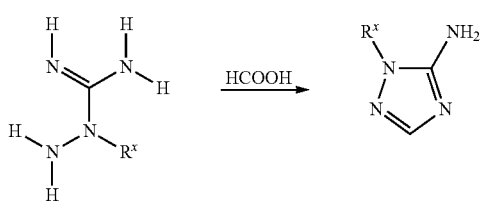

Substituted 5-aminotriazoles can also be synthesized, for example, as described in Angewandte Chemie (1963), 75, 918:

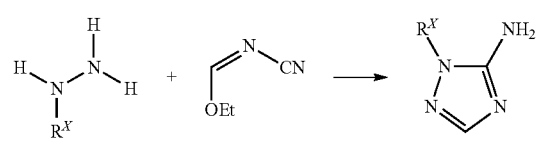

Compounds according to the invention in which Q is Q3 can be prepared, for example, stepwise, initially at the thioether stage of the formula (I-thioether) according to the method shown in Scheme 4 by base-catalyzed reaction of a benzoyl chloride (II) with a 4-amino-1,2,5-oxadiazole (VI). The thioether intermediates can be converted in accordance with Scheme 13 into the sulfin- and sulfonimidoylbenzamides of the formula (I) according to the invention.

Scheme 4

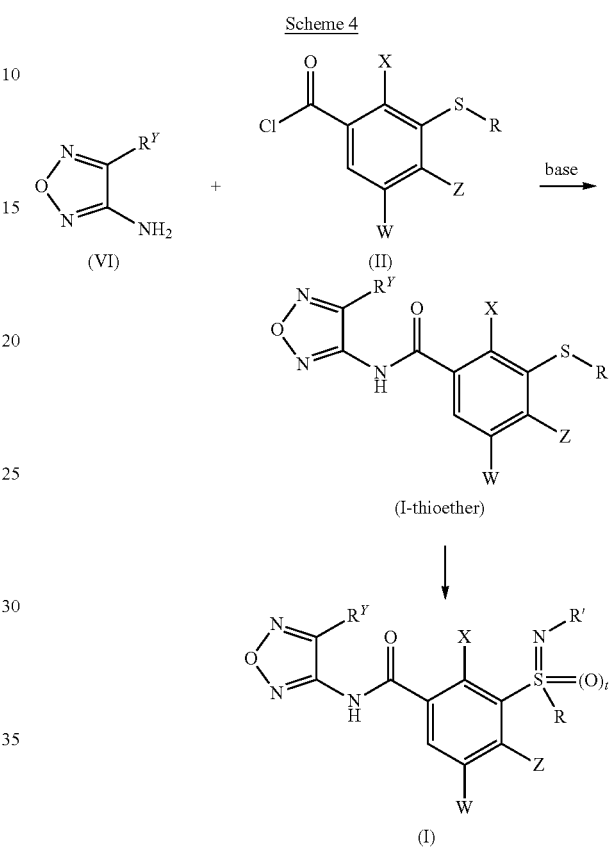

Compounds according to the invention can also be prepared stepwise, initially at the thioether stage of the formula (I-thioether) according to the method shown in Scheme 5 by reacting a benzoic acid of the formula (IV) with a 4-amino-1,2,5-oxadiazole (VI). The thioether intermediates can be converted in accordance with Scheme 13 into the sulfin- and sulfonimidoylbenzamides of the formula (I) according to the invention.

Scheme 5

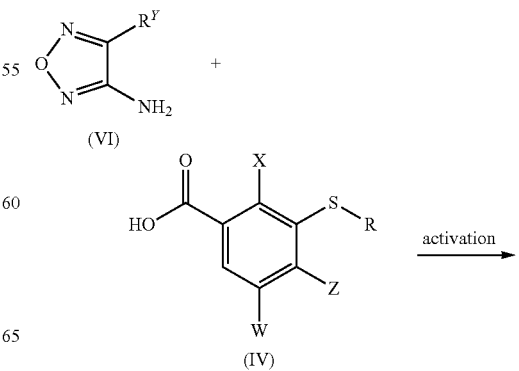

15

-continued

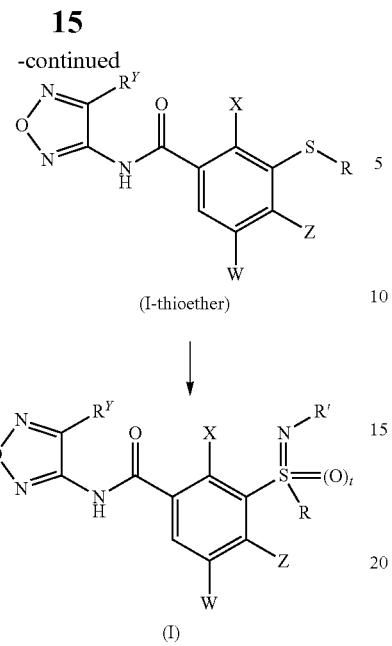

(I-thioether)

↓

(I)

For activation, it is possible to employ reagents customarily used for amidation reactions such as, for example, 1,1'-carbonyldiimidazole (CDI), dicyclohexyl-carbodiimide (DCC), 2,4,6-tripropyl-1,3,5,2,4,6-trioxatriphosphinane 2,4,6-trioxide (T3P).

The 4-amino-1,2,5-oxadiazoles of the formula (VI) are either commercially available or known or can be prepared analogously to methods known from the literature. 3-Alkyl-4-amino-1,2,5-oxadiazoles, for example, can be prepared by the method described in Russian Chemical Bulletin, Int. Ed., Vol. 54, No. 4, S. 1032-1037 (2005) from β-keto esters:

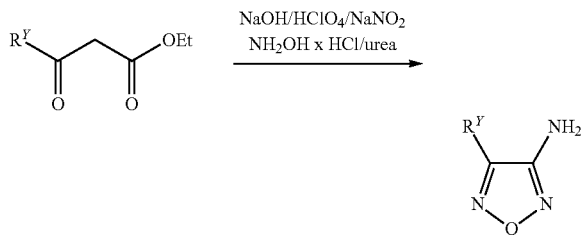

3-Aryl-4-amino-1,2,5-oxadiazoles can be synthesized, for example, as described in Russian Chemical Bulletin, 54(4), 1057-1059, (2005) or Indian Journal of Chemistry, Section B: Organic Chemistry Including Medicinal Chemistry, 26B(7), 690-2, (1987):

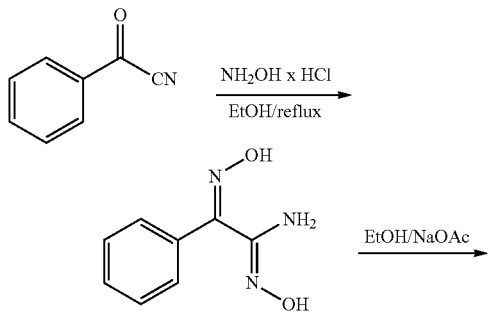

16

-continued

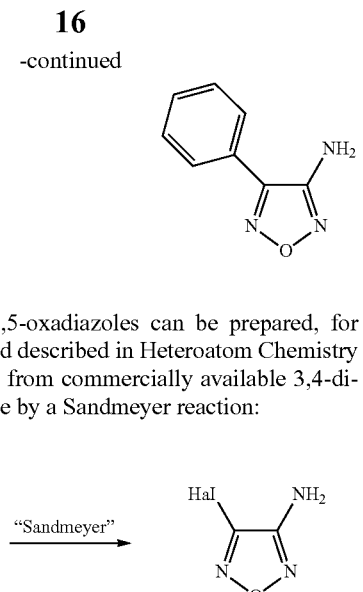

3-Amino-4-halo-1,2,5-oxadiazoles can be prepared, for example, by the method described in Heteroatom Chemistry 15(3), 199-207 (2004) from commercially available 3,4-diamino-1,2,5-oxadiazole by a Sandmeyer reaction:

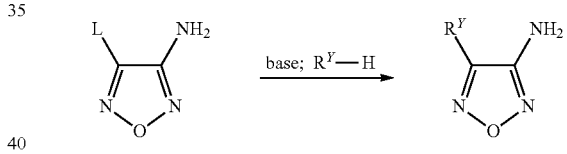

Nucleophilic radicals $R^Y$ can be introduced as described in Journal of Chemical Research, Synopses, (6), 190, 1985 or in Izvestiya Akademii Nauk SSSR, Seriya Khimicheskaya, (9), 2086-8, 1986 or in Russian Chemical Bulletin (translation of Izvestiya Akademii Nauk, Seriya Khimicheskaya), 53(3), 596-614, 2004 via substitution of the leaving group L in 3-amino-1,2,5-oxadiazoles. L is a leaving group such as, for example, chlorine, bromine, iodine, mesyloxy, tosyloxy, trifluorosulfonyloxy etc.

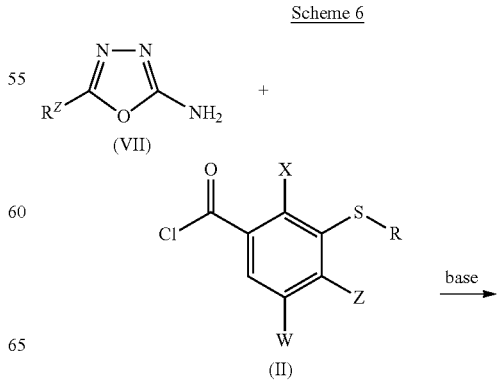

Compounds according to the invention in which Q is Q4 can be prepared, for example, stepwise, initially at the thioether stage of the formula (I-thioether) according to the method shown in Scheme 6 by base-catalyzed reaction of a benzoyl chloride (II) with a 2-amino-1,3,4-oxadiazole (VII). The thioether intermediates can then be converted in accordance with Scheme 13 into the sulfin- and sulfonimidoylbenzamides of the formula (I) according to the invention.

Scheme 6

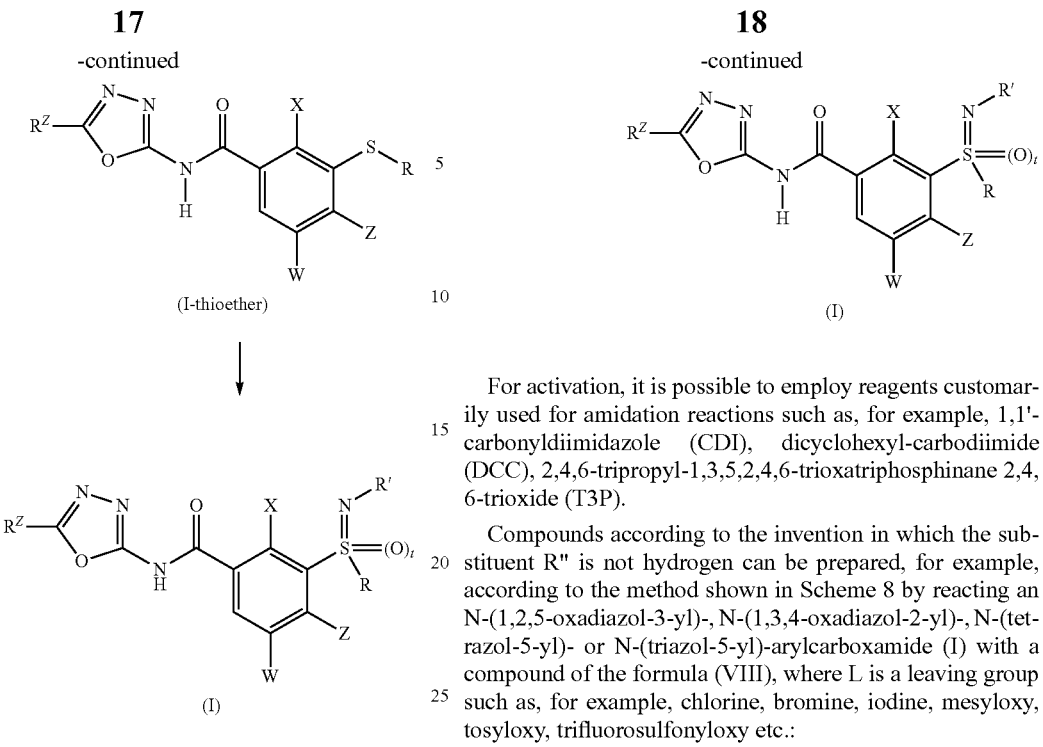

Compounds according to the invention can also be prepared stepwise, initially at the thioether stage of the formula (I-thioether) according to the method shown in Scheme 7 by reacting a benzoic acid of the formula (IV) with a 2-amino-1,3,4-oxadiazole (VII). The thioether intermediates can then be converted in accordance with Scheme 13 into the sulfin- and sulfonimidoylbenzamides according to the invention.

For activation, it is possible to employ reagents customarily used for amidation reactions such as, for example, 1,1′-carbonyldiimidazole (CDI), dicyclohexyl-carbodiimide (DCC), 2,4,6-tripropyl-1,3,5,2,4,6-trioxatriphosphinane 2,4,6-trioxide (T3P).

Compounds according to the invention in which the substituent R″ is not hydrogen can be prepared, for example, according to the method shown in Scheme 8 by reacting an N-(1,2,5-oxadiazol-3-yl)-, N-(1,3,4-oxadiazol-2-yl)-, N-(tetrazol-5-yl)- or N-(triazol-5-yl)-arylcarboxamide (I) with a compound of the formula (VIII), where L is a leaving group such as, for example, chlorine, bromine, iodine, mesyloxy, tosyloxy, trifluorosulfonyloxy etc.:

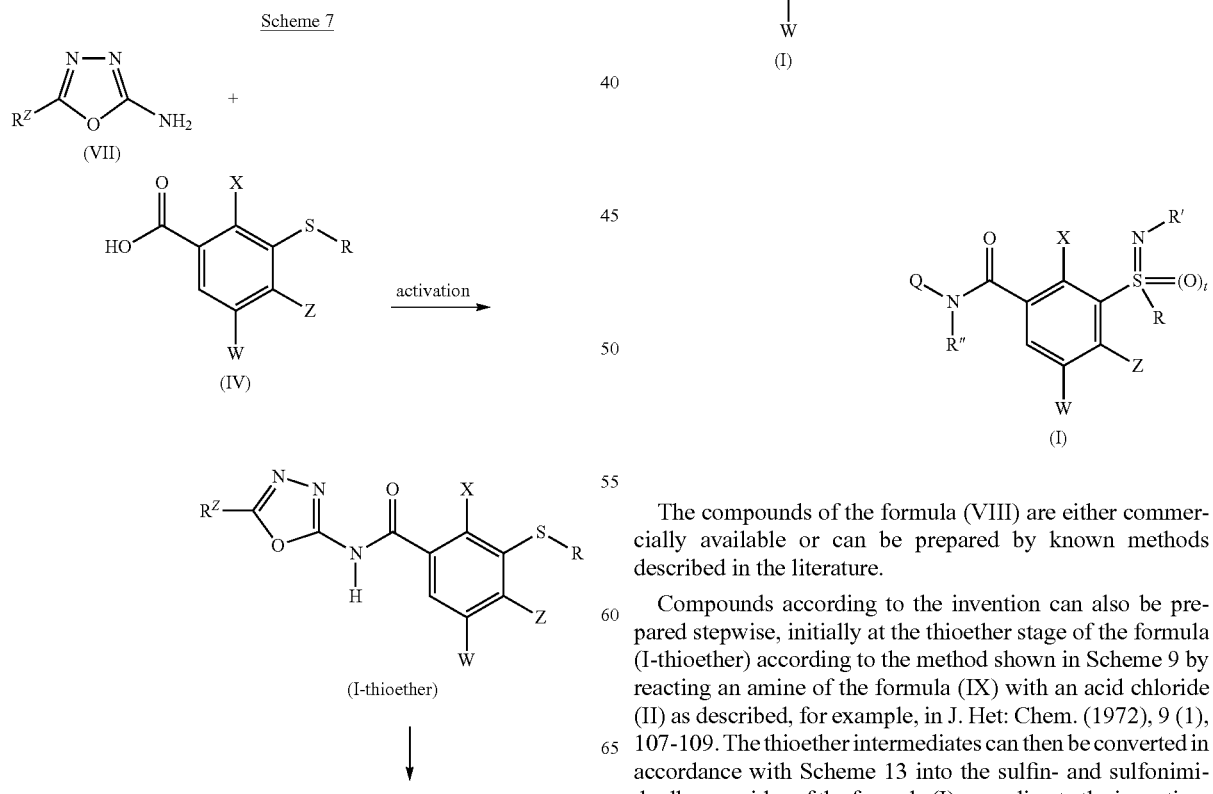

The compounds of the formula (VIII) are either commercially available or can be prepared by known methods described in the literature.

Compounds according to the invention can also be prepared stepwise, initially at the thioether stage of the formula (I-thioether) according to the method shown in Scheme 9 by reacting an amine of the formula (IX) with an acid chloride (II) as described, for example, in J. Het. Chem. (1972), 9 (1), 107-109. The thioether intermediates can then be converted in accordance with Scheme 13 into the sulfin- and sulfonimidoylbenzamides of the formula (I) according to the invention.

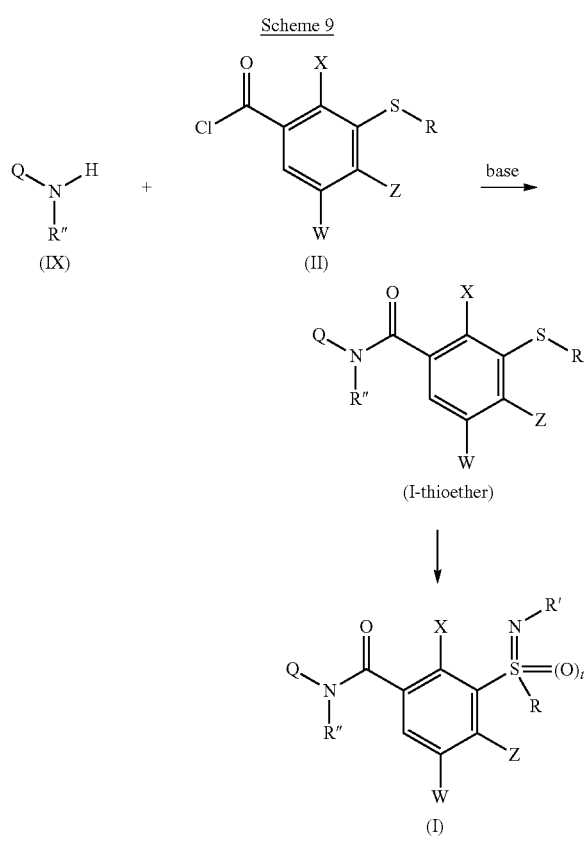

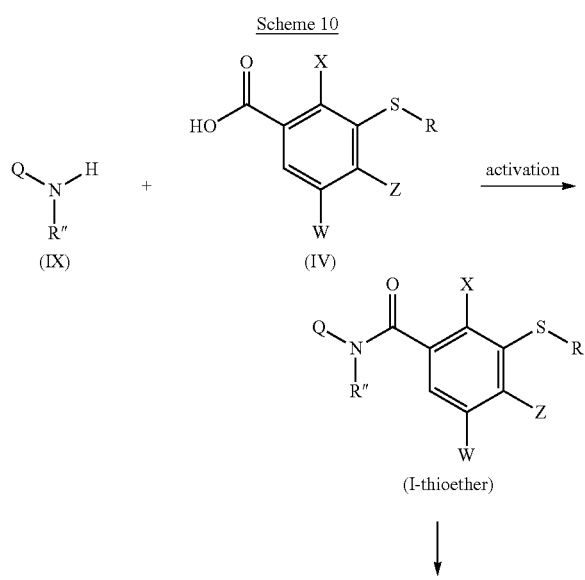

Compounds according to the invention can also be prepared stepwise, initially at the thioether stage of the formula (I-thioether) according to the method shown in Scheme 10 by reacting an amine of the formula (IX) with an acid of the formula (IV). The thioether intermediates can then be converted in accordance with Scheme 13 into the sulfin- and sulfonimidoylbenzamides of the formula (I) according to the invention.

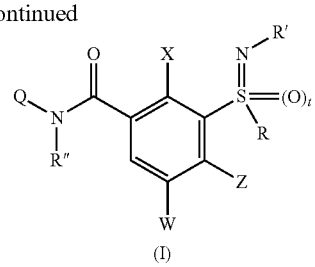

For activation, it is possible to employ reagents customarily used for amidation reactions such as, for example, 1,1'-carbonyldiimidazole (CDI), dicyclohexyl-carbodiimide (DCC), 2,4,6-tripropyl-1,3,5,2,4,6-trioxatriphosphinane 2,4,6-trioxide (T3P).

The amines of the formula (IX) are either commercially available or known from the literature or can be prepared, for example, by the methods described in Scheme 11 by base-catalyzed alkylation or by reductive amination or according to the method described in Scheme 12 by nucleophilic substitution of a leaving group L by amines R''—NH$_2$, where L is a leaving group such as, for example, chlorine, bromine, iodine, mesyloxy, tosyloxy, trifluorosulfonyloxy etc.

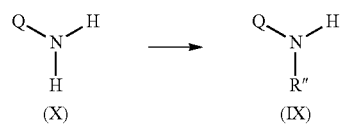

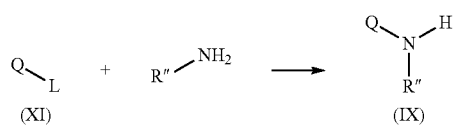

The amines of the formula (IX) can also be prepared by cyclization reactions as described, for example, in J. Org. Chem. 73(10), 3738-3744 (2008) for Q=Q1 or in Buletinul Institutului Politehnic din Iasi (1974), 20(1-2), 95-99 or in J. Org. Chem. 67(21), 7361-7364 (2002) for Q=Q4.

The compounds of the formula (I) according to the invention can be prepared from the corresponding thioethers of the formula (I-thioether) (Scheme 13). To this end, the thioether is converted, for example with cyanamide and an oxidizing agent (iodosobenzene diacetate, sodium hypochlorite or N-bromosuccinimide) into the corresponding sulfilimine, which can be oxidized further to the sulfoximine. Suitable for the oxidation to the sulfoximine are oxidizing agents such as, for example, meta-chlorperbenzoic acid, sodium permanganate or a mixture of sodium periodate and ruthenium trichloride. NH-Sulfoximines can be obtained, for example, from sulfoxides using sodium azide and sulfuric acid and can be functionalized at the nitrogen atom with reagents such as, for example cyanogen bromide, acid chlorides or acid anhydrides, chloroformic esters, nitric acid or other compounds. The oxidation of N-sulfonated sulfilimines to the corresponding sulfoximines can be achieved with hydrogen, for example. Alternatively, sulfoxides can be converted into N-acylated or N-sulfonated sulfoximines. The carboxamide or sulfonamide, respectively, can then be cleaved to give the NH-sulfoximine. Such synthesis methods for generating sulfilimines and sulfoximines from thioethers or for generating sulfoximines from sulfoxides or for derivatizing sulfilimines and sulfoximines, also NH-sulfoximines, inter alia, are described, for example, in Bolm, C. Org. Lett. 2004, 6, 1305; Bolm, C. Org. Lett. 2007, 9, 3809; Bolm, C. Synthesis 2010, 17, 2922; Bolm, C. Adv. Synth. Catal. 2010, 352, 309; WO 2007/095229, WO 2008/141843, US 2008/0207910, US 2008/0194634 and US 2010/0056534.

tert-butyl esters effectively shield the carboxyl group sterically against nucleophilic reagents, and they are easily cleaved in acidic medium (T. W. Greene, P. G. M. Wuts, Protective Groups in Organic Synthesis, 2nd Edition, John Wiley & Sons, Inc. 1991, p. 227 ff.). Also suitable are radicals which are considerably more stable than carboxyl groups, which can, however, also be easily re-converted into the free carboxylic acids. These include, for example, oxazolines (T. W. Greene, P. G. M. Wuts, Protective Groups in Organic Synthesis, 2nd Edition, John Wiley & Sons, Inc. 1991, p. 265 ff.; Z. Hell et al., Tetrahedron Letters 43 (2002), 3985-3987).

Scheme 13

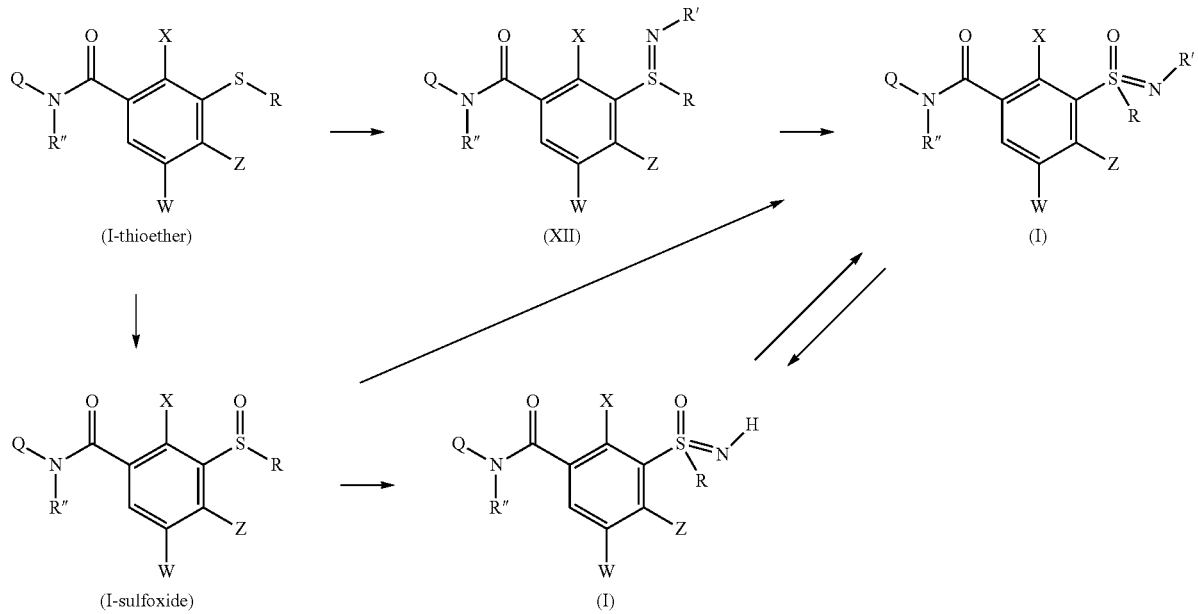

If required, protective groups have to be employed for such synthetic sequences to achieve sufficient selectivity. In particular the functionalization at the NH-sulfoximine competes in principle with the analogous functionalization at the amide nitrogen atom.

It may be expedient to change the order of reaction steps. Thus, benzoic acids carrying a sulfoxide cannot be converted directly into their acid chlorides. Here, it is expedient to form initially, at the thioether stage, the amide, and then to oxidize the thioether to the sulfoxide. Under certain conditions, sulfoximines and in particular sulfilimines are insufficiently stable (Bolm, C. Adv. Synth. Catal. 2010, 352, 309), so it may be advantageous, as shown in the schemes above, to synthesize initially, at the thioether stage, the benzamide and to generate the sulfilimine or the sulfoximine from the thioether only at the end of the synthesis sequence. However, in the case of sufficient stability, it may, depending on the substitution pattern, also be expedient to generate first, at the benzoic acid stage (or at an even earlier stage) the sulfilimine of the sulfoximine from the thioether, and only then to convert the benzoic acid into its amide.

In certain cases, it may be advantageous to use not the free benzoic acid but derivatives thereof for the reactions. Sometimes it is sufficient for the stability of a functional group to work only in acidic or only in basic media, that is to work only with the free benzoic acid or only with its salt. In many cases, esters such as methyl or ethyl esters are suitable. Frequently, Work-up of the respective reaction mixtures is generally carried out by known methods, for example by crystallization, aqueous-extractive work-up, by chromatographic methods or by a combination of these methods.

Collections of compounds of the formula (I) and/or their salts which can be synthesized in accordance with the above-mentioned reactions can also be prepared in a parallelized manner, which can be effected manually or in a partly or fully automated manner. Here, it is possible for example to automate the procedure of the reaction, the work-up or the purification of the products or intermediates. Overall, this is understood as meaning a procedure as described for example by D. Tiebes in Combinatorial Chemistry—Synthesis, Analysis, Screening (Editor Gunther Jung), Wiley 1999, on pages 1 to 34.

A number of commercially available apparatuses can be used for the parallelized reaction procedure and work-up, for example Calpyso reaction blocks from Barnstead International, Dubuque, Iowa 52004-0797, USA, or reaction stations from Radleys, Shirehill, Saffron Walden, Essex, CB 11 3AZ, England or MultiPROBE Automated Workstations from Perkin Elmar, Waltham, Mass. 02451, USA. Chromatographic apparatuses, for example from ISCO, Inc., 4700 Superior Street, Lincoln, Nebr. 68504, USA, are available, inter alia, for the parallelized purification of compounds of the formula (I) and their salts or of intermediates generated in the course of the preparation.

The apparatuses listed lead to a modular procedure in which the individual passes are automated, but manual operations must be carried out between the passes. This can be circumvented by the use of partly or fully integrated automation systems, where the relevant automation modules are operated by, for example, robots. Such automation systems can be obtained for example from Caliper, Hopkinton, Mass. 01748, USA.

The performance of individual, or a plurality of, synthesis steps can be aided by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described herein, the preparation of compounds of the formula (I) and their salts can be effected fully or in part by solid-phase-supported methods. For this purpose, individual intermediates, or all intermediates, of the synthesis or of a synthesis adapted to the relevant procedure are bound to a synthesis resin. Solid-phase-supported synthesis methods are described sufficiently in the specialist literature, for example Barry A. Bunin in "The Combinatorial Index", Academic Press, 1998 and Combinatorial Chemistry—Synthesis, Analysis, Screening (Editor Gunther Jung), Wiley, 1999. The use of solid-phase-supported synthesis methods permits a series of protocols known from the literature, which, again, can be carried out manually or in an automated manner. For example, the reactions can be carried out by means of IRORI technology in microreactors from Nexus Biosystems, 12140 Community Road, Poway, Calif. 92064, USA.

Carrying out individual or a plurality of synthesis steps, both on a solid and in the liquid phase, can be aided by the use of microwave technology. A series of experimental protocols are described in the specialist literature, for example in Microwaves in Organic and Medicinal Chemistry (Editors C. O. Kappe and A. Stadler), Wiley, 2005.

The preparation in accordance with the processes described herein generates compounds of the formula (I) and their salts in the form of substance collections, which are referred to as libraries. The present invention also relates to libraries which comprise at least two compounds of the formula (I) and their salts.

The compounds of the formula (I) according to the invention (and/or their salts), hereinbelow together referred to as "compounds according to the invention", have an outstanding herbicidal activity against a broad spectrum of economically important monocotyledonous and dicotyledonous annual harmful plants. The active substances also act efficiently on perennial harmful plants which produce shoots from rhizomes, rootstocks or other perennial organs and which are difficult to control.

The present invention therefore also relates to a method of controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, the compounds according to the invention can be applied for example pre-planting (if appropriate also by incorporation into the soil), pre-emergence or post-emergence. Examples of individual representatives of the monocotyledonous and dicotyledonous weed flora which can be controlled by the compounds according to the invention shall be mentioned, without the mention being intended as a limitation to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, either the emergence of the weed seedlings is prevented completely or the weeds grow until they have reached the cotyledon stage, but then stop their growth and, finally, die completely after three to four weeks have elapsed.

When the active substances are applied post-emergence to the green plant parts, growth stops after the treatment, and the harmful plants remain in the growth stage of the time of application or die fully after a certain period of time, so that competition by weeds, which is harmful to the crop plants, is thus eliminated at an early point in time and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, are damaged only to an insignificant extent, or not at all, depending on the structure of the respective compound according to the invention and its application rate. This is why the present compounds are highly suitable for the selective control of undesired plant growth in plant crops such as agriculturally useful plants or ornamentals.

Moreover, the compounds according to the invention (depending on their respective structure and the application rate applied) have outstanding growth-regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting undesired vegetative growth without destroying the plants in the process. Inhibiting the vegetative growth plays an important role in many monocotyledonous and dicotyledonous crops since for example lodging can be reduced, or prevented completely, hereby.

Owing to their herbicidal and plant-growth-regulatory properties, the active substances can also be employed for controlling harmful plants in crops of genetically modified plants or plants which have been modified by conventional mutagenesis. As a rule, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other special properties relate for example to the harvested material with regard to quantity, quality, storability, composition and specific constituents. Thus, transgenic plants with an increased starch content or a modified starch quality or those with a different fatty acid composition of the harvested material are known.

It is preferred to use the compounds according to the invention or their salts in economically important transgenic crops of useful plants and ornamentals, for example of cereals such as wheat, barley, rye, oats, sorghum and millet, rice, cassava and maize or else crops of sugar beet, cotton, soybean, oil seed rape, potato, tomato, peas and other vegetables. It is preferred to employ the compounds according to the invention as herbicides in crops of useful plants which are resistant, or have been made resistant by recombinant means, to the phytotoxic effects of the herbicides.

Conventional ways of generating novel plants which, in comparison with existing plants, have modified properties are, for example, traditional breeding methods and the generation of mutants. Alternatively, novel plants with modified properties can be generated with the aid of recombinant methods (see, for example, EP-A-0221044, EP-A-0131624). For example, the following have been described in several cases:

recombinant modifications of crop plants for the purposes of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or of the glyphosate type (WO 92/00377) or of the sulfonylurea type (EP-A-0257993, U.S. Pat. No. 5,013,659), transgenic crop plants, for example cotton, which are capable of producing *Bacillus thuringiensis* toxins (Bt toxins), which make the plants resistant to certain pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431.

To carry out such recombinant manipulations, it is possible to introduce nucleic acid molecules into plasmids, which permit a mutagenesis or sequence modification by recombination of DNA sequences. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim 2nd ed., 1996.

The generation of plant cells with a reduced activity for a gene product can be achieved for example by the expression of at least one corresponding antisense RNA, a sense RNA for achieving a cosuppression effect or by the expression of at least one correspondingly constructed ribozyme, which specifically cleaves transcripts of the abovementioned gene product. To do this, it is possible firstly to use DNA molecules which comprise all of the coding sequence of a gene product, including any flanking sequences which may be present, or else DNA molecules which only comprise parts of the coding sequence, it being necessary for these parts to be long enough to bring about an antisense effect in the cells. It is also possible to use DNA sequences which have a high degree of homology with the coding sequences of a gene product, but which are not entirely identical.

When expressing nucleic acid molecules in plants, the protein synthesized may be localized in any compartment of the plant cell. In order to achieve localization in a particular compartment, however, it is possible for example to link the coding region to DNA sequences which ensure the localization in a specific compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give intact plants. In principle, the transgenic plants may be plants of any plant species, that is to say both monocotyledonous and dicotyledonous plants.

Thus, transgenic plants can be obtained which feature modified properties as the result of overexpression, suppression or inhibition of homologous (=natural) genes or gene sequences or expression of heterologous (=foreign) genes or gene sequences.

It is preferred to employ the compounds according to the invention in transgenic crops which are resistant to growth regulators such as, for example, dicamba, or against herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulfonylureas, glyphosate, glufosinate or benzoylisoxazoles and analogous active substances.

When the active substances according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds according to the invention as herbicides for controlling harmful plants in transgenic crop plants.

The compounds according to the invention can be employed in the customary preparations in the form of wettable powders, emulsifiable concentrates, sprayable solutions, dusts or granules. The invention therefore also relates to herbicidal and plant-growth-regulating compositions which comprise the compounds according to the invention.

The compounds according to the invention can be formulated in various ways, depending on the prevailing biological and/or physico-chemical parameters. Examples of possible formulations are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for application by broadcasting and on the soil, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical technology], volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie" [Chemical technology], volume 7, C. Hanser Verlag Munich, 4th Ed. 1986.

Based on these formulations, it is also possible to prepare combinations with other pesticidally active substances such as, for example, insecticides, acaricides, herbicides, fungicides, and with safeners, fertilizers and/or growth regulators, for example in the form of a ready mix or a tank mix. Suitable safeners are, for example, mefenpyr-diethyl, cyprosulfamide, isoxadifen-ethyl, cloquintocet-mexyl and dichlormid.

Wettable powders are preparations which are uniformly dispersible in water and which, besides the active substance, also comprise ionic and/or nonionic surfactants (wetters, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, besides a diluent or inert substance. To prepare the wettable powders, the herbicidally active substances are ground finely, for example in customary apparatuses such as hammer mills, blower mills and air-jet mills, and mixed with the formulation auxiliaries, either simultaneously or subsequently.

Emulsifiable concentrates are prepared by dissolving the active substance in an organic solvent, for example butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylarylpolyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials such as, for example, talcum, natural clays such as kaolin, bentonite and pyrophyllite, or diatomaceous earth.

Suspension concentrates can be water- or oil-based. They can be prepared for example by wet-grinding by means of commercially available bead mills, if appropriate with addition of surfactants as already listed above for example in the case of the other formulation types.

Emulsions, for example oil-in-water emulsions (EW), can be prepared for example by means of stirrers, colloid mills and/or static mixers using aqueous organic solvents and, if appropriate, surfactants, as have already been mentioned for example above for the other formulation types.

Granules can be prepared either by spraying the active substance onto adsorptive, granulated inert material, or by applying active substance concentrates to the surface of carriers such as sand, kaolinites or granulated inert material with the aid of stickers, for example polyvinyl alcohol, sodium polyacrylate or else mineral oils. Suitable active substances can also be granulated in the manner which is customary for the production of fertilizer granules, if desired as a mixture with fertilizers.

Water-dispersible granules are generally prepared by customary methods such as spray drying, fluidized-bed granulation, disk granulation, mixing with high-speed stirrers, and extrusion without solid inert material.

To prepare disk granules, fluidized-bed granules, extruder granules and spray granules, see, for example, methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57.

For further details of the formulation of crop protection products see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise from 0.1 to 99% by weight, in particular from 0.1 to 95% by weight, of compounds according to the invention. In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise from 1 to 30% by weight of active substance, preferably in most cases from 5 to 20% by weight of active substance, and sprayable solutions comprise approximately from 0.05 to 80, preferably from 2 to 50% by weight of active substance. In the case of water-dispersible granules, the active substance content depends partly on whether the active compound is in liquid or solid form, and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the auxiliaries which are conventional in each case, such as stickers, wetting agents, dispersants, emulsifiers, penetrants, preservatives, antifreeze agents, solvents, fillers, carriers, colorants, antifoams, evaporation inhibitors, and pH and viscosity regulators.

Based on these formulations, it is also possible to prepare combinations with other pesticidally active substances such as, for example, insecticides, acaricides, herbicides, fungicides, and with safeners, fertilizers and/or growth regulators, for example in the form of a ready mix or a tank mix.

Active substances which can be employed in combination with the compounds according to the invention in mixed formulations or in the tank mix are, for example, known active substances which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoen desaturase, photosystem I, photosystem II, protoporphyrinogen oxidase, as are described in, for example, Weed Research 26 (1986) 441-445 or "The Pesticide Manual", 14th edition, The British Crop Protection Council and the Royal Soc. of Chemistry, 2003 and the literature cited therein.

For use, the formulations, which are present in commercially available form, if appropriate, are diluted in the customary manner, for example using water in the case of wettable powders, emulsifiable concentrates, dispersions and water-dispersible granules. Preparations in the form of dusts, soil granules, granules for broadcasting, and sprayable solutions, are usually not diluted further with further inert substances prior to use.

The application rate required of the compounds of the formula (I) varies as a function of the external conditions such as temperature, humidity, the nature of the herbicide used and the like. It can vary within wide limits, for example between 0.001 and 1.0 kg/ha and more of active substance, but it is preferably between 0.005 and 750 g/ha.

The examples which follow illustrate the invention.

A. CHEMICAL EXAMPLES

Synthesis of 3-(N-cyano-S-methylsulfinimidoyl)-2-methoxy-N-(1-methyl-1H-tetrazol-5-yl)-4-(trifluoromethyl)benzamide (Table Example No. 10-160) and 3-(N-cyano-S-methylsulfonimidoyl)-2-methoxy-N-(1-methyl-1H-tetrazol-5-yl)-4-(trifluoromethyl) benzamide (Table Example No. 1-160)

Step 1: Synthesis of 2-methoxy-3-(methylsulfanyl)-N-(1-methyl-1H-tetrazol-5-yl)-4-(trifluoromethyl) benzamide 1.45 g (98% by weight; 14.3 mmol) of 5-amino-1-methyl-1H-tetrazole were added to 3.00 g (11.3 mmol) of 2-methoxy-3-(methylsulfanyl)-4-(trifluoromethyl)benzoic acid in 30 ml of dry pyridine. 2.00 g (15.8 mmol) of oxalyl chloride were then added, and the mixture was subsequently stirred at room temperature (RT) for three days. Another 500 mg (3.94 mmol) of oxalyl chloride were then added, and the mixture was subsequently stirred at RT for 16 h. For work-up, the contents were substantially freed from the solvent on a rotary evaporator. The residue was stirred with dichloromethane and a saturated solution of sodium bicarbonate. The organic phases were then separated and the organic phase was freed from the solvent on a rotary evaporator. The residue was purified chromatographically, which gave 1.83 g of clean product.

Step 2: Synthesis of 3-(N-cyano-S-methylsulfinimidoyl)-2-methoxy-N-(1-methyl-1H-tetrazol-5-yl)-4-(trifluoromethyl)benzamide and 3-(N-cyano-S-methylsulfonimidoyl)-2-methoxy-N-(1-methyl-1H-tetrazol-5-yl)-4-(trifluoromethyl)benzamide At RT, 234 mg (5.56 mmol) of cyanamide and 1.06 g (5.96 mmol) of N-bromosuccinimide were added in succession to a solution of 1.14 g (3.27 mmol) of 2-methoxy-3-(methylsulfanyl)-N-(1-methyl-1H-tetrazol-5-yl)-4-(trifluoromethyl) benzamide and 440 mg (3.92 mmol) of potassium tert-butoxide in 70 ml of methanol. The contents were then stirred at RT for 16 h. For work-up, the mixture was freed from the solvent on a rotary evaporator at a temperature of at most 30° C. The residue was stirred in a mixture of 150 ml of ice-cold dichloromethane and 50 ml of ice-cold aqueous 10% by weight strength sodium bisulfate solution for about two minutes. After phase separation, the aqueous phase was extracted with 50 ml of dichloromethane. On a rotary evaporator, the combined organic phases were freed from the solvent. The residue was taken up in 60 ml of acetonitrile and 60 ml of water. 1.57 g (9.80 mmol) of sodium permanganate monohydrate were then added. The reaction mixture was stirred at RT for four days. For work-up, aqueous 10% by weight strength sodium bisulfate solution was added. Water was then added, and the mixture was extracted three times with dichloromethane. On a rotary evaporator, the combined organic phases were freed from the solvent at a temperature of at most 30° C. The residue was purified chromatographically, which gave 40 mg of 3-(N-cyano-S-methylsulfinimidoyl)-2-methoxy-N-(1-methyl-1H-tetrazol-5-yl)-4-(trifluoromethyl)benzamide and 650 mg of 3-(N-cyano-S-methylsulfonimidoyl)-2-methoxy-N-(1-methyl-1H-tetrazol-5-yl)-4-(trifluoromethyl)benzamide.

Synthesis of 2-methoxy-N-(1-methyl-1H-tetrazol-5-yl)-3-[S-methyl-N-(trifluoroacetyl)sulfonimidoyl]-4-(trifluoromethyl)benzamide (Table Example No. 1-292)

100 mg (0.248 mmol) of 3-(N-cyano-S-methylsulfinimidoyl)-2-methoxy-N-(1-methyl-1H-tetrazol-5-yl)-4-(trifluoromethyl)benzamide were initially charged in 10 ml of dry dichloromethane and cooled in an ice bath. 156 mg (0.744 mmol) of trifluoroacetic anhydride were added, and after 1.5 h the contents were thawed to RT. The mixture was stirred at RT for 16 h and then poured into water for work-up. The contents were extracted twice with dichloromethane and the mixture was then, after phase separation, freed from the solvent on a rotary evaporator at a temperature of at most 30° C. The residue was purified chromatographically, which gave 17 mg of product.

Synthesis of 2-methoxy-3-(S-methylsulfonimidoyl)-N-(1-methyl-1H-tetrazol-5-yl)-4-(trifluoromethyl) benzamide (Table Example No. 1-28)

31.5 mg (0.228 mmol) of potassium carbonate were added to 36.0 mg (0.076 mmol) of 2-methoxy-N-(1-methyl-1H- tetrazol-5-yl)-3-[S-methyl-N-(trifluoroacetyl)sulfonimidoyl]-4-(trifluoromethyl)benzamide in 5 ml of methanol. The mixture was stirred at RT for 30 minutes. For work-up, the solvent was removed at a temperature of at most 30° C. on a rotary evaporator. The residue was taken up in water and the mixture was extracted with dichloromethane. A drop of glacial acetic acid was then added to the aqueous phase, and the mixture was extracted twice with dichloromethane. On a rotary evaporator, the aqueous phase was then freed from the solvent at a temperature of at most 30° C. The residue was stirred with dichloromethane and then combined with the organic phases isolated above. The solvent was removed on a rotary evaporator, and 20 mg of product were isolated as residue.

Synthesis of 3-(N-cyano-S-methylsulfonimidoyl)-2-methoxy-N-(5-methyl-1,3,4-oxadiazol-2-yl)-4-(trifluoromethyl)benzamide (Table Example No. 7-160)

Step 1: Synthesis of 3-(N-cyano-S-methylsulfonimidoyl)-2-methoxy-4-(trifluoromethyl)benzoic acid 3.71 g (33.1 mmol) of potassium tert-butoxide were added to a solution of 4.00 g (15.0 mmol) of 2-methoxy-3-(methylsulfanyl)-4-(trifluoromethyl)benzoic acid in 250 ml of methanol. The mixture was stirred for 10 minutes, and 1.07 g (25.5 mmol) of cyanamide and 4.81 g (27.0 mmol) of N-bromosuccinimide were then added in succession. The contents were then stirred at RT for 2 h. The mixture was then freed from the solvent on a rotary evaporator and the residue was taken up in a mixture of in each case 120 ml of acetonitrile and water. 7.21 g (45.1 mmol) of sodium permanganate monohydrate were added, and the mixture was stirred at RT for one week. During this week, both after one day and after a further day, in each case 3.6 g (22.5 mmol) of sodium permanganate monohydrate were added. For work-up, a 10% by weight strength solution of sodium bisulfate was added. On a rotary evaporator, at a temperature of at most 30° C., the solvent was substantially removed. The residue was cooled in an ice bath and then acidified with 1M hydrochloric acid. The mixture was extracted three times with ice-cold dichloromethane. The combined organic phases were freed from the solvent on a rotary evaporator and the residue was purified chromatographically, which gave 1.30 g of product of a purity of 80% by weight.

Step 2: Synthesis of 3-(N-cyano-S-methylsulfonimidoyl)-2-methoxy-N-(5-methyl-1,3,4-oxadiazol-2-yl)-4-(trifluoromethyl)benzamide 350 mg (80% by weight; 0.869 mmol) of 3-(N-cyano-S-methylsulfonimidoyl)-2-methoxy-4-(trifluoromethyl)benzoic acid and 151 mg (1.52 mmol) of 2-amino-5-methyl-1,3,4-oxadiazole were initially charged in 10 ml of dry pyridine and cooled in an ice bath. 207 mg (1.63 mmol) of oxalyl chloride were added, and after 30 minutes the mixture was thawed to RT. The contents were stirred at RT for 2 h, and another 51.8 mg (0.408 mmol) of oxalyl chloride were then added. The mixture was then stirred at RT for 16 h. For work-up, the contents were freed from the solvent on a rotary evaporator and the residue was taken up in water and dichloromethane. After phase separation, the organic phase was freed from the solvent on a rotary evaporator and the residue was purified chromatographically under neutral conditions, which gave 9.80 mg of product.

The examples listed in the tables hereinbelow were prepared analogously to abovementioned methods or are obtainable analogously to abovementioned methods. These compounds are very particularly preferred.

The abbreviations used are:

| | | | |
|---|---|---|---|
| Et = ethyl | Me = methyl | n-Pr = n-propyl | i-Pr = isopropyl |
| c-Pr = cyclopropyl | Ph = phenyl | | |

TABLE 1

Compounds according to the invention of the formula (I) in which Q is Q1 and R$^x$ is a methyl group, R" and W are each hydrogen and t = 1

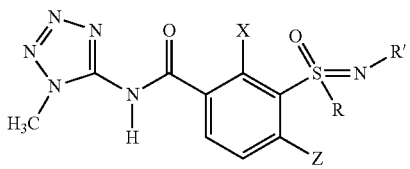

| No. | X | Z | R | R' | Physical Data ($^1$H NMR) |
|---|---|---|---|---|---|
| 1-1 | Me | Me | Me | H | |
| 1-2 | Me | F | Me | H | |
| 1-3 | Me | Cl | Me | H | |
| 1-4 | Me | Br | Me | H | |
| 1-5 | Me | I | Me | H | |
| 1-6 | Me | CF$_3$ | Me | H | |
| 1-7 | Me | CHF$_2$ | Me | H | |
| 1-8 | Me | CF$_2$Cl | Me | H | |
| 1-9 | Me | OMe | Me | H | |
| 1-10 | Me | NO$_2$ | Me | H | |
| 1-11 | Me | SO$_2$Me | Me | H | |
| 1-12 | Cl | Me | Me | H | |
| 1-13 | Cl | F | Me | H | |
| 1-14 | Cl | Cl | Me | H | |
| 1-15 | Cl | Br | Me | H | |
| 1-16 | Cl | I | Me | H | |
| 1-17 | Cl | CF$_3$ | Me | H | |
| 1-18 | Cl | CHF$_2$ | Me | H | |
| 1-19 | Cl | CF$_2$Cl | Me | H | |
| 1-20 | Cl | OMe | Me | H | |
| 1-21 | Cl | NO$_2$ | Me | H | |
| 1-22 | Cl | SO$_2$Me | Me | H | |
| 1-23 | OMe | Me | Me | H | |
| 1-24 | OMe | F | Me | H | |
| 1-25 | OMe | Cl | Me | H | |
| 1-26 | OMe | Br | Me | H | |
| 1-27 | OMe | I | Me | H | |
| 1-28 | OMe | CF$_3$ | Me | H | (400 MHz, D$_2$O δ, ppm) 7.85 (d, 1H), 7.72 (d, 1H), 3.97 (br. s, 3H), 3.81 (s, 3H), 3.46 (br. s, 3H) |
| 1-29 | OMe | CHF$_2$ | Me | H | |
| 1-30 | OMe | CF$_2$Cl | Me | H | |
| 1-31 | OMe | OMe | Me | H | |
| 1-32 | OMe | NO$_2$ | Me | H | |
| 1-33 | OMe | SO$_2$Me | Me | H | |
| 1-34 | SO$_2$Me | Me | Me | H | |
| 1-35 | SO$_2$Me | F | Me | H | |
| 1-36 | SO$_2$Me | Cl | Me | H | |
| 1-37 | SO$_2$Me | Br | Me | H | |
| 1-38 | SO$_2$Me | I | Me | H | |
| 1-39 | SO$_2$Me | CF$_3$ | Me | H | |
| 1-40 | SO$_2$Me | CHF$_2$ | Me | H | |
| 1-41 | SO$_2$Me | CF$_2$Cl | Me | H | |
| 1-42 | SO$_2$Me | OMe | Me | H | |
| 1-43 | SO$_2$Me | NO$_2$ | Me | H | |
| 1-44 | SO$_2$Me | SO$_2$Me | Me | H | |
| 1-45 | Me | Me | Et | H | |
| 1-46 | Me | F | Et | H | |
| 1-47 | Me | Cl | Et | H | |
| 1-48 | Me | Br | Et | H | |
| 1-49 | Me | I | Et | H | |

TABLE 1-continued

Compounds according to the invention of the formula (I) in which Q is Q1 and $R^x$ is a methyl group, R'' and W are each hydrogen and t = 1

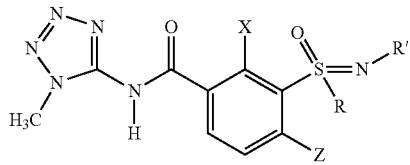

| No. | X | Z | R | R' | Physical Data ($^1$H NMR) |
|---|---|---|---|---|---|
| 1-50 | Me | CF$_3$ | Et | H | |
| 1-51 | Me | CHF$_2$ | Et | H | |
| 1-52 | Me | CF$_2$Cl | Et | H | |
| 1-53 | Me | OMe | Et | H | |
| 1-54 | Me | NO$_2$ | Et | H | |
| 1-55 | Me | SO$_2$Me | Et | H | |
| 1-56 | Cl | Me | Et | H | |
| 1-57 | Cl | F | Et | H | |
| 1-58 | Cl | Cl | Et | H | |
| 1-59 | Cl | Br | Et | H | |
| 1-60 | Cl | I | Et | H | |
| 1-61 | Cl | CF$_3$ | Et | H | |
| 1-62 | Cl | CHF$_2$ | Et | H | |
| 1-63 | Cl | CF$_2$Cl | Et | H | |
| 1-64 | Cl | OMe | Et | H | |
| 1-65 | Cl | NO$_2$ | Et | H | |
| 1-66 | Cl | SO$_2$Me | Et | H | |
| 1-67 | OMe | Me | Et | H | |
| 1-68 | OMe | F | Et | H | |
| 1-69 | OMe | Cl | Et | H | |
| 1-70 | OMe | Br | Et | H | |
| 1-71 | OMe | I | Et | H | |
| 1-72 | OMe | CF$_3$ | Et | H | |
| 1-73 | OMe | CHF$_2$ | Et | H | |
| 1-74 | OMe | CF$_2$Cl | Et | H | |
| 1-75 | OMe | OMe | Et | H | |
| 1-76 | OMe | NO$_2$ | Et | H | |
| 1-77 | OMe | SO$_2$Me | Et | H | |
| 1-78 | SO$_2$Me | Me | Et | H | |
| 1-79 | SO$_2$Me | F | Et | H | |
| 1-80 | SO$_2$Me | Cl | Et | H | |
| 1-81 | SO$_2$Me | Br | Et | H | |
| 1-82 | SO$_2$Me | I | Et | H | |
| 1-83 | SO$_2$Me | CF$_3$ | Et | H | |
| 1-84 | SO$_2$Me | CHF$_2$ | Et | H | |
| 1-85 | SO$_2$Me | CF$_2$Cl | Et | H | |
| 1-86 | SO$_2$Me | OMe | Et | H | |
| 1-87 | SO$_2$Me | NO$_2$ | Et | H | |
| 1-88 | SO$_2$Me | SO$_2$Me | Et | H | |
| 1-89 | Me | Me | CH$_2$CH$_2$OMe | H | |
| 1-90 | Me | F | CH$_2$CH$_2$OMe | H | |
| 1-91 | Me | Cl | CH$_2$CH$_2$OMe | H | |
| 1-92 | Me | Br | CH$_2$CH$_2$OMe | H | |
| 1-93 | Me | I | CH$_2$CH$_2$OMe | H | |
| 1-94 | Me | CF$_3$ | CH$_2$CH$_2$OMe | H | |
| 1-95 | Me | CHF$_2$ | CH$_2$CH$_2$OMe | H | |
| 1-96 | Me | CF$_2$Cl | CH$_2$CH$_2$OMe | H | |
| 1-97 | Me | OMe | CH$_2$CH$_2$OMe | H | |
| 1-98 | Me | NO$_2$ | CH$_2$CH$_2$OMe | H | |
| 1-99 | Me | SO$_2$Me | CH$_2$CH$_2$OMe | H | |
| 1-100 | Cl | Me | CH$_2$CH$_2$OMe | H | |
| 1-101 | Cl | F | CH$_2$CH$_2$OMe | H | |
| 1-102 | Cl | Cl | CH$_2$CH$_2$OMe | H | |
| 1-103 | Cl | Br | CH$_2$CH$_2$OMe | H | |
| 1-104 | Cl | I | CH$_2$CH$_2$OMe | H | |
| 1-105 | Cl | CF$_3$ | CH$_2$CH$_2$OMe | H | |
| 1-106 | Cl | CHF$_2$ | CH$_2$CH$_2$OMe | H | |
| 1-107 | Cl | CF$_2$Cl | CH$_2$CH$_2$OMe | H | |
| 1-108 | Cl | OMe | CH$_2$CH$_2$OMe | H | |
| 1-109 | Cl | NO$_2$ | CH$_2$CH$_2$OMe | H | |
| 1-110 | Cl | SO$_2$Me | CH$_2$CH$_2$OMe | H | |
| 1-111 | OMe | Me | CH$_2$CH$_2$OMe | H | |
| 1-112 | OMe | F | CH$_2$CH$_2$OMe | H | |
| 1-113 | OMe | Cl | CH$_2$CH$_2$OMe | H | |
| 1-114 | OMe | Br | CH$_2$CH$_2$OMe | H | |

TABLE 1-continued

Compounds according to the invention of the formula (I) in which Q is Q1 and $R^x$ is a methyl group, R'' and W are each hydrogen and t = 1

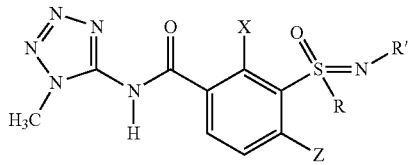

| No. | X | Z | R | R' | Physical Data ($^1$H NMR) |
|---|---|---|---|---|---|
| 1-115 | OMe | I | CH$_2$CH$_2$OMe | H | |
| 1-116 | OMe | CF$_3$ | CH$_2$CH$_2$OMe | H | |
| 1-117 | OMe | CHF$_2$ | CH$_2$CH$_2$OMe | H | |
| 1-118 | OMe | CF$_2$Cl | CH$_2$CH$_2$OMe | H | |
| 1-119 | OMe | OMe | CH$_2$CH$_2$OMe | H | |
| 1-120 | OMe | NO$_2$ | CH$_2$CH$_2$OMe | H | |
| 1-121 | OMe | SO$_2$Me | CH$_2$CH$_2$OMe | H | |
| 1-122 | SO$_2$Me | Me | CH$_2$CH$_2$OMe | H | |
| 1-123 | SO$_2$Me | F | CH$_2$CH$_2$OMe | H | |
| 1-124 | SO$_2$Me | Cl | CH$_2$CH$_2$OMe | H | |
| 1-125 | SO$_2$Me | Br | CH$_2$CH$_2$OMe | H | |
| 1-126 | SO$_2$Me | I | CH$_2$CH$_2$OMe | H | |
| 1-127 | SO$_2$Me | CF$_3$ | CH$_2$CH$_2$OMe | H | |
| 1-128 | SO$_2$Me | CHF$_2$ | CH$_2$CH$_2$OMe | H | |
| 1-129 | SO$_2$Me | CF$_2$Cl | CH$_2$CH$_2$OMe | H | |
| 1-130 | SO$_2$Me | OMe | CH$_2$CH$_2$OMe | H | |
| 1-131 | SO$_2$Me | NO$_2$ | CH$_2$CH$_2$OMe | H | |
| 1-132 | SO$_2$Me | SO$_2$Me | CH$_2$CH$_2$OMe | H | |
| 1-133 | Me | Me | Me | CN | |
| 1-134 | Me | F | Me | CN | |
| 1-135 | Me | Cl | Me | CN | |
| 1-136 | Me | Br | Me | CN | |
| 1-137 | Me | I | Me | CN | |
| 1-138 | Me | CF$_3$ | Me | CN | (400 MHz, CDCl$_3$ δ, ppm) 8.00 (s, 2H), 4.08 (s, 3H), 3.54 (s, 3H), 2.89 (s, 3H) |
| 1-139 | Me | CHF$_2$ | Me | CN | |
| 1-140 | Me | CF$_2$Cl | Me | CN | |
| 1-141 | Me | OMe | Me | CN | |
| 1-142 | Me | NO$_2$ | Me | CN | |
| 1-143 | Me | SO$_2$Me | Me | CN | |
| 1-144 | Cl | Me | Me | CN | |
| 1-145 | Cl | F | Me | CN | |
| 1-146 | Cl | Cl | Me | CN | |
| 1-147 | Cl | Br | Me | CN | |
| 1-148 | Cl | I | Me | CN | |
| 1-149 | Cl | CF$_3$ | Me | CN | |
| 1-150 | Cl | CHF$_2$ | Me | CN | |
| 1-151 | Cl | CF$_2$Cl | Me | CN | |
| 1-152 | Cl | OMe | Me | CN | |
| 1-153 | Cl | NO$_2$ | Me | CN | |
| 1-154 | Cl | SO$_2$Me | Me | CN | |
| 1-155 | OMe | Me | Me | CN | |
| 1-156 | OMe | F | Me | CN | |
| 1-157 | OMe | Cl | Me | CN | |
| 1-158 | OMe | Br | Me | CN | |
| 1-159 | OMe | I | Me | CN | |
| 1-160 | OMe | CF$_3$ | Me | CN | (400 MHz, CDCl$_3$ δ, ppm) 8.22 (d, 1H), 7.89 (d, 1H), 4.15 (s, 3H), 4.12 (s, 3H), 3.74 (s, 3H) |
| 1-161 | OMe | CHF$_2$ | Me | CN | |
| 1-162 | OMe | CF$_2$Cl | Me | CN | |
| 1-163 | OMe | OMe | Me | CN | |
| 1-164 | OMe | NO$_2$ | Me | CN | |
| 1-165 | OMe | SO$_2$Me | Me | CN | |
| 1-166 | SO$_2$Me | Me | Me | CN | |
| 1-167 | SO$_2$Me | F | Me | CN | |
| 1-168 | SO$_2$Me | Cl | Me | CN | |
| 1-169 | SO$_2$Me | Br | Me | CN | |
| 1-170 | SO$_2$Me | I | Me | CN | |
| 1-171 | SO$_2$Me | CF$_3$ | Me | CN | |
| 1-172 | SO$_2$Me | CHF$_2$ | Me | CN | |

TABLE 1-continued

Compounds according to the invention of the formula (I) in which Q is Q1 and R$^x$ is a methyl group, R″ and W are each hydrogen and t = 1

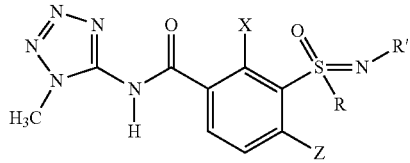
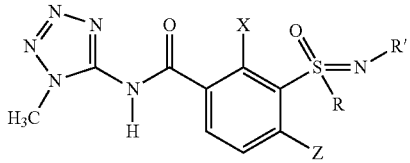

| No. | X | Z | R | R' | Physical Data ($^1$H NMR) |
|---|---|---|---|---|---|
| 1-173 | SO$_2$Me | CF$_2$Cl | Me | CN | |
| 1-174 | SO$_2$Me | OMe | Me | CN | |
| 1-175 | SO$_2$Me | NO$_2$ | Me | CN | |
| 1-176 | SO$_2$Me | SO$_2$Me | Me | CN | |
| 1-177 | Me | Me | Et | CN | |
| 1-178 | Me | F | Et | CN | |
| 1-179 | Me | Cl | Et | CN | |
| 1-180 | Me | Br | Et | CN | |
| 1-181 | Me | I | Et | CN | |
| 1-182 | Me | CF$_3$ | Et | CN | |
| 1-183 | Me | CHF$_2$ | Et | CN | |
| 1-184 | Me | CF$_2$Cl | Et | CN | |
| 1-185 | Me | OMe | Et | CN | |
| 1-186 | Me | NO$_2$ | Et | CN | |
| 1-187 | Me | SO$_2$Me | Et | CN | |
| 1-188 | Cl | Me | Et | CN | |
| 1-189 | Cl | F | Et | CN | |
| 1-190 | Cl | Cl | Et | CN | |
| 1-191 | Cl | Br | Et | CN | |
| 1-192 | Cl | I | Et | CN | |
| 1-193 | Cl | CF$_3$ | Et | CN | |
| 1-194 | Cl | CHF$_2$ | Et | CN | |
| 1-195 | Cl | CF$_2$Cl | Et | CN | |
| 1-196 | Cl | OMe | Et | CN | |
| 1-197 | Cl | NO$_2$ | Et | CN | |
| 1-198 | Cl | SO$_2$Me | Et | CN | |
| 1-199 | OMe | Me | Et | CN | |
| 1-200 | OMe | F | Et | CN | |
| 1-201 | OMe | Cl | Et | CN | |
| 1-202 | OMe | Br | Et | CN | |
| 1-203 | OMe | I | Et | CN | |
| 1-204 | OMe | CF$_3$ | Et | CN | |
| 1-205 | OMe | CHF$_2$ | Et | CN | |
| 1-206 | OMe | CF$_2$Cl | Et | CN | |
| 1-207 | OMe | OMe | Et | CN | |
| 1-208 | OMe | NO$_2$ | Et | CN | |
| 1-209 | OMe | SO$_2$Me | Et | CN | |
| 1-210 | SO$_2$Me | Me | Et | CN | |
| 1-211 | SO$_2$Me | F | Et | CN | |
| 1-212 | SO$_2$Me | Cl | Et | CN | |
| 1-213 | SO$_2$Me | Br | Et | CN | |
| 1-214 | SO$_2$Me | I | Et | CN | |
| 1-215 | SO$_2$Me | CF$_3$ | Et | CN | |
| 1-216 | SO$_2$Me | CHF$_2$ | Et | CN | |
| 1-217 | SO$_2$Me | CF$_2$Cl | Et | CN | |
| 1-218 | SO$_2$Me | OMe | Et | CN | |
| 1-219 | SO$_2$Me | NO$_2$ | Et | CN | |
| 1-220 | SO$_2$Me | SO$_2$Me | Et | CN | |
| 1-221 | Me | Me | CH$_2$CH$_2$OMe | CN | |
| 1-222 | Me | F | CH$_2$CH$_2$OMe | CN | |
| 1-223 | Me | Cl | CH$_2$CH$_2$OMe | CN | |
| 1-224 | Me | Br | CH$_2$CH$_2$OMe | CN | |
| 1-225 | Me | I | CH$_2$CH$_2$OMe | CN | |
| 1-226 | Me | CF$_3$ | CH$_2$CH$_2$OMe | CN | |
| 1-227 | Me | CHF$_2$ | CH$_2$CH$_2$OMe | CN | |
| 1-228 | Me | CF$_2$Cl | CH$_2$CH$_2$OMe | CN | |
| 1-229 | Me | OMe | CH$_2$CH$_2$OMe | CN | |
| 1-230 | Me | NO$_2$ | CH$_2$CH$_2$OMe | CN | |
| 1-231 | Me | SO$_2$Me | CH$_2$CH$_2$OMe | CN | |
| 1-232 | Cl | Me | CH$_2$CH$_2$OMe | CN | |
| 1-233 | Cl | F | CH$_2$CH$_2$OMe | CN | |
| 1-234 | Cl | Cl | CH$_2$CH$_2$OMe | CN | |
| 1-235 | Cl | Br | CH$_2$CH$_2$OMe | CN | |
| 1-236 | Cl | I | CH$_2$CH$_2$OMe | CN | |
| 1-237 | Cl | CF$_3$ | CH$_2$CH$_2$OMe | CN | |
| 1-238 | Cl | CHF$_2$ | CH$_2$CH$_2$OMe | CN | |
| 1-239 | Cl | CF$_2$Cl | CH$_2$CH$_2$OMe | CN | |
| 1-240 | Cl | OMe | CH$_2$CH$_2$OMe | CN | |
| 1-241 | Cl | NO$_2$ | CH$_2$CH$_2$OMe | CN | |
| 1-242 | Cl | SO$_2$Me | CH$_2$CH$_2$OMe | CN | |
| 1-243 | OMe | Me | CH$_2$CH$_2$OMe | CN | |
| 1-244 | OMe | F | CH$_2$CH$_2$OMe | CN | |
| 1-245 | OMe | Cl | CH$_2$CH$_2$OMe | CN | |
| 1-246 | OMe | Br | CH$_2$CH$_2$OMe | CN | |
| 1-247 | OMe | I | CH$_2$CH$_2$OMe | CN | |
| 1-248 | OMe | CF$_3$ | CH$_2$CH$_2$OMe | CN | |
| 1-249 | OMe | CHF$_2$ | CH$_2$CH$_2$OMe | CN | |
| 1-250 | OMe | CF$_2$Cl | CH$_2$CH$_2$OMe | CN | |
| 1-251 | OMe | OMe | CH$_2$CH$_2$OMe | CN | |
| 1-252 | OMe | NO$_2$ | CH$_2$CH$_2$OMe | CN | |
| 1-253 | OMe | SO$_2$Me | CH$_2$CH$_2$OMe | CN | |
| 1-254 | SO$_2$Me | Me | CH$_2$CH$_2$OMe | CN | |
| 1-255 | SO$_2$Me | F | CH$_2$CH$_2$OMe | CN | |
| 1-256 | SO$_2$Me | Cl | CH$_2$CH$_2$OMe | CN | |
| 1-257 | SO$_2$Me | Br | CH$_2$CH$_2$OMe | CN | |
| 1-258 | SO$_2$Me | I | CH$_2$CH$_2$OMe | CN | |
| 1-259 | SO$_2$Me | CF$_3$ | CH$_2$CH$_2$OMe | CN | |
| 1-260 | SO$_2$Me | CHF$_2$ | CH$_2$CH$_2$OMe | CN | |
| 1-261 | SO$_2$Me | CF$_2$Cl | CH$_2$CH$_2$OMe | CN | |
| 1-262 | SO$_2$Me | OMe | CH$_2$CH$_2$OMe | CN | |
| 1-263 | SO$_2$Me | NO$_2$ | CH$_2$CH$_2$OMe | CN | |
| 1-264 | SO$_2$Me | SO$_2$Me | CH$_2$CH$_2$OMe | CN | |
| 1-265 | Me | Me | Me | (C=O)CF$_3$ | |
| 1-266 | Me | F | Me | (C=O)CF$_3$ | |
| 1-267 | Me | Cl | Me | (C=O)CF$_3$ | |
| 1-268 | Me | Br | Me | (C=O)CF$_3$ | |
| 1-269 | Me | I | Me | (C=O)CF$_3$ | |
| 1-270 | Me | CF$_3$ | Me | (C=O)CF$_3$ | |
| 1-271 | Me | CHF$_2$ | Me | (C=O)CF$_3$ | |
| 1-272 | Me | CF$_2$Cl | Me | (C=O)CF$_3$ | |
| 1-273 | Me | OMe | Me | (C=O)CF$_3$ | |
| 1-274 | Me | NO$_2$ | Me | (C=O)CF$_3$ | |
| 1-275 | Me | SO$_2$Me | Me | (C=O)CF$_3$ | |
| 1-276 | Cl | Me | Me | (C=O)CF$_3$ | |
| 1-277 | Cl | F | Me | (C=O)CF$_3$ | |
| 1-278 | Cl | Cl | Me | (C=O)CF$_3$ | |
| 1-279 | Cl | Br | Me | (C=O)CF$_3$ | |
| 1-280 | Cl | I | Me | (C=O)CF$_3$ | |
| 1-281 | Cl | CF$_3$ | Me | (C=O)CF$_3$ | |
| 1-282 | Cl | CHF$_2$ | Me | (C=O)CF$_3$ | |
| 1-283 | Cl | CF$_2$Cl | Me | (C=O)CF$_3$ | |
| 1-284 | Cl | OMe | Me | (C=O)CF$_3$ | |
| 1-285 | Cl | NO$_2$ | Me | (C=O)CF$_3$ | |
| 1-286 | Cl | SO$_2$Me | Me | (C=O)CF$_3$ | |
| 1-287 | OMe | Me | Me | (C=O)CF$_3$ | |
| 1-288 | OMe | F | Me | (C=O)CF$_3$ | |
| 1-289 | OMe | Cl | Me | (C=O)CF$_3$ | |
| 1-290 | OMe | Br | Me | (C=O)CF$_3$ | |
| 1-291 | OMe | I | Me | (C=O)CF$_3$ | |
| 1-292 | OMe | CF$_3$ | Me | (C=O)CF$_3$ | (400 MHz, CDCl$_3$ δ, ppm) 8.18 (d, 1H), 7.90 (d, 1H), 4.12 (s, 3H), 4.04 (s, 3H), 3.82 (s, 3H) |
| 1-293 | OMe | CHF$_2$ | Me | (C=O)CF$_3$ | |
| 1-294 | OMe | CF$_2$Cl | Me | (C=O)CF$_3$ | |
| 1-295 | OMe | OMe | Me | (C=O)CF$_3$ | |
| 1-296 | OMe | NO$_2$ | Me | (C=O)CF$_3$ | |
| 1-297 | OMe | SO$_2$Me | Me | (C=O)CF$_3$ | |
| 1-298 | SO$_2$Me | Me | Me | (C=O)CF$_3$ | |

TABLE 1-continued

Compounds according to the invention of the formula (I) in which Q is Q1 and $R^x$ is a methyl group, R" and W are each hydrogen and t = 1

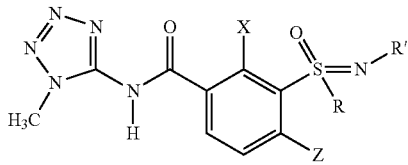

| No. | X | Z | R | R' | Physical Data ($^1$H NMR) |
|---|---|---|---|---|---|
| 1-299 | SO$_2$Me | F | Me | (C=O)CF$_3$ | |
| 1-300 | SO$_2$Me | Cl | Me | (C=O)CF$_3$ | |
| 1-301 | SO$_2$Me | Br | Me | (C=O)CF$_3$ | |
| 1-302 | SO$_2$Me | I | Me | (C=O)CF$_3$ | |
| 1-303 | SO$_2$Me | CF$_3$ | Me | (C=O)CF$_3$ | |
| 1-304 | SO$_2$Me | CHF$_2$ | Me | (C=O)CF$_3$ | |
| 1-305 | SO$_2$Me | CF$_2$Cl | Me | (C=O)CF$_3$ | |
| 1-306 | SO$_2$Me | OMe | Me | (C=O)CF$_3$ | |
| 1-307 | SO$_2$Me | NO$_2$ | Me | (C=O)CF$_3$ | |
| 1-308 | SO$_2$Me | SO$_2$Me | Me | (C=O)CF$_3$ | |

TABLE 2

Compounds according to the invention of the formula (I) in which Q is Q1 and $R^x$ is an ethyl group, R" and W are each hydrogen and t = 1

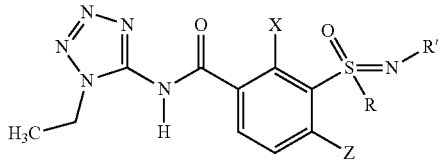

| No. | X | Z | R | R' | Physical Data ($^1$H NMR) |
|---|---|---|---|---|---|
| 2-1 | Me | Me | Me | H | |
| 2-2 | Me | F | Me | H | |
| 2-3 | Me | Cl | Me | H | |
| 2-4 | Me | Br | Me | H | |
| 2-5 | Me | I | Me | H | |
| 2-6 | Me | CF$_3$ | Me | H | |
| 2-7 | Me | CHF$_2$ | Me | H | |
| 2-8 | Me | CF$_2$Cl | Me | H | |
| 2-9 | Me | OMe | Me | H | |
| 2-10 | Me | NO$_2$ | Me | H | |
| 2-11 | Me | SO$_2$Me | Me | H | |
| 2-12 | Cl | Me | Me | H | |
| 2-13 | Cl | F | Me | H | |
| 2-14 | Cl | Cl | Me | H | |
| 2-15 | Cl | Br | Me | H | |
| 2-16 | Cl | I | Me | H | |
| 2-17 | Cl | CF$_3$ | Me | H | |
| 2-18 | Cl | CHF$_2$ | Me | H | |
| 2-19 | Cl | CF$_2$Cl | Me | H | |
| 2-20 | Cl | OMe | Me | H | |
| 2-21 | Cl | NO$_2$ | Me | H | |
| 2-22 | Cl | SO$_2$Me | Me | H | |
| 2-23 | OMe | Me | Me | H | |
| 2-24 | OMe | F | Me | H | |
| 2-25 | OMe | Cl | Me | H | |
| 2-26 | OMe | Br | Me | H | |
| 2-27 | OMe | I | Me | H | |
| 2-28 | OMe | CF$_3$ | Me | H | |
| 2-29 | OMe | CHF$_2$ | Me | H | |
| 2-30 | OMe | CF$_2$Cl | Me | H | |
| 2-31 | OMe | OMe | Me | H | |
| 2-32 | OMe | NO$_2$ | Me | H | |
| 2-33 | OMe | SO$_2$Me | Me | H | |
| 2-34 | SO$_2$Me | Me | Me | H | |
| 2-35 | SO$_2$Me | F | Me | H | |
| 2-36 | SO$_2$Me | Cl | Me | H | |

TABLE 2-continued

Compounds according to the invention of the formula (I) in which Q is Q1 and $R^x$ is an ethyl group, R" and W are each hydrogen and t = 1

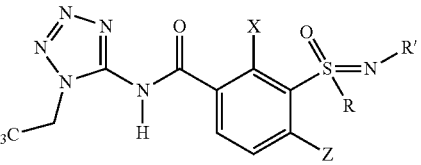

| No. | X | Z | R | R' | Physical Data ($^1$H NMR) |
|---|---|---|---|---|---|
| 2-37 | SO$_2$Me | Br | Me | H | |
| 2-38 | SO$_2$Me | I | Me | H | |
| 2-39 | SO$_2$Me | CF$_3$ | Me | H | |
| 2-40 | SO$_2$Me | CHF$_2$ | Me | H | |
| 2-41 | SO$_2$Me | CF$_2$Cl | Me | H | |
| 2-42 | SO$_2$Me | OMe | Me | H | |
| 2-43 | SO$_2$Me | NO$_2$ | Me | H | |
| 2-44 | SO$_2$Me | SO$_2$Me | Me | H | |
| 2-45 | Me | Me | Et | H | |
| 2-46 | Me | F | Et | H | |
| 2-47 | Me | Cl | Et | H | |
| 2-48 | Me | Br | Et | H | |
| 2-49 | Me | I | Et | H | |
| 2-50 | Me | CF$_3$ | Et | H | |
| 2-51 | Me | CHF$_2$ | Et | H | |
| 2-52 | Me | CF$_2$Cl | Et | H | |
| 2-53 | Me | OMe | Et | H | |
| 2-54 | Me | NO$_2$ | Et | H | |
| 2-55 | Me | SO$_2$Me | Et | H | |
| 2-56 | Cl | Me | Et | H | |
| 2-57 | Cl | F | Et | H | |
| 2-58 | Cl | Cl | Et | H | |
| 2-59 | Cl | Br | Et | H | |
| 2-60 | Cl | I | Et | H | |
| 2-61 | Cl | CF$_3$ | Et | H | |
| 2-62 | Cl | CHF$_2$ | Et | H | |
| 2-63 | Cl | CF$_2$Cl | Et | H | |
| 2-64 | Cl | OMe | Et | H | |
| 2-65 | Cl | NO$_2$ | Et | H | |
| 2-66 | Cl | SO$_2$Me | Et | H | |
| 2-67 | OMe | Me | Et | H | |
| 2-68 | OMe | F | Et | H | |
| 2-69 | OMe | Cl | Et | H | |
| 2-70 | OMe | Br | Et | H | |
| 2-71 | OMe | I | Et | H | |
| 2-72 | OMe | CF$_3$ | Et | H | |
| 2-73 | OMe | CHF$_2$ | Et | H | |
| 2-74 | OMe | CF$_2$Cl | Et | H | |
| 2-75 | OMe | OMe | Et | H | |
| 2-76 | OMe | NO$_2$ | Et | H | |
| 2-77 | OMe | SO$_2$Me | Et | H | |
| 2-78 | SO$_2$Me | Me | Et | H | |
| 2-79 | SO$_2$Me | F | Et | H | |
| 2-80 | SO$_2$Me | Cl | Et | H | |
| 2-81 | SO$_2$Me | Br | Et | H | |
| 2-82 | SO$_2$Me | I | Et | H | |
| 2-83 | SO$_2$Me | CF$_3$ | Et | H | |
| 2-84 | SO$_2$Me | CHF$_2$ | Et | H | |
| 2-85 | SO$_2$Me | CF$_2$Cl | Et | H | |
| 2-86 | SO$_2$Me | OMe | Et | H | |
| 2-87 | SO$_2$Me | NO$_2$ | Et | H | |
| 2-88 | SO$_2$Me | SO$_2$Me | Et | H | |
| 2-89 | Me | Me | CH$_2$CH$_2$OMe | H | |
| 2-90 | Me | F | CH$_2$CH$_2$OMe | H | |
| 2-91 | Me | Cl | CH$_2$CH$_2$OMe | H | |
| 2-92 | Me | Br | CH$_2$CH$_2$OMe | H | |
| 2-93 | Me | I | CH$_2$CH$_2$OMe | H | |
| 2-94 | Me | CF$_3$ | CH$_2$CH$_2$OMe | H | |
| 2-95 | Me | CHF$_2$ | CH$_2$CH$_2$OMe | H | |
| 2-96 | Me | CF$_2$Cl | CH$_2$CH$_2$OMe | H | |
| 2-97 | Me | OMe | CH$_2$CH$_2$OMe | H | |
| 2-98 | Me | NO$_2$ | CH$_2$CH$_2$OMe | H | |
| 2-99 | Me | SO$_2$Me | CH$_2$CH$_2$OMe | H | |
| 2-100 | Cl | Me | CH$_2$CH$_2$OMe | H | |
| 2-101 | Cl | F | CH$_2$CH$_2$OMe | H | |
| 2-102 | Cl | Cl | CH$_2$CH$_2$OMe | H | |

TABLE 2-continued

Compounds according to the invention of the formula (I) in which Q is Q1 and $R^x$ is an ethyl group, R" and W are each hydrogen and t = 1

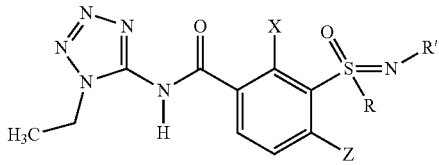

| No. | X | Z | R | R' | Physical Data ($^1$H NMR) |
|---|---|---|---|---|---|
| 2-103 | Cl | Br | CH$_2$CH$_2$OMe | H | |
| 2-104 | Cl | I | CH$_2$CH$_2$OMe | H | |
| 2-105 | Cl | CF$_3$ | CH$_2$CH$_2$OMe | H | |
| 2-106 | Cl | CHF$_2$ | CH$_2$CH$_2$OMe | H | |
| 2-107 | Cl | CF$_2$Cl | CH$_2$CH$_2$OMe | H | |
| 2-108 | Cl | OMe | CH$_2$CH$_2$OMe | H | |
| 2-109 | Cl | NO$_2$ | CH$_2$CH$_2$OMe | H | |
| 2-110 | Cl | SO$_2$Me | CH$_2$CH$_2$OMe | H | |
| 2-111 | OMe | Me | CH$_2$CH$_2$OMe | H | |
| 2-112 | OMe | F | CH$_2$CH$_2$OMe | H | |
| 2-113 | OMe | Cl | CH$_2$CH$_2$OMe | H | |
| 2-114 | OMe | Br | CH$_2$CH$_2$OMe | H | |
| 2-115 | OMe | I | CH$_2$CH$_2$OMe | H | |
| 2-116 | OMe | CF$_3$ | CH$_2$CH$_2$OMe | H | |
| 2-117 | OMe | CHF$_2$ | CH$_2$CH$_2$OMe | H | |
| 2-118 | OMe | CF$_2$Cl | CH$_2$CH$_2$OMe | H | |
| 2-119 | OMe | OMe | CH$_2$CH$_2$OMe | H | |
| 2-120 | OMe | NO$_2$ | CH$_2$CH$_2$OMe | H | |
| 2-121 | OMe | SO$_2$Me | CH$_2$CH$_2$OMe | H | |
| 2-122 | SO$_2$Me | Me | CH$_2$CH$_2$OMe | H | |
| 2-123 | SO$_2$Me | F | CH$_2$CH$_2$OMe | H | |
| 2-124 | SO$_2$Me | Cl | CH$_2$CH$_2$OMe | H | |
| 2-125 | SO$_2$Me | Br | CH$_2$CH$_2$OMe | H | |
| 2-126 | SO$_2$Me | I | CH$_2$CH$_2$OMe | H | |
| 2-127 | SO$_2$Me | CF$_3$ | CH$_2$CH$_2$OMe | H | |
| 2-128 | SO$_2$Me | CHF$_2$ | CH$_2$CH$_2$OMe | H | |
| 2-129 | SO$_2$Me | CF$_2$Cl | CH$_2$CH$_2$OMe | H | |
| 2-130 | SO$_2$Me | OMe | CH$_2$CH$_2$OMe | H | |
| 2-131 | SO$_2$Me | NO$_2$ | CH$_2$CH$_2$OMe | H | |
| 2-132 | SO$_2$Me | SO$_2$Me | CH$_2$CH$_2$OMe | H | |
| 2-133 | Me | Me | Me | CN | |
| 2-134 | Me | F | Me | CN | |
| 2-135 | Me | Cl | Me | CN | |
| 2-136 | Me | Br | Me | CN | |
| 2-137 | Me | I | Me | CN | |
| 2-138 | Me | CF$_3$ | Me | CN | |
| 2-139 | Me | CHF$_2$ | Me | CN | |
| 2-140 | Me | CF$_2$Cl | Me | CN | |
| 2-141 | Me | OMe | Me | CN | |
| 2-142 | Me | NO$_2$ | Me | CN | |
| 2-143 | Me | SO$_2$Me | Me | CN | |
| 2-144 | Cl | Me | Me | CN | |
| 2-145 | Cl | F | Me | CN | |
| 2-146 | Cl | Cl | Me | CN | |
| 2-147 | Cl | Br | Me | CN | |
| 2-148 | Cl | I | Me | CN | |
| 2-149 | Cl | CF$_3$ | Me | CN | |
| 2-150 | Cl | CHF$_2$ | Me | CN | |
| 2-151 | Cl | CF$_2$Cl | Me | CN | |
| 2-152 | Cl | OMe | Me | CN | |
| 2-153 | Cl | NO$_2$ | Me | CN | |
| 2-154 | Cl | SO$_2$Me | Me | CN | |
| 2-155 | OMe | Me | Me | CN | |
| 2-156 | OMe | F | Me | CN | |
| 2-157 | OMe | Cl | Me | CN | |
| 2-158 | OMe | Br | Me | CN | |
| 2-159 | OMe | I | Me | CN | |
| 2-160 | OMe | CF$_3$ | Me | CN | |
| 2-161 | OMe | CHF$_2$ | Me | CN | |
| 2-162 | OMe | CF$_2$Cl | Me | CN | |
| 2-163 | OMe | OMe | Me | CN | |
| 2-164 | OMe | NO$_2$ | Me | CN | |
| 2-165 | OMe | SO$_2$Me | Me | CN | |
| 2-166 | SO$_2$Me | Me | Me | CN | |
| 2-167 | SO$_2$Me | F | Me | CN | |
| 2-168 | SO$_2$Me | Cl | Me | CN | |

TABLE 2-continued

Compounds according to the invention of the formula (I) in which Q is Q1 and $R^x$ is an ethyl group, R" and W are each hydrogen and t = 1

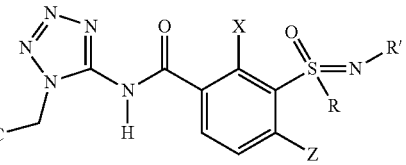

| No. | X | Z | R | R' | Physical Data ($^1$H NMR) |
|---|---|---|---|---|---|
| 2-169 | SO$_2$Me | Br | Me | CN | |
| 2-170 | SO$_2$Me | I | Me | CN | |
| 2-171 | SO$_2$Me | CF$_3$ | Me | CN | |
| 2-172 | SO$_2$Me | CHF$_2$ | Me | CN | |
| 2-173 | SO$_2$Me | CF$_2$Cl | Me | CN | |
| 2-174 | SO$_2$Me | OMe | Me | CN | |
| 2-175 | SO$_2$Me | NO$_2$ | Me | CN | |
| 2-176 | SO$_2$Me | SO$_2$Me | Me | CN | |
| 2-177 | Me | Me | Et | CN | |
| 2-178 | Me | F | Et | CN | |
| 2-179 | Me | Cl | Et | CN | |
| 2-180 | Me | Br | Et | CN | |
| 2-181 | Me | I | Et | CN | |
| 2-182 | Me | CF$_3$ | Et | CN | |
| 2-183 | Me | CHF$_2$ | Et | CN | |
| 2-184 | Me | CF$_2$Cl | Et | CN | |
| 2-185 | Me | OMe | Et | CN | |
| 2-186 | Me | NO$_2$ | Et | CN | |
| 2-187 | Me | SO$_2$Me | Et | CN | |
| 2-188 | Cl | Me | Et | CN | |
| 2-189 | Cl | F | Et | CN | |
| 2-190 | Cl | Cl | Et | CN | |
| 2-191 | Cl | Br | Et | CN | |
| 2-192 | Cl | I | Et | CN | |
| 2-193 | Cl | CF$_3$ | Et | CN | |
| 2-194 | Cl | CHF$_2$ | Et | CN | |
| 2-195 | Cl | CF$_2$Cl | Et | CN | |
| 2-196 | Cl | OMe | Et | CN | |
| 2-197 | Cl | NO$_2$ | Et | CN | |
| 2-198 | Cl | SO$_2$Me | Et | CN | |
| 2-199 | OMe | Me | Et | CN | |
| 2-200 | OMe | F | Et | CN | |
| 2-201 | OMe | Cl | Et | CN | |
| 2-202 | OMe | Br | Et | CN | |
| 2-203 | OMe | I | Et | CN | |
| 2-204 | OMe | CF$_3$ | Et | CN | |
| 2-205 | OMe | CHF$_2$ | Et | CN | |
| 2-206 | OMe | CF$_2$Cl | Et | CN | |
| 2-207 | OMe | OMe | Et | CN | |
| 2-208 | OMe | NO$_2$ | Et | CN | |
| 2-209 | OMe | SO$_2$Me | Et | CN | |
| 2-210 | SO$_2$Me | Me | Et | CN | |
| 2-211 | SO$_2$Me | F | Et | CN | |
| 2-212 | SO$_2$Me | Cl | Et | CN | |
| 2-213 | SO$_2$Me | Br | Et | CN | |
| 2-214 | SO$_2$Me | I | Et | CN | |
| 2-215 | SO$_2$Me | CF$_3$ | Et | CN | |
| 2-216 | SO$_2$Me | CHF$_2$ | Et | CN | |
| 2-217 | SO$_2$Me | CF$_2$Cl | Et | CN | |
| 2-218 | SO$_2$Me | OMe | Et | CN | |
| 2-219 | SO$_2$Me | NO$_2$ | Et | CN | |
| 2-220 | SO$_2$Me | SO$_2$Me | Et | CN | |
| 2-221 | Me | Me | CH$_2$CH$_2$OMe | CN | |
| 2-222 | Me | F | CH$_2$CH$_2$OMe | CN | |
| 2-223 | Me | Cl | CH$_2$CH$_2$OMe | CN | |
| 2-224 | Me | Br | CH$_2$CH$_2$OMe | CN | |
| 2-225 | Me | I | CH$_2$CH$_2$OMe | CN | |
| 2-226 | Me | CF$_3$ | CH$_2$CH$_2$OMe | CN | |
| 2-227 | Me | CHF$_2$ | CH$_2$CH$_2$OMe | CN | |
| 2-228 | Me | CF$_2$Cl | CH$_2$CH$_2$OMe | CN | |
| 2-229 | Me | OMe | CH$_2$CH$_2$OMe | CN | |
| 2-230 | Me | NO$_2$ | CH$_2$CH$_2$OMe | CN | |
| 2-231 | Me | SO$_2$Me | CH$_2$CH$_2$OMe | CN | |
| 2-232 | Cl | Me | CH$_2$CH$_2$OMe | CN | |
| 2-233 | Cl | F | CH$_2$CH$_2$OMe | CN | |
| 2-234 | Cl | Cl | CH$_2$CH$_2$OMe | CN | |

TABLE 2-continued

Compounds according to the invention of the formula (I) in which Q is Q1 and $R^x$ is an ethyl group, R'' and W are each hydrogen and t = 1

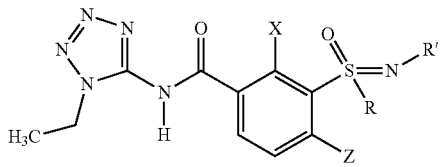

| No. | X | Z | R | R' | Physical Data ($^1$H NMR) |
|---|---|---|---|---|---|
| 2-235 | Cl | Br | CH$_2$CH$_2$OMe | CN | |
| 2-236 | Cl | I | CH$_2$CH$_2$OMe | CN | |
| 2-237 | Cl | CF$_3$ | CH$_2$CH$_2$OMe | CN | |
| 2-238 | Cl | CHF$_2$ | CH$_2$CH$_2$OMe | CN | |
| 2-239 | Cl | CF$_2$Cl | CH$_2$CH$_2$OMe | CN | |
| 2-240 | Cl | OMe | CH$_2$CH$_2$OMe | CN | |
| 2-241 | Cl | NO$_2$ | CH$_2$CH$_2$OMe | CN | |
| 2-242 | Cl | SO$_2$Me | CH$_2$CH$_2$OMe | CN | |
| 2-243 | OMe | Me | CH$_2$CH$_2$OMe | CN | |
| 2-244 | OMe | F | CH$_2$CH$_2$OMe | CN | |
| 2-245 | OMe | Cl | CH$_2$CH$_2$OMe | CN | |
| 2-246 | OMe | Br | CH$_2$CH$_2$OMe | CN | |
| 2-247 | OMe | I | CH$_2$CH$_2$OMe | CN | |
| 2-248 | OMe | CF$_3$ | CH$_2$CH$_2$OMe | CN | |
| 2-249 | OMe | CHF$_2$ | CH$_2$CH$_2$OMe | CN | |
| 2-250 | OMe | CF$_2$Cl | CH$_2$CH$_2$OMe | CN | |
| 2-251 | OMe | OMe | CH$_2$CH$_2$OMe | CN | |
| 2-252 | OMe | NO$_2$ | CH$_2$CH$_2$OMe | CN | |
| 2-253 | OMe | SO$_2$Me | CH$_2$CH$_2$OMe | CN | |
| 2-254 | SO$_2$Me | Me | CH$_2$CH$_2$OMe | CN | |
| 2-255 | SO$_2$Me | F | CH$_2$CH$_2$OMe | CN | |
| 2-256 | SO$_2$Me | Cl | CH$_2$CH$_2$OMe | CN | |
| 2-257 | SO$_2$Me | Br | CH$_2$CH$_2$OMe | CN | |
| 2-258 | SO$_2$Me | I | CH$_2$CH$_2$OMe | CN | |
| 2-259 | SO$_2$Me | CF$_3$ | CH$_2$CH$_2$OMe | CN | |
| 2-260 | SO$_2$Me | CHF$_2$ | CH$_2$CH$_2$OMe | CN | |
| 2-261 | SO$_2$Me | CF$_2$Cl | CH$_2$CH$_2$OMe | CN | |
| 2-262 | SO$_2$Me | OMe | CH$_2$CH$_2$OMe | CN | |
| 2-263 | SO$_2$Me | NO$_2$ | CH$_2$CH$_2$OMe | CN | |
| 2-264 | SO$_2$Me | SO$_2$Me | CH$_2$CH$_2$OMe | CN | |

TABLE 3

Compounds according to the invention of the formula (I) in which Q is Q1 and $R^x$ is an n-propyl group, R'' and W are each hydrogen and t = 1

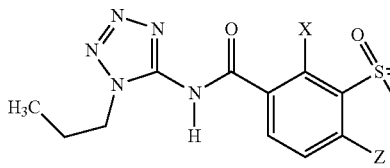

| No. | X | Z | R | R' | Physical Data ($^1$H NMR) |
|---|---|---|---|---|---|
| 3-1 | Me | Me | Me | H | |
| 3-2 | Me | F | Me | H | |
| 3-3 | Me | Cl | Me | H | |
| 3-4 | Me | Br | Me | H | |
| 3-5 | Me | I | Me | H | |
| 3-6 | Me | CF$_3$ | Me | H | |
| 3-7 | Me | CHF$_2$ | Me | H | |
| 3-8 | Me | CF$_2$Cl | Me | H | |
| 3-9 | Me | OMe | Me | H | |
| 3-10 | Me | NO$_2$ | Me | H | |
| 3-11 | Me | SO$_2$Me | Me | H | |
| 3-12 | Cl | Me | Me | H | |
| 3-13 | Cl | F | Me | H | |
| 3-14 | Cl | Cl | Me | H | |
| 3-15 | Cl | Br | Me | H | |
| 3-16 | Cl | I | Me | H | |
| 3-17 | Cl | CF$_3$ | Me | H | |

TABLE 3-continued

Compounds according to the invention of the formula (I) in which Q is Q1 and $R^x$ is an n-propyl group, R'' and W are each hydrogen and t = 1

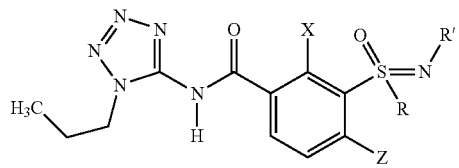

| No. | X | Z | R | R' | Physical Data ($^1$H NMR) |
|---|---|---|---|---|---|
| 3-18 | Cl | CHF$_2$ | Me | H | |
| 3-19 | Cl | CF$_2$Cl | Me | H | |
| 3-20 | Cl | OMe | Me | H | |
| 3-21 | Cl | NO$_2$ | Me | H | |
| 3-22 | Cl | SO$_2$Me | Me | H | |
| 3-23 | OMe | Me | Me | H | |
| 3-24 | OMe | F | Me | H | |
| 3-25 | OMe | Cl | Me | H | |
| 3-26 | OMe | Br | Me | H | |
| 3-27 | OMe | I | Me | H | |
| 3-28 | OMe | CF$_3$ | Me | H | |
| 3-29 | OMe | CHF$_2$ | Me | H | |
| 3-30 | OMe | CF$_2$Cl | Me | H | |
| 3-31 | OMe | OMe | Me | H | |
| 3-32 | OMe | NO$_2$ | Me | H | |
| 3-33 | OMe | SO$_2$Me | Me | H | |
| 3-34 | SO$_2$Me | Me | Me | H | |
| 3-35 | SO$_2$Me | F | Me | H | |
| 3-36 | SO$_2$Me | Cl | Me | H | |
| 3-37 | SO$_2$Me | Br | Me | H | |
| 3-38 | SO$_2$Me | I | Me | H | |
| 3-39 | SO$_2$Me | CF$_3$ | Me | H | |
| 3-40 | SO$_2$Me | CHF$_2$ | Me | H | |
| 3-41 | SO$_2$Me | CF$_2$Cl | Me | H | |
| 3-42 | SO$_2$Me | OMe | Me | H | |
| 3-43 | SO$_2$Me | NO$_2$ | Me | H | |
| 3-44 | SO$_2$Me | SO$_2$Me | Me | H | |
| 3-45 | Me | Me | Et | H | |
| 3-46 | Me | F | Et | H | |
| 3-47 | Me | Cl | Et | H | |
| 3-48 | Me | Br | Et | H | |
| 3-49 | Me | I | Et | H | |
| 3-50 | Me | CF$_3$ | Et | H | |
| 3-51 | Me | CHF$_2$ | Et | H | |
| 3-52 | Me | CF$_2$Cl | Et | H | |
| 3-53 | Me | OMe | Et | H | |
| 3-54 | Me | NO$_2$ | Et | H | |
| 3-55 | Me | SO$_2$Me | Et | H | |
| 3-56 | Cl | Me | Et | H | |
| 3-57 | Cl | F | Et | H | |
| 3-58 | Cl | Cl | Et | H | |
| 3-59 | Cl | Br | Et | H | |
| 3-60 | Cl | I | Et | H | |
| 3-61 | Cl | CF$_3$ | Et | H | |
| 3-62 | Cl | CHF$_2$ | Et | H | |
| 3-63 | Cl | CF$_2$Cl | Et | H | |
| 3-64 | Cl | OMe | Et | H | |
| 3-65 | Cl | NO$_2$ | Et | H | |
| 3-66 | Cl | SO$_2$Me | Et | H | |
| 3-67 | OMe | Me | Et | H | |
| 3-68 | OMe | F | Et | H | |
| 3-69 | OMe | Cl | Et | H | |
| 3-70 | OMe | Br | Et | H | |
| 3-71 | OMe | I | Et | H | |
| 3-72 | OMe | CF$_3$ | Et | H | |
| 3-73 | OMe | CHF$_2$ | Et | H | |
| 3-74 | OMe | CF$_2$Cl | Et | H | |
| 3-75 | OMe | OMe | Et | H | |
| 3-76 | OMe | NO$_2$ | Et | H | |
| 3-77 | OMe | SO$_2$Me | Et | H | |
| 3-78 | SO$_2$Me | Me | Et | H | |
| 3-79 | SO$_2$Me | F | Et | H | |
| 3-80 | SO$_2$Me | Cl | Et | H | |
| 3-81 | SO$_2$Me | Br | Et | H | |
| 3-82 | SO$_2$Me | I | Et | H | |
| 3-83 | SO$_2$Me | CF$_3$ | Et | H | |

TABLE 3-continued

Compounds according to the invention of the formula (I) in which Q is Q1 and R$^x$ is an n-propyl group, R″ and W are each hydrogen and t = 1

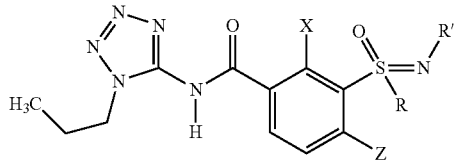

| No. | X | Z | R | R′ | Physical Data ($^1$H NMR) |
|---|---|---|---|---|---|
| 3-84 | SO$_2$Me | CHF$_2$ | Et | H | |
| 3-85 | SO$_2$Me | CF$_2$Cl | Et | H | |
| 3-86 | SO$_2$Me | OMe | Et | H | |
| 3-87 | SO$_2$Me | NO$_2$ | Et | H | |
| 3-88 | SO$_2$Me | SO$_2$Me | Et | H | |
| 3-89 | Me | Me | CH$_2$CH$_2$OMe | H | |
| 3-90 | Me | F | CH$_2$CH$_2$OMe | H | |
| 3-91 | Me | Cl | CH$_2$CH$_2$OMe | H | |
| 3-92 | Me | Br | CH$_2$CH$_2$OMe | H | |
| 3-93 | Me | I | CH$_2$CH$_2$OMe | H | |
| 3-94 | Me | CF$_3$ | CH$_2$CH$_2$OMe | H | |
| 3-95 | Me | CHF$_2$ | CH$_2$CH$_2$OMe | H | |
| 3-96 | Me | CF$_2$Cl | CH$_2$CH$_2$OMe | H | |
| 3-97 | Me | OMe | CH$_2$CH$_2$OMe | H | |
| 3-98 | Me | NO$_2$ | CH$_2$CH$_2$OMe | H | |
| 3-99 | Me | SO$_2$Me | CH$_2$CH$_2$OMe | H | |
| 3-100 | Cl | Me | CH$_2$CH$_2$OMe | H | |
| 3-101 | Cl | F | CH$_2$CH$_2$OMe | H | |
| 3-102 | Cl | Cl | CH$_2$CH$_2$OMe | H | |
| 3-103 | Cl | Br | CH$_2$CH$_2$OMe | H | |
| 3-104 | Cl | I | CH$_2$CH$_2$OMe | H | |
| 3-105 | Cl | CF$_3$ | CH$_2$CH$_2$OMe | H | |
| 3-106 | Cl | CHF$_2$ | CH$_2$CH$_2$OMe | H | |
| 3-107 | Cl | CF$_2$Cl | CH$_2$CH$_2$OMe | H | |
| 3-108 | Cl | OMe | CH$_2$CH$_2$OMe | H | |
| 3-109 | Cl | NO$_2$ | CH$_2$CH$_2$OMe | H | |
| 3-110 | Cl | SO$_2$Me | CH$_2$CH$_2$OMe | H | |
| 3-111 | OMe | Me | CH$_2$CH$_2$OMe | H | |
| 3-112 | OMe | F | CH$_2$CH$_2$OMe | H | |
| 3-113 | OMe | Cl | CH$_2$CH$_2$OMe | H | |
| 3-114 | OMe | Br | CH$_2$CH$_2$OMe | H | |
| 3-115 | OMe | I | CH$_2$CH$_2$OMe | H | |
| 3-116 | OMe | CF$_3$ | CH$_2$CH$_2$OMe | H | |
| 3-117 | OMe | CHF$_2$ | CH$_2$CH$_2$OMe | H | |
| 3-118 | OMe | CF$_2$Cl | CH$_2$CH$_2$OMe | H | |
| 3-119 | OMe | OMe | CH$_2$CH$_2$OMe | H | |
| 3-120 | OMe | NO$_2$ | CH$_2$CH$_2$OMe | H | |
| 3-121 | OMe | SO$_2$Me | CH$_2$CH$_2$OMe | H | |
| 3-122 | SO$_2$Me | Me | CH$_2$CH$_2$OMe | H | |
| 3-123 | SO$_2$Me | F | CH$_2$CH$_2$OMe | H | |
| 3-124 | SO$_2$Me | Cl | CH$_2$CH$_2$OMe | H | |
| 3-125 | SO$_2$Me | Br | CH$_2$CH$_2$OMe | H | |
| 3-126 | SO$_2$Me | I | CH$_2$CH$_2$OMe | H | |
| 3-127 | SO$_2$Me | CF$_3$ | CH$_2$CH$_2$OMe | H | |
| 3-128 | SO$_2$Me | CHF$_2$ | CH$_2$CH$_2$OMe | H | |
| 3-129 | SO$_2$Me | CF$_2$Cl | CH$_2$CH$_2$OMe | H | |
| 3-130 | SO$_2$Me | OMe | CH$_2$CH$_2$OMe | H | |
| 3-131 | SO$_2$Me | NO$_2$ | CH$_2$CH$_2$OMe | H | |
| 3-132 | SO$_2$Me | SO$_2$Me | CH$_2$CH$_2$OMe | H | |
| 3-133 | Me | Me | Me | CN | |
| 3-134 | Me | F | Me | CN | |
| 3-135 | Me | Cl | Me | CN | |
| 3-136 | Me | Br | Me | CN | |
| 3-137 | Me | I | Me | CN | |
| 3-138 | Me | CF$_3$ | Me | CN | |
| 3-139 | Me | CHF$_2$ | Me | CN | |
| 3-140 | Me | CF$_2$Cl | Me | CN | |
| 3-141 | Me | OMe | Me | CN | |
| 3-142 | Me | NO$_2$ | Me | CN | |
| 3-143 | Me | SO$_2$Me | Me | CN | |
| 3-144 | Cl | Me | Me | CN | |
| 3-145 | Cl | F | Me | CN | |
| 3-146 | Cl | Cl | Me | CN | |
| 3-147 | Cl | Br | Me | CN | |
| 3-148 | Cl | I | Me | CN | |
| 3-149 | Cl | CF$_3$ | Me | CN | |

TABLE 3-continued

Compounds according to the invention of the formula (I) in which Q is Q1 and R$^x$ is an n-propyl group, R″ and W are each hydrogen and t = 1

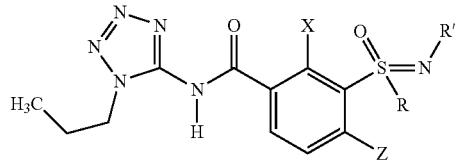

| No. | X | Z | R | R′ | Physical Data ($^1$H NMR) |
|---|---|---|---|---|---|
| 3-150 | Cl | CHF$_2$ | Me | CN | |
| 3-151 | Cl | CF$_2$Cl | Me | CN | |
| 3-152 | Cl | OMe | Me | CN | |
| 3-153 | Cl | NO$_2$ | Me | CN | |
| 3-154 | Cl | SO$_2$Me | Me | CN | |
| 3-155 | OMe | Me | Me | CN | |
| 3-156 | OMe | F | Me | CN | |
| 3-157 | OMe | Cl | Me | CN | |
| 3-158 | OMe | Br | Me | CN | |
| 3-159 | OMe | I | Me | CN | |
| 3-160 | OMe | CF$_3$ | Me | CN | |
| 3-161 | OMe | CHF$_2$ | Me | CN | |
| 3-162 | OMe | CF$_2$Cl | Me | CN | |
| 3-163 | OMe | OMe | Me | CN | |
| 3-164 | OMe | NO$_2$ | Me | CN | |
| 3-165 | OMe | SO$_2$Me | Me | CN | |
| 3-166 | SO$_2$Me | Me | Me | CN | |
| 3-167 | SO$_2$Me | F | Me | CN | |
| 3-168 | SO$_2$Me | Cl | Me | CN | |
| 3-169 | SO$_2$Me | Br | Me | CN | |
| 3-170 | SO$_2$Me | I | Me | CN | |
| 3-171 | SO$_2$Me | CF$_3$ | Me | CN | |
| 3-172 | SO$_2$Me | CHF$_2$ | Me | CN | |
| 3-173 | SO$_2$Me | CF$_2$Cl | Me | CN | |
| 3-174 | SO$_2$Me | OMe | Me | CN | |
| 3-175 | SO$_2$Me | NO$_2$ | Me | CN | |
| 3-176 | SO$_2$Me | SO$_2$Me | Me | CN | |
| 3-177 | Me | Me | Et | CN | |
| 3-178 | Me | F | Et | CN | |
| 3-179 | Me | Cl | Et | CN | |
| 3-180 | Me | Br | Et | CN | |
| 3-181 | Me | I | Et | CN | |
| 3-182 | Me | CF$_3$ | Et | CN | |
| 3-183 | Me | CHF$_2$ | Et | CN | |
| 3-184 | Me | CF$_2$Cl | Et | CN | |
| 3-185 | Me | OMe | Et | CN | |
| 3-186 | Me | NO$_2$ | Et | CN | |
| 3-187 | Me | SO$_2$Me | Et | CN | |
| 3-188 | Cl | Me | Et | CN | |
| 3-189 | Cl | F | Et | CN | |
| 3-190 | Cl | Cl | Et | CN | |
| 3-191 | Cl | Br | Et | CN | |
| 3-192 | Cl | I | Et | CN | |
| 3-193 | Cl | CF$_3$ | Et | CN | |
| 3-194 | Cl | CHF$_2$ | Et | CN | |
| 3-195 | Cl | CF$_2$Cl | Et | CN | |
| 3-196 | Cl | OMe | Et | CN | |
| 3-197 | Cl | NO$_2$ | Et | CN | |
| 3-198 | Cl | SO$_2$Me | Et | CN | |
| 3-199 | OMe | Me | Et | CN | |
| 3-200 | OMe | F | Et | CN | |
| 3-201 | OMe | Cl | Et | CN | |
| 3-202 | OMe | Br | Et | CN | |
| 3-203 | OMe | I | Et | CN | |
| 3-204 | OMe | CF$_3$ | Et | CN | |
| 3-205 | OMe | CHF$_2$ | Et | CN | |
| 3-206 | OMe | CF$_2$Cl | Et | CN | |
| 3-207 | OMe | OMe | Et | CN | |
| 3-208 | OMe | NO$_2$ | Et | CN | |
| 3-209 | OMe | SO$_2$Me | Et | CN | |
| 3-210 | SO$_2$Me | Me | Et | CN | |
| 3-211 | SO$_2$Me | F | Et | CN | |
| 3-212 | SO$_2$Me | Cl | Et | CN | |
| 3-213 | SO$_2$Me | Br | Et | CN | |
| 3-214 | SO$_2$Me | I | Et | CN | |
| 3-215 | SO$_2$Me | CF$_3$ | Et | CN | |

TABLE 3-continued

Compounds according to the invention of the formula (I) in which Q is Q1 and $R^x$ is an n-propyl group, R" and W are each hydrogen and t = 1

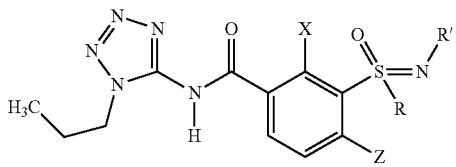

| No. | X | Z | R | R' | Physical Data ($^1$H NMR) |
|---|---|---|---|---|---|
| 3-216 | SO$_2$Me | CHF$_2$ | Et | CN | |
| 3-217 | SO$_2$Me | CF$_2$Cl | Et | CN | |
| 3-218 | SO$_2$Me | OMe | Et | CN | |
| 3-219 | SO$_2$Me | NO$_2$ | Et | CN | |
| 3-220 | SO$_2$Me | SO$_2$Me | Et | CN | |
| 3-221 | Me | Me | CH$_2$CH$_2$OMe | CN | |
| 3-222 | Me | F | CH$_2$CH$_2$OMe | CN | |
| 3-223 | Me | Cl | CH$_2$CH$_2$OMe | CN | |
| 3-224 | Me | Br | CH$_2$CH$_2$OMe | CN | |
| 3-225 | Me | I | CH$_2$CH$_2$OMe | CN | |
| 3-226 | Me | CF$_3$ | CH$_2$CH$_2$OMe | CN | |
| 3-227 | Me | CHF$_2$ | CH$_2$CH$_2$OMe | CN | |
| 3-228 | Me | CF$_2$Cl | CH$_2$CH$_2$OMe | CN | |
| 3-229 | Me | OMe | CH$_2$CH$_2$OMe | CN | |
| 3-230 | Me | NO$_2$ | CH$_2$CH$_2$OMe | CN | |
| 3-231 | Me | SO$_2$Me | CH$_2$CH$_2$OMe | CN | |
| 3-232 | Cl | Me | CH$_2$CH$_2$OMe | CN | |
| 3-233 | Cl | F | CH$_2$CH$_2$OMe | CN | |
| 3-234 | Cl | Cl | CH$_2$CH$_2$OMe | CN | |
| 3-235 | Cl | Br | CH$_2$CH$_2$OMe | CN | |
| 3-236 | Cl | I | CH$_2$CH$_2$OMe | CN | |
| 3-237 | Cl | CF$_3$ | CH$_2$CH$_2$OMe | CN | |
| 3-238 | Cl | CHF$_2$ | CH$_2$CH$_2$OMe | CN | |
| 3-239 | Cl | CF$_2$Cl | CH$_2$CH$_2$OMe | CN | |
| 3-240 | Cl | OMe | CH$_2$CH$_2$OMe | CN | |
| 3-241 | Cl | NO$_2$ | CH$_2$CH$_2$OMe | CN | |
| 3-242 | Cl | SO$_2$Me | CH$_2$CH$_2$OMe | CN | |
| 3-243 | OMe | Me | CH$_2$CH$_2$OMe | CN | |
| 3-244 | OMe | F | CH$_2$CH$_2$OMe | CN | |
| 3-245 | OMe | Cl | CH$_2$CH$_2$OMe | CN | |
| 3-246 | OMe | Br | CH$_2$CH$_2$OMe | CN | |
| 3-247 | OMe | I | CH$_2$CH$_2$OMe | CN | |
| 3-248 | OMe | CF$_3$ | CH$_2$CH$_2$OMe | CN | |
| 3-249 | OMe | CHF$_2$ | CH$_2$CH$_2$OMe | CN | |
| 3-250 | OMe | CF$_2$Cl | CH$_2$CH$_2$OMe | CN | |
| 3-251 | OMe | OMe | CH$_2$CH$_2$OMe | CN | |
| 3-252 | OMe | NO$_2$ | CH$_2$CH$_2$OMe | CN | |
| 3-253 | OMe | SO$_2$Me | CH$_2$CH$_2$OMe | CN | |
| 3-254 | SO$_2$Me | Me | CH$_2$CH$_2$OMe | CN | |
| 3-255 | SO$_2$Me | F | CH$_2$CH$_2$OMe | CN | |
| 3-256 | SO$_2$Me | Cl | CH$_2$CH$_2$OMe | CN | |
| 3-257 | SO$_2$Me | Br | CH$_2$CH$_2$OMe | CN | |
| 3-258 | SO$_2$Me | I | CH$_2$CH$_2$OMe | CN | |
| 3-259 | SO$_2$Me | CF$_3$ | CH$_2$CH$_2$OMe | CN | |
| 3-260 | SO$_2$Me | CHF$_2$ | CH$_2$CH$_2$OMe | CN | |
| 3-261 | SO$_2$Me | CF$_2$Cl | CH$_2$CH$_2$OMe | CN | |
| 3-262 | SO$_2$Me | OMe | CH$_2$CH$_2$OMe | CN | |
| 3-263 | SO$_2$Me | NO$_2$ | CH$_2$CH$_2$OMe | CN | |
| 3-264 | SO$_2$Me | SO$_2$Me | CH$_2$CH$_2$OMe | CN | |

TABLE 4

Compounds according to the invention of the formula (I) in which Q is Q1 and $R^x$ is a (2-methoxyethyl) group, R" and W are each hydrogen and t = 1

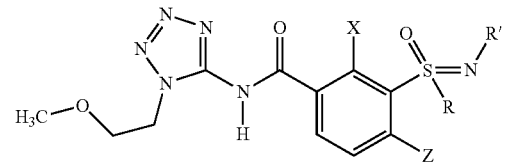

| No. | X | Z | R | R' | Physical Data ($^1$H NMR) |
|---|---|---|---|---|---|
| 4-1 | Me | Me | Me | H | |
| 4-2 | Me | F | Me | H | |
| 4-3 | Me | Cl | Me | H | |
| 4-4 | Me | Br | Me | H | |
| 4-5 | Me | I | Me | H | |
| 4-6 | Me | CF$_3$ | Me | H | |
| 4-7 | Me | CHF$_2$ | Me | H | |
| 4-8 | Me | CF$_2$Cl | Me | H | |
| 4-9 | Me | OMe | Me | H | |
| 4-10 | Me | NO$_2$ | Me | H | |
| 4-11 | Me | SO$_2$Me | Me | H | |
| 4-12 | Cl | Me | Me | H | |
| 4-13 | Cl | F | Me | H | |
| 4-14 | Cl | Cl | Me | H | |
| 4-15 | Cl | Br | Me | H | |
| 4-16 | Cl | I | Me | H | |
| 4-17 | Cl | CF$_3$ | Me | H | |
| 4-18 | Cl | CHF$_2$ | Me | H | |
| 4-19 | Cl | CF$_2$Cl | Me | H | |
| 4-20 | Cl | OMe | Me | H | |
| 4-21 | Cl | NO$_2$ | Me | H | |
| 4-22 | Cl | SO$_2$Me | Me | H | |
| 4-23 | OMe | Me | Me | H | |
| 4-24 | OMe | F | Me | H | |
| 4-25 | OMe | Cl | Me | H | |
| 4-26 | OMe | Br | Me | H | |
| 4-27 | OMe | I | Me | H | |
| 4-28 | OMe | CF$_3$ | Me | H | |
| 4-29 | OMe | CHF$_2$ | Me | H | |
| 4-30 | OMe | CF$_2$Cl | Me | H | |
| 4-31 | OMe | OMe | Me | H | |
| 4-32 | OMe | NO$_2$ | Me | H | |
| 4-33 | OMe | SO$_2$Me | Me | H | |
| 4-34 | SO$_2$Me | Me | Me | H | |
| 4-35 | SO$_2$Me | F | Me | H | |
| 4-36 | SO$_2$Me | Cl | Me | H | |
| 4-37 | SO$_2$Me | Br | Me | H | |
| 4-38 | SO$_2$Me | I | Me | H | |
| 4-39 | SO$_2$Me | CF$_3$ | Me | H | |
| 4-40 | SO$_2$Me | CHF$_2$ | Me | H | |
| 4-41 | SO$_2$Me | CF$_2$Cl | Me | H | |
| 4-42 | SO$_2$Me | OMe | Me | H | |
| 4-43 | SO$_2$Me | NO$_2$ | Me | H | |
| 4-44 | SO$_2$Me | SO$_2$Me | Me | H | |
| 4-45 | Me | Me | Et | H | |
| 4-46 | Me | F | Et | H | |
| 4-47 | Me | Cl | Et | H | |
| 4-48 | Me | Br | Et | H | |
| 4-49 | Me | I | Et | H | |
| 4-50 | Me | CF$_3$ | Et | H | |
| 4-51 | Me | CHF$_2$ | Et | H | |
| 4-52 | Me | CF$_2$Cl | Et | H | |
| 4-53 | Me | OMe | Et | H | |
| 4-54 | Me | NO$_2$ | Et | H | |
| 4-55 | Me | SO$_2$Me | Et | H | |
| 4-56 | Cl | Me | Et | H | |
| 4-57 | Cl | F | Et | H | |
| 4-58 | Cl | Cl | Et | H | |
| 4-59 | Cl | Br | Et | H | |
| 4-60 | Cl | I | Et | H | |
| 4-61 | Cl | CF$_3$ | Et | H | |
| 4-62 | Cl | CHF$_2$ | Et | H | |
| 4-63 | Cl | CF$_2$Cl | Et | H | |
| 4-64 | Cl | OMe | Et | H | |
| 4-65 | Cl | NO$_2$ | Et | H | |
| 4-66 | Cl | SO$_2$Me | Et | H | |

TABLE 4-continued

Compounds according to the invention of the formula (I) in which Q is Q1 and R$^x$ is a (2-methoxyethyl) group, R″ and W are each hydrogen and t = 1

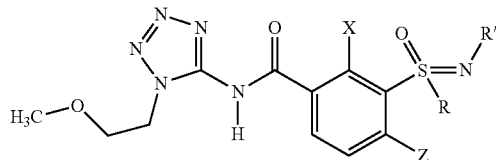

| No. | X | Z | R | R′ | Physical Data ($^1$H NMR) |
|---|---|---|---|---|---|
| 4-67 | OMe | Me | Et | H | |
| 4-68 | OMe | F | Et | H | |
| 4-69 | OMe | Cl | Et | H | |
| 4-70 | OMe | Br | Et | H | |
| 4-71 | OMe | I | Et | H | |
| 4-72 | OMe | CF$_3$ | Et | H | |
| 4-73 | OMe | CHF$_2$ | Et | H | |
| 4-74 | OMe | CF$_2$Cl | Et | H | |
| 4-75 | OMe | OMe | Et | H | |
| 4-76 | OMe | NO$_2$ | Et | H | |
| 4-77 | OMe | SO$_2$Me | Et | H | |
| 4-78 | SO$_2$Me | Me | Et | H | |
| 4-79 | SO$_2$Me | F | Et | H | |
| 4-80 | SO$_2$Me | Cl | Et | H | |
| 4-81 | SO$_2$Me | Br | Et | H | |
| 4-82 | SO$_2$Me | I | Et | H | |
| 4-83 | SO$_2$Me | CF$_3$ | Et | H | |
| 4-84 | SO$_2$Me | CHF$_2$ | Et | H | |
| 4-85 | SO$_2$Me | CF$_2$Cl | Et | H | |
| 4-86 | SO$_2$Me | OMe | Et | H | |
| 4-87 | SO$_2$Me | NO$_2$ | Et | H | |
| 4-88 | SO$_2$Me | SO$_2$Me | Et | H | |
| 4-89 | Me | Me | CH$_2$CH$_2$OMe | H | |
| 4-90 | Me | F | CH$_2$CH$_2$OMe | H | |
| 4-91 | Me | Cl | CH$_2$CH$_2$OMe | H | |
| 4-92 | Me | Br | CH$_2$CH$_2$OMe | H | |
| 4-93 | Me | I | CH$_2$CH$_2$OMe | H | |
| 4-94 | Me | CF$_3$ | CH$_2$CH$_2$OMe | H | |
| 4-95 | Me | CHF$_2$ | CH$_2$CH$_2$OMe | H | |
| 4-96 | Me | CF$_2$Cl | CH$_2$CH$_2$OMe | H | |
| 4-97 | Me | OMe | CH$_2$CH$_2$OMe | H | |
| 4-98 | Me | NO$_2$ | CH$_2$CH$_2$OMe | H | |
| 4-99 | Me | SO$_2$Me | CH$_2$CH$_2$OMe | H | |
| 4-100 | Cl | Me | CH$_2$CH$_2$OMe | H | |
| 4-101 | Cl | F | CH$_2$CH$_2$OMe | H | |
| 4-102 | Cl | Cl | CH$_2$CH$_2$OMe | H | |
| 4-103 | Cl | Br | CH$_2$CH$_2$OMe | H | |
| 4-104 | Cl | I | CH$_2$CH$_2$OMe | H | |
| 4-105 | Cl | CF$_3$ | CH$_2$CH$_2$OMe | H | |
| 4-106 | Cl | CHF$_2$ | CH$_2$CH$_2$OMe | H | |
| 4-107 | Cl | CF$_2$Cl | CH$_2$CH$_2$OMe | H | |
| 4-108 | Cl | OMe | CH$_2$CH$_2$OMe | H | |
| 4-109 | Cl | NO$_2$ | CH$_2$CH$_2$OMe | H | |
| 4-110 | Cl | SO$_2$Me | CH$_2$CH$_2$OMe | H | |
| 4-111 | OMe | Me | CH$_2$CH$_2$OMe | H | |
| 4-112 | OMe | F | CH$_2$CH$_2$OMe | H | |
| 4-113 | OMe | Cl | CH$_2$CH$_2$OMe | H | |
| 4-114 | OMe | Br | CH$_2$CH$_2$OMe | H | |
| 4-115 | OMe | I | CH$_2$CH$_2$OMe | H | |
| 4-116 | OMe | CF$_3$ | CH$_2$CH$_2$OMe | H | |
| 4-117 | OMe | CHF$_2$ | CH$_2$CH$_2$OMe | H | |
| 4-118 | OMe | CF$_2$Cl | CH$_2$CH$_2$OMe | H | |
| 4-119 | OMe | OMe | CH$_2$CH$_2$OMe | H | |
| 4-120 | OMe | NO$_2$ | CH$_2$CH$_2$OMe | H | |
| 4-121 | OMe | SO$_2$Me | CH$_2$CH$_2$OMe | H | |
| 4-122 | SO$_2$Me | Me | CH$_2$CH$_2$OMe | H | |
| 4-123 | SO$_2$Me | F | CH$_2$CH$_2$OMe | H | |
| 4-124 | SO$_2$Me | Cl | CH$_2$CH$_2$OMe | H | |
| 4-125 | SO$_2$Me | Br | CH$_2$CH$_2$OMe | H | |
| 4-126 | SO$_2$Me | I | CH$_2$CH$_2$OMe | H | |
| 4-127 | SO$_2$Me | CF$_3$ | CH$_2$CH$_2$OMe | H | |
| 4-128 | SO$_2$Me | CHF$_2$ | CH$_2$CH$_2$OMe | H | |
| 4-129 | SO$_2$Me | CF$_2$Cl | CH$_2$CH$_2$OMe | H | |
| 4-130 | SO$_2$Me | OMe | CH$_2$CH$_2$OMe | H | |
| 4-131 | SO$_2$Me | NO$_2$ | CH$_2$CH$_2$OMe | H | |
| 4-132 | SO$_2$Me | SO$_2$Me | CH$_2$CH$_2$OMe | H | |

TABLE 4-continued

Compounds according to the invention of the formula (I) in which Q is Q1 and R$^x$ is a (2-methoxyethyl) group, R″ and W are each hydrogen and t = 1

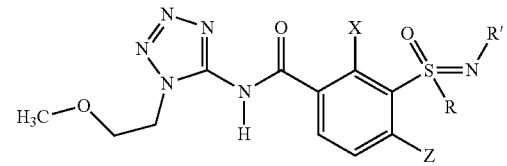

| No. | X | Z | R | R′ | Physical Data ($^1$H NMR) |
|---|---|---|---|---|---|
| 4-133 | Me | Me | Me | CN | |
| 4-134 | Me | F | Me | CN | |
| 4-135 | Me | Cl | Me | CN | |
| 4-136 | Me | Br | Me | CN | |
| 4-137 | Me | I | Me | CN | |
| 4-138 | Me | CF$_3$ | Me | CN | |
| 4-139 | Me | CHF$_2$ | Me | CN | |
| 4-140 | Me | CF$_2$Cl | Me | CN | |
| 4-141 | Me | OMe | Me | CN | |
| 4-142 | Me | NO$_2$ | Me | CN | |
| 4-143 | Me | SO$_2$Me | Me | CN | |
| 4-144 | Cl | Me | Me | CN | |
| 4-145 | Cl | F | Me | CN | |
| 4-146 | Cl | Cl | Me | CN | |
| 4-147 | Cl | Br | Me | CN | |
| 4-148 | Cl | I | Me | CN | |
| 4-149 | Cl | CF$_3$ | Me | CN | |
| 4-150 | Cl | CHF$_2$ | Me | CN | |
| 4-151 | Cl | CF$_2$Cl | Me | CN | |
| 4-152 | Cl | OMe | Me | CN | |
| 4-153 | Cl | NO$_2$ | Me | CN | |
| 4-154 | Cl | SO$_2$Me | Me | CN | |
| 4-155 | OMe | Me | Me | CN | |
| 4-156 | OMe | F | Me | CN | |
| 4-157 | OMe | Cl | Me | CN | |
| 4-158 | OMe | Br | Me | CN | |
| 4-159 | OMe | I | Me | CN | |
| 4-160 | OMe | CF$_3$ | Me | CN | |
| 4-161 | OMe | CHF$_2$ | Me | CN | |
| 4-162 | OMe | CF$_2$Cl | Me | CN | |
| 4-163 | OMe | OMe | Me | CN | |
| 4-164 | OMe | NO$_2$ | Me | CN | |
| 4-165 | OMe | SO$_2$Me | Me | CN | |
| 4-166 | SO$_2$Me | Me | Me | CN | |
| 4-167 | SO$_2$Me | F | Me | CN | |
| 4-168 | SO$_2$Me | Cl | Me | CN | |
| 4-169 | SO$_2$Me | Br | Me | CN | |
| 4-170 | SO$_2$Me | I | Me | CN | |
| 4-171 | SO$_2$Me | CF$_3$ | Me | CN | |
| 4-172 | SO$_2$Me | CHF$_2$ | Me | CN | |
| 4-173 | SO$_2$Me | CF$_2$Cl | Me | CN | |
| 4-174 | SO$_2$Me | OMe | Me | CN | |
| 4-175 | SO$_2$Me | NO$_2$ | Me | CN | |
| 4-176 | SO$_2$Me | SO$_2$Me | Me | CN | |
| 4-177 | Me | Me | Et | CN | |
| 4-178 | Me | F | Et | CN | |
| 4-179 | Me | Cl | Et | CN | |
| 4-180 | Me | Br | Et | CN | |
| 4-181 | Me | I | Et | CN | |
| 4-182 | Me | CF$_3$ | Et | CN | |
| 4-183 | Me | CHF$_2$ | Et | CN | |
| 4-184 | Me | CF$_2$Cl | Et | CN | |
| 4-185 | Me | OMe | Et | CN | |
| 4-186 | Me | NO$_2$ | Et | CN | |
| 4-187 | Me | SO$_2$Me | Et | CN | |
| 4-188 | Cl | Me | Et | CN | |
| 4-189 | Cl | F | Et | CN | |
| 4-190 | Cl | Cl | Et | CN | |
| 4-191 | Cl | Br | Et | CN | |
| 4-192 | Cl | I | Et | CN | |
| 4-193 | Cl | CF$_3$ | Et | CN | |
| 4-194 | Cl | CHF$_2$ | Et | CN | |
| 4-195 | Cl | CF$_2$Cl | Et | CN | |
| 4-196 | Cl | OMe | Et | CN | |
| 4-197 | Cl | NO$_2$ | Et | CN | |
| 4-198 | Cl | SO$_2$Me | Et | CN | |

TABLE 4-continued

Compounds according to the invention of the formula (I) in which Q is Q1 and R$^x$ is a (2-methoxyethyl) group, R'' and W are each hydrogen and t = 1

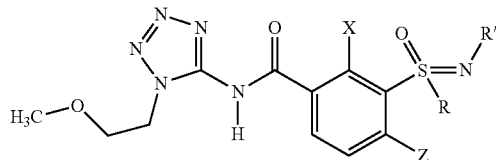

| No. | X | Z | R | R' | Physical Data ($^1$H NMR) |
|---|---|---|---|---|---|
| 4-199 | OMe | Me | Et | CN | |
| 4-200 | OMe | F | Et | CN | |
| 4-201 | OMe | Cl | Et | CN | |
| 4-202 | OMe | Br | Et | CN | |
| 4-203 | OMe | I | Et | CN | |
| 4-204 | OMe | CF$_3$ | Et | CN | |
| 4-205 | OMe | CHF$_2$ | Et | CN | |
| 4-206 | OMe | CF$_2$Cl | Et | CN | |
| 4-207 | OMe | OMe | Et | CN | |
| 4-208 | OMe | NO$_2$ | Et | CN | |
| 4-209 | OMe | SO$_2$Me | Et | CN | |
| 4-210 | SO$_2$Me | Me | Et | CN | |
| 4-211 | SO$_2$Me | F | Et | CN | |
| 4-212 | SO$_2$Me | Cl | Et | CN | |
| 4-213 | SO$_2$Me | Br | Et | CN | |
| 4-214 | SO$_2$Me | I | Et | CN | |
| 4-215 | SO$_2$Me | CF$_3$ | Et | CN | |
| 4-216 | SO$_2$Me | CHF$_2$ | Et | CN | |
| 4-217 | SO$_2$Me | CF$_2$Cl | Et | CN | |
| 4-218 | SO$_2$Me | OMe | Et | CN | |
| 4-219 | SO$_2$Me | NO$_2$ | Et | CN | |
| 4-220 | SO$_2$Me | SO$_2$Me | Et | CN | |
| 4-221 | Me | Me | CH$_2$CH$_2$OMe | CN | |
| 4-222 | Me | F | CH$_2$CH$_2$OMe | CN | |
| 4-223 | Me | Cl | CH$_2$CH$_2$OMe | CN | |
| 4-224 | Me | Br | CH$_2$CH$_2$OMe | CN | |
| 4-225 | Me | I | CH$_2$CH$_2$OMe | CN | |
| 4-226 | Me | CF$_3$ | CH$_2$CH$_2$OMe | CN | |
| 4-227 | Me | CHF$_2$ | CH$_2$CH$_2$OMe | CN | |
| 4-228 | Me | CF$_2$Cl | CH$_2$CH$_2$OMe | CN | |
| 4-229 | Me | OMe | CH$_2$CH$_2$OMe | CN | |
| 4-230 | Me | NO$_2$ | CH$_2$CH$_2$OMe | CN | |
| 4-231 | Me | SO$_2$Me | CH$_2$CH$_2$OMe | CN | |
| 4-232 | Cl | Me | CH$_2$CH$_2$OMe | CN | |
| 4-233 | Cl | F | CH$_2$CH$_2$OMe | CN | |
| 4-234 | Cl | Cl | CH$_2$CH$_2$OMe | CN | |
| 4-235 | Cl | Br | CH$_2$CH$_2$OMe | CN | |
| 4-236 | Cl | I | CH$_2$CH$_2$OMe | CN | |
| 4-237 | Cl | CF$_3$ | CH$_2$CH$_2$OMe | CN | |
| 4-238 | Cl | CHF$_2$ | CH$_2$CH$_2$OMe | CN | |
| 4-239 | Cl | CF$_2$Cl | CH$_2$CH$_2$OMe | CN | |
| 4-240 | Cl | OMe | CH$_2$CH$_2$OMe | CN | |
| 4-241 | Cl | NO$_2$ | CH$_2$CH$_2$OMe | CN | |
| 4-242 | Cl | SO$_2$Me | CH$_2$CH$_2$OMe | CN | |
| 4-243 | OMe | Me | CH$_2$CH$_2$OMe | CN | |
| 4-244 | OMe | F | CH$_2$CH$_2$OMe | CN | |
| 4-245 | OMe | Cl | CH$_2$CH$_2$OMe | CN | |
| 4-246 | OMe | Br | CH$_2$CH$_2$OMe | CN | |
| 4-247 | OMe | I | CH$_2$CH$_2$OMe | CN | |
| 4-248 | OMe | CF$_3$ | CH$_2$CH$_2$OMe | CN | |
| 4-249 | OMe | CHF$_2$ | CH$_2$CH$_2$OMe | CN | |
| 4-250 | OMe | CF$_2$Cl | CH$_2$CH$_2$OMe | CN | |
| 4-251 | OMe | OMe | CH$_2$CH$_2$OMe | CN | |
| 4-252 | OMe | NO$_2$ | CH$_2$CH$_2$OMe | CN | |
| 4-253 | OMe | SO$_2$Me | CH$_2$CH$_2$OMe | CN | |
| 4-254 | SO$_2$Me | Me | CH$_2$CH$_2$OMe | CN | |
| 4-255 | SO$_2$Me | F | CH$_2$CH$_2$OMe | CN | |
| 4-256 | SO$_2$Me | Cl | CH$_2$CH$_2$OMe | CN | |
| 4-257 | SO$_2$Me | Br | CH$_2$CH$_2$OMe | CN | |
| 4-258 | SO$_2$Me | I | CH$_2$CH$_2$OMe | CN | |
| 4-259 | SO$_2$Me | CF$_3$ | CH$_2$CH$_2$OMe | CN | |
| 4-260 | SO$_2$Me | CHF$_2$ | CH$_2$CH$_2$OMe | CN | |
| 4-261 | SO$_2$Me | CF$_2$Cl | CH$_2$CH$_2$OMe | CN | |

TABLE 4-continued

Compounds according to the invention of the formula (I) in which Q is Q1 and R$^x$ is a (2-methoxyethyl) group, R'' and W are each hydrogen and t = 1

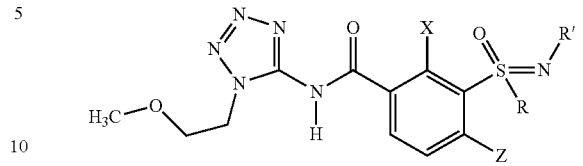

| No. | X | Z | R | R' | Physical Data ($^1$H NMR) |
|---|---|---|---|---|---|
| 4-262 | SO$_2$Me | OMe | CH$_2$CH$_2$OMe | CN | |
| 4-263 | SO$_2$Me | NO$_2$ | CH$_2$CH$_2$OMe | CN | |
| 4-264 | SO$_2$Me | SO$_2$Me | CH$_2$CH$_2$OMe | CN | |

TABLE 5

Compounds according to the invention of the formula (I) in which Q is Q2 and R$^x$ is a methyl group, R'' and W are each hydrogen and t = 1

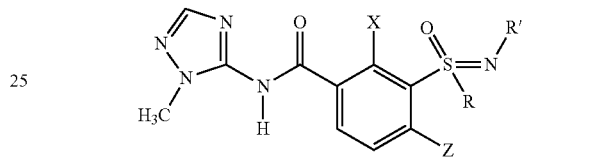

| No. | X | Z | R | R' | Physical Data ($^1$H NMR) |
|---|---|---|---|---|---|
| 5-1 | Me | Me | Me | H | |
| 5-2 | Me | F | Me | H | |
| 5-3 | Me | Cl | Me | H | |
| 5-4 | Me | Br | Me | H | |
| 5-5 | Me | I | Me | H | |
| 5-6 | Me | CF$_3$ | Me | H | |
| 5-7 | Me | CHF$_2$ | Me | H | |
| 5-8 | Me | CF$_2$Cl | Me | H | |
| 5-9 | Me | OMe | Me | H | |
| 5-10 | Me | NO$_2$ | Me | H | |
| 5-11 | Me | SO$_2$Me | Me | H | |
| 5-12 | Cl | Me | Me | H | |
| 5-13 | Cl | F | Me | H | |
| 5-14 | Cl | Cl | Me | H | |
| 5-15 | Cl | Br | Me | H | |
| 5-16 | Cl | I | Me | H | |
| 5-17 | Cl | CF$_3$ | Me | H | |
| 5-18 | Cl | CHF$_2$ | Me | H | |
| 5-19 | Cl | CF$_2$Cl | Me | H | |
| 5-20 | Cl | OMe | Me | H | |
| 5-21 | Cl | NO$_2$ | Me | H | |
| 5-22 | Cl | SO$_2$Me | Me | H | |
| 5-23 | OMe | Me | Me | H | |
| 5-24 | OMe | F | Me | H | |
| 5-25 | OMe | Cl | Me | H | |
| 5-26 | OMe | Br | Me | H | |
| 5-27 | OMe | I | Me | H | |
| 5-28 | OMe | CF$_3$ | Me | H | |
| 5-29 | OMe | CHF$_2$ | Me | H | |
| 5-30 | OMe | CF$_2$Cl | Me | H | |
| 5-31 | OMe | OMe | Me | H | |
| 5-32 | OMe | NO$_2$ | Me | H | |
| 5-33 | OMe | SO$_2$Me | Me | H | |
| 5-34 | SO$_2$Me | Me | Me | H | |
| 5-35 | SO$_2$Me | F | Me | H | |
| 5-36 | SO$_2$Me | Cl | Me | H | |
| 5-37 | SO$_2$Me | Br | Me | H | |
| 5-38 | SO$_2$Me | I | Me | H | |
| 5-39 | SO$_2$Me | CF$_3$ | Me | H | |
| 5-40 | SO$_2$Me | CHF$_2$ | Me | H | |
| 5-41 | SO$_2$Me | CF$_2$Cl | Me | H | |
| 5-42 | SO$_2$Me | OMe | Me | H | |
| 5-43 | SO$_2$Me | NO$_2$ | Me | H | |
| 5-44 | SO$_2$Me | SO$_2$Me | Me | H | |
| 5-45 | Me | Me | Et | H | |

TABLE 5-continued

Compounds according to the invention of the formula (I) in which Q is Q2 and $R^x$ is a methyl group, R″ and W are each hydrogen and t = 1

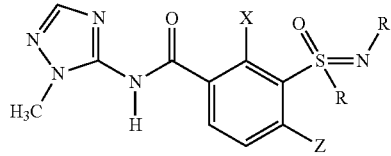

| No. | X | Z | R | R' | Physical Data ($^1$H NMR) |
|---|---|---|---|---|---|
| 5-46 | Me | F | Et | H | |
| 5-47 | Me | Cl | Et | H | |
| 5-48 | Me | Br | Et | H | |
| 5-49 | Me | I | Et | H | |
| 5-50 | Me | CF$_3$ | Et | H | |
| 5-51 | Me | CHF$_2$ | Et | H | |
| 5-52 | Me | CF$_2$Cl | Et | H | |
| 5-53 | Me | OMe | Et | H | |
| 5-54 | Me | NO$_2$ | Et | H | |
| 5-55 | Me | SO$_2$Me | Et | H | |
| 5-56 | Cl | Me | Et | H | |
| 5-57 | Cl | F | Et | H | |
| 5-58 | Cl | Cl | Et | H | |
| 5-59 | Cl | Br | Et | H | |
| 5-60 | Cl | I | Et | H | |
| 5-61 | Cl | CF$_3$ | Et | H | |
| 5-62 | Cl | CHF$_2$ | Et | H | |
| 5-63 | Cl | CF$_2$Cl | Et | H | |
| 5-64 | Cl | OMe | Et | H | |
| 5-65 | Cl | NO$_2$ | Et | H | |
| 5-66 | Cl | SO$_2$Me | Et | H | |
| 5-67 | OMe | Me | Et | H | |
| 5-68 | OMe | F | Et | H | |
| 5-69 | OMe | Cl | Et | H | |
| 5-70 | OMe | Br | Et | H | |
| 5-71 | OMe | I | Et | H | |
| 5-72 | OMe | CF$_3$ | Et | H | |
| 5-73 | OMe | CHF$_2$ | Et | H | |
| 5-74 | OMe | CF$_2$Cl | Et | H | |
| 5-75 | OMe | OMe | Et | H | |
| 5-76 | OMe | NO$_2$ | Et | H | |
| 5-77 | OMe | SO$_2$Me | Et | H | |
| 5-78 | SO$_2$Me | Me | Et | H | |
| 5-79 | SO$_2$Me | F | Et | H | |
| 5-80 | SO$_2$Me | Cl | Et | H | |
| 5-81 | SO$_2$Me | Br | Et | H | |
| 5-82 | SO$_2$Me | I | Et | H | |
| 5-83 | SO$_2$Me | CF$_3$ | Et | H | |
| 5-84 | SO$_2$Me | CHF$_2$ | Et | H | |
| 5-85 | SO$_2$Me | CF$_2$Cl | Et | H | |
| 5-86 | SO$_2$Me | OMe | Et | H | |
| 5-87 | SO$_2$Me | NO$_2$ | Et | H | |
| 5-88 | SO$_2$Me | SO$_2$Me | Et | H | |
| 5-89 | Me | Me | CH$_2$CH$_2$OMe | H | |
| 5-90 | Me | F | CH$_2$CH$_2$OMe | H | |
| 5-91 | Me | Cl | CH$_2$CH$_2$OMe | H | |
| 5-92 | Me | Br | CH$_2$CH$_2$OMe | H | |
| 5-93 | Me | I | CH$_2$CH$_2$OMe | H | |
| 5-94 | Me | CF$_3$ | CH$_2$CH$_2$OMe | H | |
| 5-95 | Me | CHF$_2$ | CH$_2$CH$_2$OMe | H | |
| 5-96 | Me | CF$_2$Cl | CH$_2$CH$_2$OMe | H | |
| 5-97 | Me | OMe | CH$_2$CH$_2$OMe | H | |
| 5-98 | Me | NO$_2$ | CH$_2$CH$_2$OMe | H | |
| 5-99 | Me | SO$_2$Me | CH$_2$CH$_2$OMe | H | |
| 5-100 | Cl | Me | CH$_2$CH$_2$OMe | H | |
| 5-101 | Cl | F | CH$_2$CH$_2$OMe | H | |
| 5-102 | Cl | Cl | CH$_2$CH$_2$OMe | H | |
| 5-103 | Cl | Br | CH$_2$CH$_2$OMe | H | |
| 5-104 | Cl | I | CH$_2$CH$_2$OMe | H | |
| 5-105 | Cl | CF$_3$ | CH$_2$CH$_2$OMe | H | |
| 5-106 | Cl | CHF$_2$ | CH$_2$CH$_2$OMe | H | |
| 5-107 | Cl | CF$_2$Cl | CH$_2$CH$_2$OMe | H | |
| 5-108 | Cl | OMe | CH$_2$CH$_2$OMe | H | |
| 5-109 | Cl | NO$_2$ | CH$_2$CH$_2$OMe | H | |
| 5-110 | Cl | SO$_2$Me | CH$_2$CH$_2$OMe | H | |
| 5-111 | OMe | Me | CH$_2$CH$_2$OMe | H | |

TABLE 5-continued

Compounds according to the invention of the formula (I) in which Q is Q2 and $R^x$ is a methyl group, R″ and W are each hydrogen and t = 1

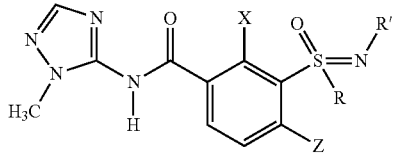

| No. | X | Z | R | R' | Physical Data ($^1$H NMR) |
|---|---|---|---|---|---|
| 5-112 | OMe | F | CH$_2$CH$_2$OMe | H | |
| 5-113 | OMe | Cl | CH$_2$CH$_2$OMe | H | |
| 5-114 | OMe | Br | CH$_2$CH$_2$OMe | H | |
| 5-115 | OMe | I | CH$_2$CH$_2$OMe | H | |
| 5-116 | OMe | CF$_3$ | CH$_2$CH$_2$OMe | H | |
| 5-117 | OMe | CHF$_2$ | CH$_2$CH$_2$OMe | H | |
| 5-118 | OMe | CF$_2$Cl | CH$_2$CH$_2$OMe | H | |
| 5-119 | OMe | OMe | CH$_2$CH$_2$OMe | H | |
| 5-120 | OMe | NO$_2$ | CH$_2$CH$_2$OMe | H | |
| 5-121 | OMe | SO$_2$Me | CH$_2$CH$_2$OMe | H | |
| 5-122 | SO$_2$Me | Me | CH$_2$CH$_2$OMe | H | |
| 5-123 | SO$_2$Me | F | CH$_2$CH$_2$OMe | H | |
| 5-124 | SO$_2$Me | Cl | CH$_2$CH$_2$OMe | H | |
| 5-125 | SO$_2$Me | Br | CH$_2$CH$_2$OMe | H | |
| 5-126 | SO$_2$Me | I | CH$_2$CH$_2$OMe | H | |
| 5-127 | SO$_2$Me | CF$_3$ | CH$_2$CH$_2$OMe | H | |
| 5-128 | SO$_2$Me | CHF$_2$ | CH$_2$CH$_2$OMe | H | |
| 5-129 | SO$_2$Me | CF$_2$Cl | CH$_2$CH$_2$OMe | H | |
| 5-130 | SO$_2$Me | OMe | CH$_2$CH$_2$OMe | H | |
| 5-131 | SO$_2$Me | NO$_2$ | CH$_2$CH$_2$OMe | H | |
| 5-132 | SO$_2$Me | SO$_2$Me | CH$_2$CH$_2$OMe | H | |
| 5-133 | Me | Me | Me | CN | |
| 5-134 | Me | F | Me | CN | |
| 5-135 | Me | Cl | Me | CN | |
| 5-136 | Me | Br | Me | CN | |
| 5-137 | Me | I | Me | CN | |
| 5-138 | Me | CF$_3$ | Me | CN | |
| 5-139 | Me | CHF$_2$ | Me | CN | |
| 5-140 | Me | CF$_2$Cl | Me | CN | |
| 5-141 | Me | OMe | Me | CN | |
| 5-142 | Me | NO$_2$ | Me | CN | |
| 5-143 | Me | SO$_2$Me | Me | CN | |
| 5-144 | Cl | Me | Me | CN | |
| 5-145 | Cl | F | Me | CN | |
| 5-146 | Cl | Cl | Me | CN | |
| 5-147 | Cl | Br | Me | CN | |
| 5-148 | Cl | I | Me | CN | |
| 5-149 | Cl | CF$_3$ | Me | CN | |
| 5-150 | Cl | CHF$_2$ | Me | CN | |
| 5-151 | Cl | CF$_2$Cl | Me | CN | |
| 5-152 | Cl | OMe | Me | CN | |
| 5-153 | Cl | NO$_2$ | Me | CN | |
| 5-154 | Cl | SO$_2$Me | Me | CN | |
| 5-155 | OMe | Me | Me | CN | |
| 5-156 | OMe | F | Me | CN | |
| 5-157 | OMe | Cl | Me | CN | |
| 5-158 | OMe | Br | Me | CN | |
| 5-159 | OMe | I | Me | CN | |
| 5-160 | OMe | CF$_3$ | Me | CN | |
| 5-161 | OMe | CHF$_2$ | Me | CN | |
| 5-162 | OMe | CF$_2$Cl | Me | CN | |
| 5-163 | OMe | OMe | Me | CN | |
| 5-164 | OMe | NO$_2$ | Me | CN | |
| 5-165 | OMe | SO$_2$Me | Me | CN | |
| 5-166 | SO$_2$Me | Me | Me | CN | |
| 5-167 | SO$_2$Me | F | Me | CN | |
| 5-168 | SO$_2$Me | Cl | Me | CN | |
| 5-169 | SO$_2$Me | Br | Me | CN | |
| 5-170 | SO$_2$Me | I | Me | CN | |
| 5-171 | SO$_2$Me | CF$_3$ | Me | CN | |
| 5-172 | SO$_2$Me | CHF$_2$ | Me | CN | |
| 5-173 | SO$_2$Me | CF$_2$Cl | Me | CN | |
| 5-174 | SO$_2$Me | OMe | Me | CN | |
| 5-175 | SO$_2$Me | NO$_2$ | Me | CN | |
| 5-176 | SO$_2$Me | SO$_2$Me | Me | CN | |
| 5-177 | Me | Me | Et | CN | |

TABLE 5-continued

Compounds according to the invention of the formula (I) in which Q is Q2 and $R^x$ is a methyl group, R" and W are each hydrogen and t = 1

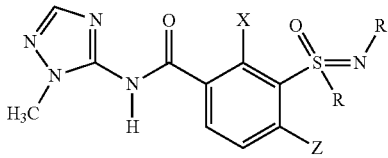

| No. | X | Z | R | R' | Physical Data ($^1$H NMR) |
|---|---|---|---|---|---|
| 5-178 | Me | F | Et | CN | |
| 5-179 | Me | Cl | Et | CN | |
| 5-180 | Me | Br | Et | CN | |
| 5-181 | Me | I | Et | CN | |
| 5-182 | Me | CF$_3$ | Et | CN | |
| 5-183 | Me | CHF$_2$ | Et | CN | |
| 5-184 | Me | CF$_2$Cl | Et | CN | |
| 5-185 | Me | OMe | Et | CN | |
| 5-186 | Me | NO$_2$ | Et | CN | |
| 5-187 | Me | SO$_2$Me | Et | CN | |
| 5-188 | Cl | Me | Et | CN | |
| 5-189 | Cl | F | Et | CN | |
| 5-190 | Cl | Cl | Et | CN | |
| 5-191 | Cl | Br | Et | CN | |
| 5-192 | Cl | I | Et | CN | |
| 5-193 | Cl | CF$_3$ | Et | CN | |
| 5-194 | Cl | CHF$_2$ | Et | CN | |
| 5-195 | Cl | CF$_2$Cl | Et | CN | |
| 5-196 | Cl | OMe | Et | CN | |
| 5-197 | Cl | NO$_2$ | Et | CN | |
| 5-198 | Cl | SO$_2$Me | Et | CN | |
| 5-199 | OMe | Me | Et | CN | |
| 5-200 | OMe | F | Et | CN | |
| 5-201 | OMe | Cl | Et | CN | |
| 5-202 | OMe | Br | Et | CN | |
| 5-203 | OMe | I | Et | CN | |
| 5-204 | OMe | CF$_3$ | Et | CN | |
| 5-205 | OMe | CHF$_2$ | Et | CN | |
| 5-206 | OMe | CF$_2$Cl | Et | CN | |
| 5-207 | OMe | OMe | Et | CN | |
| 5-208 | OMe | NO$_2$ | Et | CN | |
| 5-209 | OMe | SO$_2$Me | Et | CN | |
| 5-210 | SO$_2$Me | Me | Et | CN | |
| 5-211 | SO$_2$Me | F | Et | CN | |
| 5-212 | SO$_2$Me | Cl | Et | CN | |
| 5-213 | SO$_2$Me | Br | Et | CN | |
| 5-214 | SO$_2$Me | I | Et | CN | |
| 5-215 | SO$_2$Me | CF$_3$ | Et | CN | |
| 5-216 | SO$_2$Me | CHF$_2$ | Et | CN | |
| 5-217 | SO$_2$Me | CF$_2$Cl | Et | CN | |
| 5-218 | SO$_2$Me | OMe | Et | CN | |
| 5-219 | SO$_2$Me | NO$_2$ | Et | CN | |
| 5-220 | SO$_2$Me | SO$_2$Me | Et | CN | |
| 5-221 | Me | Me | CH$_2$CH$_2$OMe | CN | |
| 5-222 | Me | F | CH$_2$CH$_2$OMe | CN | |
| 5-223 | Me | Cl | CH$_2$CH$_2$OMe | CN | |
| 5-224 | Me | Br | CH$_2$CH$_2$OMe | CN | |
| 5-225 | Me | I | CH$_2$CH$_2$OMe | CN | |
| 5-226 | Me | CF$_3$ | CH$_2$CH$_2$OMe | CN | |
| 5-227 | Me | CHF$_2$ | CH$_2$CH$_2$OMe | CN | |
| 5-228 | Me | CF$_2$Cl | CH$_2$CH$_2$OMe | CN | |
| 5-229 | Me | OMe | CH$_2$CH$_2$OMe | CN | |
| 5-230 | Me | NO$_2$ | CH$_2$CH$_2$OMe | CN | |
| 5-231 | Me | SO$_2$Me | CH$_2$CH$_2$OMe | CN | |
| 5-232 | Cl | Me | CH$_2$CH$_2$OMe | CN | |
| 5-233 | Cl | F | CH$_2$CH$_2$OMe | CN | |
| 5-234 | Cl | Cl | CH$_2$CH$_2$OMe | CN | |
| 5-235 | Cl | Br | CH$_2$CH$_2$OMe | CN | |
| 5-236 | Cl | I | CH$_2$CH$_2$OMe | CN | |
| 5-237 | Cl | CF$_3$ | CH$_2$CH$_2$OMe | CN | |
| 5-238 | Cl | CHF$_2$ | CH$_2$CH$_2$OMe | CN | |
| 5-239 | Cl | CF$_2$Cl | CH$_2$CH$_2$OMe | CN | |
| 5-240 | Cl | OMe | CH$_2$CH$_2$OMe | CN | |
| 5-241 | Cl | NO$_2$ | CH$_2$CH$_2$OMe | CN | |
| 5-242 | Cl | SO$_2$Me | CH$_2$CH$_2$OMe | CN | |
| 5-243 | OMe | Me | CH$_2$CH$_2$OMe | CN | |

TABLE 5-continued

Compounds according to the invention of the formula (I) in which Q is Q2 and $R^x$ is a methyl group, R" and W are each hydrogen and t = 1

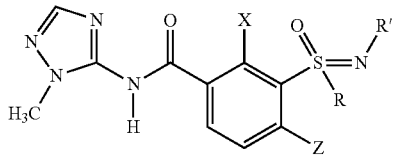

| No. | X | Z | R | R' | Physical Data ($^1$H NMR) |
|---|---|---|---|---|---|
| 5-244 | OMe | F | CH$_2$CH$_2$OMe | CN | |
| 5-245 | OMe | Cl | CH$_2$CH$_2$OMe | CN | |
| 5-246 | OMe | Br | CH$_2$CH$_2$OMe | CN | |
| 5-247 | OMe | I | CH$_2$CH$_2$OMe | CN | |
| 5-248 | OMe | CF$_3$ | CH$_2$CH$_2$OMe | CN | |
| 5-249 | OMe | CHF$_2$ | CH$_2$CH$_2$OMe | CN | |
| 5-250 | OMe | CF$_2$Cl | CH$_2$CH$_2$OMe | CN | |
| 5-251 | OMe | OMe | CH$_2$CH$_2$OMe | CN | |
| 5-252 | OMe | NO$_2$ | CH$_2$CH$_2$OMe | CN | |
| 5-253 | OMe | SO$_2$Me | CH$_2$CH$_2$OMe | CN | |
| 5-254 | SO$_2$Me | Me | CH$_2$CH$_2$OMe | CN | |
| 5-255 | SO$_2$Me | F | CH$_2$CH$_2$OMe | CN | |
| 5-256 | SO$_2$Me | Cl | CH$_2$CH$_2$OMe | CN | |
| 5-257 | SO$_2$Me | Br | CH$_2$CH$_2$OMe | CN | |
| 5-258 | SO$_2$Me | I | CH$_2$CH$_2$OMe | CN | |
| 5-259 | SO$_2$Me | CF$_3$ | CH$_2$CH$_2$OMe | CN | |
| 5-260 | SO$_2$Me | CHF$_2$ | CH$_2$CH$_2$OMe | CN | |
| 5-261 | SO$_2$Me | CF$_2$Cl | CH$_2$CH$_2$OMe | CN | |
| 5-262 | SO$_2$Me | OMe | CH$_2$CH$_2$OMe | CN | |
| 5-263 | SO$_2$Me | NO$_2$ | CH$_2$CH$_2$OMe | CN | |
| 5-264 | SO$_2$Me | SO$_2$Me | CH$_2$CH$_2$OMe | CN | |

TABLE 6

Compounds according to the invention of the formula (I) in which Q is Q3 and $R^y$ is a methyl group, R" and W are each hydrogen and t = 1

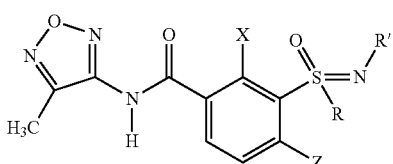

| No. | X | Z | R | R' | Physical Data ($^1$H NMR) |
|---|---|---|---|---|---|
| 6-1 | Me | Me | Me | H | |
| 6-2 | Me | F | Me | H | |
| 6-3 | Me | Cl | Me | H | |
| 6-4 | Me | Br | Me | H | |
| 6-5 | Me | I | Me | H | |
| 6-6 | Me | CF$_3$ | Me | H | |
| 6-7 | Me | CHF$_2$ | Me | H | |
| 6-8 | Me | CF$_2$Cl | Me | H | |
| 6-9 | Me | OMe | Me | H | |
| 6-10 | Me | NO$_2$ | Me | H | |
| 6-11 | Me | SO$_2$Me | Me | H | |
| 6-12 | Cl | Me | Me | H | |
| 6-13 | Cl | F | Me | H | |
| 6-14 | Cl | Cl | Me | H | |
| 6-15 | Cl | Br | Me | H | |
| 6-16 | Cl | I | Me | H | |
| 6-17 | Cl | CF$_3$ | Me | H | |
| 6-18 | Cl | CHF$_2$ | Me | H | |
| 6-19 | Cl | CF$_2$Cl | Me | H | |
| 6-20 | Cl | OMe | Me | H | |
| 6-21 | Cl | NO$_2$ | Me | H | |
| 6-22 | Cl | SO$_2$Me | Me | H | |
| 6-23 | OMe | Me | Me | H | |
| 6-24 | OMe | F | Me | H | |
| 6-25 | OMe | Cl | Me | H | |

TABLE 6-continued

Compounds according to the invention of the formula (I) in which Q is Q3 and R$^y$ is a methyl group, R" and W are each hydrogen and t = 1

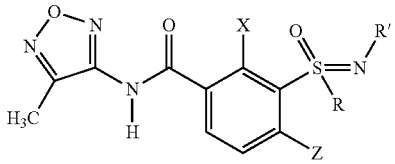

| No. | X | Z | R | R' | Physical Data ($^1$H NMR) |
|---|---|---|---|---|---|
| 6-26 | OMe | Br | Me | H | |
| 6-27 | OMe | I | Me | H | |
| 6-28 | OMe | CF$_3$ | Me | H | |
| 6-29 | OMe | CHF$_2$ | Me | H | |
| 6-30 | OMe | CF$_2$Cl | Me | H | |
| 6-31 | OMe | OMe | Me | H | |
| 6-32 | OMe | NO$_2$ | Me | H | |
| 6-33 | OMe | SO$_2$Me | Me | H | |
| 6-34 | SO$_2$Me | Me | Me | H | |
| 6-35 | SO$_2$Me | F | Me | H | |
| 6-36 | SO$_2$Me | Cl | Me | H | |
| 6-37 | SO$_2$Me | Br | Me | H | |
| 6-38 | SO$_2$Me | I | Me | H | |
| 6-39 | SO$_2$Me | CF$_3$ | Me | H | |
| 6-40 | SO$_2$Me | CHF$_2$ | Me | H | |
| 6-41 | SO$_2$Me | CF$_2$Cl | Me | H | |
| 6-42 | SO$_2$Me | OMe | Me | H | |
| 6-43 | SO$_2$Me | NO$_2$ | Me | H | |
| 6-44 | SO$_2$Me | SO$_2$Me | Me | H | |
| 6-45 | Me | Me | Et | H | |
| 6-46 | Me | F | Et | H | |
| 6-47 | Me | Cl | Et | H | |
| 6-48 | Me | Br | Et | H | |
| 6-49 | Me | I | Et | H | |
| 6-50 | Me | CF$_3$ | Et | H | |
| 6-51 | Me | CHF$_2$ | Et | H | |
| 6-52 | Me | CF$_2$Cl | Et | H | |
| 6-53 | Me | OMe | Et | H | |
| 6-54 | Me | NO$_2$ | Et | H | |
| 6-55 | Me | SO$_2$Me | Et | H | |
| 6-56 | Cl | Me | Et | H | |
| 6-57 | Cl | F | Et | H | |
| 6-58 | Cl | Cl | Et | H | |
| 6-59 | Cl | Br | Et | H | |
| 6-60 | Cl | I | Et | H | |
| 6-61 | Cl | CF$_3$ | Et | H | |
| 6-62 | Cl | CHF$_2$ | Et | H | |
| 6-63 | Cl | CF$_2$Cl | Et | H | |
| 6-64 | Cl | OMe | Et | H | |
| 6-65 | Cl | NO$_2$ | Et | H | |
| 6-66 | Cl | SO$_2$Me | Et | H | |
| 6-67 | OMe | Me | Et | H | |
| 6-68 | OMe | F | Et | H | |
| 6-69 | OMe | Cl | Et | H | |
| 6-70 | OMe | Br | Et | H | |
| 6-71 | OMe | I | Et | H | |
| 6-72 | OMe | CF$_3$ | Et | H | |
| 6-73 | OMe | CHF$_2$ | Et | H | |
| 6-74 | OMe | CF$_2$Cl | Et | H | |
| 6-75 | OMe | OMe | Et | H | |
| 6-76 | OMe | NO$_2$ | Et | H | |
| 6-77 | OMe | SO$_2$Me | Et | H | |
| 6-78 | SO$_2$Me | Me | Et | H | |
| 6-79 | SO$_2$Me | F | Et | H | |
| 6-80 | SO$_2$Me | Cl | Et | H | |
| 6-81 | SO$_2$Me | Br | Et | H | |
| 6-82 | SO$_2$Me | I | Et | H | |
| 6-83 | SO$_2$Me | CF$_3$ | Et | H | |
| 6-84 | SO$_2$Me | CHF$_2$ | Et | H | |
| 6-85 | SO$_2$Me | CF$_2$Cl | Et | H | |
| 6-86 | SO$_2$Me | OMe | Et | H | |
| 6-87 | SO$_2$Me | NO$_2$ | Et | H | |
| 6-88 | SO$_2$Me | SO$_2$Me | Et | H | |
| 6-89 | Me | Me | CH$_2$CH$_2$OMe | H | |
| 6-90 | Me | F | CH$_2$CH$_2$OMe | H | |
| 6-91 | Me | Cl | CH$_2$CH$_2$OMe | H | |
| 6-92 | Me | Br | CH$_2$CH$_2$OMe | H | |
| 6-93 | Me | I | CH$_2$CH$_2$OMe | H | |
| 6-94 | Me | CF$_3$ | CH$_2$CH$_2$OMe | H | |
| 6-95 | Me | CHF$_2$ | CH$_2$CH$_2$OMe | H | |
| 6-96 | Me | CF$_2$Cl | CH$_2$CH$_2$OMe | H | |
| 6-97 | Me | OMe | CH$_2$CH$_2$OMe | H | |
| 6-98 | Me | NO$_2$ | CH$_2$CH$_2$OMe | H | |
| 6-99 | Me | SO$_2$Me | CH$_2$CH$_2$OMe | H | |
| 6-100 | Cl | Me | CH$_2$CH$_2$OMe | H | |
| 6-101 | Cl | F | CH$_2$CH$_2$OMe | H | |
| 6-102 | Cl | Cl | CH$_2$CH$_2$OMe | H | |
| 6-103 | Cl | Br | CH$_2$CH$_2$OMe | H | |
| 6-104 | Cl | I | CH$_2$CH$_2$OMe | H | |
| 6-105 | Cl | CF$_3$ | CH$_2$CH$_2$OMe | H | |
| 6-106 | Cl | CHF$_2$ | CH$_2$CH$_2$OMe | H | |
| 6-107 | Cl | CF$_2$Cl | CH$_2$CH$_2$OMe | H | |
| 6-108 | Cl | OMe | CH$_2$CH$_2$OMe | H | |
| 6-109 | Cl | NO$_2$ | CH$_2$CH$_2$OMe | H | |
| 6-110 | Cl | SO$_2$Me | CH$_2$CH$_2$OMe | H | |
| 6-111 | OMe | Me | CH$_2$CH$_2$OMe | H | |
| 6-112 | OMe | F | CH$_2$CH$_2$OMe | H | |
| 6-113 | OMe | Cl | CH$_2$CH$_2$OMe | H | |
| 6-114 | OMe | Br | CH$_2$CH$_2$OMe | H | |
| 6-115 | OMe | I | CH$_2$CH$_2$OMe | H | |
| 6-116 | OMe | CF$_3$ | CH$_2$CH$_2$OMe | H | |
| 6-117 | OMe | CHF$_2$ | CH$_2$CH$_2$OMe | H | |
| 6-118 | OMe | CF$_2$Cl | CH$_2$CH$_2$OMe | H | |
| 6-119 | OMe | OMe | CH$_2$CH$_2$OMe | H | |
| 6-120 | OMe | NO$_2$ | CH$_2$CH$_2$OMe | H | |
| 6-121 | OMe | SO$_2$Me | CH$_2$CH$_2$OMe | H | |
| 6-122 | SO$_2$Me | Me | CH$_2$CH$_2$OMe | H | |
| 6-123 | SO$_2$Me | F | CH$_2$CH$_2$OMe | H | |
| 6-124 | SO$_2$Me | Cl | CH$_2$CH$_2$OMe | H | |
| 6-125 | SO$_2$Me | Br | CH$_2$CH$_2$OMe | H | |
| 6-126 | SO$_2$Me | I | CH$_2$CH$_2$OMe | H | |
| 6-127 | SO$_2$Me | CF$_3$ | CH$_2$CH$_2$OMe | H | |
| 6-128 | SO$_2$Me | CHF$_2$ | CH$_2$CH$_2$OMe | H | |
| 6-129 | SO$_2$Me | CF$_2$Cl | CH$_2$CH$_2$OMe | H | |
| 6-130 | SO$_2$Me | OMe | CH$_2$CH$_2$OMe | H | |
| 6-131 | SO$_2$Me | NO$_2$ | CH$_2$CH$_2$OMe | H | |
| 6-132 | SO$_2$Me | SO$_2$Me | CH$_2$CH$_2$OMe | H | |
| 6-133 | Me | Me | Me | CN | |
| 6-134 | Me | F | Me | CN | |
| 6-135 | Me | Cl | Me | CN | |
| 6-136 | Me | Br | Me | CN | |
| 6-137 | Me | I | Me | CN | |
| 6-138 | Me | CF$_3$ | Me | CN | |
| 6-139 | Me | CHF$_2$ | Me | CN | |
| 6-140 | Me | CF$_2$Cl | Me | CN | |
| 6-141 | Me | OMe | Me | CN | |
| 6-142 | Me | NO$_2$ | Me | CN | |
| 6-143 | Me | SO$_2$Me | Me | CN | |
| 6-144 | Cl | Me | Me | CN | |
| 6-145 | Cl | F | Me | CN | |
| 6-146 | Cl | Cl | Me | CN | |
| 6-147 | Cl | Br | Me | CN | |
| 6-148 | Cl | I | Me | CN | |
| 6-149 | Cl | CF$_3$ | Me | CN | |
| 6-150 | Cl | CHF$_2$ | Me | CN | |
| 6-151 | Cl | CF$_2$Cl | Me | CN | |
| 6-152 | Cl | OMe | Me | CN | |
| 6-153 | Cl | NO$_2$ | Me | CN | |

TABLE 6-continued

Compounds according to the invention of the formula (I) in which Q is Q3 and R$^y$ is a methyl group, R" and W are each hydrogen and t = 1

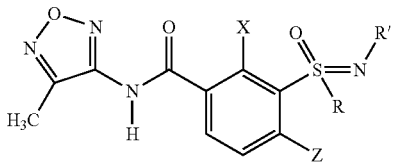

| No. | X | Z | R | R' | Physical Data ($^1$H NMR) |
|---|---|---|---|---|---|
| 6-154 | Cl | SO$_2$Me | Me | CN | |
| 6-155 | OMe | Me | Me | CN | |
| 6-156 | OMe | F | Me | CN | |
| 6-157 | OMe | Cl | Me | CN | |
| 6-158 | OMe | Br | Me | CN | |
| 6-159 | OMe | I | Me | CN | |
| 6-160 | OMe | CF$_3$ | Me | CN | |
| 6-161 | OMe | CHF$_2$ | Me | CN | |
| 6-162 | OMe | CF$_2$Cl | Me | CN | |
| 6-163 | OMe | OMe | Me | CN | |
| 6-164 | OMe | NO$_2$ | Me | CN | |
| 6-165 | OMe | SO$_2$Me | Me | CN | |
| 6-166 | SO$_2$Me | Me | Me | CN | |
| 6-167 | SO$_2$Me | F | Me | CN | |
| 6-168 | SO$_2$Me | Cl | Me | CN | |
| 6-169 | SO$_2$Me | Br | Me | CN | |
| 6-170 | SO$_2$Me | I | Me | CN | |
| 6-171 | SO$_2$Me | CF$_3$ | Me | CN | |
| 6-172 | SO$_2$Me | CHF$_2$ | Me | CN | |
| 6-173 | SO$_2$Me | CF$_2$Cl | Me | CN | |
| 6-174 | SO$_2$Me | OMe | Me | CN | |
| 6-175 | SO$_2$Me | NO$_2$ | Me | CN | |
| 6-176 | SO$_2$Me | SO$_2$Me | Me | CN | |
| 6-177 | Me | Me | Et | CN | |
| 6-178 | Me | F | Et | CN | |
| 6-179 | Me | Cl | Et | CN | |
| 6-180 | Me | Br | Et | CN | |
| 6-181 | Me | I | Et | CN | |
| 6-182 | Me | CF$_3$ | Et | CN | |
| 6-183 | Me | CHF$_2$ | Et | CN | |
| 6-184 | Me | CF$_2$Cl | Et | CN | |
| 6-185 | Me | OMe | Et | CN | |
| 6-186 | Me | NO$_2$ | Et | CN | |
| 6-187 | Me | SO$_2$Me | Et | CN | |
| 6-188 | Cl | Me | Et | CN | |
| 6-189 | Cl | F | Et | CN | |
| 6-190 | Cl | Cl | Et | CN | |
| 6-191 | Cl | Br | Et | CN | |
| 6-192 | Cl | I | Et | CN | |
| 6-193 | Cl | CF$_3$ | Et | CN | |
| 6-194 | Cl | CHF$_2$ | Et | CN | |
| 6-195 | Cl | CF$_2$Cl | Et | CN | |
| 6-196 | Cl | OMe | Et | CN | |
| 6-197 | Cl | NO$_2$ | Et | CN | |
| 6-198 | Cl | SO$_2$Me | Et | CN | |
| 6-199 | OMe | Me | Et | CN | |
| 6-200 | OMe | F | Et | CN | |
| 6-201 | OMe | Cl | Et | CN | |
| 6-202 | OMe | Br | Et | CN | |
| 6-203 | OMe | I | Et | CN | |
| 6-204 | OMe | CF$_3$ | Et | CN | |
| 6-205 | OMe | CHF$_2$ | Et | CN | |
| 6-206 | OMe | CF$_2$Cl | Et | CN | |
| 6-207 | OMe | OMe | Et | CN | |
| 6-208 | OMe | NO$_2$ | Et | CN | |
| 6-209 | OMe | SO$_2$Me | Et | CN | |
| 6-210 | SO$_2$Me | Me | Et | CN | |
| 6-211 | SO$_2$Me | F | Et | CN | |
| 6-212 | SO$_2$Me | Cl | Et | CN | |
| 6-213 | SO$_2$Me | Br | Et | CN | |
| 6-214 | SO$_2$Me | I | Et | CN | |
| 6-215 | SO$_2$Me | CF$_3$ | Et | CN | |
| 6-216 | SO$_2$Me | CHF$_2$ | Et | CN | |
| 6-217 | SO$_2$Me | CF$_2$Cl | Et | CN | |

TABLE 6-continued

Compounds according to the invention of the formula (I) in which Q is Q3 and R$^y$ is a methyl group, R" and W are each hydrogen and t = 1

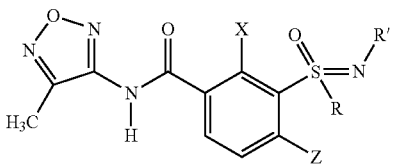

| No. | X | Z | R | R' | Physical Data ($^1$H NMR) |
|---|---|---|---|---|---|
| 6-218 | SO$_2$Me | OMe | Et | CN | |
| 6-219 | SO$_2$Me | NO$_2$ | Et | CN | |
| 6-220 | SO$_2$Me | SO$_2$Me | Et | CN | |
| 6-221 | Me | Me | CH$_2$CH$_2$OMe | CN | |
| 6-222 | Me | F | CH$_2$CH$_2$OMe | CN | |
| 6-223 | Me | Cl | CH$_2$CH$_2$OMe | CN | |
| 6-224 | Me | Br | CH$_2$CH$_2$OMe | CN | |
| 6-225 | Me | I | CH$_2$CH$_2$OMe | CN | |
| 6-226 | Me | CF$_3$ | CH$_2$CH$_2$OMe | CN | |
| 6-227 | Me | CHF$_2$ | CH$_2$CH$_2$OMe | CN | |
| 6-228 | Me | CF$_2$Cl | CH$_2$CH$_2$OMe | CN | |
| 6-229 | Me | OMe | CH$_2$CH$_2$OMe | CN | |
| 6-230 | Me | NO$_2$ | CH$_2$CH$_2$OMe | CN | |
| 6-231 | Me | SO$_2$Me | CH$_2$CH$_2$OMe | CN | |
| 6-232 | Cl | Me | CH$_2$CH$_2$OMe | CN | |
| 6-233 | Cl | F | CH$_2$CH$_2$OMe | CN | |
| 6-234 | Cl | Cl | CH$_2$CH$_2$OMe | CN | |
| 6-235 | Cl | Br | CH$_2$CH$_2$OMe | CN | |
| 6-236 | Cl | I | CH$_2$CH$_2$OMe | CN | |
| 6-237 | Cl | CF$_3$ | CH$_2$CH$_2$OMe | CN | |
| 6-238 | Cl | CHF$_2$ | CH$_2$CH$_2$OMe | CN | |
| 6-239 | Cl | CF$_2$Cl | CH$_2$CH$_2$OMe | CN | |
| 6-240 | Cl | OMe | CH$_2$CH$_2$OMe | CN | |
| 6-241 | Cl | NO$_2$ | CH$_2$CH$_2$OMe | CN | |
| 6-242 | Cl | SO$_2$Me | CH$_2$CH$_2$OMe | CN | |
| 6-243 | OMe | Me | CH$_2$CH$_2$OMe | CN | |
| 6-244 | OMe | F | CH$_2$CH$_2$OMe | CN | |
| 6-245 | OMe | Cl | CH$_2$CH$_2$OMe | CN | |
| 6-246 | OMe | Br | CH$_2$CH$_2$OMe | CN | |
| 6-247 | OMe | I | CH$_2$CH$_2$OMe | CN | |
| 6-248 | OMe | CF$_3$ | CH$_2$CH$_2$OMe | CN | |
| 6-249 | OMe | CHF$_2$ | CH$_2$CH$_2$OMe | CN | |
| 6-250 | OMe | CF$_2$Cl | CH$_2$CH$_2$OMe | CN | |
| 6-251 | OMe | OMe | CH$_2$CH$_2$OMe | CN | |
| 6-252 | OMe | NO$_2$ | CH$_2$CH$_2$OMe | CN | |
| 6-253 | OMe | SO$_2$Me | CH$_2$CH$_2$OMe | CN | |
| 6-254 | SO$_2$Me | Me | CH$_2$CH$_2$OMe | CN | |
| 6-255 | SO$_2$Me | F | CH$_2$CH$_2$OMe | CN | |
| 6-256 | SO$_2$Me | Cl | CH$_2$CH$_2$OMe | CN | |
| 6-257 | SO$_2$Me | Br | CH$_2$CH$_2$OMe | CN | |
| 6-258 | SO$_2$Me | I | CH$_2$CH$_2$OMe | CN | |
| 6-259 | SO$_2$Me | CF$_3$ | CH$_2$CH$_2$OMe | CN | |
| 6-260 | SO$_2$Me | CHF$_2$ | CH$_2$CH$_2$OMe | CN | |
| 6-261 | SO$_2$Me | CF$_2$Cl | CH$_2$CH$_2$OMe | CN | |
| 6-262 | SO$_2$Me | OMe | CH$_2$CH$_2$OMe | CN | |
| 6-263 | SO$_2$Me | NO$_2$ | CH$_2$CH$_2$OMe | CN | |
| 6-264 | SO$_2$Me | SO$_2$Me | CH$_2$CH$_2$OMe | CN | |

TABLE 7

Compounds according to the invention of the formula (I) in which Q is Q4 and R$^z$ is a methyl group, R" and W are each hydrogen and t = 1

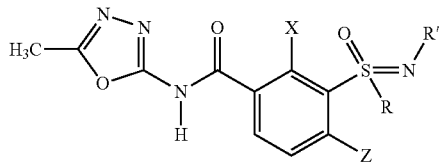

| No. | X | Z | R | R' | Physical Data ($^1$H NMR) |
|---|---|---|---|---|---|
| 7-1 | Me | Me | Me | H | |
| 7-2 | Me | F | Me | H | |
| 7-3 | Me | Cl | Me | H | |
| 7-4 | Me | Br | Me | H | |
| 7-5 | Me | I | Me | H | |
| 7-6 | Me | CF$_3$ | Me | H | |
| 7-7 | Me | CHF$_2$ | Me | H | |
| 7-8 | Me | CF$_2$Cl | Me | H | |
| 7-9 | Me | OMe | Me | H | |
| 7-10 | Me | NO$_2$ | Me | H | |
| 7-11 | Me | SO$_2$Me | Me | H | |
| 7-12 | Cl | Me | Me | H | |
| 7-13 | Cl | F | Me | H | |
| 7-14 | Cl | Cl | Me | H | |
| 7-15 | Cl | Br | Me | H | |
| 7-16 | Cl | I | Me | H | |
| 7-17 | Cl | CF$_3$ | Me | H | |
| 7-18 | Cl | CHF$_2$ | Me | H | |
| 7-19 | Cl | CF$_2$Cl | Me | H | |
| 7-20 | Cl | OMe | Me | H | |
| 7-21 | Cl | NO$_2$ | Me | H | |
| 7-22 | Cl | SO$_2$Me | Me | H | |
| 7-23 | OMe | Me | Me | H | |
| 7-24 | OMe | F | Me | H | |
| 7-25 | OMe | Cl | Me | H | |
| 7-26 | OMe | Br | Me | H | |
| 7-27 | OMe | I | Me | H | |
| 7-28 | OMe | CF$_3$ | Me | H | |
| 7-29 | OMe | CHF$_2$ | Me | H | |
| 7-30 | OMe | CF$_2$Cl | Me | H | |
| 7-31 | OMe | OMe | Me | H | |
| 7-32 | OMe | NO$_2$ | Me | H | |
| 7-33 | OMe | SO$_2$Me | Me | H | |
| 7-34 | SO$_2$Me | Me | Me | H | |
| 7-35 | SO$_2$Me | F | Me | H | |
| 7-36 | SO$_2$Me | Cl | Me | H | |
| 7-37 | SO$_2$Me | Br | Me | H | |
| 7-38 | SO$_2$Me | I | Me | H | |
| 7-39 | SO$_2$Me | CF$_3$ | Me | H | |
| 7-40 | SO$_2$Me | CHF$_2$ | Me | H | |
| 7-41 | SO$_2$Me | CF$_2$Cl | Me | H | |
| 7-42 | SO$_2$Me | OMe | Me | H | |
| 7-43 | SO$_2$Me | NO$_2$ | Me | H | |
| 7-44 | SO$_2$Me | SO$_2$Me | Me | H | |
| 7-45 | Me | Me | Et | H | |
| 7-46 | Me | F | Et | H | |
| 7-47 | Me | Cl | Et | H | |
| 7-48 | Me | Br | Et | H | |
| 7-49 | Me | I | Et | H | |
| 7-50 | Me | CF$_3$ | Et | H | |
| 7-51 | Me | CHF$_2$ | Et | H | |
| 7-52 | Me | CF$_2$Cl | Et | H | |
| 7-53 | Me | OMe | Et | H | |
| 7-54 | Me | NO$_2$ | Et | H | |
| 7-55 | Me | SO$_2$Me | Et | H | |
| 7-56 | Cl | Me | Et | H | |
| 7-57 | Cl | F | Et | H | |
| 7-58 | Cl | Cl | Et | H | |
| 7-59 | Cl | Br | Et | H | |
| 7-60 | Cl | I | Et | H | |
| 7-61 | Cl | CF$_3$ | Et | H | |
| 7-62 | Cl | CHF$_2$ | Et | H | |
| 7-63 | Cl | CF$_2$Cl | Et | H | |
| 7-64 | Cl | OMe | Et | H | |
| 7-65 | Cl | NO$_2$ | Et | H | |
| 7-66 | Cl | SO$_2$Me | Et | H | |
| 7-67 | OMe | Me | Et | H | |
| 7-68 | OMe | F | Et | H | |
| 7-69 | OMe | Cl | Et | H | |
| 7-70 | OMe | Br | Et | H | |
| 7-71 | OMe | I | Et | H | |
| 7-72 | OMe | CF$_3$ | Et | H | |
| 7-73 | OMe | CHF$_2$ | Et | H | |
| 7-74 | OMe | CF$_2$Cl | Et | H | |
| 7-75 | OMe | OMe | Et | H | |
| 7-76 | OMe | NO$_2$ | Et | H | |
| 7-77 | OMe | SO$_2$Me | Et | H | |
| 7-78 | SO$_2$Me | Me | Et | H | |
| 7-79 | SO$_2$Me | F | Et | H | |
| 7-80 | SO$_2$Me | Cl | Et | H | |
| 7-81 | SO$_2$Me | Br | Et | H | |
| 7-82 | SO$_2$Me | I | Et | H | |
| 7-83 | SO$_2$Me | CF$_3$ | Et | H | |
| 7-84 | SO$_2$Me | CHF$_2$ | Et | H | |
| 7-85 | SO$_2$Me | CF$_2$Cl | Et | H | |
| 7-86 | SO$_2$Me | OMe | Et | H | |
| 7-87 | SO$_2$Me | NO$_2$ | Et | H | |
| 7-88 | SO$_2$Me | SO$_2$Me | Et | H | |
| 7-89 | Me | Me | CH$_2$CH$_2$OMe | H | |
| 7-90 | Me | F | CH$_2$CH$_2$OMe | H | |
| 7-91 | Me | Cl | CH$_2$CH$_2$OMe | H | |
| 7-92 | Me | Br | CH$_2$CH$_2$OMe | H | |
| 7-93 | Me | I | CH$_2$CH$_2$OMe | H | |
| 7-94 | Me | CF$_3$ | CH$_2$CH$_2$OMe | H | |
| 7-95 | Me | CHF$_2$ | CH$_2$CH$_2$OMe | H | |
| 7-96 | Me | CF$_2$Cl | CH$_2$CH$_2$OMe | H | |
| 7-97 | Me | OMe | CH$_2$CH$_2$OMe | H | |
| 7-98 | Me | NO$_2$ | CH$_2$CH$_2$OMe | H | |
| 7-99 | Me | SO$_2$Me | CH$_2$CH$_2$OMe | H | |
| 7-100 | Cl | Me | CH$_2$CH$_2$OMe | H | |
| 7-101 | Cl | F | CH$_2$CH$_2$OMe | H | |
| 7-102 | Cl | Cl | CH$_2$CH$_2$OMe | H | |
| 7-103 | Cl | Br | CH$_2$CH$_2$OMe | H | |
| 7-104 | Cl | I | CH$_2$CH$_2$OMe | H | |
| 7-105 | Cl | CF$_3$ | CH$_2$CH$_2$OMe | H | |
| 7-106 | Cl | CHF$_2$ | CH$_2$CH$_2$OMe | H | |
| 7-107 | Cl | CF$_2$Cl | CH$_2$CH$_2$OMe | H | |
| 7-108 | Cl | OMe | CH$_2$CH$_2$OMe | H | |
| 7-109 | Cl | NO$_2$ | CH$_2$CH$_2$OMe | H | |
| 7-110 | Cl | SO$_2$Me | CH$_2$CH$_2$OMe | H | |
| 7-111 | OMe | Me | CH$_2$CH$_2$OMe | H | |
| 7-112 | OMe | F | CH$_2$CH$_2$OMe | H | |
| 7-113 | OMe | Cl | CH$_2$CH$_2$OMe | H | |
| 7-114 | OMe | Br | CH$_2$CH$_2$OMe | H | |
| 7-115 | OMe | I | CH$_2$CH$_2$OMe | H | |
| 7-116 | OMe | CF$_3$ | CH$_2$CH$_2$OMe | H | |
| 7-117 | OMe | CHF$_2$ | CH$_2$CH$_2$OMe | H | |
| 7-118 | OMe | CF$_2$Cl | CH$_2$CH$_2$OMe | H | |
| 7-119 | OMe | OMe | CH$_2$CH$_2$OMe | H | |
| 7-120 | OMe | NO$_2$ | CH$_2$CH$_2$OMe | H | |
| 7-121 | OMe | SO$_2$Me | CH$_2$CH$_2$OMe | H | |
| 7-122 | SO$_2$Me | Me | CH$_2$CH$_2$OMe | H | |
| 7-123 | SO$_2$Me | F | CH$_2$CH$_2$OMe | H | |
| 7-124 | SO$_2$Me | Cl | CH$_2$CH$_2$OMe | H | |
| 7-125 | SO$_2$Me | Br | CH$_2$CH$_2$OMe | H | |
| 7-126 | SO$_2$Me | I | CH$_2$CH$_2$OMe | H | |
| 7-127 | SO$_2$Me | CF$_3$ | CH$_2$CH$_2$OMe | H | |
| 7-128 | SO$_2$Me | CHF$_2$ | CH$_2$CH$_2$OMe | H | |
| 7-129 | SO$_2$Me | CF$_2$Cl | CH$_2$CH$_2$OMe | H | |
| 7-130 | SO$_2$Me | OMe | CH$_2$CH$_2$OMe | H | |
| 7-131 | SO$_2$Me | NO$_2$ | CH$_2$CH$_2$OMe | H | |
| 7-132 | SO$_2$Me | SO$_2$Me | CH$_2$CH$_2$OMe | H | |

TABLE 7-continued

Compounds according to the invention of the formula (I) in which Q is Q4 and $R^z$ is a methyl group, R" and W are each hydrogen and t = 1

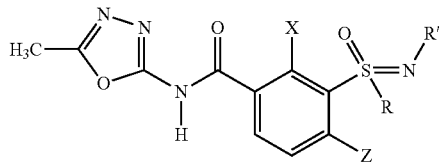

| No. | X | Z | R | R' | Physical Data ($^1$H NMR) |
|---|---|---|---|---|---|
| 7-133 | Me | Me | Me | CN | |
| 7-134 | Me | F | Me | CN | |
| 7-135 | Me | Cl | Me | CN | |
| 7-136 | Me | Br | Me | CN | |
| 7-137 | Me | I | Me | CN | |
| 7-138 | Me | CF$_3$ | Me | CN | |
| 7-139 | Me | CHF$_2$ | Me | CN | |
| 7-140 | Me | CF$_2$Cl | Me | CN | |
| 7-141 | Me | OMe | Me | CN | |
| 7-142 | Me | NO$_2$ | Me | CN | |
| 7-143 | Me | SO$_2$Me | Me | CN | |
| 7-144 | Cl | Me | Me | CN | |
| 7-145 | Cl | F | Me | CN | |
| 7-146 | Cl | Cl | Me | CN | |
| 7-147 | Cl | Br | Me | CN | |
| 7-148 | Cl | I | Me | CN | |
| 7-149 | Cl | CF$_3$ | Me | CN | |
| 7-150 | Cl | CHF$_2$ | Me | CN | |
| 7-151 | Cl | CF$_2$Cl | Me | CN | |
| 7-152 | Cl | OMe | Me | CN | |
| 7-153 | Cl | NO$_2$ | Me | CN | |
| 7-154 | Cl | SO$_2$Me | Me | CN | |
| 7-155 | OMe | Me | Me | CN | |
| 7-156 | OMe | F | Me | CN | |
| 7-157 | OMe | Cl | Me | CN | |
| 7-158 | OMe | Br | Me | CN | |
| 7-159 | OMe | I | Me | CN | |
| 7-160 | OMe | CF$_3$ | Me | CN | (400 MHz, CDCl$_3$ δ, ppm) 7.82 (d, 1H), 4.10 (s, 3H), 3.69 (s, 3H), 2.57 (s, 3H) |
| 7-161 | OMe | CHF$_2$ | Me | CN | |
| 7-162 | OMe | CF$_2$Cl | Me | CN | |
| 7-163 | OMe | OMe | Me | CN | |
| 7-164 | OMe | NO$_2$ | Me | CN | |
| 7-165 | OMe | SO$_2$Me | Me | CN | |
| 7-166 | SO$_2$Me | Me | Me | CN | |
| 7-167 | SO$_2$Me | F | Me | CN | |
| 7-168 | SO$_2$Me | Cl | Me | CN | |
| 7-169 | SO$_2$Me | Br | Me | CN | |
| 7-170 | SO$_2$Me | I | Me | CN | |
| 7-171 | SO$_2$Me | CF$_3$ | Me | CN | |
| 7-172 | SO$_2$Me | CHF$_2$ | Me | CN | |
| 7-173 | SO$_2$Me | CF$_2$Cl | Me | CN | |
| 7-174 | SO$_2$Me | OMe | Me | CN | |
| 7-175 | SO$_2$Me | NO$_2$ | Me | CN | |
| 7-176 | SO$_2$Me | SO$_2$Me | Me | CN | |
| 7-177 | Me | Me | Et | CN | |
| 7-178 | Me | F | Et | CN | |
| 7-179 | Me | Cl | Et | CN | |
| 7-180 | Me | Br | Et | CN | |
| 7-181 | Me | I | Et | CN | |
| 7-182 | Me | CF$_3$ | Et | CN | |
| 7-183 | Me | CHF$_2$ | Et | CN | |
| 7-184 | Me | CF$_2$Cl | Et | CN | |
| 7-185 | Me | OMe | Et | CN | |
| 7-186 | Me | NO$_2$ | Et | CN | |
| 7-187 | Me | SO$_2$Me | Et | CN | |
| 7-188 | Cl | Me | Et | CN | |
| 7-189 | Cl | F | Et | CN | |
| 7-190 | Cl | Cl | Et | CN | |
| 7-191 | Cl | Br | Et | CN | |
| 7-192 | Cl | I | Et | CN | |
| 7-193 | Cl | CF$_3$ | Et | CN | |
| 7-194 | Cl | CHF$_2$ | Et | CN | |
| 7-195 | Cl | CF$_2$Cl | Et | CN | |
| 7-196 | Cl | OMe | Et | CN | |

TABLE 7-continued

Compounds according to the invention of the formula (I) in which Q is Q4 and $R^z$ is a methyl group, R" and W are each hydrogen and t = 1

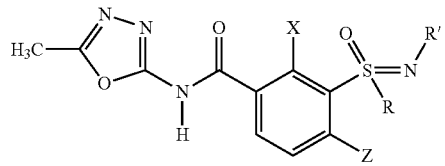

| No. | X | Z | R | R' | Physical Data ($^1$H NMR) |
|---|---|---|---|---|---|
| 7-197 | Cl | NO$_2$ | Et | CN | |
| 7-198 | Cl | SO$_2$Me | Et | CN | |
| 7-199 | OMe | Me | Et | CN | |
| 7-200 | OMe | F | Et | CN | |
| 7-201 | OMe | Cl | Et | CN | |
| 7-202 | OMe | Br | Et | CN | |
| 7-203 | OMe | I | Et | CN | |
| 7-204 | OMe | CF$_3$ | Et | CN | |
| 7-205 | OMe | CHF$_2$ | Et | CN | |
| 7-206 | OMe | CF$_2$Cl | Et | CN | |
| 7-207 | OMe | OMe | Et | CN | |
| 7-208 | OMe | NO$_2$ | Et | CN | |
| 7-209 | OMe | SO$_2$Me | Et | CN | |
| 7-210 | SO$_2$Me | Me | Et | CN | |
| 7-211 | SO$_2$Me | F | Et | CN | |
| 7-212 | SO$_2$Me | Cl | Et | CN | |
| 7-213 | SO$_2$Me | Br | Et | CN | |
| 7-214 | SO$_2$Me | I | Et | CN | |
| 7-215 | SO$_2$Me | CF$_3$ | Et | CN | |
| 7-216 | SO$_2$Me | CHF$_2$ | Et | CN | |
| 7-217 | SO$_2$Me | CF$_2$Cl | Et | CN | |
| 7-218 | SO$_2$Me | OMe | Et | CN | |
| 7-219 | SO$_2$Me | NO$_2$ | Et | CN | |
| 7-220 | SO$_2$Me | SO$_2$Me | Et | CN | |
| 7-221 | Me | Me | CH$_2$CH$_2$OMe | CN | |
| 7-222 | Me | F | CH$_2$CH$_2$OMe | CN | |
| 7-223 | Me | Cl | CH$_2$CH$_2$OMe | CN | |
| 7-224 | Me | Br | CH$_2$CH$_2$OMe | CN | |
| 7-225 | Me | I | CH$_2$CH$_2$OMe | CN | |
| 7-226 | Me | CF$_3$ | CH$_2$CH$_2$OMe | CN | |
| 7-227 | Me | CHF$_2$ | CH$_2$CH$_2$OMe | CN | |
| 7-228 | Me | CF$_2$Cl | CH$_2$CH$_2$OMe | CN | |
| 7-229 | Me | OMe | CH$_2$CH$_2$OMe | CN | |
| 7-230 | Me | NO$_2$ | CH$_2$CH$_2$OMe | CN | |
| 7-231 | Me | SO$_2$Me | CH$_2$CH$_2$OMe | CN | |
| 7-232 | Cl | Me | CH$_2$CH$_2$OMe | CN | |
| 7-233 | Cl | F | CH$_2$CH$_2$OMe | CN | |
| 7-234 | Cl | Cl | CH$_2$CH$_2$OMe | CN | |
| 7-235 | Cl | Br | CH$_2$CH$_2$OMe | CN | |
| 7-236 | Cl | I | CH$_2$CH$_2$OMe | CN | |
| 7-237 | Cl | CF$_3$ | CH$_2$CH$_2$OMe | CN | |
| 7-238 | Cl | CHF$_2$ | CH$_2$CH$_2$OMe | CN | |
| 7-239 | Cl | CF$_2$Cl | CH$_2$CH$_2$OMe | CN | |
| 7-240 | Cl | OMe | CH$_2$CH$_2$OMe | CN | |
| 7-241 | Cl | NO$_2$ | CH$_2$CH$_2$OMe | CN | |
| 7-242 | Cl | SO$_2$Me | CH$_2$CH$_2$OMe | CN | |
| 7-243 | OMe | Me | CH$_2$CH$_2$OMe | CN | |
| 7-244 | OMe | F | CH$_2$CH$_2$OMe | CN | |
| 7-245 | OMe | Cl | CH$_2$CH$_2$OMe | CN | |
| 7-246 | OMe | Br | CH$_2$CH$_2$OMe | CN | |
| 7-247 | OMe | I | CH$_2$CH$_2$OMe | CN | |
| 7-248 | OMe | CF$_3$ | CH$_2$CH$_2$OMe | CN | |
| 7-249 | OMe | CHF$_2$ | CH$_2$CH$_2$OMe | CN | |
| 7-250 | OMe | CF$_2$Cl | CH$_2$CH$_2$OMe | CN | |
| 7-251 | OMe | OMe | CH$_2$CH$_2$OMe | CN | |
| 7-252 | OMe | NO$_2$ | CH$_2$CH$_2$OMe | CN | |
| 7-253 | OMe | SO$_2$Me | CH$_2$CH$_2$OMe | CN | |
| 7-254 | SO$_2$Me | Me | CH$_2$CH$_2$OMe | CN | |
| 7-255 | SO$_2$Me | F | CH$_2$CH$_2$OMe | CN | |
| 7-256 | SO$_2$Me | Cl | CH$_2$CH$_2$OMe | CN | |
| 7-257 | SO$_2$Me | Br | CH$_2$CH$_2$OMe | CN | |
| 7-258 | SO$_2$Me | I | CH$_2$CH$_2$OMe | CN | |
| 7-259 | SO$_2$Me | CF$_3$ | CH$_2$CH$_2$OMe | CN | |
| 7-260 | SO$_2$Me | CHF$_2$ | CH$_2$CH$_2$OMe | CN | |
| 7-261 | SO$_2$Me | CF$_2$Cl | CH$_2$CH$_2$OMe | CN | |
| 7-262 | SO$_2$Me | OMe | CH$_2$CH$_2$OMe | CN | |

TABLE 7-continued

Compounds according to the invention of the formula (I) in which Q is Q4 and R$^z$ is a methyl group, R" and W are each hydrogen and t = 1

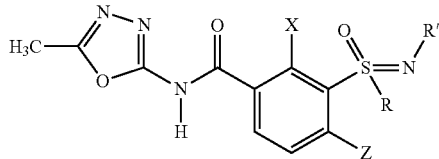

| No. | X | Z | R | R' | Physical Data ($^1$H NMR) |
|---|---|---|---|---|---|
| 7-263 | SO$_2$Me | NO$_2$ | CH$_2$CH$_2$OMe | CN | |
| 7-264 | SO$_2$Me | SO$_2$Me | CH$_2$CH$_2$OMe | CN | |

TABLE 8

Compounds according to the invention of the formula (I) in the form of the sodium salts in which Q is Q1 and R$^x$ is a methyl group, W is hydrogen and t = 1

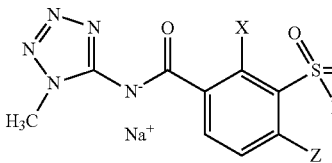

| No. | X | Z | R | R' | Physical Data ($^1$H NMR) |
|---|---|---|---|---|---|
| 8-1 | Me | Me | Me | H | |
| 8-2 | Me | Cl | Me | H | |
| 8-3 | Me | CF$_3$ | Me | H | |
| 8-4 | Me | CHF$_2$ | Me | H | |
| 8-5 | Cl | Me | Me | H | |
| 8-6 | Cl | Cl | Me | H | |
| 8-7 | Cl | CF$_3$ | Me | H | |
| 8-8 | Cl | CHF$_2$ | Me | H | |
| 8-9 | OMe | Me | Me | H | |
| 8-10 | OMe | Cl | Me | H | |
| 8-11 | OMe | CF$_3$ | Me | H | |
| 8-12 | OMe | CHF$_2$ | Me | H | |
| 8-13 | SO$_2$Me | Me | Me | H | |
| 8-14 | SO$_2$Me | Cl | Me | H | |
| 8-15 | SO$_2$Me | CF$_3$ | Me | H | |
| 8-16 | SO$_2$Me | CHF$_2$ | Me | H | |
| 8-17 | Me | Me | Et | H | |
| 8-18 | Me | Cl | Et | H | |
| 8-19 | Me | CF$_3$ | Et | H | |
| 8-20 | Me | CHF$_2$ | Et | H | |
| 8-21 | Cl | Me | Et | H | |
| 8-22 | Cl | Cl | Et | H | |
| 8-23 | Cl | CF$_3$ | Et | H | |
| 8-24 | Cl | CHF$_2$ | Et | H | |
| 8-25 | OMe | Me | Et | H | |
| 8-26 | OMe | Cl | Et | H | |
| 8-27 | OMe | CF$_3$ | Et | H | |
| 8-28 | OMe | CHF$_2$ | Et | H | |
| 8-29 | SO$_2$Me | Me | Et | H | |
| 8-30 | SO$_2$Me | Cl | Et | H | |
| 8-31 | SO$_2$Me | CF$_3$ | Et | H | |
| 8-32 | SO$_2$Me | CHF$_2$ | Et | H | |
| 8-33 | Me | Me | CH$_2$CH$_2$OMe | H | |
| 8-34 | Me | Cl | CH$_2$CH$_2$OMe | H | |
| 8-35 | Me | CF$_3$ | CH$_2$CH$_2$OMe | H | |
| 8-36 | Me | CHF$_2$ | CH$_2$CH$_2$OMe | H | |
| 8-37 | Cl | Me | CH$_2$CH$_2$OMe | H | |
| 8-38 | Cl | Cl | CH$_2$CH$_2$OMe | H | |
| 8-39 | Cl | CF$_3$ | CH$_2$CH$_2$OMe | H | |
| 8-40 | Cl | CHF$_2$ | CH$_2$CH$_2$OMe | H | |
| 8-41 | OMe | Me | CH$_2$CH$_2$OMe | H | |
| 8-42 | OMe | Cl | CH$_2$CH$_2$OMe | H | |
| 8-43 | OMe | CF$_3$ | CH$_2$CH$_2$OMe | H | |
| 8-44 | OMe | CHF$_2$ | CH$_2$CH$_2$OMe | H | |

TABLE 8-continued

Compounds according to the invention of the formula (I) in the form of the sodium salts in which Q is Q1 and R$^x$ is a methyl group, W is hydrogen and t = 1

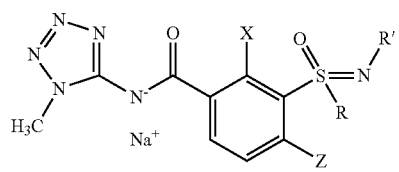

| No. | X | Z | R | R' | Physical Data ($^1$H NMR) |
|---|---|---|---|---|---|
| 8-45 | SO$_2$Me | Me | CH$_2$CH$_2$OMe | H | |
| 8-46 | SO$_2$Me | Cl | CH$_2$CH$_2$OMe | H | |
| 8-47 | SO$_2$Me | CF$_3$ | CH$_2$CH$_2$OMe | H | |
| 8-48 | SO$_2$Me | CHF$_2$ | CH$_2$CH$_2$OMe | H | |
| 8-49 | Me | Me | Me | CN | |
| 8-50 | Me | Cl | Me | CN | |
| 8-51 | Me | CF$_3$ | Me | CN | |
| 8-52 | Me | CHF$_2$ | Me | CN | |
| 8-53 | Cl | Me | Me | CN | |
| 8-54 | Cl | Cl | Me | CN | |
| 8-55 | Cl | CF$_3$ | Me | CN | |
| 8-56 | Cl | CHF$_2$ | Me | CN | |
| 8-57 | OMe | Me | Me | CN | |
| 8-58 | OMe | Cl | Me | CN | |
| 8-59 | OMe | CF$_3$ | Me | CN | |
| 8-60 | OMe | CHF$_2$ | Me | CN | |
| 8-61 | SO$_2$Me | Me | Me | CN | |
| 8-62 | SO$_2$Me | Cl | Me | CN | |
| 8-63 | SO$_2$Me | CF$_3$ | Me | CN | |
| 8-64 | SO$_2$Me | CHF$_2$ | Me | CN | |
| 8-65 | Me | Me | Et | CN | |
| 8-66 | Me | Cl | Et | CN | |
| 8-67 | Me | CF$_3$ | Et | CN | |
| 8-68 | Me | CHF$_2$ | Et | CN | |
| 8-69 | Cl | Me | Et | CN | |
| 8-70 | Cl | Cl | Et | CN | |
| 8-71 | Cl | CF$_3$ | Et | CN | |
| 8-72 | Cl | CHF$_2$ | Et | CN | |
| 8-73 | OMe | Me | Et | CN | |
| 8-74 | OMe | Cl | Et | CN | |
| 8-75 | OMe | CF$_3$ | Et | CN | |
| 8-76 | OMe | CHF$_2$ | Et | CN | |
| 8-77 | SO$_2$Me | Me | Et | CN | |
| 8-78 | SO$_2$Me | Cl | Et | CN | |
| 8-79 | SO$_2$Me | CF$_3$ | Et | CN | |
| 8-80 | SO$_2$Me | CHF$_2$ | Et | CN | |
| 8-81 | Me | Me | CH$_2$CH$_2$OMe | CN | |
| 8-82 | Me | Cl | CH$_2$CH$_2$OMe | CN | |
| 8-83 | Me | CF$_3$ | CH$_2$CH$_2$OMe | CN | |
| 8-84 | Me | CHF$_2$ | CH$_2$CH$_2$OMe | CN | |
| 8-85 | Cl | Me | CH$_2$CH$_2$OMe | CN | |
| 8-86 | Cl | Cl | CH$_2$CH$_2$OMe | CN | |
| 8-87 | Cl | CF$_3$ | CH$_2$CH$_2$OMe | CN | |
| 8-88 | Cl | CHF$_2$ | CH$_2$CH$_2$OMe | CN | |
| 8-89 | OMe | Me | CH$_2$CH$_2$OMe | CN | |
| 8-90 | OMe | Cl | CH$_2$CH$_2$OMe | CN | |
| 8-91 | OMe | CF$_3$ | CH$_2$CH$_2$OMe | CN | |
| 8-92 | OMe | CHF$_2$ | CH$_2$CH$_2$OMe | CN | |
| 8-93 | SO$_2$Me | Me | CH$_2$CH$_2$OMe | CN | |
| 8-94 | SO$_2$Me | Cl | CH$_2$CH$_2$OMe | CN | |
| 8-95 | SO$_2$Me | CF$_3$ | CH$_2$CH$_2$OMe | CN | |
| 8-96 | SO$_2$Me | CHF$_2$ | CH$_2$CH$_2$OMe | CN | |

TABLE 9

Compounds according to the invention of the formula (I) in which Q is Q3 and R$^y$ is chlorine, R'' and W are each hydrogen and t = 1

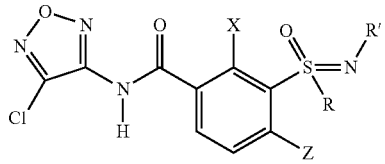

| No. | X | Z | R | R' | Physical Data ($^1$H NMR) |
|---|---|---|---|---|---|
| 9-1 | Me | Me | Me | H | |
| 9-2 | Me | F | Me | H | |
| 9-3 | Me | Cl | Me | H | |
| 9-4 | Me | Br | Me | H | |
| 9-5 | Me | I | Me | H | |
| 9-6 | Me | CF$_3$ | Me | H | |
| 9-7 | Me | CHF$_2$ | Me | H | |
| 9-8 | Me | CF$_2$Cl | Me | H | |
| 9-9 | Me | OMe | Me | H | |
| 9-10 | Me | NO$_2$ | Me | H | |
| 9-11 | Me | SO$_2$Me | Me | H | |
| 9-12 | Cl | Me | Me | H | |
| 9-13 | Cl | F | Me | H | |
| 9-14 | Cl | Cl | Me | H | |
| 9-15 | Cl | Br | Me | H | |
| 9-16 | Cl | I | Me | H | |
| 9-17 | Cl | CF$_3$ | Me | H | |
| 9-18 | Cl | CHF$_2$ | Me | H | |
| 9-19 | Cl | CF$_2$Cl | Me | H | |
| 9-20 | Cl | OMe | Me | H | |
| 9-21 | Cl | NO$_2$ | Me | H | |
| 9-22 | Cl | SO$_2$Me | Me | H | |
| 9-23 | OMe | Me | Me | H | |
| 9-24 | OMe | F | Me | H | |
| 9-25 | OMe | Cl | Me | H | |
| 9-26 | OMe | Br | Me | H | |
| 9-27 | OMe | I | Me | H | |
| 9-28 | OMe | CF$_3$ | Me | H | |
| 9-29 | OMe | CHF$_2$ | Me | H | |
| 9-30 | OMe | CF$_2$Cl | Me | H | |
| 9-31 | OMe | OMe | Me | H | |
| 9-32 | OMe | NO$_2$ | Me | H | |
| 9-33 | OMe | SO$_2$Me | Me | H | |
| 9-34 | SO$_2$Me | Me | Me | H | |
| 9-35 | SO$_2$Me | F | Me | H | |
| 9-36 | SO$_2$Me | Cl | Me | H | |
| 9-37 | SO$_2$Me | Br | Me | H | |
| 9-38 | SO$_2$Me | I | Me | H | |
| 9-39 | SO$_2$Me | CF$_3$ | Me | H | |
| 9-40 | SO$_2$Me | CHF$_2$ | Me | H | |
| 9-41 | SO$_2$Me | CF$_2$Cl | Me | H | |
| 9-42 | SO$_2$Me | OMe | Me | H | |
| 9-43 | SO$_2$Me | NO$_2$ | Me | H | |
| 9-44 | SO$_2$Me | SO$_2$Me | Me | H | |
| 9-45 | Me | Me | Et | H | |
| 9-46 | Me | F | Et | H | |
| 9-47 | Me | Cl | Et | H | |
| 9-48 | Me | Br | Et | H | |
| 9-49 | Me | I | Et | H | |
| 9-50 | Me | CF$_3$ | Et | H | |
| 9-51 | Me | CHF$_2$ | Et | H | |
| 9-52 | Me | CF$_2$Cl | Et | H | |
| 9-53 | Me | OMe | Et | H | |
| 9-54 | Me | NO$_2$ | Et | H | |
| 9-55 | Me | SO$_2$Me | Et | H | |
| 9-56 | Cl | Me | Et | H | |
| 9-57 | Cl | F | Et | H | |
| 9-58 | Cl | Cl | Et | H | |
| 9-59 | Cl | Br | Et | H | |
| 9-60 | Cl | I | Et | H | |
| 9-61 | Cl | CF$_3$ | Et | H | |
| 9-62 | Cl | CHF$_2$ | Et | H | |
| 9-63 | Cl | CF$_2$Cl | Et | H | |
| 9-64 | Cl | OMe | Et | H | |
| 9-65 | Cl | NO$_2$ | Et | H | |

TABLE 9-continued

Compounds according to the invention of the formula (I) in which Q is Q3 and R$^y$ is chlorine, R'' and W are each hydrogen and t = 1

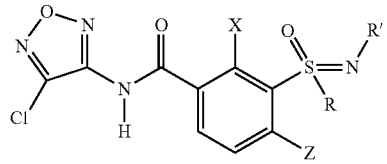

| No. | X | Z | R | R' | Physical Data ($^1$H NMR) |
|---|---|---|---|---|---|
| 9-66 | Cl | SO$_2$Me | Et | H | |
| 9-67 | OMe | Me | Et | H | |
| 9-68 | OMe | F | Et | H | |
| 9-69 | OMe | Cl | Et | H | |
| 9-70 | OMe | Br | Et | H | |
| 9-71 | OMe | I | Et | H | |
| 9-72 | OMe | CF$_3$ | Et | H | |
| 9-73 | OMe | CHF$_2$ | Et | H | |
| 9-74 | OMe | CF$_2$Cl | Et | H | |
| 9-75 | OMe | OMe | Et | H | |
| 9-76 | OMe | NO$_2$ | Et | H | |
| 9-77 | OMe | SO$_2$Me | Et | H | |
| 9-78 | SO$_2$Me | Me | Et | H | |
| 9-79 | SO$_2$Me | F | Et | H | |
| 9-80 | SO$_2$Me | Cl | Et | H | |
| 9-81 | SO$_2$Me | Br | Et | H | |
| 9-82 | SO$_2$Me | I | Et | H | |
| 9-83 | SO$_2$Me | CF$_3$ | Et | H | |
| 9-84 | SO$_2$Me | CHF$_2$ | Et | H | |
| 9-85 | SO$_2$Me | CF$_2$Cl | Et | H | |
| 9-86 | SO$_2$Me | OMe | Et | H | |
| 9-87 | SO$_2$Me | NO$_2$ | Et | H | |
| 9-88 | SO$_2$Me | SO$_2$Me | Et | H | |
| 9-89 | Me | Me | CH$_2$CH$_2$OMe | H | |
| 9-90 | Me | F | CH$_2$CH$_2$OMe | H | |
| 9-91 | Me | Cl | CH$_2$CH$_2$OMe | H | |
| 9-92 | Me | Br | CH$_2$CH$_2$OMe | H | |
| 9-93 | Me | I | CH$_2$CH$_2$OMe | H | |
| 9-94 | Me | CF$_3$ | CH$_2$CH$_2$OMe | H | |
| 9-95 | Me | CHF$_2$ | CH$_2$CH$_2$OMe | H | |
| 9-96 | Me | CF$_2$Cl | CH$_2$CH$_2$OMe | H | |
| 9-97 | Me | OMe | CH$_2$CH$_2$OMe | H | |
| 9-98 | Me | NO$_2$ | CH$_2$CH$_2$OMe | H | |
| 9-99 | Me | SO$_2$Me | CH$_2$CH$_2$OMe | H | |
| 9-100 | Cl | Me | CH$_2$CH$_2$OMe | H | |
| 9-101 | Cl | F | CH$_2$CH$_2$OMe | H | |
| 9-102 | Cl | Cl | CH$_2$CH$_2$OMe | H | |
| 9-103 | Cl | Br | CH$_2$CH$_2$OMe | H | |
| 9-104 | Cl | I | CH$_2$CH$_2$OMe | H | |
| 9-105 | Cl | CF$_3$ | CH$_2$CH$_2$OMe | H | |
| 9-106 | Cl | CHF$_2$ | CH$_2$CH$_2$OMe | H | |
| 9-107 | Cl | CF$_2$Cl | CH$_2$CH$_2$OMe | H | |
| 9-108 | Cl | OMe | CH$_2$CH$_2$OMe | H | |
| 9-109 | Cl | NO$_2$ | CH$_2$CH$_2$OMe | H | |
| 9-110 | Cl | SO$_2$Me | CH$_2$CH$_2$OMe | H | |
| 9-111 | OMe | Me | CH$_2$CH$_2$OMe | H | |
| 9-112 | OMe | F | CH$_2$CH$_2$OMe | H | |
| 9-113 | OMe | Cl | CH$_2$CH$_2$OMe | H | |
| 9-114 | OMe | Br | CH$_2$CH$_2$OMe | H | |
| 9-115 | OMe | I | CH$_2$CH$_2$OMe | H | |
| 9-116 | OMe | CF$_3$ | CH$_2$CH$_2$OMe | H | |
| 9-117 | OMe | CHF$_2$ | CH$_2$CH$_2$OMe | H | |
| 9-118 | OMe | CF$_2$Cl | CH$_2$CH$_2$OMe | H | |
| 9-119 | OMe | OMe | CH$_2$CH$_2$OMe | H | |
| 9-120 | OMe | NO$_2$ | CH$_2$CH$_2$OMe | H | |
| 9-121 | OMe | SO$_2$Me | CH$_2$CH$_2$OMe | H | |
| 9-122 | SO$_2$Me | Me | CH$_2$CH$_2$OMe | H | |
| 9-123 | SO$_2$Me | F | CH$_2$CH$_2$OMe | H | |
| 9-124 | SO$_2$Me | Cl | CH$_2$CH$_2$OMe | H | |
| 9-125 | SO$_2$Me | Br | CH$_2$CH$_2$OMe | H | |
| 9-126 | SO$_2$Me | I | CH$_2$CH$_2$OMe | H | |
| 9-127 | SO$_2$Me | CF$_3$ | CH$_2$CH$_2$OMe | H | |
| 9-128 | SO$_2$Me | CHF$_2$ | CH$_2$CH$_2$OMe | H | |
| 9-129 | SO$_2$Me | CF$_2$Cl | CH$_2$CH$_2$OMe | H | |
| 9-130 | SO$_2$Me | OMe | CH$_2$CH$_2$OMe | H | |

TABLE 9-continued

Compounds according to the invention of the formula (I) in which Q is Q3 and R<sup>y</sup> is chlorine, R" and W are each hydrogen and t = 1

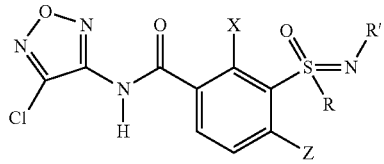

| No. | X | Z | R | R' | Physical Data ($^1$H NMR) |
|---|---|---|---|---|---|
| 9-131 | SO$_2$Me | NO$_2$ | CH$_2$CH$_2$OMe | H | |
| 9-132 | SO$_2$Me | SO$_2$Me | CH$_2$CH$_2$OMe | H | |
| 9-133 | Me | Me | Me | CN | |
| 9-134 | Me | F | Me | CN | |
| 9-135 | Me | Cl | Me | CN | |
| 9-136 | Me | Br | Me | CN | |
| 9-137 | Me | I | Me | CN | |
| 9-138 | Me | CF$_3$ | Me | CN | |
| 9-139 | Me | CHF$_2$ | Me | CN | |
| 9-140 | Me | CF$_2$Cl | Me | CN | |
| 9-141 | Me | OMe | Me | CN | |
| 9-142 | Me | NO$_2$ | Me | CN | |
| 9-143 | Me | SO$_2$Me | Me | CN | |
| 9-144 | Cl | Me | Me | CN | |
| 9-145 | Cl | F | Me | CN | |
| 9-146 | Cl | Cl | Me | CN | |
| 9-147 | Cl | Br | Me | CN | |
| 9-148 | Cl | I | Me | CN | |
| 9-149 | Cl | CF$_3$ | Me | CN | |
| 9-150 | Cl | CHF$_2$ | Me | CN | |
| 9-151 | Cl | CF$_2$Cl | Me | CN | |
| 9-152 | Cl | OMe | Me | CN | |
| 9-153 | Cl | NO$_2$ | Me | CN | |
| 9-154 | Cl | SO$_2$Me | Me | CN | |
| 9-155 | OMe | Me | Me | CN | |
| 9-156 | OMe | F | Me | CN | |
| 9-157 | OMe | Cl | Me | CN | |
| 9-158 | OMe | Br | Me | CN | |
| 9-159 | OMe | I | Me | CN | |
| 9-160 | OMe | CF$_3$ | Me | CN | |
| 9-161 | OMe | CHF$_2$ | Me | CN | |
| 9-162 | OMe | CF$_2$Cl | Me | CN | |
| 9-163 | OMe | OMe | Me | CN | |
| 9-164 | OMe | NO$_2$ | Me | CN | |
| 9-165 | OMe | SO$_2$Me | Me | CN | |
| 9-166 | SO$_2$Me | Me | Me | CN | |
| 9-167 | SO$_2$Me | F | Me | CN | |
| 9-168 | SO$_2$Me | Cl | Me | CN | |
| 9-169 | SO$_2$Me | Br | Me | CN | |
| 9-170 | SO$_2$Me | I | Me | CN | |
| 9-171 | SO$_2$Me | CF$_3$ | Me | CN | |
| 9-172 | SO$_2$Me | CHF$_2$ | Me | CN | |
| 9-173 | SO$_2$Me | CF$_2$Cl | Me | CN | |
| 9-174 | SO$_2$Me | OMe | Me | CN | |
| 9-175 | SO$_2$Me | NO$_2$ | Me | CN | |
| 9-176 | SO$_2$Me | SO$_2$Me | Me | CN | |
| 9-177 | Me | Me | Et | CN | |
| 9-178 | Me | F | Et | CN | |
| 9-179 | Me | Cl | Et | CN | |
| 9-180 | Me | Br | Et | CN | |
| 9-181 | Me | I | Et | CN | |
| 9-182 | Me | CF$_3$ | Et | CN | |
| 9-183 | Me | CHF$_2$ | Et | CN | |
| 9-184 | Me | CF$_2$Cl | Et | CN | |
| 9-185 | Me | OMe | Et | CN | |
| 9-186 | Me | NO$_2$ | Et | CN | |
| 9-187 | Me | SO$_2$Me | Et | CN | |
| 9-188 | Cl | Me | Et | CN | |
| 9-189 | Cl | F | Et | CN | |
| 9-190 | Cl | Cl | Et | CN | |
| 9-191 | Cl | Br | Et | CN | |
| 9-192 | Cl | I | Et | CN | |
| 9-193 | Cl | CF$_3$ | Et | CN | |
| 9-194 | Cl | CHF$_2$ | Et | CN | |
| 9-195 | Cl | CF$_2$Cl | Et | CN | |
| 9-196 | Cl | OMe | Et | CN | |
| 9-197 | Cl | NO$_2$ | Et | CN | |
| 9-198 | Cl | SO$_2$Me | Et | CN | |
| 9-199 | OMe | Me | Et | CN | |
| 9-200 | OMe | F | Et | CN | |
| 9-201 | OMe | Cl | Et | CN | |
| 9-202 | OMe | Br | Et | CN | |
| 9-203 | OMe | I | Et | CN | |
| 9-204 | OMe | CF$_3$ | Et | CN | |
| 9-205 | OMe | CHF$_2$ | Et | CN | |
| 9-206 | OMe | CF$_2$Cl | Et | CN | |
| 9-207 | OMe | OMe | Et | CN | |
| 9-208 | OMe | NO$_2$ | Et | CN | |
| 9-209 | OMe | SO$_2$Me | Et | CN | |
| 9-210 | SO$_2$Me | Me | Et | CN | |
| 9-211 | SO$_2$Me | F | Et | CN | |
| 9-212 | SO$_2$Me | Cl | Et | CN | |
| 9-213 | SO$_2$Me | Br | Et | CN | |
| 9-214 | SO$_2$Me | I | Et | CN | |
| 9-215 | SO$_2$Me | CF$_3$ | Et | CN | |
| 9-216 | SO$_2$Me | CHF$_2$ | Et | CN | |
| 9-217 | SO2Me | CF$_2$Cl | Et | CN | |
| 9-218 | SO$_2$Me | OMe | Et | CN | |
| 9-219 | SO$_2$Me | NO$_2$ | Et | CN | |
| 9-220 | SO$_2$Me | SO$_2$Me | Et | CN | |
| 9-221 | Me | Me | CH$_2$CH$_2$OMe | CN | |
| 9-222 | Me | F | CH$_2$CH$_2$OMe | CN | |
| 9-223 | Me | Cl | CH$_2$CH$_2$OMe | CN | |
| 9-224 | Me | Br | CH$_2$CH$_2$OMe | CN | |
| 9-225 | Me | I | CH$_2$CH$_2$OMe | CN | |
| 9-226 | Me | CF$_3$ | CH$_2$CH$_2$OMe | CN | |
| 9-227 | Me | CHF$_2$ | CH$_2$CH$_2$OMe | CN | |
| 9-228 | Me | CF$_2$Cl | CH$_2$CH$_2$OMe | CN | |
| 9-229 | Me | OMe | CH$_2$CH$_2$OMe | CN | |
| 9-230 | Me | NO$_2$ | CH$_2$CH$_2$OMe | CN | |
| 9-231 | Me | SO$_2$Me | CH$_2$CH$_2$OMe | CN | |
| 9-232 | Cl | Me | CH$_2$CH$_2$OMe | CN | |
| 9-233 | Cl | F | CH$_2$CH$_2$OMe | CN | |
| 9-234 | Cl | Cl | CH$_2$CH$_2$OMe | CN | |
| 9-235 | Cl | Br | CH$_2$CH$_2$OMe | CN | |
| 9-236 | Cl | I | CH$_2$CH$_2$OMe | CN | |
| 9-237 | Cl | CF$_3$ | CH$_2$CH$_2$OMe | CN | |
| 9-238 | Cl | CHF$_2$ | CH$_2$CH$_2$OMe | CN | |
| 9-239 | Cl | CF$_2$Cl | CH$_2$CH$_2$OMe | CN | |
| 9-240 | Cl | OMe | CH$_2$CH$_2$OMe | CN | |
| 9-241 | Cl | NO$_2$ | CH$_2$CH$_2$OMe | CN | |
| 9-242 | Cl | SO$_2$Me | CH$_2$CH$_2$OMe | CN | |
| 9-243 | OMe | Me | CH$_2$CH$_2$OMe | CN | |
| 9-244 | OMe | F | CH$_2$CH$_2$OMe | CN | |
| 9-245 | OMe | Cl | CH$_2$CH$_2$OMe | CN | |
| 9-246 | OMe | Br | CH$_2$CH$_2$OMe | CN | |
| 9-247 | OMe | I | CH$_2$CH$_2$OMe | CN | |
| 9-248 | OMe | CF$_3$ | CH$_2$CH$_2$OMe | CN | |
| 9-249 | OMe | CHF$_2$ | CH$_2$CH$_2$OMe | CN | |
| 9-250 | OMe | CF$_2$Cl | CH$_2$CH$_2$OMe | CN | |
| 9-251 | OMe | OMe | CH$_2$CH$_2$OMe | CN | |
| 9-252 | OMe | NO$_2$ | CH$_2$CH$_2$OMe | CN | |
| 9-253 | OMe | SO$_2$Me | CH$_2$CH$_2$OMe | CN | |
| 9-254 | SO$_2$Me | Me | CH$_2$CH$_2$OMe | CN | |
| 9-255 | SO$_2$Me | F | CH$_2$CH$_2$OMe | CN | |
| 9-256 | SO$_2$Me | Cl | CH$_2$CH$_2$OMe | CN | |
| 9-257 | SO$_2$Me | Br | CH$_2$CH$_2$OMe | CN | |
| 9-258 | SO$_2$Me | I | CH$_2$CH$_2$OMe | CN | |
| 9-259 | SO$_2$Me | CF$_3$ | CH$_2$CH$_2$OMe | CN | |
| 9-260 | SO$_2$Me | CHF$_2$ | CH$_2$CH$_2$OMe | CN | |

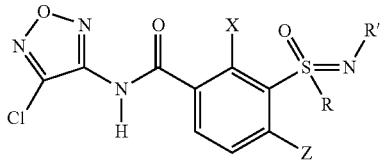

TABLE 9-continued

Compounds according to the invention of the formula (I) in which Q is Q3 and R^y is chlorine, R'' and W are each hydrogen and t = 1

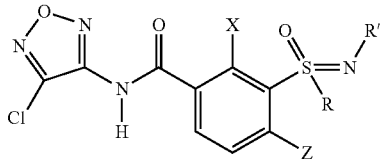

| No. | X | Z | R | R' | Physical Data ($^1$H NMR) |
|---|---|---|---|---|---|
| 9-261 | SO$_2$Me | CF$_2$Cl | CH$_2$CH$_2$OMe | CN | |
| 9-262 | SO$_2$Me | OMe | CH$_2$CH$_2$OMe | CN | |
| 9-263 | SO$_2$Me | NO$_2$ | CH$_2$CH$_2$OMe | CN | |
| 9-264 | SO$_2$Me | SO$_2$Me | CH$_2$CH$_2$OMe | CN | |

TABLE 10

Compounds according to the invention of the formula (I) in which Q is Q1 and R^x is a methyl group, R'' and W are each hydrogen and t = 0

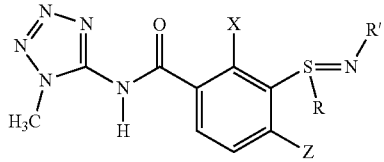

| No. | X | Z | R | R' | Physical Data ($^1$H NMR) |
|---|---|---|---|---|---|
| 10-1 | Me | Me | Me | H | |
| 10-2 | Me | F | Me | H | |
| 10-3 | Me | Cl | Me | H | |
| 10-4 | Me | Br | Me | H | |
| 10-5 | Me | I | Me | H | |
| 10-6 | Me | CF$_3$ | Me | H | |
| 10-7 | Me | CHF$_2$ | Me | H | |
| 10-8 | Me | CF$_2$Cl | Me | H | |
| 10-9 | Me | OMe | Me | H | |
| 10-10 | Me | NO$_2$ | Me | H | |
| 10-11 | Me | SO$_2$Me | Me | H | |
| 10-12 | Cl | Me | Me | H | |
| 10-13 | Cl | F | Me | H | |
| 10-14 | Cl | Cl | Me | H | |
| 10-15 | Cl | Br | Me | H | |
| 10-16 | Cl | I | Me | H | |
| 10-17 | Cl | CF$_3$ | Me | H | |
| 10-18 | Cl | CHF$_2$ | Me | H | |
| 10-19 | Cl | CF$_2$Cl | Me | H | |
| 10-20 | Cl | OMe | Me | H | |
| 10-21 | Cl | NO$_2$ | Me | H | |
| 10-22 | Cl | SO$_2$Me | Me | H | |
| 10-23 | OMe | Me | Me | H | |
| 10-24 | OMe | F | Me | H | |
| 10-25 | OMe | Cl | Me | H | |
| 10-26 | OMe | Br | Me | H | |
| 10-27 | OMe | I | Me | H | |
| 10-28 | OMe | CF$_3$ | Me | H | |
| 10-29 | OMe | CHF$_2$ | Me | H | |
| 10-30 | OMe | CF$_2$Cl | Me | H | |
| 10-31 | OMe | OMe | Me | H | |
| 10-32 | OMe | NO$_2$ | Me | H | |
| 10-33 | OMe | SO$_2$Me | Me | H | |
| 10-34 | SO$_2$Me | Me | Me | H | |
| 10-35 | SO$_2$Me | F | Me | H | |
| 10-36 | SO$_2$Me | Cl | Me | H | |
| 10-37 | SO$_2$Me | Br | Me | H | |
| 10-38 | SO$_2$Me | I | Me | H | |
| 10-39 | SO$_2$Me | CF$_3$ | Me | H | |
| 10-40 | SO$_2$Me | CHF$_2$ | Me | H | |
| 10-41 | SO$_2$Me | CF$_2$Cl | Me | H | |

TABLE 10-continued

Compounds according to the invention of the formula (I) in which Q is Q1 and R^x is a methyl group, R'' and W are each hydrogen and t = 0

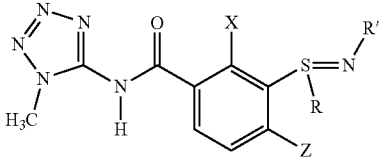

| No. | X | Z | R | R' | Physical Data ($^1$H NMR) |
|---|---|---|---|---|---|
| 10-42 | SO$_2$Me | OMe | Me | H | |
| 10-43 | SO$_2$Me | NO$_2$ | Me | H | |
| 10-44 | SO$_2$Me | SO$_2$Me | Me | H | |
| 10-45 | Me | Me | Et | H | |
| 10-46 | Me | F | Et | H | |
| 10-47 | Me | Cl | Et | H | |
| 10-48 | Me | Br | Et | H | |
| 10-49 | Me | I | Et | H | |
| 10-50 | Me | CF$_3$ | Et | H | |
| 10-51 | Me | CHF$_2$ | Et | H | |
| 10-52 | Me | CF$_2$Cl | Et | H | |
| 10-53 | Me | OMe | Et | H | |
| 10-54 | Me | NO$_2$ | Et | H | |
| 10-55 | Me | SO$_2$Me | Et | H | |
| 10-56 | Cl | Me | Et | H | |
| 10-57 | Cl | F | Et | H | |
| 10-58 | Cl | Cl | Et | H | |
| 10-59 | Cl | Br | Et | H | |
| 10-60 | Cl | I | Et | H | |
| 10-61 | Cl | CF$_3$ | Et | H | |
| 10-62 | Cl | CHF$_2$ | Et | H | |
| 10-63 | Cl | CF$_2$Cl | Et | H | |
| 10-64 | Cl | OMe | Et | H | |
| 10-65 | Cl | NO$_2$ | Et | H | |
| 10-66 | Cl | SO$_2$Me | Et | H | |
| 10-67 | OMe | Me | Et | H | |
| 10-68 | OMe | F | Et | H | |
| 10-69 | OMe | Cl | Et | H | |
| 10-70 | OMe | Br | Et | H | |
| 10-71 | OMe | I | Et | H | |
| 10-72 | OMe | CF$_3$ | Et | H | |
| 10-73 | OMe | CHF$_2$ | Et | H | |
| 10-74 | OMe | CF$_2$Cl | Et | H | |
| 10-75 | OMe | OMe | Et | H | |
| 10-76 | OMe | NO$_2$ | Et | H | |
| 10-77 | OMe | SO$_2$Me | Et | H | |
| 10-78 | SO$_2$Me | Me | Et | H | |
| 10-79 | SO$_2$Me | F | Et | H | |
| 10-80 | SO$_2$Me | Cl | Et | H | |
| 10-81 | SO$_2$Me | Br | Et | H | |
| 10-82 | SO$_2$Me | I | Et | H | |
| 10-83 | SO$_2$Me | CF$_3$ | Et | H | |
| 10-84 | SO$_2$Me | CHF$_2$ | Et | H | |
| 10-85 | SO$_2$Me | CF$_2$Cl | Et | H | |
| 10-86 | SO$_2$Me | OMe | Et | H | |
| 10-87 | SO$_2$Me | NO$_2$ | Et | H | |
| 10-88 | SO$_2$Me | SO$_2$Me | Et | H | |
| 10-89 | Me | Me | CH$_2$CH$_2$OMe | H | |
| 10-90 | Me | F | CH$_2$CH$_2$OMe | H | |
| 10-91 | Me | Cl | CH$_2$CH$_2$OMe | H | |
| 10-92 | Me | Br | CH$_2$CH$_2$OMe | H | |
| 10-93 | Me | I | CH$_2$CH$_2$OMe | H | |
| 10-94 | Me | CF$_3$ | CH$_2$CH$_2$OMe | H | |
| 10-95 | Me | CHF$_2$ | CH$_2$CH$_2$OMe | H | |
| 10-96 | Me | CF$_2$Cl | CH$_2$CH$_2$OMe | H | |
| 10-97 | Me | OMe | CH$_2$CH$_2$OMe | H | |
| 10-98 | Me | NO$_2$ | CH$_2$CH$_2$OMe | H | |
| 10-99 | Me | SO$_2$Me | CH$_2$CH$_2$OMe | H | |
| 10-100 | Cl | Me | CH$_2$CH$_2$OMe | H | |
| 10-101 | Cl | F | CH$_2$CH$_2$OMe | H | |
| 10-102 | Cl | Cl | CH$_2$CH$_2$OMe | H | |
| 10-103 | Cl | Br | CH$_2$CH$_2$OMe | H | |
| 10-104 | Cl | I | CH$_2$CH$_2$OMe | H | |
| 10-105 | Cl | CF$_3$ | CH$_2$CH$_2$OMe | H | |
| 10-106 | Cl | CHF$_2$ | CH$_2$CH$_2$OMe | H | |

TABLE 10-continued

Compounds according to the invention of the formula (I) in which Q is Q1 and R$^x$ is a methyl group, R'' and W are each hydrogen and t = 0

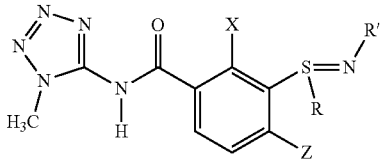

| No. | X | Z | R | R' | Physical Data ($^1$H NMR) |
|---|---|---|---|---|---|
| 10-107 | Cl | CF$_2$Cl | CH$_2$CH$_2$OMe | H | |
| 10-108 | Cl | OMe | CH$_2$CH$_2$OMe | H | |
| 10-109 | Cl | NO$_2$ | CH$_2$CH$_2$OMe | H | |
| 10-110 | Cl | SO$_2$Me | CH$_2$CH$_2$OMe | H | |
| 10-111 | OMe | Me | CH$_2$CH$_2$OMe | H | |
| 10-112 | OMe | F | CH$_2$CH$_2$OMe | H | |
| 10-113 | OMe | Cl | CH$_2$CH$_2$OMe | H | |
| 10-114 | OMe | Br | CH$_2$CH$_2$OMe | H | |
| 10-115 | OMe | I | CH$_2$CH$_2$OMe | H | |
| 10-116 | OMe | CF$_3$ | CH$_2$CH$_2$OMe | H | |
| 10-117 | OMe | CHF$_2$ | CH$_2$CH$_2$OMe | H | |
| 10-118 | OMe | CF$_2$Cl | CH$_2$CH$_2$OMe | H | |
| 10-119 | OMe | OMe | CH$_2$CH$_2$OMe | H | |
| 10-120 | OMe | NO$_2$ | CH$_2$CH$_2$OMe | H | |
| 10-121 | OMe | SO$_2$Me | CH$_2$CH$_2$OMe | H | |
| 10-122 | SO$_2$Me | Me | CH$_2$CH$_2$OMe | H | |
| 10-123 | SO$_2$Me | F | CH$_2$CH$_2$OMe | H | |
| 10-124 | SO$_2$Me | Cl | CH$_2$CH$_2$OMe | H | |
| 10-125 | SO$_2$Me | Br | CH$_2$CH$_2$OMe | H | |
| 10-126 | SO$_2$Me | I | CH$_2$CH$_2$OMe | H | |
| 10-127 | SO$_2$Me | CF$_3$ | CH$_2$CH$_2$OMe | H | |
| 10-128 | SO$_2$Me | CHF$_2$ | CH$_2$CH$_2$OMe | H | |
| 10-129 | SO$_2$Me | CF$_2$Cl | CH$_2$CH$_2$OMe | H | |
| 10-130 | SO$_2$Me | OMe | CH$_2$CH$_2$OMe | H | |
| 10-131 | SO$_2$Me | NO$_2$ | CH$_2$CH$_2$OMe | H | |
| 10-132 | SO$_2$Me | SO$_2$Me | CH$_2$CH$_2$OMe | H | |
| 10-133 | Me | Me | Me | CN | |
| 10-134 | Me | F | Me | CN | |
| 10-135 | Me | Cl | Me | CN | |
| 10-136 | Me | Br | Me | CN | |
| 10-137 | Me | I | Me | CN | |
| 10-138 | Me | CF$_3$ | Me | CN | (400 MHz, CDCl$_3$ δ, ppm) 7.88 (d, 1H), 7.79 (d, 1H), 4.08 (s, 3H), 3.19 (s, 3H), 2.98 (s, 3H) |
| 10-139 | Me | CHF$_2$ | Me | CN | |
| 10-140 | Me | CF$_2$Cl | Me | CN | |
| 10-141 | Me | OMe | Me | CN | |
| 10-142 | Me | NO$_2$ | Me | CN | |
| 10-143 | Me | SO$_2$Me | Me | CN | |
| 10-144 | Cl | Me | Me | CN | |
| 10-145 | Cl | F | Me | CN | |
| 10-146 | Cl | Cl | Me | CN | |
| 10-147 | Cl | Br | Me | CN | |
| 10-148 | Cl | I | Me | CN | |
| 10-149 | Cl | CF$_3$ | Me | CN | |
| 10-150 | Cl | CHF$_2$ | Me | CN | |
| 10-151 | Cl | CF$_2$Cl | Me | CN | |
| 10-152 | Cl | OMe | Me | CN | |
| 10-153 | Cl | NO$_2$ | Me | CN | |
| 10-154 | Cl | SO$_2$Me | Me | CN | |
| 10-155 | OMe | Me | Me | CN | |
| 10-156 | OMe | F | Me | CN | |
| 10-157 | OMe | Cl | Me | CN | |
| 10-158 | OMe | Br | Me | CN | |
| 10-159 | OMe | I | Me | CN | |
| 10-160 | OMe | CF$_3$ | Me | CN | (400 MHz, CDCl$_3$ δ, ppm) 8.12 (d, 1H), 7.69 (d, 1H), 4.22 (s, 3H), 4.11 (s, 3H), 3.37 (s, 3H) |
| 10-161 | OMe | CHF$_2$ | Me | CN | |
| 10-162 | OMe | CF$_2$Cl | Me | CN | |
| 10-163 | OMe | OMe | Me | CN | |
| 10-164 | OMe | NO$_2$ | Me | CN | |
| 10-165 | OMe | SO$_2$Me | Me | CN | |
| 10-166 | SO$_2$Me | Me | Me | CN | |
| 10-167 | SO$_2$Me | F | Me | CN | |
| 10-168 | SO$_2$Me | Cl | Me | CN | |
| 10-169 | SO$_2$Me | Br | Me | CN | |
| 10-170 | SO$_2$Me | I | Me | CN | |
| 10-171 | SO$_2$Me | CF$_3$ | Me | CN | |
| 10-172 | SO$_2$Me | CHF$_2$ | Me | CN | |
| 10-173 | SO$_2$Me | CF$_2$Cl | Me | CN | |
| 10-174 | SO$_2$Me | OMe | Me | CN | |
| 10-175 | SO$_2$Me | NO$_2$ | Me | CN | |
| 10-176 | SO$_2$Me | SO$_2$Me | Me | CN | |
| 10-177 | Me | Me | Et | CN | |
| 10-178 | Me | F | Et | CN | |
| 10-179 | Me | Cl | Et | CN | |
| 10-180 | Me | Br | Et | CN | |
| 10-181 | Me | I | Et | CN | |
| 10-182 | Me | CF$_3$ | Et | CN | |
| 10-183 | Me | CHF$_2$ | Et | CN | |
| 10-184 | Me | CF$_2$Cl | Et | CN | |
| 10-185 | Me | OMe | Et | CN | |
| 10-186 | Me | NO$_2$ | Et | CN | |
| 10-187 | Me | SO$_2$Me | Et | CN | |
| 10-188 | Cl | Me | Et | CN | |
| 10-189 | Cl | F | Et | CN | |
| 10-190 | Cl | Cl | Et | CN | |
| 10-191 | Cl | Br | Et | CN | |
| 10-192 | Cl | I | Et | CN | |
| 10-193 | Cl | CF$_3$ | Et | CN | |
| 10-194 | Cl | CHF$_2$ | Et | CN | |
| 10-195 | Cl | CF$_2$Cl | Et | CN | |
| 10-196 | Cl | OMe | Et | CN | |
| 10-197 | Cl | NO$_2$ | Et | CN | |
| 10-198 | Cl | SO$_2$Me | Et | CN | |
| 10-199 | OMe | Me | Et | CN | |
| 10-200 | OMe | F | Et | CN | |
| 10-201 | OMe | Cl | Et | CN | |
| 10-202 | OMe | Br | Et | CN | |
| 10-203 | OMe | I | Et | CN | |
| 10-204 | OMe | CF$_3$ | Et | CN | |
| 10-205 | OMe | CHF$_2$ | Et | CN | |
| 10-206 | OMe | CF$_2$Cl | Et | CN | |
| 10-207 | OMe | OMe | Et | CN | |
| 10-208 | OMe | NO$_2$ | Et | CN | |
| 10-209 | OMe | SO$_2$Me | Et | CN | |
| 10-210 | SO$_2$Me | Me | Et | CN | |
| 10-211 | SO$_2$Me | F | Et | CN | |
| 10-212 | SO$_2$Me | Cl | Et | CN | |
| 10-213 | SO$_2$Me | Br | Et | CN | |
| 10-214 | SO$_2$Me | I | Et | CN | |
| 10-215 | SO$_2$Me | CF$_3$ | Et | CN | |
| 10-216 | SO$_2$Me | CHF$_2$ | Et | CN | |
| 10-217 | SO$_2$Me | CF$_2$Cl | Et | CN | |
| 10-218 | SO$_2$Me | OMe | Et | CN | |
| 10-219 | SO$_2$Me | NO$_2$ | Et | CN | |
| 10-220 | SO$_2$Me | SO$_2$Me | Et | CN | |
| 10-221 | Me | Me | CH$_2$CH$_2$OMe | CN | |
| 10-222 | Me | F | CH$_2$CH$_2$OMe | CN | |

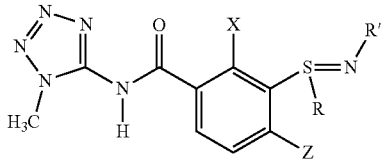

TABLE 10-continued

Compounds according to the invention of the formula (I) in which Q is Q1 and $R^x$ is a methyl group, R" and W are each hydrogen and t = 0

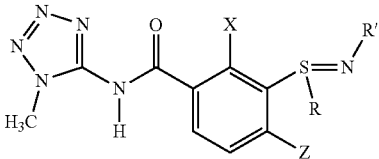

| No. | X | Z | R | R' | Physical Data ($^1$H NMR) |
|---|---|---|---|---|---|
| 10-223 | Me | Cl | CH$_2$CH$_2$OMe | CN | |
| 10-224 | Me | Br | CH$_2$CH$_2$OMe | CN | |
| 10-225 | Me | I | CH$_2$CH$_2$OMe | CN | |
| 10-226 | Me | CF$_3$ | CH$_2$CH$_2$OMe | CN | |
| 10-227 | Me | CHF$_2$ | CH$_2$CH$_2$OMe | CN | |
| 10-228 | Me | CF$_2$Cl | CH$_2$CH$_2$OMe | CN | |
| 10-229 | Me | OMe | CH$_2$CH$_2$OMe | CN | |
| 10-230 | Me | NO$_2$ | CH$_2$CH$_2$OMe | CN | |
| 10-231 | Me | SO$_2$Me | CH$_2$CH$_2$OMe | CN | |
| 10-232 | Cl | Me | CH$_2$CH$_2$OMe | CN | |
| 10-233 | Cl | F | CH$_2$CH$_2$OMe | CN | |
| 10-234 | Cl | Cl | CH$_2$CH$_2$OMe | CN | |
| 10-235 | Cl | Br | CH$_2$CH$_2$OMe | CN | |
| 10-236 | Cl | I | CH$_2$CH$_2$OMe | CN | |
| 10-237 | Cl | CF$_3$ | CH$_2$CH$_2$OMe | CN | |
| 10-238 | Cl | CHF$_2$ | CH$_2$CH$_2$OMe | CN | |
| 10-239 | Cl | CF$_2$Cl | CH$_2$CH$_2$OMe | CN | |
| 10-240 | Cl | OMe | CH$_2$CH$_2$OMe | CN | |
| 10-241 | Cl | NO$_2$ | CH$_2$CH$_2$OMe | CN | |
| 10-242 | Cl | SO$_2$Me | CH$_2$CH$_2$OMe | CN | |
| 10-243 | OMe | Me | CH$_2$CH$_2$OMe | CN | |
| 10-244 | OMe | F | CH$_2$CH$_2$OMe | CN | |
| 10-245 | OMe | Cl | CH$_2$CH$_2$OMe | CN | |
| 10-246 | OMe | Br | CH$_2$CH$_2$OMe | CN | |
| 10-247 | OMe | I | CH$_2$CH$_2$OMe | CN | |
| 10-248 | OMe | CF$_3$ | CH$_2$CH$_2$OMe | CN | |
| 10-249 | OMe | CHF$_2$ | CH$_2$CH$_2$OMe | CN | |
| 10-250 | OMe | CF$_2$Cl | CH$_2$CH$_2$OMe | CN | |
| 10-251 | OMe | OMe | CH$_2$CH$_2$OMe | CN | |
| 10-252 | OMe | NO$_2$ | CH$_2$CH$_2$OMe | CN | |
| 10-253 | OMe | SO$_2$Me | CH$_2$CH$_2$OMe | CN | |
| 10-254 | SO$_2$Me | Me | CH$_2$CH$_2$OMe | CN | |
| 10-255 | SO$_2$Me | F | CH$_2$CH$_2$OMe | CN | |
| 10-256 | SO$_2$Me | Cl | CH$_2$CH$_2$OMe | CN | |
| 10-257 | SO$_2$Me | Br | CH$_2$CH$_2$OMe | CN | |
| 10-258 | SO$_2$Me | I | CH$_2$CH$_2$OMe | CN | |
| 10-259 | SO$_2$Me | CF$_3$ | CH$_2$CH$_2$OMe | CN | |
| 10-260 | SO$_2$Me | CHF$_2$ | CH$_2$CH$_2$OMe | CN | |
| 10-261 | SO$_2$Me | CF$_2$Cl | CH$_2$CH$_2$OMe | CN | |
| 10-262 | SO$_2$Me | OMe | CH$_2$CH$_2$OMe | CN | |
| 10-263 | SO$_2$Me | NO$_2$ | CH$_2$CH$_2$OMe | CN | |
| 10-264 | SO$_2$Me | SO$_2$Me | CH$_2$CH$_2$OMe | CN | |
| 10-265 | Me | Me | Me | (C=O)CF$_3$ | |
| 10-266 | Me | F | Me | (C=O)CF$_3$ | |
| 10-267 | Me | Cl | Me | (C=O)CF$_3$ | |
| 10-268 | Me | Br | Me | (C=O)CF$_3$ | |
| 10-269 | Me | I | Me | (C=O)CF$_3$ | |
| 10-270 | Me | CF$_3$ | Me | (C=O)CF$_3$ | |
| 10-271 | Me | CHF$_2$ | Me | (C=O)CF$_3$ | |
| 10-272 | Me | CF$_2$Cl | Me | (C=O)CF$_3$ | |
| 10-273 | Me | OMe | Me | (C=O)CF$_3$ | |
| 10-274 | Me | NO$_2$ | Me | (C=O)CF$_3$ | |
| 10-275 | Me | SO$_2$Me | Me | (C=O)CF$_3$ | |
| 10-276 | Cl | Me | Me | (C=O)CF$_3$ | |
| 10-277 | Cl | F | Me | (C=O)CF$_3$ | |
| 10-278 | Cl | Cl | Me | (C=O)CF$_3$ | |
| 10-279 | Cl | Br | Me | (C=O)CF$_3$ | |
| 10-280 | Cl | I | Me | (C=O)CF$_3$ | |
| 10-281 | Cl | CF$_3$ | Me | (C=O)CF$_3$ | |
| 10-282 | Cl | CHF$_2$ | Me | (C=O)CF$_3$ | |
| 10-283 | Cl | CF$_2$Cl | Me | (C=O)CF$_3$ | |
| 10-284 | Cl | OMe | Me | (C=O)CF$_3$ | |
| 10-285 | Cl | NO$_2$ | Me | (C=O)CF$_3$ | |
| 10-286 | Cl | SO$_2$Me | Me | (C=O)CF$_3$ | |
| 10-287 | OMe | Me | Me | (C=O)CF$_3$ | |

TABLE 10-continued

Compounds according to the invention of the formula (I) in which Q is Q1 and $R^x$ is a methyl group, R" and W are each hydrogen and t = 0

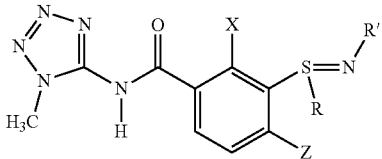

| No. | X | Z | R | R' | Physical Data ($^1$H NMR) |
|---|---|---|---|---|---|
| 10-288 | OMe | F | Me | (C=O)CF$_3$ | |
| 10-289 | OMe | Cl | Me | (C=O)CF$_3$ | |
| 10-290 | OMe | Br | Me | (C=O)CF$_3$ | |
| 10-291 | OMe | I | Me | (C=O)CF$_3$ | |
| 10-292 | OMe | CF$_3$ | Me | (C=O)CF$_3$ | |
| 10-293 | OMe | CHF$_2$ | Me | (C=O)CF$_3$ | |
| 10-294 | OMe | CF$_2$Cl | Me | (C=O)CF$_3$ | |
| 10-295 | OMe | OMe | Me | (C=O)CF$_3$ | |
| 10-296 | OMe | NO$_2$ | Me | (C=O)CF$_3$ | |
| 10-297 | OMe | SO$_2$Me | Me | (C=O)CF$_3$ | |
| 10-298 | SO$_2$Me | Me | Me | (C=O)CF$_3$ | |
| 10-299 | SO$_2$Me | F | Me | (C=O)CF$_3$ | |
| 10-300 | SO$_2$Me | Cl | Me | (C=O)CF$_3$ | |
| 10-301 | SO$_2$Me | Br | Me | (C=O)CF$_3$ | |
| 10-302 | SO$_2$Me | I | Me | (C=O)CF$_3$ | |
| 10-303 | SO$_2$Me | CF$_3$ | Me | (C=O)CF$_3$ | |
| 10-304 | SO$_2$Me | CHF$_2$ | Me | (C=O)CF$_3$ | |
| 10-305 | SO$_2$Me | CF$_2$Cl | Me | (C=O)CF$_3$ | |
| 10-306 | SO$_2$Me | OMe | Me | (C=O)CF$_3$ | |
| 10-307 | SO$_2$Me | NO$_2$ | Me | (C=O)CF$_3$ | |
| 10-308 | SO$_2$Me | SO$_2$Me | Me | (C=O)CF$_3$ | |

TABLE 11

Compounds according to the invention of the formula (I) in which Q is Q1 and $R^x$ is an ethyl group, R" and W are each hydrogen and t = 0

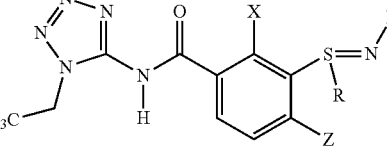

| No. | X | Z | R | R' | Physical Data ($^1$H NMR) |
|---|---|---|---|---|---|
| 11-1 | Me | Me | Me | H | |
| 11-2 | Me | F | Me | H | |
| 11-3 | Me | Cl | Me | H | |
| 11-4 | Me | Br | Me | H | |
| 11-5 | Me | I | Me | H | |
| 11-6 | Me | CF$_3$ | Me | H | |
| 11-7 | Me | CHF$_2$ | Me | H | |
| 11-8 | Me | CF$_2$Cl | Me | H | |
| 11-9 | Me | OMe | Me | H | |
| 11-10 | Me | NO$_2$ | Me | H | |
| 11-11 | Me | SO$_2$Me | Me | H | |
| 11-12 | Cl | Me | Me | H | |
| 11-13 | Cl | F | Me | H | |
| 11-14 | Cl | Cl | Me | H | |
| 11-15 | Cl | Br | Me | H | |
| 11-16 | Cl | I | Me | H | |
| 11-17 | Cl | CF$_3$ | Me | H | |
| 11-18 | Cl | CHF$_2$ | Me | H | |
| 11-19 | Cl | CF$_2$Cl | Me | H | |
| 11-20 | Cl | OMe | Me | H | |
| 11-21 | Cl | NO$_2$ | Me | H | |
| 11-22 | Cl | SO$_2$Me | Me | H | |
| 11-23 | OMe | Me | Me | H | |
| 11-24 | OMe | F | Me | H | |
| 11-25 | OMe | Cl | Me | H | |

TABLE 11-continued

Compounds according to the invention of the formula (I) in which Q is Q1 and $R^x$ is an ethyl group, R'' and W are each hydrogen and t = 0

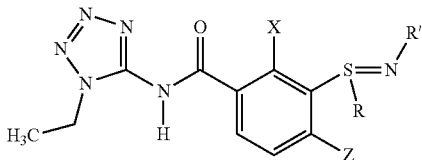

| No. | X | Z | R | R' | Physical Data ($^1$H NMR) |
|---|---|---|---|---|---|
| 11-26 | OMe | Br | Me | H | |
| 11-27 | OMe | I | Me | H | |
| 11-28 | OMe | $CF_3$ | Me | H | |
| 11-29 | OMe | $CHF_2$ | Me | H | |
| 11-30 | OMe | $CF_2Cl$ | Me | H | |
| 11-31 | OMe | OMe | Me | H | |
| 11-32 | OMe | $NO_2$ | Me | H | |
| 11-33 | OMe | $SO_2Me$ | Me | H | |
| 11-34 | $SO_2Me$ | Me | Me | H | |
| 11-35 | $SO_2Me$ | F | Me | H | |
| 11-36 | $SO_2Me$ | Cl | Me | H | |
| 11-37 | $SO_2Me$ | Br | Me | H | |
| 11-38 | $SO_2Me$ | I | Me | H | |
| 11-39 | $SO_2Me$ | $CF_3$ | Me | H | |
| 11-40 | $SO_2Me$ | $CHF_2$ | Me | H | |
| 11-41 | $SO_2Me$ | $CF_2Cl$ | Me | H | |
| 11-42 | $SO_2Me$ | OMe | Me | H | |
| 11-43 | $SO_2Me$ | $NO_2$ | Me | H | |
| 11-44 | $SO_2Me$ | $SO_2Me$ | Me | H | |
| 11-45 | Me | Me | Et | H | |
| 11-46 | Me | F | Et | H | |
| 11-47 | Me | Cl | Et | H | |
| 11-48 | Me | Br | Et | H | |
| 11-49 | Me | I | Et | H | |
| 11-50 | Me | $CF_3$ | Et | H | |
| 11-51 | Me | $CHF_2$ | Et | H | |
| 11-52 | Me | $CF_2Cl$ | Et | H | |
| 11-53 | Me | OMe | Et | H | |
| 11-54 | Me | $NO_2$ | Et | H | |
| 11-55 | Me | $SO_2Me$ | Et | H | |
| 11-56 | Cl | Me | Et | H | |
| 11-57 | Cl | F | Et | H | |
| 11-58 | Cl | Cl | Et | H | |
| 11-59 | Cl | Br | Et | H | |
| 11-60 | Cl | I | Et | H | |
| 11-61 | Cl | $CF_3$ | Et | H | |
| 11-62 | Cl | $CHF_2$ | Et | H | |
| 11-63 | Cl | $CF_2Cl$ | Et | H | |
| 11-64 | Cl | OMe | Et | H | |
| 11-65 | Cl | $NO_2$ | Et | H | |
| 11-66 | Cl | $SO_2Me$ | Et | H | |
| 11-67 | OMe | Me | Et | H | |
| 11-68 | OMe | F | Et | H | |
| 11-69 | OMe | Cl | Et | H | |
| 11-70 | OMe | Br | Et | H | |
| 11-71 | OMe | I | Et | H | |
| 11-72 | OMe | $CF_3$ | Et | H | |
| 11-73 | OMe | $CHF_2$ | Et | H | |
| 11-74 | OMe | $CF_2Cl$ | Et | H | |
| 11-75 | OMe | OMe | Et | H | |
| 11-76 | OMe | $NO_2$ | Et | H | |
| 11-77 | OMe | $SO_2Me$ | Et | H | |
| 11-78 | $SO_2Me$ | Me | Et | H | |
| 11-79 | $SO_2Me$ | F | Et | H | |
| 11-80 | $SO_2Me$ | Cl | Et | H | |
| 11-81 | $SO_2Me$ | Br | Et | H | |
| 11-82 | $SO_2Me$ | I | Et | H | |
| 11-83 | $SO_2Me$ | $CF_3$ | Et | H | |
| 11-84 | $SO_2Me$ | $CHF_2$ | Et | H | |
| 11-85 | $SO_2Me$ | $CF_2Cl$ | Et | H | |
| 11-86 | $SO_2Me$ | OMe | Et | H | |
| 11-87 | $SO_2Me$ | $NO_2$ | Et | H | |
| 11-88 | $SO_2Me$ | $SO_2Me$ | Et | H | |
| 11-89 | Me | Me | $CH_2CH_2OMe$ | H | |
| 11-90 | Me | F | $CH_2CH_2OMe$ | H | |
| 11-91 | Me | Cl | $CH_2CH_2OMe$ | H | |

TABLE 11-continued

Compounds according to the invention of the formula (I) in which Q is Q1 and $R^x$ is an ethyl group, R'' and W are each hydrogen and t = 0

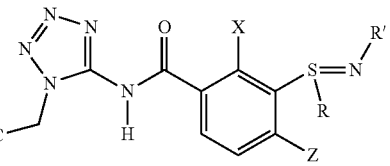

| No. | X | Z | R | R' | Physical Data ($^1$H NMR) |
|---|---|---|---|---|---|
| 11-92 | Me | Br | $CH_2CH_2OMe$ | H | |
| 11-93 | Me | I | $CH_2CH_2OMe$ | H | |
| 11-94 | Me | $CF_3$ | $CH_2CH_2OMe$ | H | |
| 11-95 | Me | $CHF_2$ | $CH_2CH_2OMe$ | H | |
| 11-96 | Me | $CF_2Cl$ | $CH_2CH_2OMe$ | H | |
| 11-97 | Me | OMe | $CH_2CH_2OMe$ | H | |
| 11-98 | Me | $NO_2$ | $CH_2CH_2OMe$ | H | |
| 11-99 | Me | $SO_2Me$ | $CH_2CH_2OMe$ | H | |
| 11-100 | Cl | Me | $CH_2CH_2OMe$ | H | |
| 11-101 | Cl | F | $CH_2CH_2OMe$ | H | |
| 11-102 | Cl | Cl | $CH_2CH_2OMe$ | H | |
| 11-103 | Cl | Br | $CH_2CH_2OMe$ | H | |
| 11-104 | Cl | I | $CH_2CH_2OMe$ | H | |
| 11-105 | Cl | $CF_3$ | $CH_2CH_2OMe$ | H | |
| 11-106 | Cl | $CHF_2$ | $CH_2CH_2OMe$ | H | |
| 11-107 | Cl | $CF_2Cl$ | $CH_2CH_2OMe$ | H | |
| 11-108 | Cl | OMe | $CH_2CH_2OMe$ | H | |
| 11-109 | Cl | $NO_2$ | $CH_2CH_2OMe$ | H | |
| 11-110 | Cl | $SO_2Me$ | $CH_2CH_2OMe$ | H | |
| 11-111 | OMe | Me | $CH_2CH_2OMe$ | H | |
| 11-112 | OMe | F | $CH_2CH_2OMe$ | H | |
| 11-113 | OMe | Cl | $CH_2CH_2OMe$ | H | |
| 11-114 | OMe | Br | $CH_2CH_2OMe$ | H | |
| 11-115 | OMe | I | $CH_2CH_2OMe$ | H | |
| 11-116 | OMe | $CF_3$ | $CH_2CH_2OMe$ | H | |
| 11-117 | OMe | $CHF_2$ | $CH_2CH_2OMe$ | H | |
| 11-118 | OMe | $CF_2Cl$ | $CH_2CH_2OMe$ | H | |
| 11-119 | OMe | OMe | $CH_2CH_2OMe$ | H | |
| 11-120 | OMe | $NO_2$ | $CH_2CH_2OMe$ | H | |
| 11-121 | OMe | $SO_2Me$ | $CH_2CH_2OMe$ | H | |
| 11-122 | $SO_2Me$ | Me | $CH_2CH_2OMe$ | H | |
| 11-123 | $SO_2Me$ | F | $CH_2CH_2OMe$ | H | |
| 11-124 | $SO_2Me$ | Cl | $CH_2CH_2OMe$ | H | |
| 11-125 | $SO_2Me$ | Br | $CH_2CH_2OMe$ | H | |
| 11-126 | $SO_2Me$ | I | $CH_2CH_2OMe$ | H | |
| 11-127 | $SO_2Me$ | $CF_3$ | $CH_2CH_2OMe$ | H | |
| 11-128 | $SO_2Me$ | $CHF_2$ | $CH_2CH_2OMe$ | H | |
| 11-129 | $SO_2Me$ | $CF_2Cl$ | $CH_2CH_2OMe$ | H | |
| 11-130 | $SO_2Me$ | OMe | $CH_2CH_2OMe$ | H | |
| 11-131 | $SO_2Me$ | $NO_2$ | $CH_2CH_2OMe$ | H | |
| 11-132 | $SO_2Me$ | $SO_2Me$ | $CH_2CH_2OMe$ | H | |
| 11-133 | Me | Me | Me | CN | |
| 11-134 | Me | F | Me | CN | |
| 11-135 | Me | Cl | Me | CN | |
| 11-136 | Me | Br | Me | CN | |
| 11-137 | Me | I | Me | CN | |
| 11-138 | Me | $CF_3$ | Me | CN | |
| 11-139 | Me | $CHF_2$ | Me | CN | |
| 11-140 | Me | $CF_2Cl$ | Me | CN | |
| 11-141 | Me | OMe | Me | CN | |
| 11-142 | Me | $NO_2$ | Me | CN | |
| 11-143 | Me | $SO_2Me$ | Me | CN | |
| 11-144 | Cl | Me | Me | CN | |
| 11-145 | Cl | F | Me | CN | |
| 11-146 | Cl | Cl | Me | CN | |
| 11-147 | Cl | Br | Me | CN | |
| 11-148 | Cl | I | Me | CN | |
| 11-149 | Cl | $CF_3$ | Me | CN | |
| 11-150 | Cl | $CHF_2$ | Me | CN | |
| 11-151 | Cl | $CF_2Cl$ | Me | CN | |
| 11-152 | Cl | OMe | Me | CN | |
| 11-153 | Cl | $NO_2$ | Me | CN | |
| 11-154 | Cl | $SO_2Me$ | Me | CN | |
| 11-155 | OMe | Me | Me | CN | |
| 11-156 | OMe | F | Me | CN | |
| 11-157 | OMe | Cl | Me | CN | |

TABLE 11-continued

Compounds according to the invention of the formula (I) in which Q is Q1 and R$^x$ is an ethyl group, R'' and W are each hydrogen and t = 0

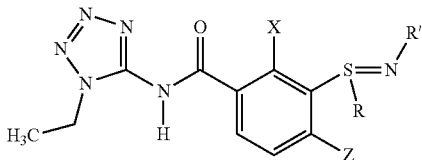

| No. | X | Z | R | R' | Physical Data ($^1$H NMR) |
|---|---|---|---|---|---|
| 11-158 | OMe | Br | Me | CN | |
| 11-159 | OMe | I | Me | CN | |
| 11-160 | OMe | CF$_3$ | Me | CN | |
| 11-161 | OMe | CHF$_2$ | Me | CN | |
| 11-162 | OMe | CF$_2$Cl | Me | CN | |
| 11-163 | OMe | OMe | Me | CN | |
| 11-164 | OMe | NO$_2$ | Me | CN | |
| 11-165 | OMe | SO$_2$Me | Me | CN | |
| 11-166 | SO$_2$Me | Me | Me | CN | |
| 11-167 | SO$_2$Me | F | Me | CN | |
| 11-168 | SO$_2$Me | Cl | Me | CN | |
| 11-169 | SO$_2$Me | Br | Me | CN | |
| 11-170 | SO$_2$Me | I | Me | CN | |
| 11-171 | SO$_2$Me | CF$_3$ | Me | CN | |
| 11-172 | SO$_2$Me | CHF$_2$ | Me | CN | |
| 11-173 | SO$_2$Me | CF$_2$Cl | Me | CN | |
| 11-174 | SO$_2$Me | OMe | Me | CN | |
| 11-175 | SO$_2$Me | NO$_2$ | Me | CN | |
| 11-176 | SO$_2$Me | SO$_2$Me | Me | CN | |
| 11-177 | Me | Me | Et | CN | |
| 11-178 | Me | F | Et | CN | |
| 11-179 | Me | Cl | Et | CN | |
| 11-180 | Me | Br | Et | CN | |
| 11-181 | Me | I | Et | CN | |
| 11-182 | Me | CF$_3$ | Et | CN | |
| 11-183 | Me | CHF$_2$ | Et | CN | |
| 11-184 | Me | CF$_2$Cl | Et | CN | |
| 11-185 | Me | OMe | Et | CN | |
| 11-186 | Me | NO$_2$ | Et | CN | |
| 11-187 | Me | SO$_2$Me | Et | CN | |
| 11-188 | Cl | Me | Et | CN | |
| 11-189 | Cl | F | Et | CN | |
| 11-190 | Cl | Cl | Et | CN | |
| 11-191 | Cl | Br | Et | CN | |
| 11-192 | Cl | I | Et | CN | |
| 11-193 | Cl | CF$_3$ | Et | CN | |
| 11-194 | Cl | CHF$_2$ | Et | CN | |
| 11-195 | Cl | CF$_2$Cl | Et | CN | |
| 11-196 | Cl | OMe | Et | CN | |
| 11-197 | Cl | NO$_2$ | Et | CN | |
| 11-198 | Cl | SO$_2$Me | Et | CN | |
| 11-199 | OMe | Me | Et | CN | |
| 11-200 | OMe | F | Et | CN | |
| 11-201 | OMe | Cl | Et | CN | |
| 11-202 | OMe | Br | Et | CN | |
| 11-203 | OMe | I | Et | CN | |
| 11-204 | OMe | CF$_3$ | Et | CN | |
| 11-205 | OMe | CHF$_2$ | Et | CN | |
| 11-206 | OMe | CF$_2$Cl | Et | CN | |
| 11-207 | OMe | OMe | Et | CN | |
| 11-208 | OMe | NO$_2$ | Et | CN | |
| 11-209 | OMe | SO$_2$Me | Et | CN | |
| 11-210 | SO$_2$Me | Me | Et | CN | |
| 11-211 | SO$_2$Me | F | Et | CN | |
| 11-212 | SO$_2$Me | Cl | Et | CN | |
| 11-213 | SO$_2$Me | Br | Et | CN | |
| 11-214 | SO$_2$Me | I | Et | CN | |
| 11-215 | SO$_2$Me | CF$_3$ | Et | CN | |
| 11-216 | SO$_2$Me | CHF$_2$ | Et | CN | |
| 11-217 | SO$_2$Me | CF$_2$Cl | Et | CN | |
| 11-218 | SO$_2$Me | OMe | Et | CN | |
| 11-219 | SO$_2$Me | NO$_2$ | Et | CN | |
| 11-220 | SO$_2$Me | SO$_2$Me | Et | CN | |
| 11-221 | Me | Me | CH$_2$CH$_2$OMe | CN | |
| 11-222 | Me | F | CH$_2$CH$_2$OMe | CN | |
| 11-223 | Me | Cl | CH$_2$CH$_2$OMe | CN | |
| 11-224 | Me | Br | CH$_2$CH$_2$OMe | CN | |
| 11-225 | Me | I | CH$_2$CH$_2$OMe | CN | |
| 11-226 | Me | CF$_3$ | CH$_2$CH$_2$OMe | CN | |
| 11-227 | Me | CHF$_2$ | CH$_2$CH$_2$OMe | CN | |
| 11-228 | Me | CF$_2$Cl | CH$_2$CH$_2$OMe | CN | |
| 11-229 | Me | OMe | CH$_2$CH$_2$OMe | CN | |
| 11-230 | Me | NO$_2$ | CH$_2$CH$_2$OMe | CN | |
| 11-231 | Me | SO$_2$Me | CH$_2$CH$_2$OMe | CN | |
| 11-232 | Cl | Me | CH$_2$CH$_2$OMe | CN | |
| 11-233 | Cl | F | CH$_2$CH$_2$OMe | CN | |
| 11-234 | Cl | Cl | CH$_2$CH$_2$OMe | CN | |
| 11-235 | Cl | Br | CH$_2$CH$_2$OMe | CN | |
| 11-236 | Cl | I | CH$_2$CH$_2$OMe | CN | |
| 11-237 | Cl | CF$_3$ | CH$_2$CH$_2$OMe | CN | |
| 11-238 | Cl | CHF$_2$ | CH$_2$CH$_2$OMe | CN | |
| 11-239 | Cl | CF$_2$Cl | CH$_2$CH$_2$OMe | CN | |
| 11-240 | Cl | OMe | CH$_2$CH$_2$OMe | CN | |
| 11-241 | Cl | NO$_2$ | CH$_2$CH$_2$OMe | CN | |
| 11-242 | Cl | SO$_2$Me | CH$_2$CH$_2$OMe | CN | |
| 11-243 | OMe | Me | CH$_2$CH$_2$OMe | CN | |
| 11-244 | OMe | F | CH$_2$CH$_2$OMe | CN | |
| 11-245 | OMe | Cl | CH$_2$CH$_2$OMe | CN | |
| 11-246 | OMe | Br | CH$_2$CH$_2$OMe | CN | |
| 11-247 | OMe | I | CH$_2$CH$_2$OMe | CN | |
| 11-248 | OMe | CF$_3$ | CH$_2$CH$_2$OMe | CN | |
| 11-249 | OMe | CHF$_2$ | CH$_2$CH$_2$OMe | CN | |
| 11-250 | OMe | CF$_2$Cl | CH$_2$CH$_2$OMe | CN | |
| 11-251 | OMe | OMe | CH$_2$CH$_2$OMe | CN | |
| 11-252 | OMe | NO$_2$ | CH$_2$CH$_2$OMe | CN | |
| 11-253 | OMe | SO$_2$Me | CH$_2$CH$_2$OMe | CN | |
| 11-254 | SO$_2$Me | Me | CH$_2$CH$_2$OMe | CN | |
| 11-255 | SO$_2$Me | F | CH$_2$CH$_2$OMe | CN | |
| 11-256 | SO$_2$Me | Cl | CH$_2$CH$_2$OMe | CN | |
| 11-257 | SO$_2$Me | Br | CH$_2$CH$_2$OMe | CN | |
| 11-258 | SO$_2$Me | I | CH$_2$CH$_2$OMe | CN | |
| 11-259 | SO$_2$Me | CF$_3$ | CH$_2$CH$_2$OMe | CN | |
| 11-260 | SO$_2$Me | CHF$_2$ | CH$_2$CH$_2$OMe | CN | |
| 11-261 | SO$_2$Me | CF$_2$Cl | CH$_2$CH$_2$OMe | CN | |
| 11-262 | SO$_2$Me | OMe | CH$_2$CH$_2$OMe | CN | |
| 11-263 | SO$_2$Me | NO$_2$ | CH$_2$CH$_2$OMe | CN | |
| 11-264 | SO$_2$Me | SO$_2$Me | CH$_2$CH$_2$OMe | CN | |

TABLE 12

Compounds according to the invention of the formula (I) in which Q is Q1 and R$^x$ is an n-propyl group, R'' and W are each hydrogen and t = 0

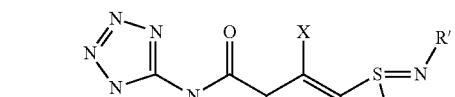

| No. | X | Z | R | R' | Physical Data ($^1$H NMR) |
|---|---|---|---|---|---|
| 12-1 | Me | Me | Me | H | |
| 12-2 | Me | F | Me | H | |
| 12-3 | Me | Cl | Me | H | |
| 12-4 | Me | Br | Me | H | |
| 12-5 | Me | I | Me | H | |
| 12-6 | Me | CF$_3$ | Me | H | |

TABLE 12-continued

Compounds according to the invention of the formula (I) in which Q is Q1 and $R^x$ is an n-propyl group, R″ and W are each hydrogen and t = 0

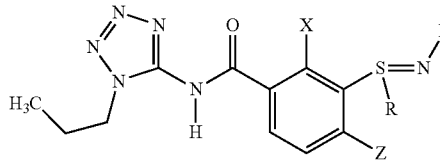

| No. | X | Z | R | R' | Physical Data ($^1$H NMR) |
|---|---|---|---|---|---|
| 12-7 | Me | CHF$_2$ | Me | H | |
| 12-8 | Me | CF$_2$Cl | Me | H | |
| 12-9 | Me | OMe | Me | H | |
| 12-10 | Me | NO$_2$ | Me | H | |
| 12-11 | Me | SO$_2$Me | Me | H | |
| 12-12 | Cl | Me | Me | H | |
| 12-13 | Cl | F | Me | H | |
| 12-14 | Cl | Cl | Me | H | |
| 12-15 | Cl | Br | Me | H | |
| 12-16 | Cl | I | Me | H | |
| 12-17 | Cl | CF$_3$ | Me | H | |
| 12-18 | Cl | CHF$_2$ | Me | H | |
| 12-19 | Cl | CF$_2$Cl | Me | H | |
| 12-20 | Cl | OMe | Me | H | |
| 12-21 | Cl | NO$_2$ | Me | H | |
| 12-22 | Cl | SO$_2$Me | Me | H | |
| 12-23 | OMe | Me | Me | H | |
| 12-24 | OMe | F | Me | H | |
| 12-25 | OMe | Cl | Me | H | |
| 12-26 | OMe | Br | Me | H | |
| 12-27 | OMe | I | Me | H | |
| 12-28 | OMe | CF$_3$ | Me | H | |
| 12-29 | OMe | CHF$_2$ | Me | H | |
| 12-30 | OMe | CF$_2$Cl | Me | H | |
| 12-31 | OMe | OMe | Me | H | |
| 12-32 | OMe | NO$_2$ | Me | H | |
| 12-33 | OMe | SO$_2$Me | Me | H | |
| 12-34 | SO$_2$Me | Me | Me | H | |
| 12-35 | SO$_2$Me | F | Me | H | |
| 12-36 | SO$_2$Me | Cl | Me | H | |
| 12-37 | SO$_2$Me | Br | Me | H | |
| 12-38 | SO$_2$Me | I | Me | H | |
| 12-39 | SO$_2$Me | CF$_3$ | Me | H | |
| 12-40 | SO$_2$Me | CHF$_2$ | Me | H | |
| 12-41 | SO$_2$Me | CF$_2$Cl | Me | H | |
| 12-42 | SO$_2$Me | OMe | Me | H | |
| 12-43 | SO$_2$Me | NO$_2$ | Me | H | |
| 12-44 | SO$_2$Me | SO$_2$Me | Me | H | |
| 12-45 | Me | Me | Et | H | |
| 12-46 | Me | F | Et | H | |
| 12-47 | Me | Cl | Et | H | |
| 12-48 | Me | Br | Et | H | |
| 12-49 | Me | I | Et | H | |
| 12-50 | Me | CF$_3$ | Et | H | |
| 12-51 | Me | CHF$_2$ | Et | H | |
| 12-52 | Me | CF$_2$Cl | Et | H | |
| 12-53 | Me | OMe | Et | H | |
| 12-54 | Me | NO$_2$ | Et | H | |
| 12-55 | Me | SO$_2$Me | Et | H | |
| 12-56 | Cl | Me | Et | H | |
| 12-57 | Cl | F | Et | H | |
| 12-58 | Cl | Cl | Et | H | |
| 12-59 | Cl | Br | Et | H | |
| 12-60 | Cl | I | Et | H | |
| 12-61 | Cl | CF$_3$ | Et | H | |
| 12-62 | Cl | CHF$_2$ | Et | H | |
| 12-63 | Cl | CF$_2$Cl | Et | H | |
| 12-64 | Cl | OMe | Et | H | |
| 12-65 | Cl | NO$_2$ | Et | H | |
| 12-66 | Cl | SO$_2$Me | Et | H | |
| 12-67 | OMe | Me | Et | H | |
| 12-68 | OMe | F | Et | H | |
| 12-69 | OMe | Cl | Et | H | |
| 12-70 | OMe | Br | Et | H | |
| 12-71 | OMe | I | Et | H | |
| 12-72 | OMe | CF$_3$ | Et | H | |

TABLE 12-continued

Compounds according to the invention of the formula (I) in which Q is Q1 and $R^x$ is an n-propyl group, R″ and W are each hydrogen and t = 0

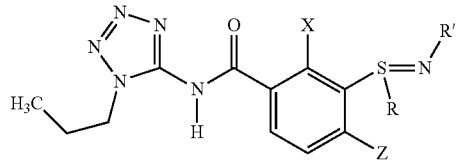

| No. | X | Z | R | R' | Physical Data ($^1$H NMR) |
|---|---|---|---|---|---|
| 12-73 | OMe | CHF$_2$ | Et | H | |
| 12-74 | OMe | CF$_2$Cl | Et | H | |
| 12-75 | OMe | OMe | Et | H | |
| 12-76 | OMe | NO$_2$ | Et | H | |
| 12-77 | OMe | SO$_2$Me | Et | H | |
| 12-78 | SO$_2$Me | Me | Et | H | |
| 12-79 | SO$_2$Me | F | Et | H | |
| 12-80 | SO$_2$Me | Cl | Et | H | |
| 12-81 | SO$_2$Me | Br | Et | H | |
| 12-82 | SO$_2$Me | I | Et | H | |
| 12-83 | SO$_2$Me | CF$_3$ | Et | H | |
| 12-84 | SO$_2$Me | CHF$_2$ | Et | H | |
| 12-85 | SO$_2$Me | CF$_2$Cl | Et | H | |
| 12-86 | SO$_2$Me | OMe | Et | H | |
| 12-87 | SO$_2$Me | NO$_2$ | Et | H | |
| 12-88 | SO$_2$Me | SO$_2$Me | Et | H | |
| 12-89 | Me | Me | CH$_2$CH$_2$OMe | H | |
| 12-90 | Me | F | CH$_2$CH$_2$OMe | H | |
| 12-91 | Me | Cl | CH$_2$CH$_2$OMe | H | |
| 12-92 | Me | Br | CH$_2$CH$_2$OMe | H | |
| 12-93 | Me | I | CH$_2$CH$_2$OMe | H | |
| 12-94 | Me | CF$_3$ | CH$_2$CH$_2$OMe | H | |
| 12-95 | Me | CHF$_2$ | CH$_2$CH$_2$OMe | H | |
| 12-96 | Me | CF$_2$Cl | CH$_2$CH$_2$OMe | H | |
| 12-97 | Me | OMe | CH$_2$CH$_2$OMe | H | |
| 12-98 | Me | NO$_2$ | CH$_2$CH$_2$OMe | H | |
| 12-99 | Me | SO$_2$Me | CH$_2$CH$_2$OMe | H | |
| 12-100 | Cl | Me | CH$_2$CH$_2$OMe | H | |
| 12-101 | Cl | F | CH$_2$CH$_2$OMe | H | |
| 12-102 | Cl | Cl | CH$_2$CH$_2$OMe | H | |
| 12-103 | Cl | Br | CH$_2$CH$_2$OMe | H | |
| 12-104 | Cl | I | CH$_2$CH$_2$OMe | H | |
| 12-105 | Cl | CF$_3$ | CH$_2$CH$_2$OMe | H | |
| 12-106 | Cl | CHF$_2$ | CH$_2$CH$_2$OMe | H | |
| 12-107 | Cl | CF$_2$Cl | CH$_2$CH$_2$OMe | H | |
| 12-108 | Cl | OMe | CH$_2$CH$_2$OMe | H | |
| 12-109 | Cl | NO$_2$ | CH$_2$CH$_2$OMe | H | |
| 12-110 | Cl | SO$_2$Me | CH$_2$CH$_2$OMe | H | |
| 12-111 | OMe | Me | CH$_2$CH$_2$OMe | H | |
| 12-112 | OMe | F | CH$_2$CH$_2$OMe | H | |
| 12-113 | OMe | Cl | CH$_2$CH$_2$OMe | H | |
| 12-114 | OMe | Br | CH$_2$CH$_2$OMe | H | |
| 12-115 | OMe | I | CH$_2$CH$_2$OMe | H | |
| 12-116 | OMe | CF$_3$ | CH$_2$CH$_2$OMe | H | |
| 12-117 | OMe | CHF$_2$ | CH$_2$CH$_2$OMe | H | |
| 12-118 | OMe | CF$_2$Cl | CH$_2$CH$_2$OMe | H | |
| 12-119 | OMe | OMe | CH$_2$CH$_2$OMe | H | |
| 12-120 | OMe | NO$_2$ | CH$_2$CH$_2$OMe | H | |
| 12-121 | OMe | SO$_2$Me | CH$_2$CH$_2$OMe | H | |
| 12-122 | SO$_2$Me | Me | CH$_2$CH$_2$OMe | H | |
| 12-123 | SO$_2$Me | F | CH$_2$CH$_2$OMe | H | |
| 12-124 | SO$_2$Me | Cl | CH$_2$CH$_2$OMe | H | |
| 12-125 | SO$_2$Me | Br | CH$_2$CH$_2$OMe | H | |
| 12-126 | SO$_2$Me | I | CH$_2$CH$_2$OMe | H | |
| 12-127 | SO$_2$Me | CF$_3$ | CH$_2$CH$_2$OMe | H | |
| 12-128 | SO$_2$Me | CHF$_2$ | CH$_2$CH$_2$OMe | H | |
| 12-129 | SO$_2$Me | CF$_2$Cl | CH$_2$CH$_2$OMe | H | |
| 12-130 | SO$_2$Me | OMe | CH$_2$CH$_2$OMe | H | |
| 12-131 | SO$_2$Me | NO$_2$ | CH$_2$CH$_2$OMe | H | |
| 12-132 | SO$_2$Me | SO$_2$Me | CH$_2$CH$_2$OMe | H | |
| 12-133 | Me | Me | Me | CN | |
| 12-134 | Me | F | Me | CN | |
| 12-135 | Me | Cl | Me | CN | |
| 12-136 | Me | Br | Me | CN | |
| 12-137 | Me | I | Me | CN | |
| 12-138 | Me | CF$_3$ | Me | CN | |

TABLE 12-continued

Compounds according to the invention of the formula (I) in which Q is Q1 and R$^x$ is an n-propyl group, R" and W are each hydrogen and t = 0

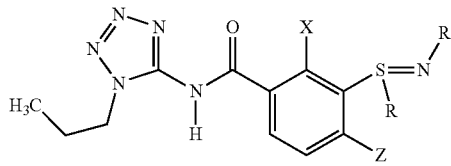

| No. | X | Z | R | R' | Physical Data ($^1$H NMR) |
|---|---|---|---|---|---|
| 12-139 | Me | CHF$_2$ | Me | CN | |
| 12-140 | Me | CF$_2$Cl | Me | CN | |
| 12-141 | Me | OMe | Me | CN | |
| 12-142 | Me | NO$_2$ | Me | CN | |
| 12-143 | Me | SO$_2$Me | Me | CN | |
| 12-144 | Cl | Me | Me | CN | |
| 12-145 | Cl | F | Me | CN | |
| 12-146 | Cl | Cl | Me | CN | |
| 12-147 | Cl | Br | Me | CN | |
| 12-148 | Cl | I | Me | CN | |
| 12-149 | Cl | CF$_3$ | Me | CN | |
| 12-150 | Cl | CHF$_2$ | Me | CN | |
| 12-151 | Cl | CF$_2$Cl | Me | CN | |
| 12-152 | Cl | OMe | Me | CN | |
| 12-153 | Cl | NO$_2$ | Me | CN | |
| 12-154 | Cl | SO$_2$Me | Me | CN | |
| 12-155 | OMe | Me | Me | CN | |
| 12-156 | OMe | F | Me | CN | |
| 12-157 | OMe | Cl | Me | CN | |
| 12-158 | OMe | Br | Me | CN | |
| 12-159 | OMe | I | Me | CN | |
| 12-160 | OMe | CF$_3$ | Me | CN | |
| 12-161 | OMe | CHF$_2$ | Me | CN | |
| 12-162 | OMe | CF$_2$Cl | Me | CN | |
| 12-163 | OMe | OMe | Me | CN | |
| 12-164 | OMe | NO$_2$ | Me | CN | |
| 12-165 | OMe | SO$_2$Me | Me | CN | |
| 12-166 | SO$_2$Me | Me | Me | CN | |
| 12-167 | SO$_2$Me | F | Me | CN | |
| 12-168 | SO$_2$Me | Cl | Me | CN | |
| 12-169 | SO$_2$Me | Br | Me | CN | |
| 12-170 | SO$_2$Me | I | Me | CN | |
| 12-171 | SO$_2$Me | CF$_3$ | Me | CN | |
| 12-172 | SO$_2$Me | CHF$_2$ | Me | CN | |
| 12-173 | SO$_2$Me | CF$_2$Cl | Me | CN | |
| 12-174 | SO$_2$Me | OMe | Me | CN | |
| 12-175 | SO$_2$Me | NO$_2$ | Me | CN | |
| 12-176 | SO$_2$Me | SO$_2$Me | Me | CN | |
| 12-177 | Me | Me | Et | CN | |
| 12-178 | Me | F | Et | CN | |
| 12-179 | Me | Cl | Et | CN | |
| 12-180 | Me | Br | Et | CN | |
| 12-181 | Me | I | Et | CN | |
| 12-182 | Me | CF$_3$ | Et | CN | |
| 12-183 | Me | CHF$_2$ | Et | CN | |
| 12-184 | Me | CF$_2$Cl | Et | CN | |
| 12-185 | Me | OMe | Et | CN | |
| 12-186 | Me | NO$_2$ | Et | CN | |
| 12-187 | Me | SO$_2$Me | Et | CN | |
| 12-188 | Cl | Me | Et | CN | |
| 12-189 | Cl | F | Et | CN | |
| 12-190 | Cl | Cl | Et | CN | |
| 12-191 | Cl | Br | Et | CN | |
| 12-192 | Cl | I | Et | CN | |
| 12-193 | Cl | CF$_3$ | Et | CN | |
| 12-194 | Cl | CHF$_2$ | Et | CN | |
| 12-195 | Cl | CF$_2$Cl | Et | CN | |
| 12-196 | Cl | OMe | Et | CN | |
| 12-197 | Cl | NO$_2$ | Et | CN | |
| 12-198 | Cl | SO$_2$Me | Et | CN | |
| 12-199 | OMe | Me | Et | CN | |
| 12-200 | OMe | F | Et | CN | |
| 12-201 | OMe | Cl | Et | CN | |
| 12-202 | OMe | Br | Et | CN | |
| 12-203 | OMe | I | Et | CN | |
| 12-204 | OMe | CF$_3$ | Et | CN | |

TABLE 12-continued

Compounds according to the invention of the formula (I) in which Q is Q1 and R$^x$ is an n-propyl group, R" and W are each hydrogen and t = 0

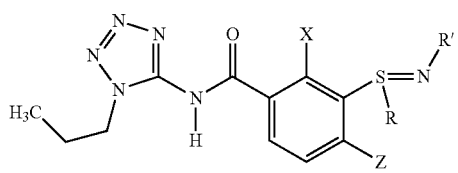

| No. | X | Z | R | R' | Physical Data ($^1$H NMR) |
|---|---|---|---|---|---|
| 12-205 | OMe | CHF$_2$ | Et | CN | |
| 12-206 | OMe | CF$_2$Cl | Et | CN | |
| 12-207 | OMe | OMe | Et | CN | |
| 12-208 | OMe | NO$_2$ | Et | CN | |
| 12-209 | OMe | SO$_2$Me | Et | CN | |
| 12-210 | SO$_2$Me | Me | Et | CN | |
| 12-211 | SO$_2$Me | F | Et | CN | |
| 12-212 | SO$_2$Me | Cl | Et | CN | |
| 12-213 | SO$_2$Me | Br | Et | CN | |
| 12-214 | SO$_2$Me | I | Et | CN | |
| 12-215 | SO$_2$Me | CF$_3$ | Et | CN | |
| 12-216 | SO$_2$Me | CHF$_2$ | Et | CN | |
| 12-217 | SO$_2$Me | CF$_2$Cl | Et | CN | |
| 12-218 | SO$_2$Me | OMe | Et | CN | |
| 12-219 | SO$_2$Me | NO$_2$ | Et | CN | |
| 12-220 | SO$_2$Me | SO$_2$Me | Et | CN | |
| 12-221 | Me | Me | CH$_2$CH$_2$OMe | CN | |
| 12-222 | Me | F | CH$_2$CH$_2$OMe | CN | |
| 12-223 | Me | Cl | CH$_2$CH$_2$OMe | CN | |
| 12-224 | Me | Br | CH$_2$CH$_2$OMe | CN | |
| 12-225 | Me | I | CH$_2$CH$_2$OMe | CN | |
| 12-226 | Me | CF$_3$ | CH$_2$CH$_2$OMe | CN | |
| 12-227 | Me | CHF$_2$ | CH$_2$CH$_2$OMe | CN | |
| 12-228 | Me | CF$_2$Cl | CH$_2$CH$_2$OMe | CN | |
| 12-229 | Me | OMe | CH$_2$CH$_2$OMe | CN | |
| 12-230 | Me | NO$_2$ | CH$_2$CH$_2$OMe | CN | |
| 12-231 | Me | SO$_2$Me | CH$_2$CH$_2$OMe | CN | |
| 12-232 | Cl | Me | CH$_2$CH$_2$OMe | CN | |
| 12-233 | Cl | F | CH$_2$CH$_2$OMe | CN | |
| 12-234 | Cl | Cl | CH$_2$CH$_2$OMe | CN | |
| 12-235 | Cl | Br | CH$_2$CH$_2$OMe | CN | |
| 12-236 | Cl | I | CH$_2$CH$_2$OMe | CN | |
| 12-237 | Cl | CF$_3$ | CH$_2$CH$_2$OMe | CN | |
| 12-238 | Cl | CHF$_2$ | CH$_2$CH$_2$OMe | CN | |
| 12-239 | Cl | CF$_2$Cl | CH$_2$CH$_2$OMe | CN | |
| 12-240 | Cl | OMe | CH$_2$CH$_2$OMe | CN | |
| 12-241 | Cl | NO$_2$ | CH$_2$CH$_2$OMe | CN | |
| 12-242 | Cl | SO$_2$Me | CH$_2$CH$_2$OMe | CN | |
| 12-243 | OMe | Me | CH$_2$CH$_2$OMe | CN | |
| 12-244 | OMe | F | CH$_2$CH$_2$OMe | CN | |
| 12-245 | OMe | Cl | CH$_2$CH$_2$OMe | CN | |
| 12-246 | OMe | Br | CH$_2$CH$_2$OMe | CN | |
| 12-247 | OMe | I | CH$_2$CH$_2$OMe | CN | |
| 12-248 | OMe | CF$_3$ | CH$_2$CH$_2$OMe | CN | |
| 12-249 | OMe | CHF$_2$ | CH$_2$CH$_2$OMe | CN | |
| 12-250 | OMe | CF$_2$Cl | CH$_2$CH$_2$OMe | CN | |
| 12-251 | OMe | OMe | CH$_2$CH$_2$OMe | CN | |
| 12-252 | OMe | NO$_2$ | CH$_2$CH$_2$OMe | CN | |
| 12-253 | OMe | SO$_2$Me | CH$_2$CH$_2$OMe | CN | |
| 12-254 | SO$_2$Me | Me | CH$_2$CH$_2$OMe | CN | |
| 12-255 | SO$_2$Me | F | CH$_2$CH$_2$OMe | CN | |
| 12-256 | SO$_2$Me | Cl | CH$_2$CH$_2$OMe | CN | |
| 12-257 | SO$_2$Me | Br | CH$_2$CH$_2$OMe | CN | |
| 12-258 | SO$_2$Me | I | CH$_2$CH$_2$OMe | CN | |
| 12-259 | SO$_2$Me | CF$_3$ | CH$_2$CH$_2$OMe | CN | |
| 12-260 | SO$_2$Me | CHF$_2$ | CH$_2$CH$_2$OMe | CN | |
| 12-261 | SO$_2$Me | CF$_2$Cl | CH$_2$CH$_2$OMe | CN | |
| 12-262 | SO$_2$Me | OMe | CH$_2$CH$_2$OMe | CN | |
| 12-263 | SO$_2$Me | NO$_2$ | CH$_2$CH$_2$OMe | CN | |
| 12-264 | SO$_2$Me | SO$_2$Me | CH$_2$CH$_2$OMe | CN | |

TABLE 13

Compounds according to the invention of the formula (I) in which Q is Q1 and R$^x$ is a (2-methoxyethyl) group, R" and W are each hydrogen and t = 0

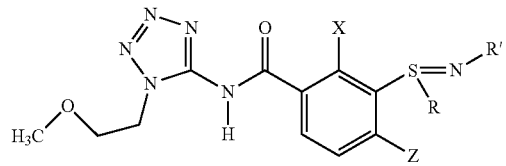

| No. | X | Z | R | R' | Physical Data ($^1$H NMR) |
|---|---|---|---|---|---|
| 13-1 | Me | Me | Me | H | |
| 13-2 | Me | F | Me | H | |
| 13-3 | Me | Cl | Me | H | |
| 13-4 | Me | Br | Me | H | |
| 13-5 | Me | I | Me | H | |
| 13-6 | Me | CF$_3$ | Me | H | |
| 13-7 | Me | CHF$_2$ | Me | H | |
| 13-8 | Me | CF$_2$Cl | Me | H | |
| 13-9 | Me | OMe | Me | H | |
| 13-10 | Me | NO$_2$ | Me | H | |
| 13-11 | Me | SO$_2$Me | Me | H | |
| 13-12 | Cl | Me | Me | H | |
| 13-13 | Cl | F | Me | H | |
| 13-14 | Cl | Cl | Me | H | |
| 13-15 | Cl | Br | Me | H | |
| 13-16 | Cl | I | Me | H | |
| 13-17 | Cl | CF$_3$ | Me | H | |
| 13-18 | Cl | CHF$_2$ | Me | H | |
| 13-19 | Cl | CF$_2$Cl | Me | H | |
| 13-20 | Cl | OMe | Me | H | |
| 13-21 | Cl | NO$_2$ | Me | H | |
| 13-22 | Cl | SO$_2$Me | Me | H | |
| 13-23 | OMe | Me | Me | H | |
| 13-24 | OMe | F | Me | H | |
| 13-25 | OMe | Cl | Me | H | |
| 13-26 | OMe | Br | Me | H | |
| 13-27 | OMe | I | Me | H | |
| 13-28 | OMe | CF$_3$ | Me | H | |
| 13-29 | OMe | CHF$_2$ | Me | H | |
| 13-30 | OMe | CF$_2$Cl | Me | H | |
| 13-31 | OMe | OMe | Me | H | |
| 13-32 | OMe | NO$_2$ | Me | H | |
| 13-33 | OMe | SO$_2$Me | Me | H | |
| 13-34 | SO$_2$Me | Me | Me | H | |
| 13-35 | SO$_2$Me | F | Me | H | |
| 13-36 | SO$_2$Me | Cl | Me | H | |
| 13-37 | SO$_2$Me | Br | Me | H | |
| 13-38 | SO$_2$Me | I | Me | H | |
| 13-39 | SO$_2$Me | CF$_3$ | Me | H | |
| 13-40 | SO$_2$Me | CHF$_2$ | Me | H | |
| 13-41 | SO$_2$Me | CF$_2$Cl | Me | H | |
| 13-42 | SO$_2$Me | OMe | Me | H | |
| 13-43 | SO$_2$Me | NO$_2$ | Me | H | |
| 13-44 | SO$_2$Me | SO$_2$Me | Me | H | |
| 13-45 | Me | Me | Et | H | |
| 13-46 | Me | F | Et | H | |
| 13-47 | Me | Cl | Et | H | |
| 13-48 | Me | Br | Et | H | |
| 13-49 | Me | I | Et | H | |
| 13-50 | Me | CF$_3$ | Et | H | |
| 13-51 | Me | CHF$_2$ | Et | H | |
| 13-52 | Me | CF$_2$Cl | Et | H | |
| 13-53 | Me | OMe | Et | H | |
| 13-54 | Me | NO$_2$ | Et | H | |
| 13-55 | Me | SO$_2$Me | Et | H | |
| 13-56 | Cl | Me | Et | H | |
| 13-57 | Cl | F | Et | H | |
| 13-58 | Cl | Cl | Et | H | |
| 13-59 | Cl | Br | Et | H | |
| 13-60 | Cl | I | Et | H | |
| 13-61 | Cl | CF$_3$ | Et | H | |
| 13-62 | Cl | CHF$_2$ | Et | H | |
| 13-63 | Cl | CF$_2$Cl | Et | H | |
| 13-64 | Cl | OMe | Et | H | |
| 13-65 | Cl | NO$_2$ | Et | H | |
| 13-66 | Cl | SO$_2$Me | Et | H | |
| 13-67 | OMe | Me | Et | H | |
| 13-68 | OMe | F | Et | H | |
| 13-69 | OMe | Cl | Et | H | |
| 13-70 | OMe | Br | Et | H | |
| 13-71 | OMe | I | Et | H | |
| 13-72 | OMe | CF$_3$ | Et | H | |
| 13-73 | OMe | CHF$_2$ | Et | H | |
| 13-74 | OMe | CF$_2$Cl | Et | H | |
| 13-75 | OMe | OMe | Et | H | |
| 13-76 | OMe | NO$_2$ | Et | H | |
| 13-77 | OMe | SO$_2$Me | Et | H | |
| 13-78 | SO$_2$Me | Me | Et | H | |
| 13-79 | SO$_2$Me | F | Et | H | |
| 13-80 | SO$_2$Me | Cl | Et | H | |
| 13-81 | SO$_2$Me | Br | Et | H | |
| 13-82 | SO$_2$Me | I | Et | H | |
| 13-83 | SO$_2$Me | CF$_3$ | Et | H | |
| 13-84 | SO$_2$Me | CHF$_2$ | Et | H | |
| 13-85 | SO$_2$Me | CF$_2$Cl | Et | H | |
| 13-86 | SO$_2$Me | OMe | Et | H | |
| 13-87 | SO$_2$Me | NO$_2$ | Et | H | |
| 13-88 | SO$_2$Me | SO$_2$Me | Et | H | |
| 13-89 | Me | Me | CH$_2$CH$_2$OMe | H | |
| 13-90 | Me | F | CH$_2$CH$_2$OMe | H | |
| 13-91 | Me | Cl | CH$_2$CH$_2$OMe | H | |
| 13-92 | Me | Br | CH$_2$CH$_2$OMe | H | |
| 13-93 | Me | I | CH$_2$CH$_2$OMe | H | |
| 13-94 | Me | CF$_3$ | CH$_2$CH$_2$OMe | H | |
| 13-95 | Me | CHF$_2$ | CH$_2$CH$_2$OMe | H | |
| 13-96 | Me | CF$_2$Cl | CH$_2$CH$_2$OMe | H | |
| 13-97 | Me | OMe | CH$_2$CH$_2$OMe | H | |
| 13-98 | Me | NO$_2$ | CH$_2$CH$_2$OMe | H | |
| 13-99 | Me | SO$_2$Me | CH$_2$CH$_2$OMe | H | |
| 13-100 | Cl | Me | CH$_2$CH$_2$OMe | H | |
| 13-101 | Cl | F | CH$_2$CH$_2$OMe | H | |
| 13-102 | Cl | Cl | CH$_2$CH$_2$OMe | H | |
| 13-103 | Cl | Br | CH$_2$CH$_2$OMe | H | |
| 13-104 | Cl | I | CH$_2$CH$_2$OMe | H | |
| 13-105 | Cl | CF$_3$ | CH$_2$CH$_2$OMe | H | |
| 13-106 | Cl | CHF$_2$ | CH$_2$CH$_2$OMe | H | |
| 13-107 | Cl | CF$_2$Cl | CH$_2$CH$_2$OMe | H | |
| 13-108 | Cl | OMe | CH$_2$CH$_2$OMe | H | |
| 13-109 | Cl | NO$_2$ | CH$_2$CH$_2$OMe | H | |
| 13-110 | Cl | SO$_2$Me | CH$_2$CH$_2$OMe | H | |
| 13-111 | OMe | Me | CH$_2$CH$_2$OMe | H | |
| 13-112 | OMe | F | CH$_2$CH$_2$OMe | H | |
| 13-113 | OMe | Cl | CH$_2$CH$_2$OMe | H | |
| 13-114 | OMe | Br | CH$_2$CH$_2$OMe | H | |
| 13-115 | OMe | I | CH$_2$CH$_2$OMe | H | |
| 13-116 | OMe | CF$_3$ | CH$_2$CH$_2$OMe | H | |
| 13-117 | OMe | CHF$_2$ | CH$_2$CH$_2$OMe | H | |
| 13-118 | OMe | CF$_2$Cl | CH$_2$CH$_2$OMe | H | |
| 13-119 | OMe | OMe | CH$_2$CH$_2$OMe | H | |
| 13-120 | OMe | NO$_2$ | CH$_2$CH$_2$OMe | H | |
| 13-121 | OMe | SO$_2$Me | CH$_2$CH$_2$OMe | H | |
| 13-122 | SO$_2$Me | Me | CH$_2$CH$_2$OMe | H | |
| 13-123 | SO$_2$Me | F | CH$_2$CH$_2$OMe | H | |
| 13-124 | SO$_2$Me | Cl | CH$_2$CH$_2$OMe | H | |
| 13-125 | SO$_2$Me | Br | CH$_2$CH$_2$OMe | H | |
| 13-126 | SO$_2$Me | I | CH$_2$CH$_2$OMe | H | |
| 13-127 | SO$_2$Me | CF$_3$ | CH$_2$CH$_2$OMe | H | |
| 13-128 | SO$_2$Me | CHF$_2$ | CH$_2$CH$_2$OMe | H | |
| 13-129 | SO$_2$Me | CF$_2$Cl | CH$_2$CH$_2$OMe | H | |
| 13-130 | SO$_2$Me | OMe | CH$_2$CH$_2$OMe | H | |

TABLE 13-continued

Compounds according to the invention of the formula (I) in which Q is Q1 and $R^x$ is a (2-methoxyethyl) group, R'' and W are each hydrogen and t = 0

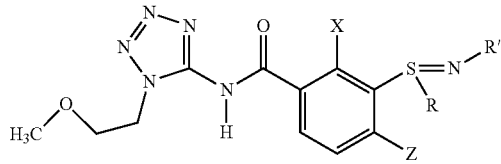

| No. | X | Z | R | R' | Physical Data ($^1$H NMR) |
|---|---|---|---|---|---|
| 13-131 | SO$_2$Me | NO$_2$ | CH$_2$CH$_2$OMe | H | |
| 13-132 | SO$_2$Me | SO$_2$Me | CH$_2$CH$_2$OMe | H | |
| 13-133 | Me | Me | Me | CN | |
| 13-134 | Me | F | Me | CN | |
| 13-135 | Me | Cl | Me | CN | |
| 13-136 | Me | Br | Me | CN | |
| 13-137 | Me | I | Me | CN | |
| 13-138 | Me | CF$_3$ | Me | CN | |
| 13-139 | Me | CHF$_2$ | Me | CN | |
| 13-140 | Me | CF$_2$Cl | Me | CN | |
| 13-141 | Me | OMe | Me | CN | |
| 13-142 | Me | NO$_2$ | Me | CN | |
| 13-143 | Me | SO$_2$Me | Me | CN | |
| 13-144 | Cl | Me | Me | CN | |
| 13-145 | Cl | F | Me | CN | |
| 13-146 | Cl | Cl | Me | CN | |
| 13-147 | Cl | Br | Me | CN | |
| 13-148 | Cl | I | Me | CN | |
| 13-149 | Cl | CF$_3$ | Me | CN | |
| 13-150 | Cl | CHF$_2$ | Me | CN | |
| 13-151 | Cl | CF$_2$Cl | Me | CN | |
| 13-152 | Cl | OMe | Me | CN | |
| 13-153 | Cl | NO$_2$ | Me | CN | |
| 13-154 | Cl | SO$_2$Me | Me | CN | |
| 13-155 | OMe | Me | Me | CN | |
| 13-156 | OMe | F | Me | CN | |
| 13-157 | OMe | Cl | Me | CN | |
| 13-158 | OMe | Br | Me | CN | |
| 13-159 | OMe | I | Me | CN | |
| 13-160 | OMe | CF$_3$ | Me | CN | |
| 13-161 | OMe | CHF$_2$ | Me | CN | |
| 13-162 | OMe | CF$_2$Cl | Me | CN | |
| 13-163 | OMe | OMe | Me | CN | |
| 13-164 | OMe | NO$_2$ | Me | CN | |
| 13-165 | OMe | SO$_2$Me | Me | CN | |
| 13-166 | SO$_2$Me | Me | Me | CN | |
| 13-167 | SO$_2$Me | F | Me | CN | |
| 13-168 | SO$_2$Me | Cl | Me | CN | |
| 13-169 | SO$_2$Me | Br | Me | CN | |
| 13-170 | SO$_2$Me | I | Me | CN | |
| 13-171 | SO$_2$Me | CF$_3$ | Me | CN | |
| 13-172 | SO$_2$Me | CHF$_2$ | Me | CN | |
| 13-173 | SO$_2$Me | CF$_2$Cl | Me | CN | |
| 13-174 | SO$_2$Me | OMe | Me | CN | |
| 13-175 | SO$_2$Me | NO$_2$ | Me | CN | |
| 13-176 | SO$_2$Me | SO$_2$Me | Me | CN | |
| 13-177 | Me | Me | Et | CN | |
| 13-178 | Me | F | Et | CN | |
| 13-179 | Me | Cl | Et | CN | |
| 13-180 | Me | Br | Et | CN | |
| 13-181 | Me | I | Et | CN | |
| 13-182 | Me | CF$_3$ | Et | CN | |
| 13-183 | Me | CHF$_2$ | Et | CN | |
| 13-184 | Me | CF$_2$Cl | Et | CN | |
| 13-185 | Me | OMe | Et | CN | |
| 13-186 | Me | NO$_2$ | Et | CN | |
| 13-187 | Me | SO$_2$Me | Et | CN | |
| 13-188 | Cl | Me | Et | CN | |
| 13-189 | Cl | F | Et | CN | |
| 13-190 | Cl | Cl | Et | CN | |
| 13-191 | Cl | Br | Et | CN | |
| 13-192 | Cl | I | Et | CN | |
| 13-193 | Cl | CF$_3$ | Et | CN | |
| 13-194 | Cl | CHF$_2$ | Et | CN | |
| 13-195 | Cl | CF$_2$Cl | Et | CN | |

TABLE 13-continued

Compounds according to the invention of the formula (I) in which Q is Q1 and $R^x$ is a (2-methoxyethyl) group, R'' and W are each hydrogen and t = 0

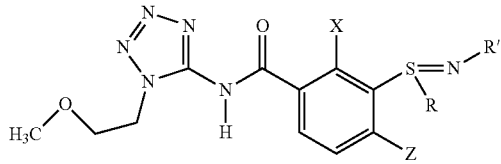

| No. | X | Z | R | R' | Physical Data ($^1$H NMR) |
|---|---|---|---|---|---|
| 13-196 | Cl | OMe | Et | CN | |
| 13-197 | Cl | NO$_2$ | Et | CN | |
| 13-198 | Cl | SO$_2$Me | Et | CN | |
| 13-199 | OMe | Me | Et | CN | |
| 13-200 | OMe | F | Et | CN | |
| 13-201 | OMe | Cl | Et | CN | |
| 13-202 | OMe | Br | Et | CN | |
| 13-203 | OMe | I | Et | CN | |
| 13-204 | OMe | CF$_3$ | Et | CN | |
| 13-205 | OMe | CHF$_2$ | Et | CN | |
| 13-206 | OMe | CF$_2$Cl | Et | CN | |
| 13-207 | OMe | OMe | Et | CN | |
| 13-208 | OMe | NO$_2$ | Et | CN | |
| 13-209 | OMe | SO$_2$Me | Et | CN | |
| 13-210 | SO$_2$Me | Me | Et | CN | |
| 13-211 | SO$_2$Me | F | Et | CN | |
| 13-212 | SO$_2$Me | Cl | Et | CN | |
| 13-213 | SO$_2$Me | Br | Et | CN | |
| 13-214 | SO$_2$Me | I | Et | CN | |
| 13-215 | SO$_2$Me | CF$_3$ | Et | CN | |
| 13-216 | SO$_2$Me | CHF$_2$ | Et | CN | |
| 13-217 | SO$_2$Me | CF$_2$Cl | Et | CN | |
| 13-218 | SO$_2$Me | OMe | Et | CN | |
| 13-219 | SO$_2$Me | NO$_2$ | Et | CN | |
| 13-220 | SO$_2$Me | SO$_2$Me | Et | CN | |
| 13-221 | Me | Me | CH$_2$CH$_2$OMe | CN | |
| 13-222 | Me | F | CH$_2$CH$_2$OMe | CN | |
| 13-223 | Me | Cl | CH$_2$CH$_2$OMe | CN | |
| 13-224 | Me | Br | CH$_2$CH$_2$OMe | CN | |
| 13-225 | Me | I | CH$_2$CH$_2$OMe | CN | |
| 13-226 | Me | CF$_3$ | CH$_2$CH$_2$OMe | CN | |
| 13-227 | Me | CHF$_2$ | CH$_2$CH$_2$OMe | CN | |
| 13-228 | Me | CF$_2$Cl | CH$_2$CH$_2$OMe | CN | |
| 13-229 | Me | OMe | CH$_2$CH$_2$OMe | CN | |
| 13-230 | Me | NO$_2$ | CH$_2$CH$_2$OMe | CN | |
| 13-231 | Me | SO$_2$Me | CH$_2$CH$_2$OMe | CN | |
| 13-232 | Cl | Me | CH$_2$CH$_2$OMe | CN | |
| 13-233 | Cl | F | CH$_2$CH$_2$OMe | CN | |
| 13-234 | Cl | Cl | CH$_2$CH$_2$OMe | CN | |
| 13-235 | Cl | Br | CH$_2$CH$_2$OMe | CN | |
| 13-236 | Cl | I | CH$_2$CH$_2$OMe | CN | |
| 13-237 | Cl | CF$_3$ | CH$_2$CH$_2$OMe | CN | |
| 13-238 | Cl | CHF$_2$ | CH$_2$CH$_2$OMe | CN | |
| 13-239 | Cl | CF$_2$Cl | CH$_2$CH$_2$OMe | CN | |
| 13-240 | Cl | OMe | CH$_2$CH$_2$OMe | CN | |
| 13-241 | Cl | NO$_2$ | CH$_2$CH$_2$OMe | CN | |
| 13-242 | Cl | SO$_2$Me | CH$_2$CH$_2$OMe | CN | |
| 13-243 | OMe | Me | CH$_2$CH$_2$OMe | CN | |
| 13-244 | OMe | F | CH$_2$CH$_2$OMe | CN | |
| 13-245 | OMe | Cl | CH$_2$CH$_2$OMe | CN | |
| 13-246 | OMe | Br | CH$_2$CH$_2$OMe | CN | |
| 13-247 | OMe | I | CH$_2$CH$_2$OMe | CN | |
| 13-248 | OMe | CF$_3$ | CH$_2$CH$_2$OMe | CN | |
| 13-249 | OMe | CHF$_2$ | CH$_2$CH$_2$OMe | CN | |
| 13-250 | OMe | CF$_2$Cl | CH$_2$CH$_2$OMe | CN | |
| 13-251 | OMe | OMe | CH$_2$CH$_2$OMe | CN | |
| 13-252 | OMe | NO$_2$ | CH$_2$CH$_2$OMe | CN | |
| 13-253 | OMe | SO$_2$Me | CH$_2$CH$_2$OMe | CN | |
| 13-254 | SO$_2$Me | Me | CH$_2$CH$_2$OMe | CN | |
| 13-255 | SO$_2$Me | F | CH$_2$CH$_2$OMe | CN | |
| 13-256 | SO$_2$Me | Cl | CH$_2$CH$_2$OMe | CN | |
| 13-257 | SO$_2$Me | Br | CH$_2$CH$_2$OMe | CN | |
| 13-258 | SO$_2$Me | I | CH$_2$CH$_2$OMe | CN | |
| 13-259 | SO$_2$Me | CF$_3$ | CH$_2$CH$_2$OMe | CN | |
| 13-260 | SO$_2$Me | CHF$_2$ | CH$_2$CH$_2$OMe | CN | |

TABLE 13-continued

Compounds according to the invention of the formula (I) in which Q is Q1 and $R^x$ is a (2-methoxyethyl) group, R'' and W are each hydrogen and t = 0

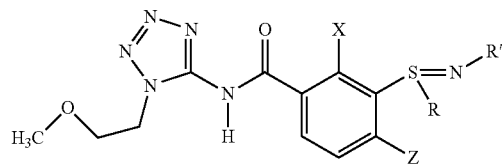

| No. | X | Z | R | R' | Physical Data ($^1$H NMR) |
|---|---|---|---|---|---|
| 13-261 | SO$_2$Me | CF$_2$Cl | CH$_2$CH$_2$OMe | CN | |
| 13-262 | SO$_2$Me | OMe | CH$_2$CH$_2$OMe | CN | |
| 13-263 | SO$_2$Me | NO$_2$ | CH$_2$CH$_2$OMe | CN | |
| 13-264 | SO$_2$Me | SO$_2$Me | CH$_2$CH$_2$OMe | CN | |

TABLE 14

Compounds according to the invention of the formula (I) in which Q is Q2 and $R^x$ is a methyl group, R'' and W are each hydrogen and t = 0

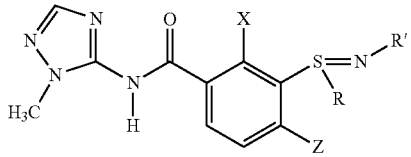

| No. | X | Z | R | R' | Physical Data ($^1$H NMR) |
|---|---|---|---|---|---|
| 14-1 | Me | Me | Me | H | |
| 14-2 | Me | F | Me | H | |
| 14-3 | Me | Cl | Me | H | |
| 14-4 | Me | Br | Me | H | |
| 14-5 | Me | I | Me | H | |
| 14-6 | Me | CF$_3$ | Me | H | |
| 14-7 | Me | CHF$_2$ | Me | H | |
| 14-8 | Me | CF$_2$Cl | Me | H | |
| 14-9 | Me | OMe | Me | H | |
| 14-10 | Me | NO$_2$ | Me | H | |
| 14-11 | Me | SO$_2$Me | Me | H | |
| 14-12 | Cl | Me | Me | H | |
| 14-13 | Cl | F | Me | H | |
| 14-14 | Cl | Cl | Me | H | |
| 14-15 | Cl | Br | Me | H | |
| 14-16 | Cl | I | Me | H | |
| 14-17 | Cl | CF$_3$ | Me | H | |
| 14-18 | Cl | CHF$_2$ | Me | H | |
| 14-19 | Cl | CF$_2$Cl | Me | H | |
| 14-20 | Cl | OMe | Me | H | |
| 14-21 | Cl | NO$_2$ | Me | H | |
| 14-22 | Cl | SO$_2$Me | Me | H | |
| 14-23 | OMe | Me | Me | H | |
| 14-24 | OMe | F | Me | H | |
| 14-25 | OMe | Cl | Me | H | |
| 14-26 | OMe | Br | Me | H | |
| 14-27 | OMe | I | Me | H | |
| 14-28 | OMe | CF$_3$ | Me | H | |
| 14-29 | OMe | CHF$_2$ | Me | H | |
| 14-30 | OMe | CF$_2$Cl | Me | H | |
| 14-31 | OMe | OMe | Me | H | |
| 14-32 | OMe | NO$_2$ | Me | H | |
| 14-33 | OMe | SO$_2$Me | Me | H | |
| 14-34 | SO$_2$Me | Me | Me | H | |
| 14-35 | SO$_2$Me | F | Me | H | |
| 14-36 | SO$_2$Me | Cl | Me | H | |
| 14-37 | SO$_2$Me | Br | Me | H | |
| 14-38 | SO$_2$Me | I | Me | H | |
| 14-39 | SO$_2$Me | CF$_3$ | Me | H | |
| 14-40 | SO$_2$Me | CHF$_2$ | Me | H | |
| 14-41 | SO$_2$Me | CF$_2$Cl | Me | H | |
| 14-42 | SO$_2$Me | OMe | Me | H | |
| 14-43 | SO$_2$Me | NO$_2$ | Me | H | |
| 14-44 | SO$_2$Me | SO$_2$Me | Me | H | |
| 14-45 | Me | Me | Et | H | |
| 14-46 | Me | F | Et | H | |
| 14-47 | Me | Cl | Et | H | |
| 14-48 | Me | Br | Et | H | |
| 14-49 | Me | I | Et | H | |
| 14-50 | Me | CF$_3$ | Et | H | |
| 14-51 | Me | CHF$_2$ | Et | H | |
| 14-52 | Me | CF$_2$Cl | Et | H | |
| 14-53 | Me | OMe | Et | H | |
| 14-54 | Me | NO$_2$ | Et | H | |
| 14-55 | Me | SO$_2$Me | Et | H | |
| 14-56 | Cl | Me | Et | H | |
| 14-57 | Cl | F | Et | H | |
| 14-58 | Cl | Cl | Et | H | |
| 14-59 | Cl | Br | Et | H | |
| 14-60 | Cl | I | Et | H | |
| 14-61 | Cl | CF$_3$ | Et | H | |
| 14-62 | Cl | CHF$_2$ | Et | H | |
| 14-63 | Cl | CF$_2$Cl | Et | H | |
| 14-64 | Cl | OMe | Et | H | |
| 14-65 | Cl | NO$_2$ | Et | H | |
| 14-66 | Cl | SO$_2$Me | Et | H | |
| 14-67 | OMe | Me | Et | H | |
| 14-68 | OMe | F | Et | H | |
| 14-69 | OMe | Cl | Et | H | |
| 14-70 | OMe | Br | Et | H | |
| 14-71 | OMe | I | Et | H | |
| 14-72 | OMe | CF$_3$ | Et | H | |
| 14-73 | OMe | CHF$_2$ | Et | H | |
| 14-74 | OMe | CF$_2$Cl | Et | H | |
| 14-75 | OMe | OMe | Et | H | |
| 14-76 | OMe | NO$_2$ | Et | H | |
| 14-77 | OMe | SO$_2$Me | Et | H | |
| 14-78 | SO$_2$Me | Me | Et | H | |
| 14-79 | SO$_2$Me | F | Et | H | |
| 14-80 | SO$_2$Me | Cl | Et | H | |
| 14-81 | SO$_2$Me | Br | Et | H | |
| 14-82 | SO$_2$Me | I | Et | H | |
| 14-83 | SO$_2$Me | CF$_3$ | Et | H | |
| 14-84 | SO$_2$Me | CHF$_2$ | Et | H | |
| 14-85 | SO$_2$Me | CF$_2$Cl | Et | H | |
| 14-86 | SO$_2$Me | OMe | Et | H | |
| 14-87 | SO$_2$Me | NO$_2$ | Et | H | |
| 14-88 | SO$_2$Me | SO$_2$Me | Et | H | |
| 14-89 | Me | Me | CH$_2$CH$_2$OMe | H | |
| 14-90 | Me | F | CH$_2$CH$_2$OMe | H | |
| 14-91 | Me | Cl | CH$_2$CH$_2$OMe | H | |
| 14-92 | Me | Br | CH$_2$CH$_2$OMe | H | |
| 14-93 | Me | I | CH$_2$CH$_2$OMe | H | |
| 14-94 | Me | CF$_3$ | CH$_2$CH$_2$OMe | H | |
| 14-95 | Me | CHF$_2$ | CH$_2$CH$_2$OMe | H | |
| 14-96 | Me | CF$_2$Cl | CH$_2$CH$_2$OMe | H | |
| 14-97 | Me | OMe | CH$_2$CH$_2$OMe | H | |
| 14-98 | Me | NO$_2$ | CH$_2$CH$_2$OMe | H | |
| 14-99 | Me | SO$_2$Me | CH$_2$CH$_2$OMe | H | |
| 14-100 | Cl | Me | CH$_2$CH$_2$OMe | H | |
| 14-101 | Cl | F | CH$_2$CH$_2$OMe | H | |
| 14-102 | Cl | Cl | CH$_2$CH$_2$OMe | H | |
| 14-103 | Cl | Br | CH$_2$CH$_2$OMe | H | |
| 14-104 | Cl | I | CH$_2$CH$_2$OMe | H | |
| 14-105 | Cl | CF$_3$ | CH$_2$CH$_2$OMe | H | |
| 14-106 | Cl | CHF$_2$ | CH$_2$CH$_2$OMe | H | |
| 14-107 | Cl | CF$_2$Cl | CH$_2$CH$_2$OMe | H | |
| 14-108 | Cl | OMe | CH$_2$CH$_2$OMe | H | |

TABLE 14-continued

Compounds according to the invention of the formula (I) in which Q is Q2 and $R^x$ is a methyl group, R″ and W are each hydrogen and t = 0

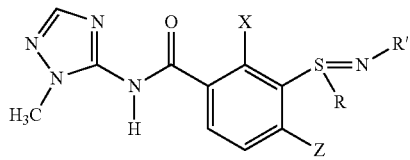

| No. | X | Z | R | R' | Physical Data ($^1$H NMR) |
|---|---|---|---|---|---|
| 14-109 | Cl | NO$_2$ | CH$_2$CH$_2$OMe | H | |
| 14-110 | Cl | SO$_2$Me | CH$_2$CH$_2$OMe | H | |
| 14-111 | OMe | Me | CH$_2$CH$_2$OMe | H | |
| 14-112 | OMe | F | CH$_2$CH$_2$OMe | H | |
| 14-113 | OMe | Cl | CH$_2$CH$_2$OMe | H | |
| 14-114 | OMe | Br | CH$_2$CH$_2$OMe | H | |
| 14-115 | OMe | I | CH$_2$CH$_2$OMe | H | |
| 14-116 | OMe | CF$_3$ | CH$_2$CH$_2$OMe | H | |
| 14-117 | OMe | CHF$_2$ | CH$_2$CH$_2$OMe | H | |
| 14-118 | OMe | CF$_2$Cl | CH$_2$CH$_2$OMe | H | |
| 14-119 | OMe | OMe | CH$_2$CH$_2$OMe | H | |
| 14-120 | OMe | NO$_2$ | CH$_2$CH$_2$OMe | H | |
| 14-121 | OMe | SO$_2$Me | CH$_2$CH$_2$OMe | H | |
| 14-122 | SO$_2$Me | Me | CH$_2$CH$_2$OMe | H | |
| 14-123 | SO$_2$Me | F | CH$_2$CH$_2$OMe | H | |
| 14-124 | SO$_2$Me | Cl | CH$_2$CH$_2$OMe | H | |
| 14-125 | SO$_2$Me | Br | CH$_2$CH$_2$OMe | H | |
| 14-126 | SO$_2$Me | I | CH$_2$CH$_2$OMe | H | |
| 14-127 | SO$_2$Me | CF$_3$ | CH$_2$CH$_2$OMe | H | |
| 14-128 | SO$_2$Me | CHF$_2$ | CH$_2$CH$_2$OMe | H | |
| 14-129 | SO$_2$Me | CF$_2$Cl | CH$_2$CH$_2$OMe | H | |
| 14-130 | SO$_2$Me | OMe | CH$_2$CH$_2$OMe | H | |
| 14-131 | SO$_2$Me | NO$_2$ | CH$_2$CH$_2$OMe | H | |
| 14-132 | SO$_2$Me | SO$_2$Me | CH$_2$CH$_2$OMe | H | |
| 14-133 | Me | Me | Me | CN | |
| 14-134 | Me | F | Me | CN | |
| 14-135 | Me | Cl | Me | CN | |
| 14-136 | Me | Br | Me | CN | |
| 14-137 | Me | I | Me | CN | |
| 14-138 | Me | CF$_3$ | Me | CN | |
| 14-139 | Me | CHF$_2$ | Me | CN | |
| 14-140 | Me | CF$_2$Cl | Me | CN | |
| 14-141 | Me | OMe | Me | CN | |
| 14-142 | Me | NO$_2$ | Me | CN | |
| 14-143 | Me | SO$_2$Me | Me | CN | |
| 14-144 | Cl | Me | Me | CN | |
| 14-145 | Cl | F | Me | CN | |
| 14-146 | Cl | Cl | Me | CN | |
| 14-147 | Cl | Br | Me | CN | |
| 14-148 | Cl | I | Me | CN | |
| 14-149 | Cl | CF$_3$ | Me | CN | |
| 14-150 | Cl | CHF$_2$ | Me | CN | |
| 14-151 | Cl | CF$_2$Cl | Me | CN | |
| 14-152 | Cl | OMe | Me | CN | |
| 14-153 | Cl | NO$_2$ | Me | CN | |
| 14-154 | Cl | SO$_2$Me | Me | CN | |
| 14-155 | OMe | Me | Me | CN | |
| 14-156 | OMe | F | Me | CN | |
| 14-157 | OMe | Cl | Me | CN | |
| 14-158 | OMe | Br | Me | CN | |
| 14-159 | OMe | I | Me | CN | |
| 14-160 | OMe | CF$_3$ | Me | CN | |
| 14-161 | OMe | CHF$_2$ | Me | CN | |
| 14-162 | OMe | CF$_2$Cl | Me | CN | |
| 14-163 | OMe | OMe | Me | CN | |
| 14-164 | OMe | NO$_2$ | Me | CN | |
| 14-165 | OMe | SO$_2$Me | Me | CN | |
| 14-166 | SO$_2$Me | Me | Me | CN | |
| 14-167 | SO$_2$Me | F | Me | CN | |
| 14-168 | SO$_2$Me | Cl | Me | CN | |
| 14-169 | SO$_2$Me | Br | Me | CN | |
| 14-170 | SO$_2$Me | I | Me | CN | |
| 14-171 | SO$_2$Me | CF$_3$ | Me | CN | |
| 14-172 | SO$_2$Me | CHF$_2$ | Me | CN | |
| 14-173 | SO$_2$Me | CF$_2$Cl | Me | CN | |
| 14-174 | SO$_2$Me | OMe | Me | CN | |

TABLE 14-continued

Compounds according to the invention of the formula (I) in which Q is Q2 and $R^x$ is a methyl group, R″ and W are each hydrogen and t = 0

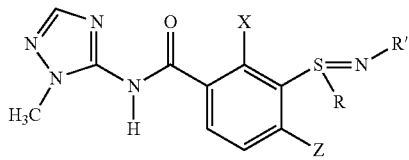

| No. | X | Z | R | R' | Physical Data ($^1$H NMR) |
|---|---|---|---|---|---|
| 14-175 | SO$_2$Me | NO$_2$ | Me | CN | |
| 14-176 | SO$_2$Me | SO$_2$Me | Me | CN | |
| 14-177 | Me | Me | Et | CN | |
| 14-178 | Me | F | Et | CN | |
| 14-179 | Me | Cl | Et | CN | |
| 14-180 | Me | Br | Et | CN | |
| 14-181 | Me | I | Et | CN | |
| 14-182 | Me | CF$_3$ | Et | CN | |
| 14-183 | Me | CHF$_2$ | Et | CN | |
| 14-184 | Me | CF$_2$Cl | Et | CN | |
| 14-185 | Me | OMe | Et | CN | |
| 14-186 | Me | NO$_2$ | Et | CN | |
| 14-187 | Me | SO$_2$Me | Et | CN | |
| 14-188 | Cl | Me | Et | CN | |
| 14-189 | Cl | F | Et | CN | |
| 14-190 | Cl | Cl | Et | CN | |
| 14-191 | Cl | Br | Et | CN | |
| 14-192 | Cl | I | Et | CN | |
| 14-193 | Cl | CF$_3$ | Et | CN | |
| 14-194 | Cl | CHF$_2$ | Et | CN | |
| 14-195 | Cl | CF$_2$Cl | Et | CN | |
| 14-196 | Cl | OMe | Et | CN | |
| 14-197 | Cl | NO$_2$ | Et | CN | |
| 14-198 | Cl | SO$_2$Me | Et | CN | |
| 14-199 | OMe | Me | Et | CN | |
| 14-200 | OMe | F | Et | CN | |
| 14-201 | OMe | Cl | Et | CN | |
| 14-202 | OMe | Br | Et | CN | |
| 14-203 | OMe | I | Et | CN | |
| 14-204 | OMe | CF$_3$ | Et | CN | |
| 14-205 | OMe | CHF$_2$ | Et | CN | |
| 14-206 | OMe | CF$_2$Cl | Et | CN | |
| 14-207 | OMe | OMe | Et | CN | |
| 14-208 | OMe | NO$_2$ | Et | CN | |
| 14-209 | OMe | SO$_2$Me | Et | CN | |
| 14-210 | SO$_2$Me | Me | Et | CN | |
| 14-211 | SO$_2$Me | F | Et | CN | |
| 14-212 | SO$_2$Me | Cl | Et | CN | |
| 14-213 | SO$_2$Me | Br | Et | CN | |
| 14-214 | SO$_2$Me | I | Et | CN | |
| 14-215 | SO$_2$Me | CF$_3$ | Et | CN | |
| 14-216 | SO$_2$Me | CHF$_2$ | Et | CN | |
| 14-217 | SO$_2$Me | CF$_2$Cl | Et | CN | |
| 14-218 | SO$_2$Me | OMe | Et | CN | |
| 14-219 | SO$_2$Me | NO$_2$ | Et | CN | |
| 14-220 | SO$_2$Me | SO$_2$Me | Et | CN | |
| 14-221 | Me | Me | CH$_2$CH$_2$OMe | CN | |
| 14-222 | Me | F | CH$_2$CH$_2$OMe | CN | |
| 14-223 | Me | Cl | CH$_2$CH$_2$OMe | CN | |
| 14-224 | Me | Br | CH$_2$CH$_2$OMe | CN | |
| 14-225 | Me | I | CH$_2$CH$_2$OMe | CN | |
| 14-226 | Me | CF$_3$ | CH$_2$CH$_2$OMe | CN | |
| 14-227 | Me | CHF$_2$ | CH$_2$CH$_2$OMe | CN | |
| 14-228 | Me | CF$_2$Cl | CH$_2$CH$_2$OMe | CN | |
| 14-229 | Me | OMe | CH$_2$CH$_2$OMe | CN | |
| 14-230 | Me | NO$_2$ | CH$_2$CH$_2$OMe | CN | |
| 14-231 | Me | SO$_2$Me | CH$_2$CH$_2$OMe | CN | |
| 14-232 | Cl | Me | CH$_2$CH$_2$OMe | CN | |
| 14-233 | Cl | F | CH$_2$CH$_2$OMe | CN | |
| 14-234 | Cl | Cl | CH$_2$CH$_2$OMe | CN | |
| 14-235 | Cl | Br | CH$_2$CH$_2$OMe | CN | |
| 14-236 | Cl | I | CH$_2$CH$_2$OMe | CN | |
| 14-237 | Cl | CF$_3$ | CH$_2$CH$_2$OMe | CN | |
| 14-238 | Cl | CHF$_2$ | CH$_2$CH$_2$OMe | CN | |
| 14-239 | Cl | CF$_2$Cl | CH$_2$CH$_2$OMe | CN | |
| 14-240 | Cl | OMe | CH$_2$CH$_2$OMe | CN | |

TABLE 14-continued

Compounds according to the invention of the formula (I) in which Q is Q2 and $R^x$ is a methyl group, R'' and W are each hydrogen and t = 0

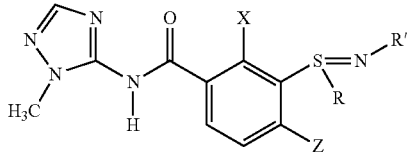

| No. | X | Z | R | R' | Physical Data ($^1$H NMR) |
|---|---|---|---|---|---|
| 14-241 | Cl | NO$_2$ | CH$_2$CH$_2$OMe | CN | |
| 14-242 | Cl | SO$_2$Me | CH$_2$CH$_2$OMe | CN | |
| 14-243 | OMe | Me | CH$_2$CH$_2$OMe | CN | |
| 14-244 | OMe | F | CH$_2$CH$_2$OMe | CN | |
| 14-245 | OMe | Cl | CH$_2$CH$_2$OMe | CN | |
| 14-246 | OMe | Br | CH$_2$CH$_2$OMe | CN | |
| 14-247 | OMe | I | CH$_2$CH$_2$OMe | CN | |
| 14-248 | OMe | CF$_3$ | CH$_2$CH$_2$OMe | CN | |
| 14-249 | OMe | CHF$_2$ | CH$_2$CH$_2$OMe | CN | |
| 14-250 | OMe | CF$_2$Cl | CH$_2$CH$_2$OMe | CN | |
| 14-251 | OMe | OMe | CH$_2$CH$_2$OMe | CN | |
| 14-252 | OMe | NO$_2$ | CH$_2$CH$_2$OMe | CN | |
| 14-253 | OMe | SO$_2$Me | CH$_2$CH$_2$OMe | CN | |
| 14-254 | SO$_2$Me | Me | CH$_2$CH$_2$OMe | CN | |
| 14-255 | SO$_2$Me | F | CH$_2$CH$_2$OMe | CN | |
| 14-256 | SO$_2$Me | Cl | CH$_2$CH$_2$OMe | CN | |
| 14-257 | SO$_2$Me | Br | CH$_2$CH$_2$OMe | CN | |
| 14-258 | SO$_2$Me | I | CH$_2$CH$_2$OMe | CN | |
| 14-259 | SO$_2$Me | CF$_3$ | CH$_2$CH$_2$OMe | CN | |
| 14-260 | SO$_2$Me | CHF$_2$ | CH$_2$CH$_2$OMe | CN | |
| 14-261 | SO$_2$Me | CF$_2$Cl | CH$_2$CH$_2$OMe | CN | |
| 14-262 | SO$_2$Me | OMe | CH$_2$CH$_2$OMe | CN | |
| 14-263 | SO$_2$Me | NO$_2$ | CH$_2$CH$_2$OMe | CN | |
| 14-264 | SO$_2$Me | SO$_2$Me | CH$_2$CH$_2$OMe | CN | |

TABLE 15

Compounds according to the invention of the formula (I) in which Q is Q3 and $R^y$ is a methyl group, R'' and W are each hydrogen and t = 0

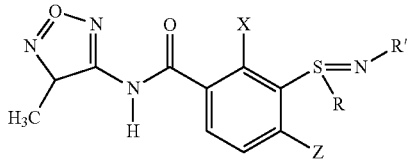

| No. | X | Z | R | R' | Physical Data ($^1$H NMR) |
|---|---|---|---|---|---|
| 15-1 | Me | Me | Me | H | |
| 15-2 | Me | F | Me | H | |
| 15-3 | Me | Cl | Me | H | |
| 15-4 | Me | Br | Me | H | |
| 15-5 | Me | I | Me | H | |
| 15-6 | Me | CF$_3$ | Me | H | |
| 15-7 | Me | CHF$_2$ | Me | H | |
| 15-8 | Me | CF$_2$Cl | Me | H | |
| 15-9 | Me | OMe | Me | H | |
| 15-10 | Me | NO$_2$ | Me | H | |
| 15-11 | Me | SO$_2$Me | Me | H | |
| 15-12 | Cl | Me | Me | H | |
| 15-13 | Cl | F | Me | H | |
| 15-14 | Cl | Cl | Me | H | |
| 15-15 | Cl | Br | Me | H | |
| 15-16 | Cl | I | Me | H | |
| 15-17 | Cl | CF$_3$ | Me | H | |
| 15-18 | Cl | CHF$_2$ | Me | H | |
| 15-19 | Cl | CF$_2$Cl | Me | H | |
| 15-20 | Cl | OMe | Me | H | |
| 15-21 | Cl | NO$_2$ | Me | H | |
| 15-22 | Cl | SO$_2$Me | Me | H | |
| 15-23 | OMe | Me | Me | H | |

TABLE 15-continued

Compounds according to the invention of the formula (I) in which Q is Q3 and $R^y$ is a methyl group, R'' and W are each hydrogen and t = 0

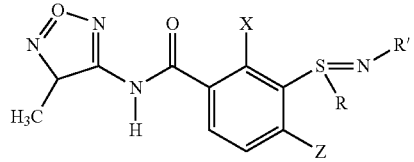

| No. | X | Z | R | R' | Physical Data ($^1$H NMR) |
|---|---|---|---|---|---|
| 15-24 | OMe | F | Me | H | |
| 15-25 | OMe | Cl | Me | H | |
| 15-26 | OMe | Br | Me | H | |
| 15-27 | OMe | I | Me | H | |
| 15-28 | OMe | CF$_3$ | Me | H | |
| 15-29 | OMe | CHF$_2$ | Me | H | |
| 15-30 | OMe | CF$_2$Cl | Me | H | |
| 15-31 | OMe | OMe | Me | H | |
| 15-32 | OMe | NO$_2$ | Me | H | |
| 15-33 | OMe | SO$_2$Me | Me | H | |
| 15-34 | SO$_2$Me | Me | Me | H | |
| 15-35 | SO$_2$Me | F | Me | H | |
| 15-36 | SO$_2$Me | Cl | Me | H | |
| 15-37 | SO$_2$Me | Br | Me | H | |
| 15-38 | SO$_2$Me | I | Me | H | |
| 15-39 | SO$_2$Me | CF$_3$ | Me | H | |
| 15-40 | SO$_2$Me | CHF$_2$ | Me | H | |
| 15-41 | SO$_2$Me | CF$_2$Cl | Me | H | |
| 15-42 | SO$_2$Me | OMe | Me | H | |
| 15-43 | SO$_2$Me | NO$_2$ | Me | H | |
| 15-44 | SO$_2$Me | SO$_2$Me | Me | H | |
| 15-45 | Me | Me | Et | H | |
| 15-46 | Me | F | Et | H | |
| 15-47 | Me | Cl | Et | H | |
| 15-48 | Me | Br | Et | H | |
| 15-49 | Me | I | Et | H | |
| 15-50 | Me | CF$_3$ | Et | H | |
| 15-51 | Me | CHF$_2$ | Et | H | |
| 15-52 | Me | CF$_2$Cl | Et | H | |
| 15-53 | Me | OMe | Et | H | |
| 15-54 | Me | NO$_2$ | Et | H | |
| 15-55 | Me | SO$_2$Me | Et | H | |
| 15-56 | Cl | Me | Et | H | |
| 15-57 | Cl | F | Et | H | |
| 15-58 | Cl | Cl | Et | H | |
| 15-59 | Cl | Br | Et | H | |
| 15-60 | Cl | I | Et | H | |
| 15-61 | Cl | CF$_3$ | Et | H | |
| 15-62 | Cl | CHF$_2$ | Et | H | |
| 15-63 | Cl | CF$_2$Cl | Et | H | |
| 15-64 | Cl | OMe | Et | H | |
| 15-65 | Cl | NO$_2$ | Et | H | |
| 15-66 | Cl | SO$_2$Me | Et | H | |
| 15-67 | OMe | Me | Et | H | |
| 15-68 | OMe | F | Et | H | |
| 15-69 | OMe | Cl | Et | H | |
| 15-70 | OMe | Br | Et | H | |
| 15-71 | OMe | I | Et | H | |
| 15-72 | OMe | CF$_3$ | Et | H | |
| 15-73 | OMe | CHF$_2$ | Et | H | |
| 15-74 | OMe | CF$_2$Cl | Et | H | |
| 15-75 | OMe | OMe | Et | H | |
| 15-76 | OMe | NO$_2$ | Et | H | |
| 15-77 | OMe | SO$_2$Me | Et | H | |
| 15-78 | SO$_2$Me | Me | Et | H | |
| 15-79 | SO$_2$Me | F | Et | H | |
| 15-80 | SO$_2$Me | Cl | Et | H | |
| 15-81 | SO$_2$Me | Br | Et | H | |
| 15-82 | SO$_2$Me | I | Et | H | |
| 15-83 | SO$_2$Me | CF$_3$ | Et | H | |
| 15-84 | SO$_2$Me | CHF$_2$ | Et | H | |
| 15-85 | SO$_2$Me | CF$_2$Cl | Et | H | |
| 15-86 | SO$_2$Me | OMe | Et | H | |
| 15-87 | SO$_2$Me | NO$_2$ | Et | H | |
| 15-88 | SO$_2$Me | SO$_2$Me | Et | H | |
| 15-89 | Me | Me | CH$_2$CH$_2$OMe | H | |

TABLE 15-continued

Compounds according to the invention of the formula (I) in which Q is Q3 and R$^y$ is a methyl group, R" and W are each hydrogen and t = 0

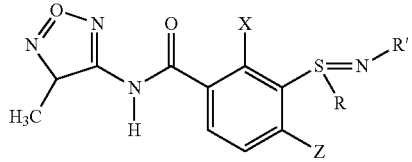
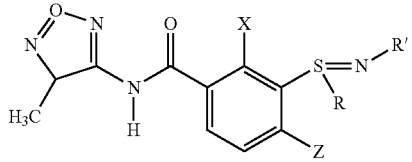

| No. | X | Z | R | R' | Physical Data ($^1$H NMR) |
|---|---|---|---|---|---|
| 15-90 | Me | F | CH$_2$CH$_2$OMe | H | |
| 15-91 | Me | Cl | CH$_2$CH$_2$OMe | H | |
| 15-92 | Me | Br | CH$_2$CH$_2$OMe | H | |
| 15-93 | Me | I | CH$_2$CH$_2$OMe | H | |
| 15-94 | Me | CF$_3$ | CH$_2$CH$_2$OMe | H | |
| 15-95 | Me | CHF$_2$ | CH$_2$CH$_2$OMe | H | |
| 15-96 | Me | CF$_2$Cl | CH$_2$CH$_2$OMe | H | |
| 15-97 | Me | OMe | CH$_2$CH$_2$OMe | H | |
| 15-98 | Me | NO$_2$ | CH$_2$CH$_2$OMe | H | |
| 15-99 | Me | SO$_2$Me | CH$_2$CH$_2$OMe | H | |
| 15-100 | Cl | Me | CH$_2$CH$_2$OMe | H | |
| 15-101 | Cl | F | CH$_2$CH$_2$OMe | H | |
| 15-102 | Cl | Cl | CH$_2$CH$_2$OMe | H | |
| 15-103 | Cl | Br | CH$_2$CH$_2$OMe | H | |
| 15-104 | Cl | I | CH$_2$CH$_2$OMe | H | |
| 15-105 | Cl | CF$_3$ | CH$_2$CH$_2$OMe | H | |
| 15-106 | Cl | CHF$_2$ | CH$_2$CH$_2$OMe | H | |
| 15-107 | Cl | CF$_2$Cl | CH$_2$CH$_2$OMe | H | |
| 15-108 | Cl | OMe | CH$_2$CH$_2$OMe | H | |
| 15-109 | Cl | NO$_2$ | CH$_2$CH$_2$OMe | H | |
| 15-110 | Cl | SO$_2$Me | CH$_2$CH$_2$OMe | H | |
| 15-111 | OMe | Me | CH$_2$CH$_2$OMe | H | |
| 15-112 | OMe | F | CH$_2$CH$_2$OMe | H | |
| 15-113 | OMe | Cl | CH$_2$CH$_2$OMe | H | |
| 15-114 | OMe | Br | CH$_2$CH$_2$OMe | H | |
| 15-115 | OMe | I | CH$_2$CH$_2$OMe | H | |
| 15-116 | OMe | CF$_3$ | CH$_2$CH$_2$OMe | H | |
| 15-117 | OMe | CHF$_2$ | CH$_2$CH$_2$OMe | H | |
| 15-118 | OMe | CF$_2$Cl | CH$_2$CH$_2$OMe | H | |
| 15-119 | OMe | OMe | CH$_2$CH$_2$OMe | H | |
| 15-120 | OMe | NO$_2$ | CH$_2$CH$_2$OMe | H | |
| 15-121 | OMe | SO$_2$Me | CH$_2$CH$_2$OMe | H | |
| 15-122 | SO$_2$Me | Me | CH$_2$CH$_2$OMe | H | |
| 15-123 | SO$_2$Me | F | CH$_2$CH$_2$OMe | H | |
| 15-124 | SO$_2$Me | Cl | CH$_2$CH$_2$OMe | H | |
| 15-125 | SO$_2$Me | Br | CH$_2$CH$_2$OMe | H | |
| 15-126 | SO$_2$Me | I | CH$_2$CH$_2$OMe | H | |
| 15-127 | SO$_2$Me | CF$_3$ | CH$_2$CH$_2$OMe | H | |
| 15-128 | SO$_2$Me | CHF$_2$ | CH$_2$CH$_2$OMe | H | |
| 15-129 | SO$_2$Me | CF$_2$Cl | CH$_2$CH$_2$OMe | H | |
| 15-130 | SO$_2$Me | OMe | CH$_2$CH$_2$OMe | H | |
| 15-131 | SO$_2$Me | NO$_2$ | CH$_2$CH$_2$OMe | H | |
| 15-132 | SO$_2$Me | SO$_2$Me | CH$_2$CH$_2$OMe | H | |
| 15-133 | Me | Me | Me | CN | |
| 15-134 | Me | F | Me | CN | |
| 15-135 | Me | Cl | Me | CN | |
| 15-136 | Me | Br | Me | CN | |
| 15-137 | Me | I | Me | CN | |
| 15-138 | Me | CF$_3$ | Me | CN | |
| 15-139 | Me | CHF$_2$ | Me | CN | |
| 15-140 | Me | CF$_2$Cl | Me | CN | |
| 15-141 | Me | OMe | Me | CN | |
| 15-142 | Me | NO$_2$ | Me | CN | |
| 15-143 | Me | SO$_2$Me | Me | CN | |
| 15-144 | Cl | Me | Me | CN | |
| 15-145 | Cl | F | Me | CN | |
| 15-146 | Cl | Cl | Me | CN | |
| 15-147 | Cl | Br | Me | CN | |
| 15-148 | Cl | I | Me | CN | |
| 15-149 | Cl | CF$_3$ | Me | CN | |
| 15-150 | Cl | CHF$_2$ | Me | CN | |
| 15-151 | Cl | CF$_2$Cl | Me | CN | |
| 15-152 | Cl | OMe | Me | CN | |
| 15-153 | Cl | NO$_2$ | Me | CN | |
| 15-154 | Cl | SO$_2$Me | Me | CN | |
| 15-155 | OMe | Me | Me | CN | |
| 15-156 | OMe | F | Me | CN | |
| 15-157 | OMe | Cl | Me | CN | |
| 15-158 | OMe | Br | Me | CN | |
| 15-159 | OMe | I | Me | CN | |
| 15-160 | OMe | CF$_3$ | Me | CN | |
| 15-161 | OMe | CHF$_2$ | Me | CN | |
| 15-162 | OMe | CF$_2$Cl | Me | CN | |
| 15-163 | OMe | OMe | Me | CN | |
| 15-164 | OMe | NO$_2$ | Me | CN | |
| 15-165 | OMe | SO$_2$Me | Me | CN | |
| 15-166 | SO$_2$Me | Me | Me | CN | |
| 15-167 | SO$_2$Me | F | Me | CN | |
| 15-168 | SO$_2$Me | Cl | Me | CN | |
| 15-169 | SO$_2$Me | Br | Me | CN | |
| 15-170 | SO$_2$Me | I | Me | CN | |
| 15-171 | SO$_2$Me | CF$_3$ | Me | CN | |
| 15-172 | SO$_2$Me | CHF$_2$ | Me | CN | |
| 15-173 | SO$_2$Me | CF$_2$Cl | Me | CN | |
| 15-174 | SO$_2$Me | OMe | Me | CN | |
| 15-175 | SO$_2$Me | NO$_2$ | Me | CN | |
| 15-176 | SO$_2$Me | SO$_2$Me | Me | CN | |
| 15-177 | Me | Me | Et | CN | |
| 15-178 | Me | F | Et | CN | |
| 15-179 | Me | Cl | Et | CN | |
| 15-180 | Me | Br | Et | CN | |
| 15-181 | Me | I | Et | CN | |
| 15-182 | Me | CF$_3$ | Et | CN | |
| 15-183 | Me | CHF$_2$ | Et | CN | |
| 15-184 | Me | CF$_2$Cl | Et | CN | |
| 15-185 | Me | OMe | Et | CN | |
| 15-186 | Me | NO$_2$ | Et | CN | |
| 15-187 | Me | SO$_2$Me | Et | CN | |
| 15-188 | Cl | Me | Et | CN | |
| 15-189 | Cl | F | Et | CN | |
| 15-190 | Cl | Cl | Et | CN | |
| 15-191 | Cl | Br | Et | CN | |
| 15-192 | Cl | I | Et | CN | |
| 15-193 | Cl | CF$_3$ | Et | CN | |
| 15-194 | Cl | CHF$_2$ | Et | CN | |
| 15-195 | Cl | CF$_2$Cl | Et | CN | |
| 15-196 | Cl | OMe | Et | CN | |
| 15-197 | Cl | NO$_2$ | Et | CN | |
| 15-198 | Cl | SO$_2$Me | Et | CN | |
| 15-199 | OMe | Me | Et | CN | |
| 15-200 | OMe | F | Et | CN | |
| 15-201 | OMe | Cl | Et | CN | |
| 15-202 | OMe | Br | Et | CN | |
| 15-203 | OMe | I | Et | CN | |
| 15-204 | OMe | CF$_3$ | Et | CN | |
| 15-205 | OMe | CHF$_2$ | Et | CN | |
| 15-206 | OMe | CF$_2$Cl | Et | CN | |
| 15-207 | OMe | OMe | Et | CN | |
| 15-208 | OMe | NO$_2$ | Et | CN | |
| 15-209 | OMe | SO$_2$Me | Et | CN | |
| 15-210 | SO$_2$Me | Me | Et | CN | |
| 15-211 | SO$_2$Me | F | Et | CN | |
| 15-212 | SO$_2$Me | Cl | Et | CN | |
| 15-213 | SO$_2$Me | Br | Et | CN | |
| 15-214 | SO$_2$Me | I | Et | CN | |
| 15-215 | SO$_2$Me | CF$_3$ | Et | CN | |
| 15-216 | SO$_2$Me | CHF$_2$ | Et | CN | |
| 15-217 | SO$_2$Me | CF$_2$Cl | Et | CN | |
| 15-218 | SO$_2$Me | OMe | Et | CN | |
| 15-219 | SO$_2$Me | NO$_2$ | Et | CN | |
| 15-220 | SO$_2$Me | SO$_2$Me | Et | CN | |
| 15-221 | Me | Me | CH$_2$CH$_2$OMe | CN | |

TABLE 15-continued

Compounds according to the invention of the formula (I) in which Q is Q3 and R$^y$ is a methyl group, R" and W are each hydrogen and t = 0

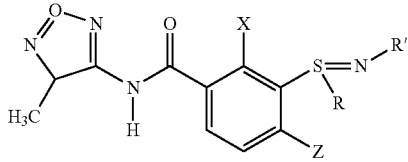

| No. | X | Z | R | R' | Physical Data ($^1$H NMR) |
|---|---|---|---|---|---|
| 15-222 | Me | F | CH$_2$CH$_2$OMe | CN | |
| 15-223 | Me | Cl | CH$_2$CH$_2$OMe | CN | |
| 15-224 | Me | Br | CH$_2$CH$_2$OMe | CN | |
| 15-225 | Me | I | CH$_2$CH$_2$OMe | CN | |
| 15-226 | Me | CF$_3$ | CH$_2$CH$_2$OMe | CN | |
| 15-227 | Me | CHF$_2$ | CH$_2$CH$_2$OMe | CN | |
| 15-228 | Me | CF$_2$Cl | CH$_2$CH$_2$OMe | CN | |
| 15-229 | Me | OMe | CH$_2$CH$_2$OMe | CN | |
| 15-230 | Me | NO$_2$ | CH$_2$CH$_2$OMe | CN | |
| 15-231 | Me | SO$_2$Me | CH$_2$CH$_2$OMe | CN | |
| 15-232 | Cl | Me | CH$_2$CH$_2$OMe | CN | |
| 15-233 | Cl | F | CH$_2$CH$_2$OMe | CN | |
| 15-234 | Cl | Cl | CH$_2$CH$_2$OMe | CN | |
| 15-235 | Cl | Br | CH$_2$CH$_2$OMe | CN | |
| 15-236 | Cl | I | CH$_2$CH$_2$OMe | CN | |
| 15-237 | Cl | CF$_3$ | CH$_2$CH$_2$OMe | CN | |
| 15-238 | Cl | CHF$_2$ | CH$_2$CH$_2$OMe | CN | |
| 15-239 | Cl | CF$_2$Cl | CH$_2$CH$_2$OMe | CN | |
| 15-240 | Cl | OMe | CH$_2$CH$_2$OMe | CN | |
| 15-241 | Cl | NO$_2$ | CH$_2$CH$_2$OMe | CN | |
| 15-242 | Cl | SO$_2$Me | CH$_2$CH$_2$OMe | CN | |
| 15-243 | OMe | Me | CH$_2$CH$_2$OMe | CN | |
| 15-244 | OMe | F | CH$_2$CH$_2$OMe | CN | |
| 15-245 | OMe | Cl | CH$_2$CH$_2$OMe | CN | |
| 15-246 | OMe | Br | CH$_2$CH$_2$OMe | CN | |
| 15-247 | OMe | I | CH$_2$CH$_2$OMe | CN | |
| 15-248 | OMe | CF$_3$ | CH$_2$CH$_2$OMe | CN | |
| 15-249 | OMe | CHF$_2$ | CH$_2$CH$_2$OMe | CN | |
| 15-250 | OMe | CF$_2$Cl | CH$_2$CH$_2$OMe | CN | |
| 15-251 | OMe | OMe | CH$_2$CH$_2$OMe | CN | |
| 15-252 | OMe | NO$_2$ | CH$_2$CH$_2$OMe | CN | |
| 15-253 | OMe | SO$_2$Me | CH$_2$CH$_2$OMe | CN | |
| 15-254 | SO$_2$Me | Me | CH$_2$CH$_2$OMe | CN | |
| 15-255 | SO$_2$Me | F | CH$_2$CH$_2$OMe | CN | |
| 15-256 | SO$_2$Me | Cl | CH$_2$CH$_2$OMe | CN | |
| 15-257 | SO$_2$Me | Br | CH$_2$CH$_2$OMe | CN | |
| 15-258 | SO$_2$Me | I | CH$_2$CH$_2$OMe | CN | |
| 15-259 | SO$_2$Me | CF$_3$ | CH$_2$CH$_2$OMe | CN | |
| 15-260 | SO$_2$Me | CHF$_2$ | CH$_2$CH$_2$OMe | CN | |
| 15-261 | SO$_2$Me | CF$_2$Cl | CH$_2$CH$_2$OMe | CN | |
| 15-262 | SO$_2$Me | OMe | CH$_2$CH$_2$OMe | CN | |
| 15-263 | SO$_2$Me | NO$_2$ | CH$_2$CH$_2$OMe | CN | |
| 15-264 | SO$_2$Me | SO$_2$Me | CH$_2$CH$_2$OMe | CN | |

TABLE 16

Compounds according to the invention of the formula (I) in which Q is Q4 and R$^z$ is a methyl group, R" and W are each hydrogen and t = 0

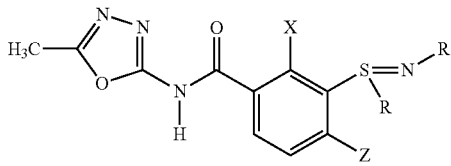

| No. | X | Z | R | R' | Physical Data ($^1$H NMR) |
|---|---|---|---|---|---|
| 16-1 | Me | Me | Me | H | |
| 16-2 | Me | F | Me | H | |
| 16-3 | Me | Cl | Me | H | |
| 16-4 | Me | Br | Me | H | |

TABLE 16-continued

Compounds according to the invention of the formula (I) in which Q is Q4 and R$^z$ is a methyl group, R" and W are each hydrogen and t = 0

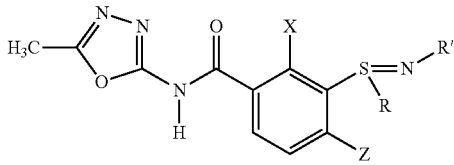

| No. | X | Z | R | R' | Physical Data ($^1$H NMR) |
|---|---|---|---|---|---|
| 16-5 | Me | I | Me | H | |
| 16-6 | Me | CF$_3$ | Me | H | |
| 16-7 | Me | CHF$_2$ | Me | H | |
| 16-8 | Me | CF$_2$Cl | Me | H | |
| 16-9 | Me | OMe | Me | H | |
| 16-10 | Me | NO$_2$ | Me | H | |
| 16-11 | Me | SO$_2$Me | Me | H | |
| 16-12 | Cl | Me | Me | H | |
| 16-13 | Cl | F | Me | H | |
| 16-14 | Cl | Cl | Me | H | |
| 16-15 | Cl | Br | Me | H | |
| 16-16 | Cl | I | Me | H | |
| 16-17 | Cl | CF$_3$ | Me | H | |
| 16-18 | Cl | CHF$_2$ | Me | H | |
| 16-19 | Cl | CF$_2$Cl | Me | H | |
| 16-20 | Cl | OMe | Me | H | |
| 16-21 | Cl | NO$_2$ | Me | H | |
| 16-22 | Cl | SO$_2$Me | Me | H | |
| 16-23 | OMe | Me | Me | H | |
| 16-24 | OMe | F | Me | H | |
| 16-25 | OMe | Cl | Me | H | |
| 16-26 | OMe | Br | Me | H | |
| 16-27 | OMe | I | Me | H | |
| 16-28 | OMe | CF$_3$ | Me | H | |
| 16-29 | OMe | CHF$_2$ | Me | H | |
| 16-30 | OMe | CF$_2$Cl | Me | H | |
| 16-31 | OMe | OMe | Me | H | |
| 16-32 | OMe | NO$_2$ | Me | H | |
| 16-33 | OMe | SO$_2$Me | Me | H | |
| 16-34 | SO$_2$Me | Me | Me | H | |
| 16-35 | SO$_2$Me | F | Me | H | |
| 16-36 | SO$_2$Me | Cl | Me | H | |
| 16-37 | SO$_2$Me | Br | Me | H | |
| 16-38 | SO$_2$Me | I | Me | H | |
| 16-39 | SO$_2$Me | CF$_3$ | Me | H | |
| 16-40 | SO$_2$Me | CHF$_2$ | Me | H | |
| 16-41 | SO$_2$Me | CF$_2$Cl | Me | H | |
| 16-42 | SO$_2$Me | OMe | Me | H | |
| 16-43 | SO$_2$Me | NO$_2$ | Me | H | |
| 16-44 | SO$_2$Me | SO$_2$Me | Me | H | |
| 16-45 | Me | Me | Et | H | |
| 16-46 | Me | F | Et | H | |
| 16-47 | Me | Cl | Et | H | |
| 16-48 | Me | Br | Et | H | |
| 16-49 | Me | I | Et | H | |
| 16-50 | Me | CF$_3$ | Et | H | |
| 16-51 | Me | CHF$_2$ | Et | H | |
| 16-52 | Me | CF$_2$Cl | Et | H | |
| 16-53 | Me | OMe | Et | H | |
| 16-54 | Me | NO$_2$ | Et | H | |
| 16-55 | Me | SO$_2$Me | Et | H | |
| 16-56 | Cl | Me | Et | H | |
| 16-57 | Cl | F | Et | H | |
| 16-58 | Cl | Cl | Et | H | |
| 16-59 | Cl | Br | Et | H | |
| 16-60 | Cl | I | Et | H | |
| 16-61 | Cl | CF$_3$ | Et | H | |
| 16-62 | Cl | CHF$_2$ | Et | H | |
| 16-63 | Cl | CF$_2$Cl | Et | H | |
| 16-64 | Cl | OMe | Et | H | |
| 16-65 | Cl | NO$_2$ | Et | H | |
| 16-66 | Cl | SO$_2$Me | Et | H | |
| 16-67 | OMe | Me | Et | H | |
| 16-68 | OMe | F | Et | H | |
| 16-69 | OMe | Cl | Et | H | |
| 16-70 | OMe | Br | Et | H | |

TABLE 16-continued

Compounds according to the invention of the formula (I) in which Q is Q4 and $R^z$ is a methyl group, R" and W are each hydrogen and t = 0

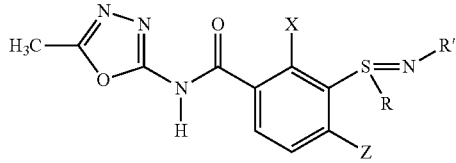

| No. | X | Z | R | R' | Physical Data ($^1$H NMR) |
|---|---|---|---|---|---|
| 16-71 | OMe | I | Et | H | |
| 16-72 | OMe | CF$_3$ | Et | H | |
| 16-73 | OMe | CHF$_2$ | Et | H | |
| 16-74 | OMe | CF$_2$Cl | Et | H | |
| 16-75 | OMe | OMe | Et | H | |
| 16-76 | OMe | NO$_2$ | Et | H | |
| 16-77 | OMe | SO$_2$Me | Et | H | |
| 16-78 | SO$_2$Me | Me | Et | H | |
| 16-79 | SO$_2$Me | F | Et | H | |
| 16-80 | SO$_2$Me | Cl | Et | H | |
| 16-81 | SO$_2$Me | Br | Et | H | |
| 16-82 | SO$_2$Me | I | Et | H | |
| 16-83 | SO$_2$Me | CF$_3$ | Et | H | |
| 16-84 | SO$_2$Me | CHF$_2$ | Et | H | |
| 16-85 | SO$_2$Me | CF$_2$Cl | Et | H | |
| 16-86 | SO$_2$Me | OMe | Et | H | |
| 16-87 | SO$_2$Me | NO$_2$ | Et | H | |
| 16-88 | SO$_2$Me | SO$_2$Me | Et | H | |
| 16-89 | Me | Me | CH$_2$CH$_2$OMe | H | |
| 16-90 | Me | F | CH$_2$CH$_2$OMe | H | |
| 16-91 | Me | Cl | CH$_2$CH$_2$OMe | H | |
| 16-92 | Me | Br | CH$_2$CH$_2$OMe | H | |
| 16-93 | Me | I | CH$_2$CH$_2$OMe | H | |
| 16-94 | Me | CF$_3$ | CH$_2$CH$_2$OMe | H | |
| 16-95 | Me | CHF$_2$ | CH$_2$CH$_2$OMe | H | |
| 16-96 | Me | CF$_2$Cl | CH$_2$CH$_2$OMe | H | |
| 16-97 | Me | OMe | CH$_2$CH$_2$OMe | H | |
| 16-98 | Me | NO$_2$ | CH$_2$CH$_2$OMe | H | |
| 16-99 | Me | SO$_2$Me | CH$_2$CH$_2$OMe | H | |
| 16-100 | Cl | Me | CH$_2$CH$_2$OMe | H | |
| 16-101 | Cl | F | CH$_2$CH$_2$OMe | H | |
| 16-102 | Cl | Cl | CH$_2$CH$_2$OMe | H | |
| 16-103 | Cl | Br | CH$_2$CH$_2$OMe | H | |
| 16-104 | Cl | I | CH$_2$CH$_2$OMe | H | |
| 16-105 | Cl | CF$_3$ | CH$_2$CH$_2$OMe | H | |
| 16-106 | Cl | CHF$_2$ | CH$_2$CH$_2$OMe | H | |
| 16-107 | Cl | CF$_2$Cl | CH$_2$CH$_2$OMe | H | |
| 16-108 | Cl | OMe | CH$_2$CH$_2$OMe | H | |
| 16-109 | Cl | NO$_2$ | CH$_2$CH$_2$OMe | H | |
| 16-110 | Cl | SO$_2$Me | CH$_2$CH$_2$OMe | H | |
| 16-111 | OMe | Me | CH$_2$CH$_2$OMe | H | |
| 16-112 | OMe | F | CH$_2$CH$_2$OMe | H | |
| 16-113 | OMe | Cl | CH$_2$CH$_2$OMe | H | |
| 16-114 | OMe | Br | CH$_2$CH$_2$OMe | H | |
| 16-115 | OMe | I | CH$_2$CH$_2$OMe | H | |
| 16-116 | OMe | CF$_3$ | CH$_2$CH$_2$OMe | H | |
| 16-117 | OMe | CHF$_2$ | CH$_2$CH$_2$OMe | H | |
| 16-118 | OMe | CF$_2$Cl | CH$_2$CH$_2$OMe | H | |
| 16-119 | OMe | OMe | CH$_2$CH$_2$OMe | H | |
| 16-120 | OMe | NO$_2$ | CH$_2$CH$_2$OMe | H | |
| 16-121 | OMe | SO$_2$Me | CH$_2$CH$_2$OMe | H | |
| 16-122 | SO$_2$Me | Me | CH$_2$CH$_2$OMe | H | |
| 16-123 | SO$_2$Me | F | CH$_2$CH$_2$OMe | H | |
| 16-124 | SO$_2$Me | Cl | CH$_2$CH$_2$OMe | H | |
| 16-125 | SO$_2$Me | Br | CH$_2$CH$_2$OMe | H | |
| 16-126 | SO$_2$Me | I | CH$_2$CH$_2$OMe | H | |
| 16-127 | SO$_2$Me | CF$_3$ | CH$_2$CH$_2$OMe | H | |
| 16-128 | SO$_2$Me | CHF$_2$ | CH$_2$CH$_2$OMe | H | |
| 16-129 | SO$_2$Me | CF$_2$Cl | CH$_2$CH$_2$OMe | H | |
| 16-130 | SO$_2$Me | OMe | CH$_2$CH$_2$OMe | H | |
| 16-131 | SO$_2$Me | NO$_2$ | CH$_2$CH$_2$OMe | H | |
| 16-132 | SO$_2$Me | SO$_2$Me | CH$_2$CH$_2$OMe | H | |
| 16-133 | Me | Me | Me | CN | |
| 16-134 | Me | F | Me | CN | |
| 16-135 | Me | Cl | Me | CN | |
| 16-136 | Me | Br | Me | CN | |

TABLE 16-continued

Compounds according to the invention of the formula (I) in which Q is Q4 and $R^z$ is a methyl group, R" and W are each hydrogen and t = 0

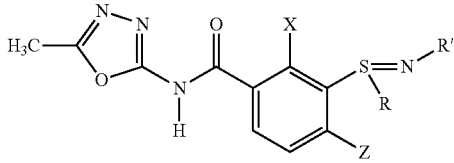

| No. | X | Z | R | R' | Physical Data ($^1$H NMR) |
|---|---|---|---|---|---|
| 16-137 | Me | I | Me | CN | |
| 16-138 | Me | CF$_3$ | Me | CN | |
| 16-139 | Me | CHF$_2$ | Me | CN | |
| 16-140 | Me | CF$_2$Cl | Me | CN | |
| 16-141 | Me | OMe | Me | CN | |
| 16-142 | Me | NO$_2$ | Me | CN | |
| 16-143 | Me | SO$_2$Me | Me | CN | |
| 16-144 | Cl | Me | Me | CN | |
| 16-145 | Cl | F | Me | CN | |
| 16-146 | Cl | Cl | Me | CN | |
| 16-147 | Cl | Br | Me | CN | |
| 16-148 | Cl | I | Me | CN | |
| 16-149 | Cl | CF$_3$ | Me | CN | |
| 16-150 | Cl | CHF$_2$ | Me | CN | |
| 16-151 | Cl | CF$_2$Cl | Me | CN | |
| 16-152 | Cl | OMe | Me | CN | |
| 16-153 | Cl | NO$_2$ | Me | CN | |
| 16-154 | Cl | SO$_2$Me | Me | CN | |
| 16-155 | OMe | Me | Me | CN | |
| 16-156 | OMe | F | Me | CN | |
| 16-157 | OMe | Cl | Me | CN | |
| 16-158 | OMe | Br | Me | CN | |
| 16-159 | OMe | I | Me | CN | |
| 16-160 | OMe | CF$_3$ | Me | CN | |
| 16-161 | OMe | CHF$_2$ | Me | CN | |
| 16-162 | OMe | CF$_2$Cl | Me | CN | |
| 16-163 | OMe | OMe | Me | CN | |
| 16-164 | OMe | NO$_2$ | Me | CN | |
| 16-165 | OMe | SO$_2$Me | Me | CN | |
| 16-166 | SO$_2$Me | Me | Me | CN | |
| 16-167 | SO$_2$Me | F | Me | CN | |
| 16-168 | SO$_2$Me | Cl | Me | CN | |
| 16-169 | SO$_2$Me | Br | Me | CN | |
| 16-170 | SO$_2$Me | I | Me | CN | |
| 16-171 | SO$_2$Me | CF$_3$ | Me | CN | |
| 16-172 | SO$_2$Me | CHF$_2$ | Me | CN | |
| 16-173 | SO$_2$Me | CF$_2$Cl | Me | CN | |
| 16-174 | SO$_2$Me | OMe | Me | CN | |
| 16-175 | SO$_2$Me | NO$_2$ | Me | CN | |
| 16-176 | SO$_2$Me | SO$_2$Me | Me | CN | |
| 16-177 | Me | Me | Et | CN | |
| 16-178 | Me | F | Et | CN | |
| 16-179 | Me | Cl | Et | CN | |
| 16-180 | Me | Br | Et | CN | |
| 16-181 | Me | I | Et | CN | |
| 16-182 | Me | CF$_3$ | Et | CN | |
| 16-183 | Me | CHF$_2$ | Et | CN | |
| 16-184 | Me | CF$_2$Cl | Et | CN | |
| 16-185 | Me | OMe | Et | CN | |
| 16-186 | Me | NO$_2$ | Et | CN | |
| 16-187 | Me | SO$_2$Me | Et | CN | |
| 16-188 | Cl | Me | Et | CN | |
| 16-189 | Cl | F | Et | CN | |
| 16-190 | Cl | Cl | Et | CN | |
| 16-191 | Cl | Br | Et | CN | |
| 16-192 | Cl | I | Et | CN | |
| 16-193 | Cl | CF$_3$ | Et | CN | |
| 16-194 | Cl | CHF$_2$ | Et | CN | |
| 16-195 | Cl | CF$_2$Cl | Et | CN | |
| 16-196 | Cl | OMe | Et | CN | |
| 16-197 | Cl | NO$_2$ | Et | CN | |
| 16-198 | Cl | SO$_2$Me | Et | CN | |
| 16-199 | OMe | Me | Et | CN | |
| 16-200 | OMe | F | Et | CN | |
| 16-201 | OMe | Cl | Et | CN | |
| 16-202 | OMe | Br | Et | CN | |

TABLE 16-continued

Compounds according to the invention of the formula (I) in which Q is Q4 and $R^z$ is a methyl group, R" and W are each hydrogen and t = 0

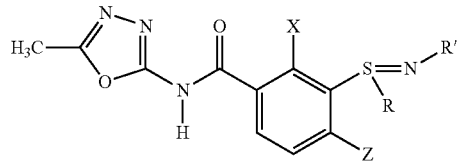

| No. | X | Z | R | R' | Physical Data ($^1$H NMR) |
|---|---|---|---|---|---|
| 16-203 | OMe | I | Et | CN | |
| 16-204 | OMe | CF$_3$ | Et | CN | |
| 16-205 | OMe | CHF$_2$ | Et | CN | |
| 16-206 | OMe | CF$_2$Cl | Et | CN | |
| 16-207 | OMe | OMe | Et | CN | |
| 16-208 | OMe | NO$_2$ | Et | CN | |
| 16-209 | OMe | SO$_2$Me | Et | CN | |
| 16-210 | SO$_2$Me | Me | Et | CN | |
| 16-211 | SO$_2$Me | F | Et | CN | |
| 16-212 | SO$_2$Me | Cl | Et | CN | |
| 16-213 | SO$_2$Me | Br | Et | CN | |
| 16-214 | SO$_2$Me | I | Et | CN | |
| 16-215 | SO$_2$Me | CF$_3$ | Et | CN | |
| 16-216 | SO$_2$Me | CHF$_2$ | Et | CN | |
| 16-217 | SO$_2$Me | CF$_2$Cl | Et | CN | |
| 16-218 | SO$_2$Me | OMe | Et | CN | |
| 16-219 | SO$_2$Me | NO$_2$ | Et | CN | |
| 16-220 | SO$_2$Me | SO$_2$Me | Et | CN | |
| 16-221 | Me | Me | CH$_2$CH$_2$OMe | CN | |
| 16-222 | Me | F | CH$_2$CH$_2$OMe | CN | |
| 16-223 | Me | Cl | CH$_2$CH$_2$OMe | CN | |
| 16-224 | Me | Br | CH$_2$CH$_2$OMe | CN | |
| 16-225 | Me | I | CH$_2$CH$_2$OMe | CN | |
| 16-226 | Me | CF$_3$ | CH$_2$CH$_2$OMe | CN | |
| 16-227 | Me | CHF$_2$ | CH$_2$CH$_2$OMe | CN | |
| 16-228 | Me | CF$_2$Cl | CH$_2$CH$_2$OMe | CN | |
| 16-229 | Me | OMe | CH$_2$CH$_2$OMe | CN | |
| 16-230 | Me | NO$_2$ | CH$_2$CH$_2$OMe | CN | |
| 16-231 | Me | SO$_2$Me | CH$_2$CH$_2$OMe | CN | |
| 16-232 | Cl | Me | CH$_2$CH$_2$OMe | CN | |
| 16-233 | Cl | F | CH$_2$CH$_2$OMe | CN | |
| 16-234 | Cl | Cl | CH$_2$CH$_2$OMe | CN | |
| 16-235 | Cl | Br | CH$_2$CH$_2$OMe | CN | |
| 16-236 | Cl | I | CH$_2$CH$_2$OMe | CN | |
| 16-237 | Cl | CF$_3$ | CH$_2$CH$_2$OMe | CN | |
| 16-238 | Cl | CHF$_2$ | CH$_2$CH$_2$OMe | CN | |
| 16-239 | Cl | CF$_2$Cl | CH$_2$CH$_2$OMe | CN | |
| 16-240 | Cl | OMe | CH$_2$CH$_2$OMe | CN | |
| 16-241 | Cl | NO$_2$ | CH$_2$CH$_2$OMe | CN | |
| 16-242 | Cl | SO$_2$Me | CH$_2$CH$_2$OMe | CN | |
| 16-243 | OMe | Me | CH$_2$CH$_2$OMe | CN | |
| 16-244 | OMe | F | CH$_2$CH$_2$OMe | CN | |
| 16-245 | OMe | Cl | CH$_2$CH$_2$OMe | CN | |
| 16-246 | OMe | Br | CH$_2$CH$_2$OMe | CN | |
| 16-247 | OMe | I | CH$_2$CH$_2$OMe | CN | |
| 16-248 | OMe | CF$_3$ | CH$_2$CH$_2$OMe | CN | |
| 16-249 | OMe | CHF$_2$ | CH$_2$CH$_2$OMe | CN | |
| 16-250 | OMe | CF$_2$Cl | CH$_2$CH$_2$OMe | CN | |
| 16-251 | OMe | OMe | CH$_2$CH$_2$OMe | CN | |
| 16-252 | OMe | NO$_2$ | CH$_2$CH$_2$OMe | CN | |
| 16-253 | OMe | SO$_2$Me | CH$_2$CH$_2$OMe | CN | |
| 16-254 | SO$_2$Me | Me | CH$_2$CH$_2$OMe | CN | |
| 16-255 | SO$_2$Me | F | CH$_2$CH$_2$OMe | CN | |
| 16-256 | SO$_2$Me | Cl | CH$_2$CH$_2$OMe | CN | |
| 16-257 | SO$_2$Me | Br | CH$_2$CH$_2$OMe | CN | |
| 16-258 | SO$_2$Me | I | CH$_2$CH$_2$OMe | CN | |
| 16-259 | SO$_2$Me | CF$_3$ | CH$_2$CH$_2$OMe | CN | |
| 16-260 | SO$_2$Me | CHF$_2$ | CH$_2$CH$_2$OMe | CN | |
| 16-261 | SO$_2$Me | CF$_2$Cl | CH$_2$CH$_2$OMe | CN | |
| 16-262 | SO$_2$Me | OMe | CH$_2$CH$_2$OMe | CN | |
| 16-263 | SO$_2$Me | NO$_2$ | CH$_2$CH$_2$OMe | CN | |
| 16-264 | SO$_2$Me | SO$_2$Me | CH$_2$CH$_2$OMe | CN | |

TABLE 17

Compounds according to the invention of the formula (I) in the form of the sodium salts in which Q is Q1 and $R^x$ is a methyl group, W is hydrogen and t = 0

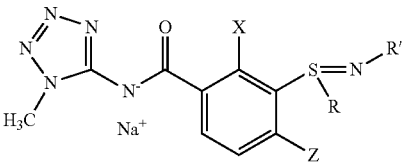

| No. | X | Z | R | R' | Physical Data ($^1$H NMR) |
|---|---|---|---|---|---|
| 17-1 | Me | Me | Me | H | |
| 17-2 | Me | Cl | Me | H | |
| 17-3 | Me | CF$_3$ | Me | H | |
| 17-4 | Me | CHF$_2$ | Me | H | |
| 17-5 | Cl | Me | Me | H | |
| 17-6 | Cl | Cl | Me | H | |
| 17-7 | Cl | CF$_3$ | Me | H | |
| 17-8 | Cl | CHF$_2$ | Me | H | |
| 17-9 | OMe | Me | Me | H | |
| 17-10 | OMe | Cl | Me | H | |
| 17-11 | OMe | CF$_3$ | Me | H | |
| 17-12 | OMe | CHF$_2$ | Me | H | |
| 17-13 | SO$_2$Me | Me | Me | H | |
| 17-14 | SO$_2$Me | Cl | Me | H | |
| 17-15 | SO$_2$Me | CF$_3$ | Me | H | |
| 17-16 | SO$_2$Me | CHF$_2$ | Me | H | |
| 17-17 | Me | Me | Et | H | |
| 17-18 | Me | Cl | Et | H | |
| 17-19 | Me | CF$_3$ | Et | H | |
| 17-20 | Me | CHF$_2$ | Et | H | |
| 17-21 | Cl | Me | Et | H | |
| 17-22 | Cl | Cl | Et | H | |
| 17-23 | Cl | CF$_3$ | Et | H | |
| 17-24 | Cl | CHF$_2$ | Et | H | |
| 17-25 | OMe | Me | Et | H | |
| 17-26 | OMe | Cl | Et | H | |
| 17-27 | OMe | CF$_3$ | Et | H | |
| 17-28 | OMe | CHF$_2$ | Et | H | |
| 17-29 | SO$_2$Me | Me | Et | H | |
| 17-30 | SO$_2$Me | Cl | Et | H | |
| 17-31 | SO$_2$Me | CF$_3$ | Et | H | |
| 17-32 | SO$_2$Me | CHF$_2$ | Et | H | |
| 17-33 | Me | Me | CH$_2$CH$_2$OMe | H | |
| 17-34 | Me | Cl | CH$_2$CH$_2$OMe | H | |
| 17-35 | Me | CF$_3$ | CH$_2$CH$_2$OMe | H | |
| 17-36 | Me | CHF$_2$ | CH$_2$CH$_2$OMe | H | |
| 17-37 | Cl | Me | CH$_2$CH$_2$OMe | H | |
| 17-38 | Cl | Cl | CH$_2$CH$_2$OMe | H | |
| 17-39 | Cl | CF$_3$ | CH$_2$CH$_2$OMe | H | |
| 17-40 | Cl | CHF$_2$ | CH$_2$CH$_2$OMe | H | |
| 17-41 | OMe | Me | CH$_2$CH$_2$OMe | H | |
| 17-42 | OMe | Cl | CH$_2$CH$_2$OMe | H | |
| 17-43 | OMe | CF$_3$ | CH$_2$CH$_2$OMe | H | |
| 17-44 | OMe | CHF$_2$ | CH$_2$CH$_2$OMe | H | |
| 17-45 | SO$_2$Me | Me | CH$_2$CH$_2$OMe | H | |
| 17-46 | SO$_2$Me | Cl | CH$_2$CH$_2$OMe | H | |
| 17-47 | SO$_2$Me | CF$_3$ | CH$_2$CH$_2$OMe | H | |
| 17-48 | SO$_2$Me | CHF$_2$ | CH$_2$CH$_2$OMe | H | |
| 17-49 | Me | Me | Me | CN | |
| 17-50 | Me | Cl | Me | CN | |
| 17-51 | Me | CF$_3$ | Me | CN | |
| 17-52 | Me | CHF$_2$ | Me | CN | |
| 17-53 | Cl | Me | Me | CN | |
| 17-54 | Cl | Cl | Me | CN | |
| 17-55 | Cl | CF$_3$ | Me | CN | |
| 17-56 | Cl | CHF$_2$ | Me | CN | |
| 17-57 | OMe | Me | Me | CN | |
| 17-58 | OMe | Cl | Me | CN | |
| 17-59 | OMe | CF$_3$ | Me | CN | |
| 17-60 | OMe | CHF$_2$ | Me | CN | |
| 17-61 | SO$_2$Me | Me | Me | CN | |
| 17-62 | SO$_2$Me | Cl | Me | CN | |
| 17-63 | SO$_2$Me | CF$_3$ | Me | CN | |
| 17-64 | SO$_2$Me | CHF$_2$ | Me | CN | |
| 17-65 | Me | Me | Et | CN | |

TABLE 17-continued

Compounds according to the invention of the formula (I) in the form of the sodium salts in which Q is Q1 and $R^x$ is a methyl group, W is hydrogen and t = 0

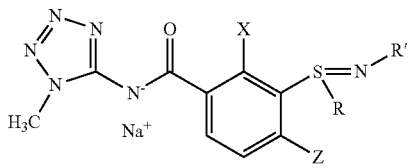

| No. | X | Z | R | R' | Physical Data ($^1$H NMR) |
|---|---|---|---|---|---|
| 17-66 | Me | Cl | Et | CN | |
| 17-67 | Me | CF$_3$ | Et | CN | |
| 17-68 | Me | CHF$_2$ | Et | CN | |
| 17-69 | Cl | Me | Et | CN | |
| 17-70 | Cl | Cl | Et | CN | |
| 17-71 | Cl | CF$_3$ | Et | CN | |
| 17-72 | Cl | CHF$_2$ | Et | CN | |
| 17-73 | OMe | Me | Et | CN | |
| 17-74 | OMe | Cl | Et | CN | |
| 17-75 | OMe | CF$_3$ | Et | CN | |
| 17-76 | OMe | CHF$_2$ | Et | CN | |
| 17-77 | SO$_2$Me | Me | Et | CN | |
| 17-78 | SO$_2$Me | Cl | Et | CN | |
| 17-79 | SO$_2$Me | CF$_3$ | Et | CN | |
| 17-80 | SO$_2$Me | CHF$_2$ | Et | CN | |
| 17-81 | Me | Me | CH$_2$CH$_2$OMe | CN | |
| 17-82 | Me | Cl | CH$_2$CH$_2$OMe | CN | |
| 17-83 | Me | CF$_3$ | CH$_2$CH$_2$OMe | CN | |
| 17-84 | Me | CHF$_2$ | CH$_2$CH$_2$OMe | CN | |
| 17-85 | Cl | Me | CH$_2$CH$_2$OMe | CN | |
| 17-86 | Cl | Cl | CH$_2$CH$_2$OMe | CN | |
| 17-87 | Cl | CF$_3$ | CH$_2$CH$_2$OMe | CN | |
| 17-88 | Cl | CHF$_2$ | CH$_2$CH$_2$OMe | CN | |
| 17-89 | OMe | Me | CH$_2$CH$_2$OMe | CN | |
| 17-90 | OMe | Cl | CH$_2$CH$_2$OMe | CN | |
| 17-91 | OMe | CF$_3$ | CH$_2$CH$_2$OMe | CN | |
| 17-92 | OMe | CHF$_2$ | CH$_2$CH$_2$OMe | CN | |
| 17-93 | SO$_2$Me | Me | CH$_2$CH$_2$OMe | CN | |
| 17-94 | SO$_2$Me | Cl | CH$_2$CH$_2$OMe | CN | |
| 17-95 | SO$_2$Me | CF$_3$ | CH$_2$CH$_2$OMe | CN | |
| 17-96 | SO$_2$Me | CHF$_2$ | CH$_2$CH$_2$OMe | CN | |

TABLE 18

Compounds according to the invention of the formula (I) in which Q is Q3 and $R^y$ is chlorine, R" and W are each hydrogen and t = 0

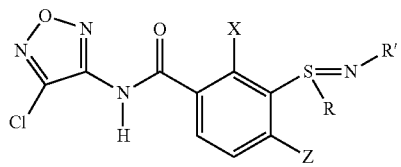

| No. | X | Z | R | R' | Physical Data ($^1$H NMR) |
|---|---|---|---|---|---|
| 18-1 | Me | Me | Me | H | |
| 18-2 | Me | F | Me | H | |
| 18-3 | Me | Cl | Me | H | |
| 18-4 | Me | Br | Me | H | |
| 18-5 | Me | I | Me | H | |
| 18-6 | Me | CF$_3$ | Me | H | |
| 18-7 | Me | CHF$_2$ | Me | H | |
| 18-8 | Me | CF$_2$Cl | Me | H | |
| 18-9 | Me | OMe | Me | H | |
| 18-10 | Me | NO$_2$ | Me | H | |
| 18-11 | Me | SO$_2$Me | Me | H | |
| 18-12 | Cl | Me | Me | H | |
| 18-13 | Cl | F | Me | H | |
| 18-14 | Cl | Cl | Me | H | |
| 18-15 | Cl | Br | Me | H | |

TABLE 18-continued

Compounds according to the invention of the formula (I) in which Q is Q3 and $R^y$ is chlorine, R" and W are each hydrogen and t = 0

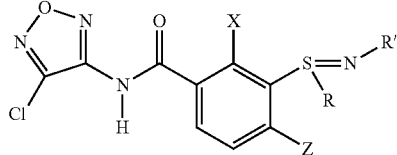

| No. | X | Z | R | R' | Physical Data ($^1$H NMR) |
|---|---|---|---|---|---|
| 18-16 | Cl | I | Me | H | |
| 18-17 | Cl | CF$_3$ | Me | H | |
| 18-18 | Cl | CHF$_2$ | Me | H | |
| 18-19 | Cl | CF$_2$Cl | Me | H | |
| 18-20 | Cl | OMe | Me | H | |
| 18-21 | Cl | NO$_2$ | Me | H | |
| 18-22 | Cl | SO$_2$Me | Me | H | |
| 18-23 | OMe | Me | Me | H | |
| 18-24 | OMe | F | Me | H | |
| 18-25 | OMe | Cl | Me | H | |
| 18-26 | OMe | Br | Me | H | |
| 18-27 | OMe | I | Me | H | |
| 18-28 | OMe | CF$_3$ | Me | H | |
| 18-29 | OMe | CHF$_2$ | Me | H | |
| 18-30 | OMe | CF$_2$Cl | Me | H | |
| 18-31 | OMe | OMe | Me | H | |
| 18-32 | OMe | NO$_2$ | Me | H | |
| 18-33 | OMe | SO$_2$Me | Me | H | |
| 18-34 | SO$_2$Me | Me | Me | H | |
| 18-35 | SO$_2$Me | F | Me | H | |
| 18-36 | SO$_2$Me | Cl | Me | H | |
| 18-37 | SO$_2$Me | Br | Me | H | |
| 18-38 | SO$_2$Me | I | Me | H | |
| 18-39 | SO$_2$Me | CF$_3$ | Me | H | |
| 18-40 | SO$_2$Me | CHF$_2$ | Me | H | |
| 18-41 | SO$_2$Me | CF$_2$Cl | Me | H | |
| 18-42 | SO$_2$Me | OMe | Me | H | |
| 18-43 | SO$_2$Me | NO$_2$ | Me | H | |
| 18-44 | SO$_2$Me | SO$_2$Me | Me | H | |
| 18-45 | Me | Me | Et | H | |
| 18-46 | Me | F | Et | H | |
| 18-47 | Me | Cl | Et | H | |
| 18-48 | Me | Br | Et | H | |
| 18-49 | Me | I | Et | H | |
| 18-50 | Me | CF$_3$ | Et | H | |
| 18-51 | Me | CHF$_2$ | Et | H | |
| 18-52 | Me | CF$_2$Cl | Et | H | |
| 18-53 | Me | OMe | Et | H | |
| 18-54 | Me | NO$_2$ | Et | H | |
| 18-55 | Me | SO$_2$Me | Et | H | |
| 18-56 | Cl | Me | Et | H | |
| 18-57 | Cl | F | Et | H | |
| 18-58 | Cl | Cl | Et | H | |
| 18-59 | Cl | Br | Et | H | |
| 18-60 | Cl | I | Et | H | |
| 18-61 | Cl | CF$_3$ | Et | H | |
| 18-62 | Cl | CHF$_2$ | Et | H | |
| 18-63 | Cl | CF$_2$Cl | Et | H | |
| 18-64 | Cl | OMe | Et | H | |
| 18-65 | Cl | NO$_2$ | Et | H | |
| 18-66 | Cl | SO$_2$Me | Et | H | |
| 18-67 | OMe | Me | Et | H | |
| 18-68 | OMe | F | Et | H | |
| 18-69 | OMe | Cl | Et | H | |
| 18-70 | OMe | Br | Et | H | |
| 18-71 | OMe | I | Et | H | |
| 18-72 | OMe | CF$_3$ | Et | H | |
| 18-73 | OMe | CHF$_2$ | Et | H | |
| 18-74 | OMe | CF$_2$Cl | Et | H | |
| 18-75 | OMe | OMe | Et | H | |
| 18-76 | OMe | NO$_2$ | Et | H | |
| 18-77 | OMe | SO$_2$Me | Et | H | |
| 18-78 | SO$_2$Me | Me | Et | H | |
| 18-79 | SO$_2$Me | F | Et | H | |
| 18-80 | SO$_2$Me | Cl | Et | H | |
| 18-81 | SO$_2$Me | Br | Et | H | |

TABLE 18-continued

Compounds according to the invention of the formula (I) in which Q is Q3 and $R^y$ is chlorine, R" and W are each hydrogen and t = 0

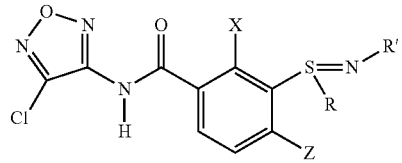

| No. | X | Z | R | R' | Physical Data ($^1$H NMR) |
|---|---|---|---|---|---|
| 18-82 | SO$_2$Me | I | Et | H | |
| 18-83 | SO$_2$Me | CF$_3$ | Et | H | |
| 18-84 | SO$_2$Me | CHF$_2$ | Et | H | |
| 18-85 | SO$_2$Me | CF$_2$Cl | Et | H | |
| 18-86 | SO$_2$Me | OMe | Et | H | |
| 18-87 | SO$_2$Me | NO$_2$ | Et | H | |
| 18-88 | SO$_2$Me | SO$_2$Me | Et | H | |
| 18-89 | Me | Me | CH$_2$CH$_2$OMe | H | |
| 18-90 | Me | F | CH$_2$CH$_2$OMe | H | |
| 18-91 | Me | Cl | CH$_2$CH$_2$OMe | H | |
| 18-92 | Me | Br | CH$_2$CH$_2$OMe | H | |
| 18-93 | Me | I | CH$_2$CH$_2$OMe | H | |
| 18-94 | Me | CF$_3$ | CH$_2$CH$_2$OMe | H | |
| 18-95 | Me | CHF$_2$ | CH$_2$CH$_2$OMe | H | |
| 18-96 | Me | CF$_2$Cl | CH$_2$CH$_2$OMe | H | |
| 18-97 | Me | OMe | CH$_2$CH$_2$OMe | H | |
| 18-98 | Me | NO$_2$ | CH$_2$CH$_2$OMe | H | |
| 18-99 | Me | SO$_2$Me | CH$_2$CH$_2$OMe | H | |
| 18-100 | Cl | Me | CH$_2$CH$_2$OMe | H | |
| 18-101 | Cl | F | CH$_2$CH$_2$OMe | H | |
| 18-102 | Cl | Cl | CH$_2$CH$_2$OMe | H | |
| 18-103 | Cl | Br | CH$_2$CH$_2$OMe | H | |
| 18-104 | Cl | I | CH$_2$CH$_2$OMe | H | |
| 18-105 | Cl | CF$_3$ | CH$_2$CH$_2$OMe | H | |
| 18-106 | Cl | CHF$_2$ | CH$_2$CH$_2$OMe | H | |
| 18-107 | Cl | CF$_2$Cl | CH$_2$CH$_2$OMe | H | |
| 18-108 | Cl | OMe | CH$_2$CH$_2$OMe | H | |
| 18-109 | Cl | NO$_2$ | CH$_2$CH$_2$OMe | H | |
| 18-110 | Cl | SO$_2$Me | CH$_2$CH$_2$OMe | H | |
| 18-111 | OMe | Me | CH$_2$CH$_2$OMe | H | |
| 18-112 | OMe | F | CH$_2$CH$_2$OMe | H | |
| 18-113 | OMe | Cl | CH$_2$CH$_2$OMe | H | |
| 18-114 | OMe | Br | CH$_2$CH$_2$OMe | H | |
| 18-115 | OMe | I | CH$_2$CH$_2$OMe | H | |
| 18-116 | OMe | CF$_3$ | CH$_2$CH$_2$OMe | H | |
| 18-117 | OMe | CHF$_2$ | CH$_2$CH$_2$OMe | H | |
| 18-118 | OMe | CF$_2$Cl | CH$_2$CH$_2$OMe | H | |
| 18-119 | OMe | OMe | CH$_2$CH$_2$OMe | H | |
| 18-120 | OMe | NO$_2$ | CH$_2$CH$_2$OMe | H | |
| 18-121 | OMe | SO$_2$Me | CH$_2$CH$_2$OMe | H | |
| 18-122 | SO$_2$Me | Me | CH$_2$CH$_2$OMe | H | |
| 18-123 | SO$_2$Me | F | CH$_2$CH$_2$OMe | H | |
| 18-124 | SO$_2$Me | Cl | CH$_2$CH$_2$OMe | H | |
| 18-125 | SO$_2$Me | Br | CH$_2$CH$_2$OMe | H | |
| 18-126 | SO$_2$Me | I | CH$_2$CH$_2$OMe | H | |
| 18-127 | SO$_2$Me | CF$_3$ | CH$_2$CH$_2$OMe | H | |
| 18-128 | SO$_2$Me | CHF$_2$ | CH$_2$CH$_2$OMe | H | |
| 18-129 | SO$_2$Me | CF$_2$Cl | CH$_2$CH$_2$OMe | H | |
| 18-130 | SO$_2$Me | OMe | CH$_2$CH$_2$OMe | H | |
| 18-131 | SO$_2$Me | NO$_2$ | CH$_2$CH$_2$OMe | H | |
| 18-132 | SO$_2$Me | SO$_2$Me | CH$_2$CH$_2$OMe | H | |
| 18-133 | Me | Me | Me | CN | |
| 18-134 | Me | F | Me | CN | |
| 18-135 | Me | Cl | Me | CN | |
| 18-136 | Me | Br | Me | CN | |
| 18-137 | Me | I | Me | CN | |
| 18-138 | Me | CF$_3$ | Me | CN | |
| 18-139 | Me | CHF$_2$ | Me | CN | |
| 18-140 | Me | CF$_2$Cl | Me | CN | |
| 18-141 | Me | OMe | Me | CN | |
| 18-142 | Me | NO$_2$ | Me | CN | |
| 18-143 | Me | SO$_2$Me | Me | CN | |
| 18-144 | Cl | Me | Me | CN | |
| 18-145 | Cl | F | Me | CN | |
| 18-146 | Cl | Cl | Me | CN | |
| 18-147 | Cl | Br | Me | CN | |

TABLE 18-continued

Compounds according to the invention of the formula (I) in which Q is Q3 and $R^y$ is chlorine, R" and W are each hydrogen and t = 0

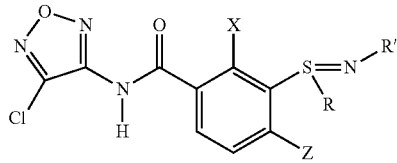

| No. | X | Z | R | R' | Physical Data ($^1$H NMR) |
|---|---|---|---|---|---|
| 18-148 | Cl | I | Me | CN | |
| 18-149 | Cl | CF$_3$ | Me | CN | |
| 18-150 | Cl | CHF$_2$ | Me | CN | |
| 18-151 | Cl | CF$_2$Cl | Me | CN | |
| 18-152 | Cl | OMe | Me | CN | |
| 18-153 | Cl | NO$_2$ | Me | CN | |
| 18-154 | Cl | SO$_2$Me | Me | CN | |
| 18-155 | OMe | Me | Me | CN | |
| 18-156 | OMe | F | Me | CN | |
| 18-157 | OMe | Cl | Me | CN | |
| 18-158 | OMe | Br | Me | CN | |
| 18-159 | OMe | I | Me | CN | |
| 18-160 | OMe | CF$_3$ | Me | CN | |
| 18-161 | OMe | CHF$_2$ | Me | CN | |
| 18-162 | OMe | CF$_2$Cl | Me | CN | |
| 18-163 | OMe | OMe | Me | CN | |
| 18-164 | OMe | NO$_2$ | Me | CN | |
| 18-165 | OMe | SO$_2$Me | Me | CN | |
| 18-166 | SO$_2$Me | Me | Me | CN | |
| 18-167 | SO$_2$Me | F | Me | CN | |
| 18-168 | SO$_2$Me | Cl | Me | CN | |
| 18-169 | SO$_2$Me | Br | Me | CN | |
| 18-170 | SO$_2$Me | I | Me | CN | |
| 18-171 | SO$_2$Me | CF$_3$ | Me | CN | |
| 18-172 | SO$_2$Me | CHF$_2$ | Me | CN | |
| 18-173 | SO$_2$Me | CF$_2$Cl | Me | CN | |
| 18-174 | SO$_2$Me | OMe | Me | CN | |
| 18-175 | SO$_2$Me | NO$_2$ | Me | CN | |
| 18-176 | SO$_2$Me | SO$_2$Me | Me | CN | |
| 18-177 | Me | Me | Et | CN | |
| 18-178 | Me | F | Et | CN | |
| 18-179 | Me | Cl | Et | CN | |
| 18-180 | Me | Br | Et | CN | |
| 18-181 | Me | I | Et | CN | |
| 18-182 | Me | CF$_3$ | Et | CN | |
| 18-183 | Me | CHF$_2$ | Et | CN | |
| 18-184 | Me | CF$_2$Cl | Et | CN | |
| 18-185 | Me | OMe | Et | CN | |
| 18-186 | Me | NO$_2$ | Et | CN | |
| 18-187 | Me | SO$_2$Me | Et | CN | |
| 18-188 | Cl | Me | Et | CN | |
| 18-189 | Cl | F | Et | CN | |
| 18-190 | Cl | Cl | Et | CN | |
| 18-191 | Cl | Br | Et | CN | |
| 18-192 | Cl | I | Et | CN | |
| 18-193 | Cl | CF$_3$ | Et | CN | |
| 18-194 | Cl | CHF$_2$ | Et | CN | |
| 18-195 | Cl | CF$_2$Cl | Et | CN | |
| 18-196 | Cl | OMe | Et | CN | |
| 18-197 | Cl | NO$_2$ | Et | CN | |
| 18-198 | Cl | SO$_2$Me | Et | CN | |
| 18-199 | OMe | Me | Et | CN | |
| 18-200 | OMe | F | Et | CN | |
| 18-201 | OMe | Cl | Et | CN | |
| 18-202 | OMe | Br | Et | CN | |
| 18-203 | OMe | I | Et | CN | |
| 18-204 | OMe | CF$_3$ | Et | CN | |
| 18-205 | OMe | CHF$_2$ | Et | CN | |
| 18-206 | OMe | CF$_2$Cl | Et | CN | |
| 18-207 | OMe | OMe | Et | CN | |
| 18-208 | OMe | NO$_2$ | Et | CN | |
| 18-209 | OMe | SO$_2$Me | Et | CN | |
| 18-210 | SO$_2$Me | Me | Et | CN | |
| 18-211 | SO$_2$Me | F | Et | CN | |
| 18-212 | SO$_2$Me | Cl | Et | CN | |
| 18-213 | SO$_2$Me | Br | Et | CN | |

TABLE 18-continued

Compounds according to the invention of the formula (I) in which Q is Q3 and R<sup>y</sup> is chlorine, R" and W are each hydrogen and t = 0

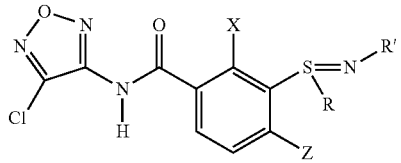

| No. | X | Z | R | R' | Physical Data ($^1$H NMR) |
|---|---|---|---|---|---|
| 18-214 | SO$_2$Me | I | Et | CN | |
| 18-215 | SO$_2$Me | CF$_3$ | Et | CN | |
| 18-216 | SO$_2$Me | CHF$_2$ | Et | CN | |
| 18-217 | SO$_2$Me | CF$_2$Cl | Et | CN | |
| 18-218 | SO$_2$Me | OMe | Et | CN | |
| 18-219 | SO$_2$Me | NO$_2$ | Et | CN | |
| 18-220 | SO$_2$Me | SO$_2$Me | Et | CN | |
| 18-221 | Me | Me | CH$_2$CH$_2$OMe | CN | |
| 18-222 | Me | F | CH$_2$CH$_2$OMe | CN | |
| 18-223 | Me | Cl | CH$_2$CH$_2$OMe | CN | |
| 18-224 | Me | Br | CH$_2$CH$_2$OMe | CN | |
| 18-225 | Me | I | CH$_2$CH$_2$OMe | CN | |
| 18-226 | Me | CF$_3$ | CH$_2$CH$_2$OMe | CN | |
| 18-227 | Me | CHF$_2$ | CH$_2$CH$_2$OMe | CN | |
| 18-228 | Me | CF$_2$Cl | CH$_2$CH$_2$OMe | CN | |
| 18-229 | Me | OMe | CH$_2$CH$_2$OMe | CN | |
| 18-230 | Me | NO$_2$ | CH$_2$CH$_2$OMe | CN | |
| 18-231 | Me | SO$_2$Me | CH$_2$CH$_2$OMe | CN | |
| 18-232 | Cl | Me | CH$_2$CH$_2$OMe | CN | |
| 18-233 | Cl | F | CH$_2$CH$_2$OMe | CN | |
| 18-234 | Cl | Cl | CH$_2$CH$_2$OMe | CN | |
| 18-235 | Cl | Br | CH$_2$CH$_2$OMe | CN | |
| 18-236 | Cl | I | CH$_2$CH$_2$OMe | CN | |
| 18-237 | Cl | CF$_3$ | CH$_2$CH$_2$OMe | CN | |
| 18-238 | Cl | CHF$_2$ | CH$_2$CH$_2$OMe | CN | |
| 18-239 | Cl | CF$_2$Cl | CH$_2$CH$_2$OMe | CN | |
| 18-240 | Cl | OMe | CH$_2$CH$_2$OMe | CN | |
| 18-241 | Cl | NO$_2$ | CH$_2$CH$_2$OMe | CN | |
| 18-242 | Cl | SO$_2$Me | CH$_2$CH$_2$OMe | CN | |
| 18-243 | OMe | Me | CH$_2$CH$_2$OMe | CN | |
| 18-244 | OMe | F | CH$_2$CH$_2$OMe | CN | |
| 18-245 | OMe | Cl | CH$_2$CH$_2$OMe | CN | |
| 18-246 | OMe | Br | CH$_2$CH$_2$OMe | CN | |
| 18-247 | OMe | I | CH$_2$CH$_2$OMe | CN | |
| 18-248 | OMe | CF$_3$ | CH$_2$CH$_2$OMe | CN | |
| 18-249 | OMe | CHF$_2$ | CH$_2$CH$_2$OMe | CN | |
| 18-250 | OMe | CF$_2$Cl | CH$_2$CH$_2$OMe | CN | |
| 18-251 | OMe | OMe | CH$_2$CH$_2$OMe | CN | |
| 18-252 | OMe | NO$_2$ | CH$_2$CH$_2$OMe | CN | |
| 18-253 | OMe | SO$_2$Me | CH$_2$CH$_2$OMe | CN | |
| 18-254 | SO$_2$Me | Me | CH$_2$CH$_2$OMe | CN | |
| 18-255 | SO$_2$Me | F | CH$_2$CH$_2$OMe | CN | |
| 18-256 | SO$_2$Me | Cl | CH$_2$CH$_2$OMe | CN | |
| 18-257 | SO$_2$Me | Br | CH$_2$CH$_2$OMe | CN | |
| 18-258 | SO$_2$Me | I | CH$_2$CH$_2$OMe | CN | |
| 18-259 | SO$_2$Me | CF$_3$ | CH$_2$CH$_2$OMe | CN | |
| 18-260 | SO$_2$Me | CHF$_2$ | CH$_2$CH$_2$OMe | CN | |
| 18-261 | SO$_2$Me | CF$_2$Cl | CH$_2$CH$_2$OMe | CN | |
| 18-262 | SO$_2$Me | OMe | CH$_2$CH$_2$OMe | CN | |
| 18-263 | SO$_2$Me | NO$_2$ | CH$_2$CH$_2$OMe | CN | |
| 18-264 | SO$_2$Me | SO$_2$Me | CH$_2$CH$_2$OMe | CN | |

B. FORMULATION EXAMPLES a) A dust is obtained by mixing 10 parts by weight of a compound of the formula (I) and/or its salts and 90 parts by weight of talc as inert substance and comminuting the mixture in a hammer mill.

b) A wettable powder which is readily dispersible in water is obtained by mixing 25 parts by weight of a compound of the formula (I) and/or its salts, 64 parts by weight of kaolin-containing quartz as inert substance, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is obtained by mixing 20 parts by weight of a compound of the formula (I) and/or its salts with 6 parts by weight of alkylphenol polyglycol ether (®Triton X 207), 3 parts by weight of isotridecanol polyglycol ether (8 EO) and 71 parts by weight of paraffinic mineral oil (boiling range for example approximately 255 up to over 277° C.) and grinding the mixture in a bowl mill to a fineness of below 5 microns.

d) An emulsifiable concentrate is obtained from 15 parts by weight of a compound of the formula (I) and/or its salts, 75 parts by weight of cyclohexanone as solvent and 10 parts by weight of ethoxylated nonylphenol as emulsifier.

e) Water-dispersible granules are obtained by mixing
75 parts by weight of a compound of the formula (I) and/or its salts,
10 parts by weight of calcium lignosulfonate,
5 parts by weight of sodium lauryl sulfate,
3 parts by weight of polyvinyl alcohol and
7 parts by weight of kaolin, grinding the mixture in a pinned-disk mill and granulating the powder in a fluidized bed by spraying on water as granulation liquid.

f) Water-dispersible granules are also obtained by homogenizing and precomminuting, in a colloid mill,
25 parts by weight of a compound of the formula (I) and/or its salts,
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water,
subsequently grinding the mixture in a bead mill, and atomizing and drying the resulting suspension in a spray tower by means of a single-substance nozzle.

C. BIOLOGICAL EXAMPLES

1. Herbicidal Pre-Emergence Effect Against Harmful Plants

Seeds of monocotyledonous or dicotyledonous weeds or crop plants are placed in sandy loam soil in wood-fiber pots and covered with soil. The compounds according to the invention, formulated in the form of wettable powders (WP) or emulsion concentrates (EC), are then applied to the surface of the soil cover in the form of an aqueous suspension or emulsion at a water application rate of 600 to 800 l/ha (converted), with addition of 0.2% wetter. After the treatment, the pots are placed in the greenhouse and kept under good growth conditions for the test plants. The damage to the test plants is scored visually in comparison with untreated controls after an experimental time of 3 weeks has elapsed (herbicidal activity in percent (%): 100% activity=plants have died, 0% activity=like control plants). Here, for example the compounds Nos. 1-028, 1-138 and 1-270 show, at an application rate of 320 g/ha, each at least 80% strength activity against *Abutilon theophrasti, Amaranthus retroflexus, Cyperus serotinus, Echinochloa crus galli, Matricaria inodora, Setaria viridis, Stellaria media, Veronica persica* and *Viola tricolor.*

2. Herbicidal Post-Emergence Activity Against Harmful Plants

Seeds of monocotyledonous or dicotyledonous weeds or crop plants are placed in sandy loam soil in wood-fiber pots, covered with soil and grown in the greenhouse under good growth conditions. 2 to 3 weeks after sowing, the test plants are treated in the one-leaf stage. The compounds according to the invention, formulated in the form of wettable powders (WP) or emulsion concentrates (EC), are then sprayed onto the green plant parts in the form of an aqueous suspension or emulsion at a water application rate of 600 to 800 l/ha (converted), with addition of 0.2% wetter. After the test plants have been left to stand under optimal growth conditions in the greenhouse for approximately 3 weeks, the activity of the preparations is scored visually in comparison with untreated controls (herbicidal activity in percent (%): 100% activity=plants have died, 0% activity=like control plants). Here, for example the compounds Nos. 1-028, 1-138 and 1-270 show, at an application rate of 80 g/ha, each at least 80% strength activity against *Abutilon theophrasti, Echinochloa crus galli, Matricaria inodora, Setaria viridis, Stellaria media* and *Veronica persica*.

The invention claimed is:

1. A sulfin- or sulfonimidoylbenzamide of formula (I) and/or a salt thereof

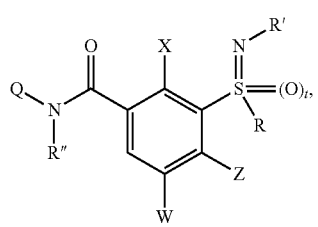
(I)

in which

Q is a radical Q1, Q2, or Q3,

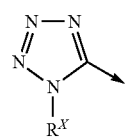
(Q1)

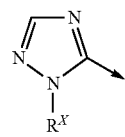
(Q2)

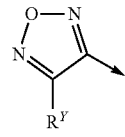
(Q3)

X is nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkenyl, halo-$(C_3-C_6)$-cycloalkenyl, $(C_3-C_6)$-cycloalkyl-$(C_1-C_6)$-alkyl, halo-$(C_3-C_6)$-cycloalkyl-$(C_1-C_6)$-alkyl, $(C_3-C_6)$-cycloalkenyl-$(C_1-C_6)$-alkyl, halo-$(C_3-C_6)$-cycloalkenyl-$(C_1-C_6)$-alkyl, $R^1O(O)C$, $R^1(R^1ON=)C$, $R^1O(O)C$, $(R^1)_2N(O)C$, $R^1(R^1O)N(O)C$, $(R^1)_2N(R^1)N(O)C$, $R^1(O)C(R^1)N(O)C$, $R^2O(O)C(R^1)N(O)C$, $(R^1)_2N(O)C(R^1)N(O)C$, $R^2(O)_2S(R^1)N(O)C$, $R^1O(O)_2S(R^1)N(O)$ C, $(R^1)_2N(O)_2S(R^1)N(O)C$, $R^1O$, $R^1(O)CO$, $R^2(O)_2SO$, $R^2(O)CO$, $(R^1)_2N(O)CO$, $(R^1)_2N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1O$ $(O)_2S$, $(R^1)_2N(O)_2S$, $R^1(O)C(R^1)N(O)_2S$, $R^2O(O)C$ $(R^1)N(O)_2S$, $(R^1)_2N(O)C(R^1)N(O)_2S$, $(R^5O)_2(O)P$, $R^1(O)C—(C_1-C_6)$-alkyl, $R^1O(O)C—(C_1-C_6)$-alkyl, $(R^1)_2N(O)C—(C_1-C_6)$-alkyl, $(R^1O)(R^1)N(O)C—(C_1-C_6)$-alkyl, $(R^1)_2N(R^1)N(O)$ $C—(C_1-C_6)$-alkyl, $R^1(O)C(R^1)N(O)C—(C_1-C_6)$-alkyl, $R^2O(O)C(R^1)N(O)C—(C_1-C_6)$-alkyl, $(R^1)_2N(O)C(R^1)$ $N(O)C—(C_1-C_6)$-alkyl, $R^2(O)_2S(R^1)N(O)C—(C_1-C_6)$-alkyl, $R^1O(O)_2S(R^1)N(O)C—(C_1-C_6)$-alkyl, $(R^1)_2N$ $(O)_2S(R^1)N(O)C—(C_1-C_6)$-alkyl, NC—$(C_1-C_6)$-alkyl, $R^1O—(C_1-C_6)$-alkyl, $R^1(O)CO—(C_1-C_6)$-alkyl, $R^2(O)_2SO—(C_1-C_6)$-alkyl, $R^2O(O)CO—(C_1-C_6)$-alkyl, $(R^1)_2N(O)CO—(C_1-C_6)$-alkyl, $(R^1)_2N—(C_1-C_6)$-alkyl, $R^1(O)C(R^1)N—(C_1-C_6)$-alkyl, $R^2(O)_2S(R^1)$ $N—(C_1-C_6)$-alkyl, $R^2O(O)C(R^1)N—(C_1-C_6)$-alkyl, $(R^1)_2N(O)C(R^1)N—(C_1-C_6)$-alkyl, $R^1O(O)_2S(R^1)N—(C_1-C_6)$-alkyl, $(R^1)_2N(O)_2S(R^1)N—(C_1-C_6)$-alkyl, $R^2(O)S—(C_1-C_6)$-alkyl, $R^1O(O)_2S—(C_1-C_6)$-alkyl, $(R^1)_2N(O)_2S—(C_1-C_6)$-alkyl, $R^1(O)C(R^1)N(O)_2S—(C_1-C_6)$-alkyl, $R^2O(O)C(R^1)N(O)_2S—(C_1-C_6)$-alkyl, $(R^1)_2N(O)C(R^1)N(O)_2S—(C_1-C_6)$-alkyl, $(R^5O)_2(O)$ P—$(C_1-C_6)$-alkyl, phenyl, heteroaryl, heterocyclyl, phenyl-$(C_1-C_6)$-alkyl, heteroaryl-$(C_1-C_6)$-alkyl, heterocyclyl-$(C_1-C_6)$-alkyl, where the six last-mentioned radicals are each substituted by s radicals from the group consisting of nitro, halogen, cyano, thiocyanato, $(C_1-C_6)$-alkyl, halo-$(C_1-C_6)$-alkyl, $(C_3-C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O—(C_1-C_6)$-alkyl, and where heterocyclyl carries n oxo groups, Z is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkenyl, halo-$(C_3-C_6)$-cycloalkenyl, $(C_3-C_6)$-cycloalkyl-$(C_1-C_6)$-alkyl, halo-$(C_3-C_6)$-cycloalkyl-$(C_1-C_6)$-alkyl, $(C_3-C_6)$-cycloalkenyl-$(C_1-C_6)$-alkyl, halo-$(C_3-C_6)$-cycloalkenyl-$(C_1-C_6)$-alkyl, $R^1(O)C$, $R^1(R^1ON=)C$, $R^1O(O)C$, $(R^1)_2N(O)C$, $R^1(R^1O)N(O)C$, $(R^1)_2N(R^1)N(O)C$, $R^1(O)C(R^1)N(O)C$, $R^2O(O)C(R^1)N(O)C$, $(R^1)_2N(O)C(R^1)N(O)C$, $R^2(O)_2S$ $(R^1)N(O)C$, $R^1O(O)_2S(R^1)N(O)C$, $(R^1)_2N(O)_2S(R^1)N$ $(O)C$, $R^1O$, $R^1(O)CO$, $R^2(O)_2SO$, $R^2O(O)CO$, $(R^1)_2N$ $(O)CO$, $(R^1)_2N$, $R^1(O)C(R^1)N$, $R^2(O)_2S(R^1)N$, $R^2O(O)$ $C(R^1)N$, $(R^1)_2N(O)C(R^1)N$, $R^1O(O)_2S(R^1)N$, $(R^1)_2N$ $(O)_2S(R^1)N$, $R^2(O)_nS$, $R^1O(O)_2S$, $(R^1)_2N(O)_2S$, $R^1(O)$ $C(R^1)N(O)_2S$, $R^2O(O)C(R^1)N(O)_2S$, $(R^1)_2N(O)C(R^1)$ $N(O)_2S$, $(R^5O)_2(O)P$, $R^1(O)C—(C_1-C_6)$-alkyl, $R^1O(O)$ $C—(C_1-C_6)$-alkyl, $(R^1)_2N(O)C—(C_1-C_6)$-alkyl, $(R^1O)$ $(R^1)N(O)C—(C_1-C_6)$-alkyl, $(R^1)_2N(R^1)N(O)C—(C_1-C_6)$-alkyl, $R^1(O)C(R^1)N(O)C—(C_1-C_6)$-alkyl, $R^2O(O)$ $C(R^1)N(O)C—(C_1-C_6)$-alkyl, $(R^1)_2N(O)C(R^1)N(O)$ $C—(C_1-C_6)$-alkyl, $R^2(O)_2S(R^1)N(O)C—(C_1-C_6)$-alkyl, $R^1O(O)_2S(R^1)N(O)C—(C_1-C_6)$-alkyl, $(R^1)_2N$ $(O)_2S(R^1)N(O)C—(C_1-C_6)$-alkyl, NC—$(C_1-C_6)$-alkyl, $R^1O—(C_1-C_6)$-alkyl, $R^1(O)CO—(C_1-C_6)$-alkyl, $R^2(O)_2SO—(C_1-C_6)$-alkyl, $R^2O(O)CO—(C_1-C_6)$-alkyl, $(R^1)_2N(O)CO—(C_1-C_6)$-alkyl, $(R^1)_2N—(C_1-C_6)$-alkyl, $R^1(O)C(R^1)N—(C_1-C_6)$-alkyl, $R^2(O)_2S(R^1)$ $N—(C_1-C_6)$-alkyl, $R^2O(O)C(R^1)N—(C_1-C_6)$-alkyl, $(R^1)_2N(O)C(R^1)N—(C_1-C_6)$-alkyl, $R^1O(O)_2S(R^1)N—(C_1-C_6)$-alkyl, $(R^1)_2N(O)_2S(R^1)N—(C_1-C_6)$-alkyl, $R^2(O)_nS—(C_1-C_6)$-alkyl, $R^1O(O)_2S—(C_1-C_6)$-alkyl, $(R^1)_2N(O)_2S$—$(C_1$-$C_6)$-alkyl, $R^1(O)C(R^1)N(O)_nS$—$(C_1$-$C_6)$-alkyl, $R^2O(O)C(R^1)N(O)_2S$—$(C_1$-$C_6)$-alkyl, $(R^1)_2N(O)C(R^1)N(O)_2S$—$(C_1$-$C_6)$-alkyl, $(R^5O)_2(O)P$—$(C_1$-$C_6)$-alkyl, phenyl, heteroaryl, heterocyclyl, phenyl-$(C_1$-$C_6)$-alkyl, heteroaryl-$(C_1$-$C_6)$-alkyl, heterocyclyl-$(C_1$-$C_6)$-alkyl, where the six last-mentioned radicals are each substituted by s radicals from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^1O$ $(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1$-$C_6)$-alkyl, and where heterocyclyl carries n oxo groups, W is hydrogen, halogen, nitro, cyano, thiocyanato, $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, $(C_3$-$C_7)$-cycloalkyl, halo-$(C_3$-$C_7)$-cycloalkyl, $(C_1$-$C_6)$-alkoxy, halo-$(C_1$-$C_6)$-alkoxy, $(C_1$-$C_6)$-alkyl-$(O)_nS$—, $(C_1$-$C_6)$-haloalkyl-$(O)_nS$—, $(C_1$-$C_6)$-alkoxy-$(C_1$-$C_4)$-alkyl, $(C_1$-$C_6)$-alkoxy-$(C_1$-$C_4)$-haloalkyl, $R^1(O)C$, $R^1(R^1ON\!\!=\!\!)C$, $R^1O(O)C$, $(R^1)_2N$, $R^1(O)C(R^1)N$ or $R^2(O)_2S(R^1)N$, R is $(C_1$-$C_6)$-alkyl, $(C_2$-$C_6)$-alkenyl or $(C_2$-$C_6)$-alkynyl, each of which is substituted by s radicals from the group consisting of nitro, halogen, cyano, thiocyanato, $(C_3$-$C_6)$-cycloalkyl, $R^1(O)C$, $R^1(R^1ON\!\!=\!\!)C$, $R^1O(O)C$, $(R^1)_2N(O)C$, $R^1(R^1O)N(O)C$, $R^2(O)_2S(R^1)N(O)C$, $R^1O(O)_2S(R^1)N(O)C$, $(R^1)_2N(O)_2S(R^1)N(O)C$, $R^1S(O)C$, $R^1O$, $R^1(O)CO$, $R^2(O)_2SO$, $R^2O(O)CO$, $(R^1)_2N(O)CO$, $(R^1)_2N$, $R^1O$ $(R^1)N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1C(O)S$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$ and $(R^5O)_2(O)P$, or is $(C_3$-$C_6)$-cycloalkyl, $(C_3$-$C_6)$-cycloalkenyl, phenyl, phenyl-$(C_1$-$C_6)$-alkyl, heteroaryl, heteroaryl-$(C_1$-$C_6)$-alkyl, heterocyclyl, heterocyclyl-$(C_1$-$C_6)$-alkyl, phenyl-$O$—$(C_1$-$C_6)$-alkyl, heteroaryl-$O$—$(C_1$-$C_6)$-alkyl, heterocyclyl-$O$—$(C_1$-$C_6)$-alkyl, phenyl-$N(R^1)$—$(C_1$-$C_6)$-alkyl, heteroaryl-$N(R^1)$—$(C_1$-$C_6)$-alkyl, heterocyclyl-$N(R^1)$—$(C_1$-$C_6)$-alkyl, phenyl—$S(O)_n$—$(C_1$-$C_6)$-alkyl, heteroaryl—$S(O)_n$—$(C_1$-$C_6)$-alkyl or heterocyclyl—$S(O)_n$—$(C_1$-$C_6)$-alkyl, each of which is substituted in the cyclic moiety by s radicals from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^1(O)C$, $R^1(R^1ON\!\!=\!\!)C$, $R^1O(O)C$, $(R^1)_2N(O)C$, $R^1(R^1O)N(O)C$, $R^2(O)_2S(R^1)N(O)C$, $R^1O(O)_2S(R^1)N(O)C$, $(R^1)_2N(O)_2S(R^1)N(O)C$, $R^1S(O)C$, $R^1O$, $R^1(O)CO$, $R^2(O)_2SO$, $R^2O(O)CO$, $(R^1)_2N(O)CO$, $(R^1)_2N$, $R^1O$ $(R^1)N$, $R^1(O)C(R^1)N$, $R^2(O)_2S(R^1)N$, $R^2O(O)C(R^1)N$, $(R^1)_2N(O)C(R^1)N$, $R^1O(O)_2S(R^1)N$, $(R^1)_2N(O)_2S(R^1)N$, $R^2(O)_nS$, $R^1C(O)S$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $(R^5O)_2(O)P$ and $R^1O$—$(C_1$-$C_6)$-alkyl, and where heterocyclyl carries n oxo groups, R' is hydrogen, nitro, halogen, cyano, $(C_1$-$C_6)$-alkyl, halo-$(C_1$-$C_6)$-alkyl, $(C_3$-$C_6)$-alkenyl, halo-$(C_3$-$C_6)$-alkenyl, $(C_2$-$C_6)$-alkynyl, halo-$(C_3$-$C_6)$-alkynyl, $(C_3$-$C_6)$-cycloalkyl, halo-$(C_3$-$C_6)$-cycloalkyl, $(C_3$-$C_6)$-cycloalkyl-$(C_1$-$C_6)$-alkyl, halo-$(C_3$-$C_6)$-cycloalkyl-$(C_1$-$C_6)$-alkyl, $R^1(O)C$, $R^2O(O)C$, $(R^1)_2N(O)C$, $R^2S(O)C$, $(R^1)_2N(S)C$, $R^1(R^1O)N(O)C$, $R^2(O)_2S(R^1)N(O)C$, $(R^1)_2N(O)_2S(R^1)N(O)C$, $R^1O$, $(R^1)_2N$, $R^2(O)_nS$, $(R^2)_3Si$—$(C_1$-$C_6)$-alkyl-$(O)_nS$, $R^1O(O)_2S$, $(R^1)_2N(O)_2S$, $R^1(O)C(R^1)N(O)_2S$, $R^2O(O)C(R^1)N(O)_2S$, $(R^1)_2N(O)C(R^1)N(O)_2S$, $R^2(O)_2S(R^1)N(O)_2S$, $(R^5O)_2(O)P$, $(R^2)_3Si$, $R^1(O)C$—$(C_1$-$C_6)$-alkyl, $R^1O(O)C$—$(C_1$-$C_6)$-alkyl, $(R^1)_2N(O)C$—$(C_1$-$C_6)$-alkyl, $(R^1O)(R^1)N(O)C$—$(C_1$-$C_6)$-alkyl, $R^2(O)_2S(R^1)N(O)C$—$(C_1$-$C_6)$-alkyl, $R^1O(O)_2S(R^1)N(O)C$—$(C_1$-$C_6)$-alkyl, $(R^1)_2N(O)_2S(R^1)N(O)C$—$(C_1$-$C_6)$-alkyl, $R^1O$—$(C_1$-$C_6)$-alkyl, $R^1(O)CO$—$(C_1$-$C_6)$-alkyl, $R^2(O)_2SO$—$(C_1$-$C_6)$-alkyl, $R^2O(O)CO$—$(C_1$-$C_6)$-alkyl, $(R^1)_2N(O)CO$—$(C_1$-$C_6)$-alkyl, $(R^1)_2N$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, $R^2O(O)C(R^1)N$—$(C_1$-$C_6)$-alkyl, $(R^1)_2N(O)C(R^1)N$—$(C_1$-$C_6)$-alkyl, $R^1O(O)_2S(R^1)N$—$(C_1$-$C_6)$-alkyl, $(R^1)_2N(O)_2S(R^1)N$—$(C_1$-$C_6)$-alkyl, $R^2(O)_nS$—$(C_1$-$C_6)$-alkyl, $R^1O(O)_2S$—$(C_1$-$C_6)$-alkyl, $(R^1)_2N(O)_2S$—$(C_1$-$C_6)$-alkyl, $R^1(O)C(R^1)N(O)_2S$—$(C_1$-$C_6)$-alkyl, $R^2O(O)C(R^1)N(O)_2S$—$(C_1$-$C_6)$-alkyl, $(R^1)_2N(O)C(R^1)N(O)_2S$—$(C_1$-$C_6)$-alkyl, $(R^5O)_2(O)P$—$(C_1$-$C_6)$-alkyl, $(R^2)_3Si$—$(C_1$-$C_6)$-alkyl, or is phenyl, heteroaryl, heterocyclyl, phenyl-$(C_1$-$C_6)$-alkyl, heteroaryl-$(C_1$-$C_6)$-alkyl or heterocyclyl-$(C_1$-$C_6)$-alkyl, each of which is substituted in the cyclic moiety by s radicals from the group consisting of nitro, halogen, cyano, thiocyanato, $(C_1$-$C_6)$-alkyl, halo-$(C_1$-$C_6)$-alkyl, $(C_3$-$C_6)$-cycloalkyl, $R^1O(O)C$, $(R^1)_2N(O)C$, $R^1O$, $(R^1)_2N$, $R^2(O)_nS$, $R^1O(O)_2S$, $(R^1)_2N(O)_2S$ and $R^1O$—$(C_1$-$C_6)$-alkyl, and where heterocyclyl carries n oxo groups, R" is hydrogen, $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, $(C_3$-$C_6)$-cycloalkyl, halo-$(C_3$-$C_6)$-cycloalkyl, $(C_3$-$C_6)$—cycloalkyl-$(C_1$-$C_6)$-alkyl, halo-$(C_3$-$C_6)$-cycloalkyl-$(C_1$-$C_6)$-alkyl, $R^1(O)C$—$(C_1$-$C_6)$-alkyl, $R^1O(O)C$—$(C_1$-$C_6)$-alkyl, $(R^1)_2N(O)C$—$(C_1$-$C_6)$-alkyl, $NC$—$(C_1$-$C_6)$-alkyl, $R^1O$—$(C_1$-$C_6)$-alkyl, $R^1(O)CO$—$(C_1$-$C_6)$-alkyl, $R^2(O)_2SO$—$(C_1$-$C_6)$-alkyl, $(R^1)_2N$—$(C_1$-$C_6)$-alkyl, $R^1(O)C(R^1)N$—$(C_1$-$C_6)$-alkyl, $R^2(O)_2S(R^1)N$—$(C_1$-$C_6)$-alkyl, $R^2(O)_nS$—$(C_1$-$C_6)$-alkyl, $R^1O(O)_2S$—$(C_1$-$C_6)$-alkyl, $(R^1)_2N(O)_2S$—$(C_1$-$C_6)$-alkyl, $R^1(O)C$, $R^1O(O)C$, $(R^1)_2N(O)C$, $R^1O$, $(R^1)_2N$, $R^2O(O)C(R^1)N$, $(R^1)_2N(O)C(R^1)N$, $R^2(O)_2S$, or is benzyl which is in each case substituted by s radicals from the group consisting of methyl, ethyl, methoxy, nitro, trifluoromethyl and halogen-substituted benzyl, $R^x$ is $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, where the six above-mentioned radicals are each substituted by s radicals from the group consisting of nitro, cyano, $(R^6)_3Si$, $(R^5O)_2(O)P$, $R^2(O)_nS$, $(R^1)_2N$, $R^1O$, $R^1(O)C$, $R^1O(O)C$, $R^1(O)CO$, $R^2O(O)CO$, $R^1(O)C(R^1)N$, $R^2(O)_2S(R^1)N$, $(C_3$-$C_6)$-cycloalkyl, heteroaryl, heterocyclyl and phenyl, where the four last-mentioned radicals are substituted by s radicals from the group consisting of $(C_1$-$C_6)$-alkyl, halo-$(C_1$-$C_6)$-alkyl, $(C_1$-$C_6)$-alkoxy, halo-$(C_1$-$C_6)$-alkoxy and halogen, and where heterocyclyl carries n oxo groups, or $R^x$ is $(C_3$-$C_7)$-cycloalkyl, heteroaryl, heterocyclyl or phenyl, where the four above-mentioned radicals are each substituted by s radicals from the group consisting of halogen, nitro, cyano, $(C_1$-$C_6)$-alkyl, halo-$(C_1$-$C_6)$-alkyl, $(C_3$-$C_6)$-cycloalkyl, $(C_1$-$C_6)$-alkyl-$S(O)_n$, $(C_1$-$C_6)$-alkoxy, halo-$(C_1$-$C_6)$-alkoxy and $(C_1$-$C_6)$-alkoxy-$(C_1$-$C_4)$-alkyl, $R^Y$ is hydrogen, $(C_1$-$C_6)$-alkyl, halo-$(C_1$-$C_6)$-alkyl, $(C_2$-$C_6)$-alkenyl, halo-$(C_2$-$C_6)$-alkenyl, $(C_2$-$C_6)$-alkynyl, halo-$(C_3$-$C_6)$-alkynyl, $(C_3$-$C_7)$-cycloalkyl, $(C_1$-$C_6)$-alkoxy, halo-$(C_1$-$C_6)$-alkoxy, $(C_2$-$C_6)$-alkenyloxy, ($C_2$-$C_6$)-alkynyloxy, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or is heteroaryl, heterocyclyl or phenyl, each of which is substituted by s radicals from the group consisting of ($C_1$-$C_6$)-alkyl, halo-($C_1$-$C_6$)-alkyl, ($C_1$-$C_6$)-alkoxy, halo-($C_1$-$C_6$)-alkoxy and halogen, and where heterocyclyl carries n oxo groups, $R^1$ is hydrogen, ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_3$-$C_6$)-alkynyl, ($C_3$-$C_6$)-cycloalkyl, ($C_3$-$C_6$)-cycloalkenyl, halo-($C_3$-$C_6$)-cycloalkyl, ($C_3$-$C_6$)-cycloalkyl-($C_1$-$C_6$)-alkyl, ($C_1$-$C_6$)-alkyl-O—($C_1$-$C_6$)-alkyl, cycloalkyl-($C_1$-$C_6$)-alkyl-O—($C_1$-$C_6$)-alkyl, phenyl, phenyl-($C_1$-$C_6$)-alkyl, heteroaryl, heteroaryl-($C_1$-$C_6$)-alkyl, heterocyclyl, heterocyclyl-($C_1$-$C_6$)-alkyl, phenyl-O—($C_1$-$C_6$)-alkyl, heteroaryl-O—($C_1$-$C_6$)-alkyl, heterocyclyl-O—($C_1$-$C_6$)-alkyl, phenyl-N($R^3$)—($C_1$-$C_6$)-alkyl, heteroaryl-N($R^3$)—($C_1$-$C_6$)-alkyl, heterocyclyl-N($R^3$)—($C_1$-$C_6$)-alkyl, phenyl-S(O)$_n$—($C_1$-$C_6$)-alkyl, heteroaryl-S(O)$_n$—($C_1$-$C_6$)-alkyl, heterocyclyl-S(O)$_n$—($C_1$-$C_6$)-alkyl, where the fifteen last-mentioned radicals are each substituted by s radicals from the group consisting of nitro, halogen, cyano, thiocyanato, ($C_1$-$C_6$)-alkyl, halo-($C_1$-$C_6$)-alkyl, ($C_3$-$C_6$)-cycloalkyl, $R^3$O(O)C, ($R^3$)$_2$N(O)C, $R^3$O, ($R^3$)$_2$N, $R^4$(O)$_n$S, $R^3$O(O)$_2$S, ($R^3$)$_2$N(O)$_2$S and $R^3$O—($C_1$-$C_6$)-alkyl, and where heterocyclyl carries n oxo groups, $R^2$ is ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_3$-$C_6$)-alkynyl, ($C_3$-$C_6$)-cycloalkyl, ($C_3$-$C_6$)-cycloalkenyl, halo-($C_3$-$C_6$)-cycloalkyl, ($C_3$-$C_6$)-cycloalkyl-($C_1$-$C_6$)-alkyl, ($C_1$-$C_6$)-alkyl-O—($C_1$-$C_6$)-alkyl, cycloalkyl-($C_1$-$C_6$)-alkyl-O—($C_1$-$C_6$)-alkyl, phenyl, phenyl-($C_1$-$C_6$)-alkyl, heteroaryl, heteroaryl-($C_1$-$C_6$)-alkyl, heterocyclyl, heterocyclyl-($C_1$-$C_6$)-alkyl, phenyl-O—($C_1$-$C_6$)-alkyl, heteroaryl-O—($C_1$-$C_6$)-alkyl, heterocyclyl-O—($C_1$-$C_6$)-alkyl, phenyl-N($R^3$)—($C_1$-$C_6$)-alkyl, heteroaryl-N($R^3$)—($C_1$-$C_6$)-alkyl, heterocyclyl-N($R^3$)—($C_1$-$C_6$)-alkyl, phenyl-S(O)$_n$—($C_1$-$C_6$)-alkyl, heteroaryl-S(O)$_n$—($C_1$-$C_6$)-alkyl, heterocyclyl-S(O)$_n$—($C_1$-$C_6$)-alkyl, where the fifteen last-mentioned radicals are each substituted by s radicals from the group consisting of nitro, halogen, cyano, thiocyanato, ($C_1$-$C_6$)-alkyl, halo-($C_1$-$C_6$)-alkyl, ($C_3$-$C_6$)-cycloalkyl, $R^3$O(O)C, ($R^3$)$_2$N(O)C, $R^3$O, ($R^3$)$_2$N, $R^4$(O)$_n$S, $R^3$O(O)$_2$S, ($R^3$)$_2$N(O)$_2$S and $R^3$O—($C_1$-$C_6$)-alkyl, and where heterocyclyl carries n oxo groups, $R^3$ is hydrogen, ($C_1$-$C_6$)-alkyl, halo-($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkyl-($C_1$-$C_6$)-alkyl or phenyl, $R^4$ is ($C_1$-$C_6$)-alkyl, halo-($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkyl-($C_1$-$C_6$)-alkyl or phenyl, $R^5$ is hydrogen or ($C_1$-$C_4$)-alkyl, $R^6$ is ($C_1$-$C_4$)-alkyl, n is 0, 1 or 2, s is 0, 1, 2 or 3, t is 0 or 1.

2. The sulfin- or sulfonimidoylbenzamide and/or salt as claimed in claim 1 in which Q is a radical Q1, Q2, or Q3

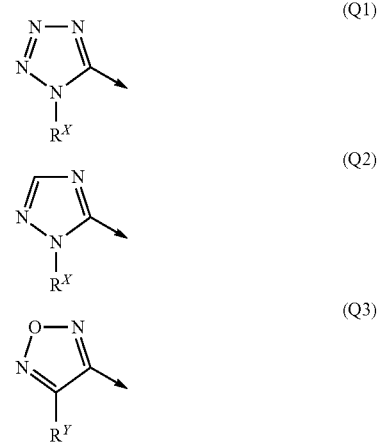

X is nitro, halogen, cyano, ($C_1$-$C_6$)-alkyl, halo-($C_1$-$C_6$)-alkyl, ($C_2$-$C_6$)-alkenyl, ($C_2$-$C_6$)-alkynyl, ($C_3$-$C_6$)-cycloalkyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, $R^1$(O)C, $R^1$($R^1$ON═)C, $R^1$O(O)C, ($R^1$)$_2$N(O)C, $R^1$O, ($R^1$)$_2$N, $R^1$(O)C($R^1$)N, $R^2$(O)$_2$S($R^1$)N, $R^2$O(O)C($R^1$)N, ($R^1$)$_2$N(O)C($R^1$)N, $R^2$(O)$_n$S, $R^1$O(O)$_2$S, ($R^1$)$_2$N(O)$_2$S, ($R^5$O)$_2$(O)P, $R^1$(O)C—($C_1$-$C_6$)-alkyl, $R^1$O(O)C—($C_1$-$C_6$)-alkyl, ($R^1$)$_2$N(O)C—($C_1$-$C_6$)-alkyl, NC—($C_1$-$C_6$)-alkyl, $R^1$O—($C_1$-$C_6$)-alkyl, ($R^1$)$_2$N—($C_1$-$C_6$)-alkyl, $R^1$(O)C($R^1$)N—($C_1$-$C_6$)-alkyl, $R^2$(O)$_2$S($R^1$)N—($C_1$-$C_6$)-alkyl, $R^2$O(O)C($R^1$)N—($C_1$-$C_6$)-alkyl, ($R^1$)$_2$N(O)C($R^1$)N—($C_1$-$C_6$)-alkyl, $R^2$(O)$_n$S—($C_1$-$C_6$)-alkyl, $R^1$O(O)$_2$S—($C_1$-$C_6$)-alkyl, ($R^1$)$_2$N(O)$_2$S—($C_1$-$C_6$)-alkyl, ($R^5$O)$_2$(O)P—($C_1$-$C_6$)-alkyl, phenyl, heteroaryl, heterocyclyl, phenyl-($C_1$-$C_6$)-alkyl, heteroaryl-($C_1$-$C_6$)-alkyl, heterocyclyl-($C_1$-$C_6$)-alkyl, where the six last-mentioned radicals are each substituted by s radicals from the group consisting of nitro, halogen, cyano, thiocyanato, ($C_1$-$C_6$)-alkyl, halo-($C_1$-$C_6$)-alkyl, $R^1$O, ($R^1$)$_2$N, $R^2$(O)$_n$S, $R^1$O(O)$_2$S, ($R^1$)$_2$N(O)$_2$S and $R^1$O—($C_1$-$C_6$)-alkyl and where heterocyclyl carries n oxo groups, Z is hydrogen, nitro, halogen, cyano, ($C_1$-$C_6$)-alkyl, halo-($C_1$-$C_6$)-alkyl, ($C_2$-$C_6$)-alkenyl, ($C_2$-$C_6$)-alkynyl, ($C_3$-$C_6$)-cycloalkyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, $R^1$(O)C, $R^1$($R^1$ON═)C, $R^1$O(O)C, ($R^1$)$_2$N(O)C, $R^1$O, ($R^1$)$_2$N, $R^1$(O)C($R^1$)N, $R^2$(O)$_2$S($R^1$)N, $R^2$O(O)C($R^1$)N, ($R^1$)$_2$N(O)C($R^1$)N, $R^2$(O)$_n$S, $R^1$O(O)$_2$S, ($R^1$)$_2$N(O)$_2$S, ($R^5$O)$_2$(O)P, $R^1$(O)C—($C_1$-$C_6$)-alkyl, $R^1$O(O)C—($C_1$-$C_6$)-alkyl, ($R^1$)$_2$N(O)C—($C_1$-$C_6$)-alkyl, NC—($C_1$-$C_6$)-alkyl, $R^1$O—($C_1$-$C_6$)-alkyl, ($R^1$)$_2$N—($C_1$-$C_6$)-alkyl, $R^1$(O)C($R^1$)N—($C_1$-$C_6$)-alkyl, $R^2$(O)$_2$S($R^1$)N—($C_1$-$C_6$)-alkyl, $R^2$O(O)C($R^1$)N—($C_1$-$C_6$)-alkyl, ($R^1$)$_2$N(O)C($R^1$)N—($C_1$-$C_6$)-alkyl, $R^2$(O)$_n$S—($C_1$-$C_6$)-alkyl, $R^1$O(O)$_2$S—($C_1$-$C_6$)-alkyl, ($R^1$)$_2$N(O)$_2$S—($C_1$-$C_6$)-alkyl, ($R^5$O)$_2$(O)P—($C_1$-$C_6$)-alkyl, phenyl, heteroaryl, heterocyclyl, phenyl-($C_1$-$C_6$)-alkyl, heteroaryl-($C_1$-$C_6$)-alkyl, heterocyclyl-($C_1$-$C_6$)-alkyl, where the six last-mentioned radicals are each substituted by s radicals from the group consisting of nitro, halogen, cyano, thiocyanato, ($C_1$-$C_6$)-alkyl, halo- $(C_1-C_6)$-alkyl, $R^1O$, $(R^1)_2N$, $R^2(O)_nS$, $R^1O(O)_2S$, $(R^1)_2N(O)_2S$ and $R^1O$—$(C_1-C_6)$-alkyl and where heterocyclyl carries n oxo groups, W is hydrogen, halogen, nitro, cyano, $(C_1-C_6)$-alkyl, halo-$(C_1-C_6)$-alkyl, $(C_3-C_7)$-cycloalkyl, $(C_1-C_6)$-alkoxy, $(C_1-C_6)$-alkyl-$(O)_nS$—, $R^1O(O)C$, $(R^1)_2N$, $R^1(O)C(R^1)N$ or $R^2(O)_2S(R^1)N$, R is $(C_1-C_6)$-alkyl which is in each case substituted by s radicals from the group consisting of halogen, cyano, $(C_3-C_6)$-cycloalkyl, $R^1(O)C$, $R^1(R^1ON=)C$, $R^1O(O)C$, $(R^1)_2N(O)C$, $R^2(O)_2S(R^1)N(O)C$, $R^1O$, $(R^1)_2N$, $R^1(O)C(R^1)N$, $R^2(O)_2S(R^1)N$, $R^2O(O)C(R^1)N$, $(R^1)_2N(O)C(R^1)N$, $R^2(O)S$, $R^1O(O)_2S$, $(R^1)_2N(O)_2S$, $R^1(O)C(R^1)N(O)_2S$, $R^2O(O)C(R^1)N(O)_2S$ and $(R^1)_2N(O)C(R^1)N(O)_2S$ or is $(C_3-C_6)$-cycloalkyl which is in each case substituted by s radicals from the group consisting of halogen, $(C_1-C_6)$-alkyl, halo-$(C_1-C_6)$-alkyl, $(C_3-C_6)$-cycloalkyl, $R^1O(O)C$ and $(R^1)_2N(O)C$, R' is hydrogen, nitro, cyano, $(C_1-C_6)$-alkyl, halo-$(C_1-C_6)$-alkyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^1(O)C$, $R^2O(O)C$, $(R^1)_2N(O)C$, $R^2(O)_2S$, $R^1(O)C$—$(C_1-C_6)$-alkyl, $R^1O(O)C$—$(C_1-C_6)$-alkyl, $(R^1)_2N(O)C$—$(C_1-C_6)$-alkyl, $R^1O$—$(C_1-C_6)$-alkyl, $(R^1)_2N$—$(C_1-C_6)$-alkyl, $R^2(O)_nS$—$(C_1-C_6)$-alkyl, R" is hydrogen, $R^x$ is $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, where the six above-mentioned radicals are each substituted by s radicals from the group consisting of $R^2(O)_nS$, $(R^1)_2N$, $R^1O$, $R^1(O)C$, $R^1O(O)C$, $R^1(O)CO$, $R^2O(O)CO$, $R^1(O)C(R^1)N$, $R^2(O)_2S(R^1)N$, $(C_3-C_6)$-cycloalkyl, heteroaryl, heterocyclyl and phenyl, where the four last-mentioned radicals for their part are substituted by s radicals from the group consisting of $(C_1-C_6)$-alkyl, halo-$(C_1-C_6)$-alkyl, $(C_1-C_6)$-alkoxy and halogen, and where heterocyclyl carries n oxo groups, or $R^x$ is $(C_3-C_7)$-cycloalkyl, where this radical is in each case substituted by s radicals from the group consisting of halogen, $(C_1-C_6)$-alkyl and halo-$(C_1-C_6)$-alkyl, $R^Y$ is hydrogen, $(C_1-C_6)$-alkyl, halo-$(C_1-C_6)$-alkyl, $(C_3-C_7)$-cycloalkyl, $(C_1-C_6)$-alkoxy, methoxycarbonyl, methoxycarbonylmethyl, halogen, amino, aminocarbonyl or methoxymethyl, $R^1$ is hydrogen, $(C_1-C_6)$-alkyl, halo-$(C_1-C_6)$-alkyl, $(C_3-C_6)$-cycloalkyl, halo-$(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl, heterocyclyl-O—$(C_1-C_6)$-alkyl, where the nine last-mentioned radicals are in each case substituted by s radicals from the group consisting of nitro, halogen, $(C_1-C_6)$-alkyl, halo-$(C_1-C_6)$-alkyl, $R^3O(O)C$, $(R^3)_2N(O)C$, $R^3O$, $(R^3)_2N$, $R^4(O)_nS$ and $R^3O$—$(C_1-C_6)$-alkyl, and where heterocyclyl carries n oxo groups, $R^2$ is $(C_1-C_6)$-alkyl, halo-$(C_1-C_6)$-alkyl, $(C_3-C_6)$-cycloalkyl, halo-$(C_3-C_6)$-cycloalkyl, $(C_3-C_6)$-cycloalkyl-$(C_1-C_6)$-alkyl, $(C_1-C_6)$-alkyl-O—$(C_1-C_6)$-alkyl, cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, hetero aryl-O—$(C_1-C_6)$-alkyl, heterocyclyl-O—$(C_1-C_6)$-alkyl, where the nine last-mentioned radicals are in each case substituted by s radicals from the group consisting of nitro, halogen, $(C_1-C_6)$-alkyl, halo-$(C_1-C_6)$-alkyl, $R^3O(O)C$, $(R^3)_2N(O)C$, $R^3$, $(R^3)_2N$, $R^4(O)_nS$ and $R^3O$—$(C_1-C_6)$-alkyl, and where heterocyclyl carries n oxo groups, $R^3$ is hydrogen or $(C_1-C_6)$-alkyl, $R^4$ is $(C_1-C_6)$-alkyl, $R^5$ is hydrogen or $(C_1-C_4)$-alkyl, n is 0, 1 or 2, s is 0, 1, 2 or 3, t is 0 or 1.

3. The sulfin- or sulfonimidoylbenzamide and/or salt as claimed in claim 1 in which Q is a radical Q1, Q2, or Q3,

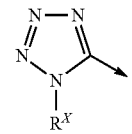
(Q1)

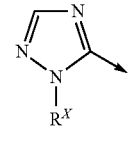
(Q2)

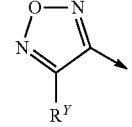
(Q3)

X is nitro, halogen, methyl, ethyl, n-propyl, isopropyl, trifluoromethyl, difluoromethyl, chlorodifluoromethyl, dichlorofluoromethyl, trichloromethyl, pentafluoroethyl, heptafluoroisopropyl, cyclopropyl, methoxy, ethoxy, methylsulfanyl, methylsulfinyl, methylsulfonyl, methoxymethyl, ethoxymethyl, methoxyethyl, methoxyethoxymethyl, methylthiomethyl, methylsulfinylmethyl or methylsulfonylmethyl, Z is hydrogen, nitro, cyano, halogen, methyl, ethyl, n-propyl, isopropyl, trifluoromethyl, difluoromethyl, chlorodifluoromethyl, dichlorofluoromethyl, trichloromethyl, pentafluoroethyl, heptafluoroisopropyl, cyclopropyl, methoxy, ethoxy, methylsulfanyl, methylsulfinyl or methylsulfonyl, W is hydrogen, chlorine or methyl, R is methyl, ethyl or n-propyl, R' is hydrogen, cyano or trifluoroacetyl, R" is hydrogen, $R^x$ is methyl, ethyl, n-propyl, prop-2-en-1-yl, methoxyethyl, ethoxyethyl or methoxyethoxyethyl, $R^Y$ is methyl, ethyl, n-propyl, chlorine or amino, t is 0 or 1.

4. A herbicidal composition which comprises a herbicidally active amount of at least one compound of formula (I) as claimed in claim 1 and/or a salt thereof.

5. The herbicidal composition as claimed in claim 4 in a mixture with one or more formulation auxiliaries.

6. The herbicidal composition as claimed in claim 4 which comprises at least one further pesticidally active compound selected from the group consisting of insecticides, acaricides, herbicides, fungicides, safeners and growth regulators.

7. The herbicidal composition as claimed in claim 6 which comprises a safener.

8. The herbicidal composition as claimed in claim 7 which comprises cyprosulfamide, cloquintocet-mexyl, mefenpyr-diethyl or isoxadifen-ethyl.

9. The herbicidal composition as claimed in claim 6 which comprises a further herbicide.

10. A method of controlling one or more unwanted plants, which comprises applying an effective amount of at least one compound of formula (I) and/or a salt thereof as claimed in claim 1 to the plants or to a location of unwanted plant growth.

11. A method as claimed in claim 10, wherein the compound of the formula (I) and/or a salt thereof is employed for controlling one or more unwanted plants in one or more crops of useful plants.

12. A method as claimed in claim 11, wherein the useful plants are transgenic useful plants.

13. The sulfin- or sulfonimidoylbenzamide and/or salt as claimed in claim 1 in which Q is a radical Q1.

14. The sulfin- or sulfonimidoylbenzamide and/or salt as claimed in claim 1 in which Q is a radical Q2.

15. The sulfin- or sulfonimidoylbenzamide and/or salt as claimed in claim 1 in which Q is a radical Q3.

16. The sulfin- or sulfonimidoylbenzamide and/or salt as claimed in claim 3 in which Q is a radical Q1.

17. The sulfin- or sulfonimidoylbenzamide and/or salt as claimed in claim 3 in which Q is a radical Q2.

18. The sulfin- or sulfonimidoylbenzamide and/or salt as claimed in claim 3 in which Q is a radical Q3.

\* \* \* \* \*